United States Patent [19]
Craig et al.

[11] Patent Number: 6,057,123
[45] Date of Patent: May 2, 2000

[54] STEM CELL INHIBITING PROTEINS

[75] Inventors: Stewart Craig, Oxford; Michael George Hunter, Buckinghamshire; Richard Mark Edwards, Oxford; Lloyd George Czaplewski, Oxford; Richard James Gilbert, Oxford, all of United Kingdom

[73] Assignee: British Biotech Pharmaceuticals Limited, Oxford, United Kingdom

[21] Appl. No.: 07/982,759

[22] PCT Filed: Dec. 23, 1992

[86] PCT No.: PCT/GB92/02390

§ 371 Date: Mar. 8, 1993

§ 102(e) Date: Mar. 8, 1993

[87] PCT Pub. No.: WO93/13206

PCT Pub. Date: Jul. 8, 1993

[30] Foreign Application Priority Data

Dec. 23, 1991 [GB] United Kingdom ............... 9127319
Oct. 14, 1992 [GB] United Kingdom ............... 9221587

[51] Int. Cl.[7] ............... C12N 1/21; C07H 21/02; C07K 14/52
[52] U.S. Cl. ............... 435/69.1; 435/69.5; 435/320.1; 435/325; 435/252.3; 530/350; 530/351; 536/23.5
[58] Field of Search ............... 536/23.5; 435/69.1, 435/69.5, 320.1, 325, 252.3; 514/12; 530/350, 351

[56] References Cited

U.S. PATENT DOCUMENTS 4,929,555  5/1990  Cregg et al. .

FOREIGN PATENT DOCUMENTS 3228683   10/1991  Japan .
WO9104274  9/1990  WIPO .
WO9205198  9/1991  WIPO .

OTHER PUBLICATIONS

Graham et al., Nature, 344:422 (1990).
Schall, Cytokine, 3:165–183 (1991).
Dunlop et al., Blood, 79:2221–2225 (1992).
Oppenheim et al., Annual Rev. Immunol., 9:617–648 (1991).
Clore et al., Biochemistry, 29:1689–1696 (1990).
Gronenborn and Clore, Protein Engineering, 4:263–269 (1991).
Lodi et al., Science, 263:1762–1767 (1994).
McKie and Douglas, Drug Design and Discovery, 11:47–59 (1994).
Skelton et al., Biochemistry, 34:5329–5342 (1995).
Chung et al., Biochemistry, 34:9307–9314 (1995).
Covell et al., Protein Science, 3:2604–2072 (1994).
Broxmeyer et al., J. Immunology, 150(8):3448–3458 (1993).
Mantel et al., Expt. Haematol., 20: No. 368,800 (1992).
Graham & Pragnell, Dev. Biol., 151:377–381 (1992).
W. R. Paukovits, et al., "Hemoregulatory Peptide pGlu–Glu–Asp–Cys–Lys: A New Synthetic Derivative for Avoiding Dimerization and Loss of Inhibitory Activity," *Molecular Pharmacology*, 38:401–409 (Jun. 1990).

*Primary Examiner*—Patricia Duffy
*Attorney, Agent, or Firm*—Hale and Dorr LLP

[57] ABSTRACT

Proteinaceous molecules with stem cell inhibition activity are analogues of LD78 or MIP-1α which have mutations to prevent or reduce multimer formation beyond certain stages (for example a dodecamer). Aggregate formation is therefore inhibited, and the resulting low molecular weight monomers (or oligomers) have improved solution properties leading to enhanced productivity and greater therapeutic utility as stem cell protective agents, which are useful in tumour therapy.

23 Claims, 23 Drawing Sheets

FIG. 1A

```
LD78         -SLAADTPTA CCFSYTSRQI   PQNFIADYFE TSSQCSKPGV IFLTKRSRQV   49
ACT-2        APMGSDPPTA CCFSYTARKL   PRNFVVDYYE TSSLCSQPAV VFQTKRSKQV   50
MIP-1 Alpha  APYGADTPTA CCFSYSRK-I   PRQFIVDYFE TSSLCSQPGV IFLTKRNRQI   49

LD78         CADPSEEWVQ KYVSDLELSA                                       69
ACT-2        CADPSESWVQ EYVYDLEIN-                                       69
MIP-1 Alpha  CADSKETWVQ EYITDLELNA                                       69
```

| LANE | SAMPLE |
|---|---|
| 1 | markers |
| 2 | MIP-1a |
| 3 | Act-2 |
| 4 | LD78 |

| LANE | SAMPLE |
|---|---|
| 1 | EGF |
| 2 | MIP-1a |
| 3 | Act-2 |
| 4 | Ld78 |
| 5 | markers |

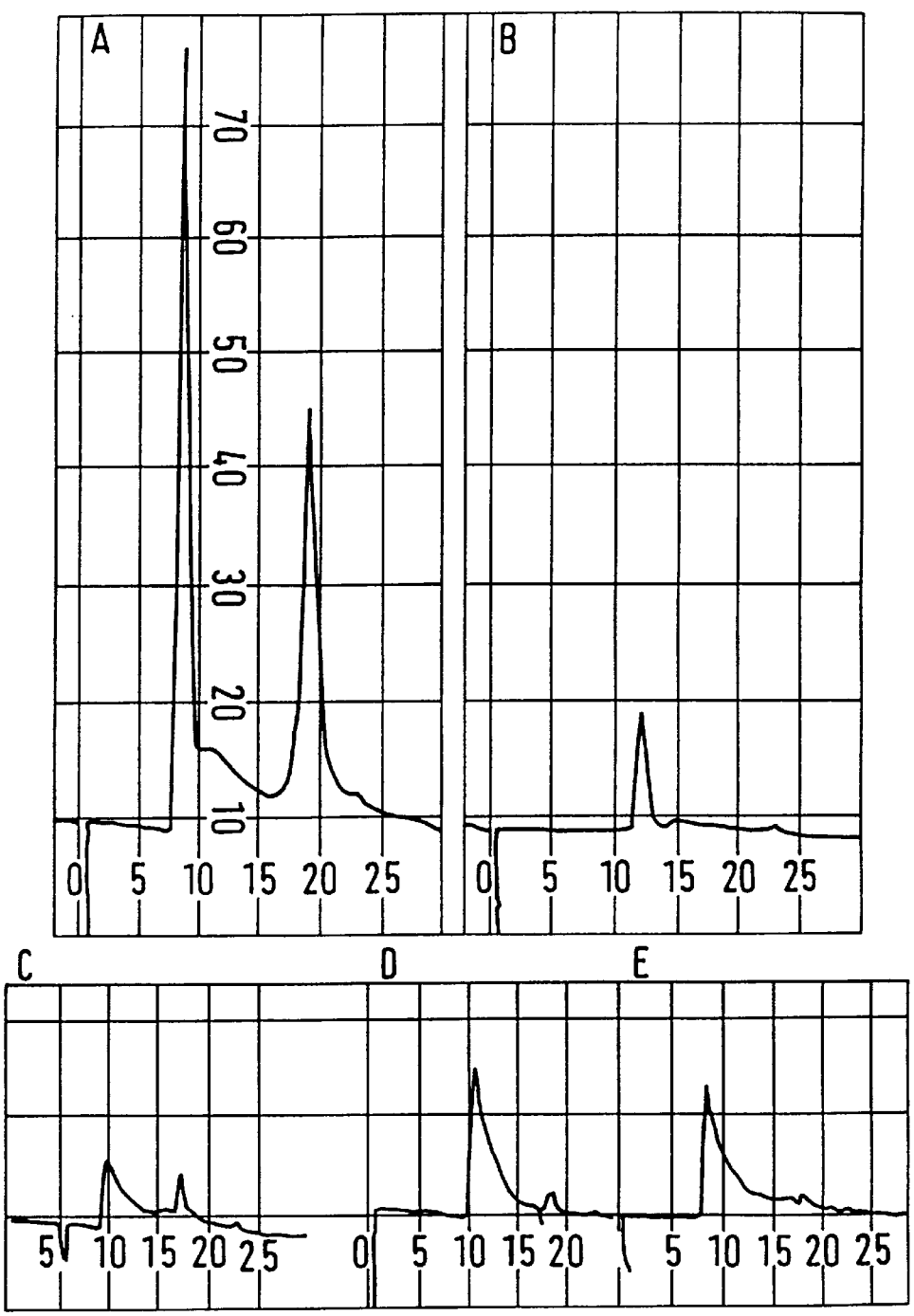

Tracks from left to right:

Mutant 30

Mutant 29

Mutant 26

Mutant 15

Mutant 10

Mutant 2

Mutant 1

Wild type

Markers

FIG. 21

```
          BB5615
AGCTTGGAT AAAGATCCT TGGCTGCTGA CACTCCAACC GCTTGT    TGTT TCTCTTACAC
||||||||| ||||||||| |||||||||| |||||||||| ||||||         ||||||||||
   ACCTA TTTTCTAGGA ACCGACGACT GTGAGGTTGG CGAACAACAA AGA GAATGTG
                BB5616

BB5617
CTCTAGACAA ATTCCACAAA ATTTCATTGC TGACTA   CTTT GAAACTTCTT CTCAATGTTC
|||||||||| |||||||||| |||||||||| ||||||   |||| |||||||||| ||||||||||
GAGATCTGTT TAAGGTGTTT TAAAGTAACG ACTGATGAAA CTT TGAAGAA GAGTTACAAG
                   BB5618

BB5619                                                BB5621
CAAGCCAGGT GTCATCTTCT TGAC    TAAGCG CTCGAGACAA GTCTGTGCTG ACCCATCTGA
|||||||||| |||||||||| ||||           |||||||||| |||||||||| ||||||||||
GTTCGGTCCA CAGTAGAAGA ACTGATTCGC G    AGCTCTGTT CAGACACGAC TGGGTAGACT
               BB5620                                    BB5622

BB5623
AGAATGGGTT  CAAAAATATG TTTCTGACTT GGAATTGTCT GCCTAATAAG
||||||||||  |||||||||| |||||||||| |||||||||| ||||||||||
TCTTACCCAA GTTTTTA    TAC AAAGACTGAA CCTTAACAGA CGGATTATTC CTAG
                     BB5624
```

FIG. 22

```
           BB3374
AGCTTACCT GCCATGGCGC CTTATGGAGC TGACACCCC  G ACTGCATGCT GCTTCTCCTA
     ||||  ||||||||||  ||||||||||  |||||||||     ||||||||||  ||||||||||
     ATGGA CGGTACCGCG GAATACCTCG ACTGTGGGGC TGACGT   ACGA CGAAGAGGAT
                              BB3375

BB3376                                       BB3378
CAGCCGGAAG ATTCCACGCC AAT   TCATCGT CGACTATTTT GAAACTAGTA GCCTTTGCTC
 |||||||||  |||||||||  |||    ||||||| |||||||||| ||||||||||  ||||||||||
GTCGGCCTTC TAAGGTGCGG TTAAGTAGCA   GCTGATAAAA CTTTGATCAT CGGAAACGAG
              BB3377                                      BB3379

BB3380
CC AGCCAGGT GTCATTTTCC TGACTAAGAG AAAACCGGCA  G ATCTGCGCTG ACTCCAAAGA
    ||||||||  ||||||||||  ||||||||||  ||||||||||     ||||||||||  ||||||||||
GGTCGGTCC A CAGTAAAAGG ACTGATTCTC TTTGGCCGTC TAGACG   CGAC TGAGGTTTCT
                              BB3381

BB3382                            BB3384
GACCTGGGTC CAAGAATACA TCA   CTGACCT CGAGCTGAAT GCCTGATAGG ATCCG
 ||||||||||  ||||||||||  |||    ||||||| |||||||||| ||||||||||  |||||
CTGGACCCAG GTTCTTATGT AGTGACTGGA   GCTCGACTTA CGGACTATCC TAGGCTTAA
              BB3383                              BB3385
```

FIG. 23

```
BB5424
AGCTTGGAT AAAAGAGCAC CAATGGGTTC AGACCCTCCA ACCGCAT      GCT            GCTTTCTTA
    ||||| |||||||||| |||||||||| |||||||||| |||||||      |||            |||||||||
    ACCTA TTTTCTCGTG GTTACCCAAG TCTGGGAGGT TGGCGTACGA    CGAA           AAGAAT
          BB5425

BB5426                                                      BB5428
CA CCGCTAGG AAGTTGCCTA GAAACTTTGT GGTC     GACTAC TATGAGACCT CTTCTTTGTG
|| |||||||| |||||||||| |||||||||| ||||     |||||| |||||||||| ||||||||||
GT GGCGATCC TTCAACGGAT CTTTGAAACA CCAGCTGATG A      TACTCTGGA GAAGAAACAC
   BB5427                                                  BB5430
                                                           CAAGTCTGTG CTGACCCGAG
                                                           |||||||||| ||||||||||
                                                           GTTCAGACAC GACTGGGCTC
                                                                      BB5431
CTCCCAGCCA GCTGTGGTAT    TCCAAACCAA AAGATCCAAG
|||||||||| ||||||||||    |||||||||| ||||||||||
GAGGGTCGGT CGACACCATA AGGTTTG      GTT TTCTAGGTTC
BB5429

BB5432
TGAATCC   TGG GTCCAGGAGT ACGTGTATGA CTTGGAATTG AACTGATAAG
|||||||   ||| |||||||||| |||||||||| |||||||||| ||||||||||
ACTTAGGACC CAGG    TCCTCA TGCACATACT GAACCTTAAC TTGACTATTC CTAG
                                               BB5433
```

STEM CELL INHIBITING PROTEINS

This application is the national stage of PCT/GB92/02390 filed Dec. 23, 1992.

This invention relates to proteinaceous compounds having the properties of inhibitors of stem cell proliferation. In particular, the invention relates to engineered variants of protein molecules with stem cell inhibition activity, their preparation and pharmaceutical compositions containing them and their use as adjuncts to chemotherapy or radiotherapy, for example in the treatment of cancer.

The diverse cells of the haemopoietic system are derived from multipotential stem cells by a process of sequential division and differentiation. The proliferation of the stem cell population is controlled in part by an inhibitory molecule produced by bone marrow macrophages (Lord et al., *Brit. J. Haematol.* 34 441, (1976)). The murine haemopoietic stem cell inhibitor has been shown to be an 8 kDa protein, macrophage inflammatory protein-1 alpha (MIP-1α (Graham et al., *Nature* 344 442, (1990)). The properties of the stem cell inhibitor include protecting stem cells from the toxic effects of cell cycle specific cytotoxic agents (Lord and Wright, *Blood Cells,* 6 581 (1980)). Stem cell inhibitors therefore have enormous clinical potential as agents to protect the stem cells from the chemotherapy or radiotherapy regimes used in tumour therapy. Additionally, stem cell inhibitors may be used in the treatment of hyperproliferative diseases such as psoriasis, either alone or in conjunction with cytotoxic agents. Amino acid sequence homologies suggested that either the human LD78 or ACT2 gene products were the human homologues of the murine stem cell inhibitor (FIG. 1*a*) (Schall, *Cytokine* 3 165–183 (1991)). It has been demonstrated that the human LD78 gene product is the functional homologue of murine MIP-1α, (Pragnell CRC Beatson Laboratory Scientific Report pp 21–25, (1990), Dunlop et al., *Blood* 79: 2221–2225 (1992)).

As a component of the present invention, the secondary and tertiary structure of LD78 and MIP-1α have been shown to be almost identical. Only a difference in the nature of a side-chain or charge interaction in the vicinity of Trp-57 is observed for the two proteins. Despite having a similar secondary structure to LD78 and MIP-1α, near u.v. c.d. studies show ACT2 has a different tertiary conformation as highlighted by the shape and intensity of the spectrum. This provides strong evidence that LD78 and not ACT2 is the human bomologue of MIP-1α.

A major problem shared by murine MIP-1α and human LD78, which limits their potential clinical utility, is that at concentrations as low as 25 μg/ml in physiological ionic strength buffer they form large soluble multimeric complexes which have a tendency to aggregate. The native MIP-1α and LD78 protein molecules have a molecular weight of 7,966 Da and 7,712 Da respectively. For both proteins, the soluble multimeric complexes show a broad heterogeneous mixture of molecular weights ranging from 100,000 Da to >>200,000 Da. The principal consequence of the multimerisation and aggregation phenomena is that clinical administration of the protein is compromised. Aggregation and multimerisation can lead to varying efficacy, impaired tissue penetration and enhanced immunogenicity. Another important shortcoming is that, during production and formulation, aggregation will result in heterogeneous pharmaceutical preparations.

Cloudy aggregates are often observed upon reconstitution of pure, lyophilised LD78 or MIP-1α protein in physiological ionic strength buffer at pH 7.4. Aggregates are removed by centrifugation prior to further analysis. Size exclusion chromatography (Comparative Example 3) of the soluble reconstituted MIP-1α and LD78 following clarification show that the majority of the protein chromatographs as broad peaks of molecular weights of 100,000–800,000 Da. The broad trailing edge of the peaks demonstrates the existence of a range of high molecular weight complexes for each protein. The size exclusion profile of MIP-1α also reveals a population of tetrameric molecules in equilibrium with the large multimers.

Although the problem of aggregation of stem cell inhibitors (and LD78 in particular) has been recognised in the art, those working in the field have hitherto attempted to address it by formulating unusual buffering systems (Mantel et al., *Expt. Haematol.* 20: No. 368 800 (1992), Dunlop et al., *Blood* 79: 2221–2225 (1992) and Graham & Pragnell *Dev. Biol.* 151 377–81 (1992)) to keep the otherwise multimeric molecule in a low molecular weight form. This approach has its disadvantages, not least that, whatever the ingredients of the buffer, the molecule may well reaggregate on administration in vivo.

The present invention approaches the problem in a radically different way. It has been discovered not only how stem cell inhibitors such as LD78 and MIP-1α aggregate but also that it is possible to inhibit the aggregation or multimerisation at certain stages in the aggregation process, while still retaining biological activity.

MIP-1α, LD78 and ACT-2 show sequence homology to the chemotactic cytokine superfamily of proteins which contains Interleukin-8 (IL-8), platelet factor 4 (PF-4) and monocyte chemo-attractant and activating protein (MCAF). Of these related proteins, it is known that IL-8 exists as a dimer (Clore et al., *Biochemistry* 29 1689–1696 (1990)) and PF-4 is a tetramer at physiological ionic strength (Moore et al, *Biochim. Biophys. Acta.* 379, 379–384, 1975). The model of MCAF built using IL-8 as a template (Gronenborn & Clore, *Protein Engineering* 4 263–269 (1991)) is consistent with a basic dimeric structure. However, trimerisation of tetramers to dodecamers has not previously been reported.

It has now been found that the high-order multimers of MIP-1α and LD78 are formed via intermediate dimers, tetramers and dodecamers (three associated tetramer units). So to prevent the undesirable higher order multimerisation and aggregation, it is necessary to prevent multimerisation either at the level of or lower than the dodecamer. At its broadest, therefore, in a first aspect the invention provides a proteinaceous molecule with stem cell inhibition (SCI) activity, the molecule being substantially incapable at physiological ionic strength of forming a stable multimer higher than a dodecamer. The molecular weight of molecules in accordance with the invention will generally be about or less than 100,000 Da at physiological ionic strength. Such variants would require no further formulation, at least in respect of the multimerisation properties, and would therefore represent a clinical advantage in terms of ease of use and a manufacturing advantage as its homogeneity would better lend itself to GMP. Additionally, the increased molecular surface area may lead to advantages in tissue penetrability and increased efficacy.

Preferred embodiments of the invention are substantially incapable at physiological ionic strength of forming a stable multimer higher than a tetramer; the molecular weight in such cases will generally be about or less than 32,000 Da. Some embodiments are substantially incapable at physiological ionic strength of forming a stable multimer higher than a dimer; in these cases, the molecular weight will generally be about or less than 16,000 Da. Certain embodiments of the invention are substantially incapable of forming multimers at all; their molecular weight will generally be about or less than 8,000 Da, which is the monomeric molecular weight of LD78 and MIP-1α, based on amino acid sequences.

Molecules which form substantially homogenous populations of multimers (or monomers) are preferred.

The molecular weight and/or degree of multimerisation of molecules of the invention can be assessed by any suitable means. Electrophoresis (for example native PAGE), size-exclusion chromatography and, particularly, ultracentrifuge sedimentation coefficient analysis are methods of choice.

When it is stated in this specification that a molecule is "substantially incapable" of forming a multimer higher than a given order, it should be understood that a minor proportion of higher order multimers can be tolerated and may in fact be inevitable from a consideration of thermodynamic equilibria. While it is not possible to put precise quantitative limits on this proportion, in general no more than 15, 10 or even 5% of the species present will be above the threshold stated.

The term "stem cell inhibition activity" (or "SCI activity") is known to those skilled in the art. It may be taken to refer to a biological activity exhibited by MIP-1α and/or LD78 and in particular to the inhibition of proliferation of stem cells or, more precisely, to the prevention of movement of stem cells through a proliferative cell cycle. Proteinaceous molecules in accordance with the invention may therefore be regarded as analogues of MIP-1α and/or LD78. "Stem cells", as generally indicated above, are dividing cells which maintain cells of various lineages, particularly cells of the haemapoietic system or the epithelial system; more particularly, haemapoietic stem cells are cells which are capable of self renewal and are capable of giving long term repopulation of cells of the haemapoietic system when transplanted into a lethally irradiated animal.

Stem cell inhibition activity can be determined experimentally in a variety of ways. For example, an in vitro assay of activity can be made. Such an assay is preferably a receptor binding assay: molecules in accordance with the invention are assessed for their ability to displace LD78 (or MIP-1α), which may be appropriately detectably labelled, from a suitable source of receptors, such as the murine stem cell line FDCP cell mix (A4 cells). Details of such an assay are given in Example 164 below; stem cell inhibition activity may be said to be exhibited by a molecule if a statistically significant proportion of wild type activity (for example at least 1%, 5%, 10%, or 20%, in increasing order of preference, of the activity of the corresponding wild type molecule) is observed for a preparation of given concentration. Receptor binding activity which is as good as, or even better than, wild type is not essential but may well be preferred.

An alternative but functional, although still in vitro assay for experimental determination is an assay which measures the inhibition of proliferation of murine day 12 CFU-S cells. Molecules are assayed for their ability to inhibit colony formation of day 12 CFU-S cells sorted from murine bone marrow. Details can be found in:

Lord and Spooner *Lymphokine Research* B 59 (1986) and Lord and Marsh in "Haemapoiesis, A Practical Approach" IRL Press, Oxford, 1992, Testa and Molineux, Eds., page 21 (for murine bone marrow cell sorting);

Heyworth and Spooner in "Haemapoiesis, A Practical Approach" IRL Press, Oxford, 1992, Testa and Molineux, Eds., page 37 (for general cell culture techniques); and Pragnell et al. *Blood* 72 196 (1988) (for assay and conditioned medium).

More precise details of such an assay are given in Example 165 below. Molecules possess stem cell inhibition activity if they inhibit colony formation in this assay. Inhibition which is as good as or even better than wild type is not essential but may be preferred.

A further alternative functional, but still in vitro, assay is to be found in WO-A-9104274, Pragnell et al., *Blood* 72 196–201 (1988) and Lorimer et al. *Leukemia Research* 14 481–489 (1990).

Alternatively or additionally, activity in vivo can be assessed. First, a CFU-S in vivo assay, in which the ability of the candidate stem cell inhibitor is used to protect the stem cell population (measured as CFU-S) against the cytotoxic effects of chemotherapeutic agents such as hydroxyurea or cytosine arabinoside (ara-C). A suitable assay is described in Lord et al., *Blood* 79: 2605–2609 (1992) and also by Lord in "Haemopoiesis—A Practical Approach", pages 1–20, IRL Press, Oxford, 1992, (Testa and Molineux, Eds.), pages 1–20 and by Lord and Schofield in "Cell Clones: Manual of Mammalian Cell Techniques", Churchill Livingstone, 1985 (Potten and Henry, Eds.), pages 13–26.

Further in the alternative, or in addition, an assay which indirectly reflects the CFU-S population measures the recovery of neutrophil numbers following chemotherapy with ara-C; such an assay is described in Dunlop et al., *Blood* 79: 2221–2225.

A molecule can be regarded as having stem cell inhibiting activity if it gives a significant improvement over negative control (whether or not an improvement over the wild type molecule) in any or all of the above assays. Certain preferred molecules show such an improvement over negative control in more than one, or even all, of the assays.

The term "physiological ionic strength" is well known to those skilled in the art. It is generally equivalent to about 137 mM NaCl, 3 mM KCl and about 10 mM phosphate. Physiological pH is about 7.4.

The invention enables the preparation of analogues of LD78 and MIP-1α in dodecameric, tetrameric, homodimeric and monomeric forms, wherein each form is substantially incapable of forming a stable higher order complex under conditions of physiological ionic strength and pH. The analogues may form a substantially homogeneous population of multimers; analogues which form a substantially homogeneous preparation of tetramers are preferred.

The term "analogue" is used, broadly, in a functional sense. As a practical matter, though, most analogues will have a high degree of homology with the prototype molecule if biological activity is to be substantially preserved. It will be realised that the nature of changes from the prototype molecule is more important than the number of them. As guidance, though, at the amino acid level, it may be that (in increasing order of preference) at least 40, 50, 60, 65, 67 or 68 of the residues will be the same as the prototype molecule; at the nucleic acid level, nucleic acid coding for an analogue may for example hybridise under stringent conditions (such as at approximately 35° C. to 65° C. in a salt solution of approximately 0.9 molar) to nucleic acid coding for the prototype molecule, or would do so but for the degeneracy of the genetic code.

Many analogue MIP-1α and LD78 molecules of this invention reproducibly form a stable quaternary structure no greater than either a tetramer or three associated tetramer units (a dodecamer). It may well be that the stability of dimers, tetramers, dodecamers or other multimers will vary depending on the environment of the molecules; if so, it will be preferably at physiological ionic strength and more preferably when the analogue is presented in a clinically administrable (usually aqueous) formulation, and at a clinically acceptable dose, that multimerisation beyond a dodecamer cannot (or at least does not) substantially occur. Often the clinically administrable formulation will be reconstituted from a lyophilised protein preparation. Preferably, multimers beyond dodecamers will not substantially occur in conditions likely to be encountered during production, formulation and administration. The absence of multimers of molecular weight greater than a tetramer or dodecamer reduces the aggregation of recombinant or other analogues of MIP-1α and LD78. Such stable preparations of MIP-1α and LD78 analogues with a defined, reproducible quaternary structure represent a distinct advantage in production, formulation and administration of the therapeutic entity.

A stable monomeric, dimeric, tetrameric or dodecameric variant may have improved pharmaceutical and pharmacokinetic properties, such as: the advantage of improved tissue penetration; a lesser likelihood of being immunogenic; and much more reproducible efficacy, by virtue of a stable quaternary structure. An added advantage of this approach lies in the fact that some of these surface residues may be involved in receptor activation and modify the pharmacology. Identification of biologically important residues can therefore be used to improve the pharmacokinetics of stem cell proliferation inhibition and lead to the design of low molecular weight mimics. Stable monomers, dimers, tetramers and dodecamers should provide powerful research tools, being particularly useful in the identification and characterisation of receptors for SCIs, of which little is known (Oh et al., *J. Immunol.* 147 2978–2983 (1991)). Disruption of the dimer interface interactions to produce a monomer would provide a useful research tool. A further advantage of this approach is the possibility of eliminating any cross reaction of LD78 or MIP-1α with the murine inflammatory protein-1β receptor or its human equivalent. Activation of the MIP-1β receptor elicits a major part of the inflammatory response of the body to these molecules and represents a potential unwanted side-effect during therapy. Elimination of this response would therefore provide a further clinical advantage.

An unexpected additional advantage conferred by the lack of multimerisation is the greatly enhanced productivity of such variants in eukaryotic cells, for example yeast species such as *Saccharomyces cerevisiae* and *Pichia pastoris*. The invention therefore relates additionally to a method of increasing protein expression levels in a system in which the desired protein normally forms multimeric complexes (which may be soluble) at physiological ionic strength (the "multimeric protein"), which method comprises using in the expression system cells which are transformed or transfected with a vector comprising DNA coding, not for the multimeric protein, but instead for a mutant thereof which has a reduced tendency to form (eg soluble) multimeric complexes relative to the multimeric protein. Such a method may be of general applicability, but has particular utility when applied to the production of proteins having stem cell inhibitor activity.

From studies involved in the making of this invention, it appears that LD78 and MIP-1α associate along the following pathway:

M+M←→D; D+D←→T; 3×T←→dodecamer;

n×dodecamer←→multimer; n×multimer→aggregate.

wherein M represents a monomer, D represents a homodimer and T represents a tetramer. FIGS. 1c and 1d illustrate how this putatively comes about. Circumstantial evidence in support of this proposal comes from Mayo and Chen (*Biochemistry* 28 9469–9478 (1989)), who demonstrated that tetramers of PF-4 form via a similar pathway.

The pathway proposed above consists of a series of reversible equilibria up to the point of the irreversible aggregation of multimers. There are in principle four stages in the association mechanism at which it is possible to prevent the formation of large multimers (and therefore aggregates) of SCIs. Inhibition of each of these stages could be influenced by a mutation in a different region of the SCI molecule.

First, further association of tetramers can be inhibited. Secondly, if the SCI dimers are prevented from associating to tetramers, then further multimerisation will be inhibited. Thirdly, SCI monomers may be prevented from dimerising. Fourthly, further association of dodecamers to higher order multimers can be inhibited. Any of these options can be implemented by specific mutation of residues involved in promoting and/or stabilising the association events. A further option would be to use a combination of mutations simultaneously to block two or all of the association events.

The following amino acid residues are preferred for modification:

(i) amino acid residues which could be involved in stabilising the interaction between two dimers; and (ii) amino acid residues at surface regions, on the external faces of the tetramer, which could act as sites for higher order association.

Radical mutation of individual or combinations of key residues stabilising the association of dimers into tetramers will yield a dimeric recombinant SCI variant or analogue molecule. Similarly, mutation of residues at the sites of association of tetramers to multimers will yield a tetrameric SCI variant or analogue molecule. The amino acid modification preferably involves a substitution, although deletions and additions are contemplated within the scope of the invention.

The types of mutation preferred for producing the desired effects are:

(i) charge repulsions (successfully used to produce monomeric insulin; Dodson, *Prospects in Protein Engineering Meeting Abstracts*, 49–53, (1989));

(ii) hydrophobic to hydrophilic changes;

(iii) neutral/hydrophobic to charged.

It is generally better not to substitute very hydrophobic residues into the protein in order to avoid contributing to the hydrophobic effect in association. Equally, it is preferred to avoid mutations which significantly disrupt secondary structural elements of the protein: so, for example, known β-breakers are preferably not introduced into β-sheet regions.

Certain types of mutation are most effective in producing desirable changes within the SCI molecule. These are:

charge reversal;

charged residue to neutral;

hydrophobic to hydrophilic.

For optimum results substitutions should be made at particular sites within the molecule. The residues which should be altered are dependent on the level of multimerisation which is to be prevented.

The following discussion of preferred sites for mutation deals primarily with LD78, the proposed structure of which is shown in FIG. 1b. In FIG. 1b, the ribbon traces the predicted path of backbone atoms for the LD78 monomer. The labelled residues define the putative secondary structure elements. β-sheet strand 1 runs from Phe23 to Thr30; β-sheet strand 2 runs from Lys35 to Thr43; β-sheet strand 3 runs from Ser46 to Pro53; and the C-terminal helix runs from Trp57 to Ala69. Analogous secondary structural elements may be inferred for other SCIs, including MIP-1α, for example using the amino acid alignment shown in FIG. 1a.

It is apparent that some faces of the monomer are involved in more than one part of the multimerisation pathway. The extent of disruption/inhibition of self-association in those faces is related to the nature of the amino acid substitution.

Inhibition of monomer to dimer formation can be achieved by one or more mutations, for example at residue 19 (Ile) or 39 (Val). Either residue may be changed to Ala.

Dimer to tetramer formation is affected by mutations in residues projecting away from the surface of the dimer in strand 1 of the βsheet, and/or in the turn between strands 2 and 3 of the sheet. Examples of the first region are amino acids 24–29 of LD78 and of the second region are amino acids 43–47 of LD78. In particular, Ile24>Asn, Tyr27>Asn, Phe28>Glu, Glu29>Arg, Lys44>Glu (especially with Arg45>Gln) and Arg 45>Glu are preferred.

Tetramer to dodecamer formation can be inhibited or disrupted by mutations of the nature described above in either the residues which form a chain N-terminal to the turn into strand 1 of the sheet (where two changes are preferred), particularly residues 16–21, especially 17–19 or at position 4, 12, 26, 44, 48 or 66 of LD78. In particular, Ala4>Glu, Phe12>Asp, Arg17>Ser, Asp26>Ala (especially with Gln18>Glu), Arg17>Glu (again especially with Gln18>Glu), Asp26>Ala, Lys44>Ser, Gln48>Glu (especially with Phe28>Glu) and Glu66>Ser are preferred.

Dodecamer to higher order multimer formation is prevented or disrupted by mutations at positions 12 to 21, especially positions 12, 18 and 21, of LD78, or at position 65. In particular, Phe12>Gln, Gln18>Glu, Gln21>Ser and Leu65>Ala are preferred.

Generally preferred LD78 analogues of the invention include molecules which comprise a sequence substantially corresponding to LD78, but with a mutation at one or more (but preferably no more than two) of the following amino acid residues: Ser1, Leu2, Ala3, Ala4, Asp5, Thr6, Ala9, Phe12, Ser13, Tyr14, Ser16, Arg17, Gln18, Ile19, Pro20, Gln21, Phe23, Ile24, Asp26, Tyr27, Phe28, Glu29, Ser31, Ser32, Gln33, Ser35, Lys36, Pro37, Gly38, Val39, Ile40, Leu42, Thr43, Lys44, Arg45, Ser46, Arg47, Gln48, Asp52, Glu55, Glu56, Gln59, Lys60, Tyr61, Val62, Asp64, Leu65, Leu67, Glu66, Ser68, and Ala69.

Preferred LD78 analogues in accordance with the invention include Lys44>Glu (with Arg45>Gln), Arg47>Glu, Phe28>Glu, Phe28>Glu (with Gln48>Glu), Phe28>Glu (with Arg47>Glu), Arg17>Ser (with Gln18>Glu), Phe12>Ala, Val39>Ala, Ile40>Ala, Asp26>Ala (with Glu29>Arg and Arg47>Glu). More preferred LD78 analogues in accordance with the invention include Arg17>Ser, Glu29>Arg, Gln18>Glu, Asp26>Ser, Gln48>Ser, Thr15>Ala, Gln21>Ser, Phe23>Ala, Ser32>Ala, Ala51>Ser, Ala4>Glu, Phe12>Asp, Asp26>Gln, Lys36>Glu, Lys44>Glu, Arg45>Glu, Glu66>Gln. The most preferred LD78 analogues in accordance with the invention are Phe12>Gln, Lys44>Ser, Arg17>Glu (with Gln18>Glu) and, especially, Asp26>Ala and Glu66>Ser. Generally preferred MIP-1α analogues of the invention include molecules which comprise a sequence substantially corresponding to MIP-1α, but with a mutation at one or more (but preferably not more than two) of the following amino acid residues: Ala1, Pro2, Tyr3, Gly4, Ala5, Asp6, Thr7, Ala10, Phe13, Ser14, Tyr15, Ser16, Arg17, Lys18, Ile19, Pro20, Arg21, Phe23, Ile24, Asp26, Phe28, Glu29, Ser31, Ser32, Glu33, Ser35, Gln36, Pro37, Gly38, Val39, Ile40, Leu42, Thr43, Lys44, Arg45, Asn46, Arg47, Gln48, Asp52, Glu55, Thr56, Gln59, Glu60, Tyr61, Ile62, Asp64, Leu65, Glu66, Leu67, Asn68 and Ala69.

Preferred MIP-1α analogues of the invention correspond to the preferred LD78 analogues described above.

Molecules in accordance with the invention will for preference be free of N-terminal extensions preceding Ser-1 (in the case of LD78) or Ala-1 (in the case of MIP-1α). This is because such N-terminally extended forms of the molecule are compromised with respect to their ability to bind to the LD78 receptor present on stem cells. Such molecules can still give rise to active species in functional in vitro assays, such as CFU-A or mitogenesis assays, possibly due to processing by aminopeptidases. It is preferable, however, not to depend on such processing events for the clinical application of a stem cell inhibitor, as it leads to greater uncertainty over the pharmacokinetics of the active species, and increased variation in the response.

In contrast to the N-terminally extended variants, molecules carrying N-terminal deletions of between 1 and 7 residues are active in receptor binding, though the full length form with serine at position 1 is preferred.

SCI analogues in accordance with the invention can in principle be made by any convenient method including chemical modification of existing (for example natural) proteins and/or chemical coupling of two or more oligo- or polypeptide chains. Far greater flexibility, though, can be obtained by using recombinant DNA methodology, which enables successive amino acid residues to be coupled together in vivo.

According to a second aspect of the invention, therefore, there is provided nucleic acid coding for a protein as described above. Both DNA and RNA are within the scope of the invention. DNA may be chemically synthesised and/or recombinant.

Mutations may be introduced by de novo polynucleotide synthesis, by site-directed mutagenesis using appropriately designed oligonucleotide primers or by any other convenient method.

Recombinant DNA in accordance with the invention may be in the form of a vector. The vector may for example be a plasmid, cosmid or phage. Vectors will frequently include one or more selectable markers to enable the selection of cells transformed (or transfected: the terms are used interchangeably in this specification) with them and, preferably, to enable selection of cells harbouring vectors incorporating heterologous DNA. Appropriate translational initiating and termination signals will generally be present. Additionally, if the vector is intended for expression, sufficient transcriptional regulatory sequences to drive expression will be included. Vectors not including regulatory sequences are useful as cloning vectors.

Cloning vectors can be introduced into *E. coli* or any other suitable hosts which facilitate their manipulation. Expression vectors may be adapted for prokaryotic expression but for preference are adapted for expression in a microbial eukaryotic cell, such as a yeast (including but not limited to *Saccharomyces cerevisiae* and *Pichia pastoris*) or a higher eukaryotic cell such as insect or mammalian cells.

Performance of the invention is neither dependent on nor limited to any particular strain of microorganism or cell type: those suitable for use with the invention will be apparent to those skilled in the art, following the teaching of this specification. According to a third aspect of the invention there is provided a host cell transfected or transformed with DNA described above. Host cells may be of any suitable source; eukaryotic host cells are preferred; yeast cells may be those of choice.

Production of stem cell inhibitors, whether wild type or altered as described above has been found to be particularly advantageous when carried out in the yeast host *Pichia pastoris*. According to a fourth aspect of the invention, therefore, there is provided a process for the production of a molecule having stem cell inhibitor activity, the process comprising culturing a yeast of the genus Pichia, and preferably of the species *pastoris*, the yeast having expressible heterologous nucleic acid coding for the molecule.

DNA in accordance with the invention can be prepared by any convenient method involving coupling together successive nucleotides, and/or ligating oligo- and/or polynucleotides, including in vitro processes, but recombinant DNA technology forms the method of choice.

However the proteinaceous compounds of the invention are made, they may be useful either as research tools or in medicine. Other uses are not ruled out. In a fifth aspect, the invention provides proteinaceous compounds as described above for use in medicine, particularly in the protection of stem cells, for example in tumour therapy (whether radiotherapy or chemotherapy).

The invention therefore provides in a sixth aspect the use of a proteinaceous compound as described above in the preparation of an agent for use as a stem cell protective agent, particularly in tumour therapy. The invention can be used in a method for the protection of stem cells, particularly in conjunction with tumour therapy, the method comprising administering to a patient an effective amount of a proteinaceous compound as described above. This method is preferably performed in vivo. Alternatively, the method may be performed ex vivo where the resulting marrow is purged of leukaemia cells by the chemotherapeutic agent and then reinjected into the patient.

Formulations of the proteinaceous compounds described above themselves form an aspect of the invention and comprise active compound and a pharmaceutically acceptable carrier. While oral formulations which lead to bioactive and bioavailable active compound may in principle be preferred, in practice the compounds of the invention may have to be administered parenterally. Parenterally administrable formulations will generally be sterile and may comprise one or more proteinaceous compounds dissolved in a suitable liquid excipient such as water for injections, PBS or physiological saline. Dosages will be determinable by the clinician or physician and will generally be such as to ensure an active dose is delivered.

Compounds of the invention may also be used to treat psoriasis or other disorders related to hyper-proliferative stem cells either alone or in conjunction with cytotoxic agents. Topical or transdermal formulations of compounds of the invention, as well as parenteral formulations, may advantageously be used in this aspect of the invention.

It is to be understood that preferred features for each aspect of the invention are as for each other aspect of the invention, *mutatis mutandis.*

Certain preferred embodiments of the invention will now be described with reference to the accompanying drawings, in which:

FIG. 1*a* illustrates the alignment of the LD78 (SEQ ID NO. 2) amino acid sequence with those of MIP-1α (SEQ ID NO. 18) and ACT-2(SEQ ID NO. 35);

FIG. 1*b* shows the structural model of the LD78 monomer. The ribbon traces the predicted path of the backbone atoms for the LD78 monomer. The labelled residues define the predicted secondary structure elements. Strand 1 of the β-sheet is from Phe23 to Thr36, strand 2 is from Lys35 to Thr43, strand 3 is from Ser46 to Pro53 and the C-terminal helix is from Trp57 to Ala69.

FIG. 1*c* shows schematically the putative multimer interfaces on the LD78 monomer.

FIG. 1*d* shows how the LD78 monomer shown in FIG. 1*c* are proposed to form dimers, tetramers, dodecamers and aggregates.

FIG. 2 illustrates the plasmid of yeast expression vector pSW6.

FIG. 3 demonstrates that the tertiary conformation of LD78 and MIP-1α are identical as determined by near ultra-violet circular dichroism.

FIG. 4 demonstrates that the tertiary conformation of ACT2 differs from that of MIP-1α as determined by near ultra-violet circular dichroism.

FIG. 6 shows a representative size exclusion chromatographic profile of MIP-1α, LD78 and ACT2, reconstituted as described in Comparative Example 4. Also shown is the elution profile of proteins used as standard of molecular weights demonstrating the correct separation of standard proteins and a table of molecular weight species determined for reconstituted LD78, MIP-1α and ACT-2.

Figure 12:
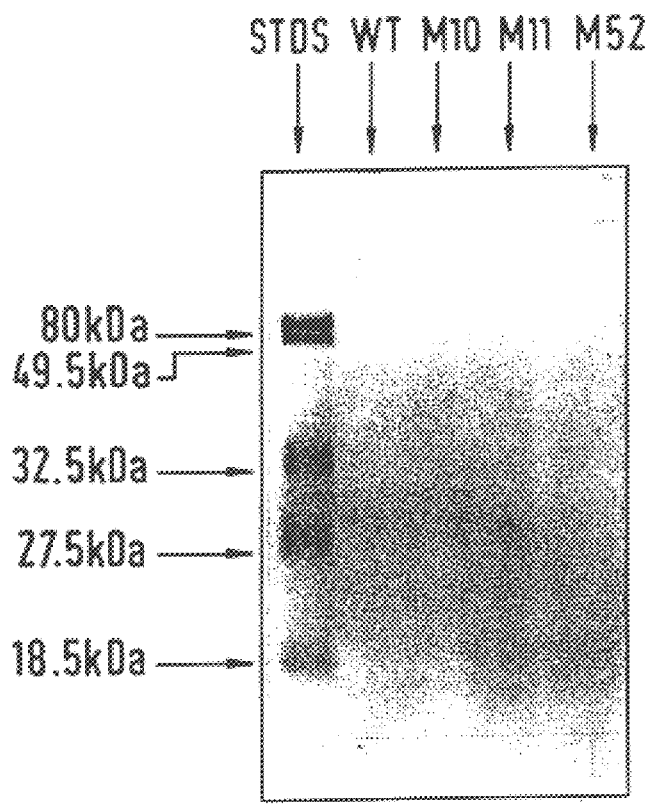

FIG. 12 shows a coomassie stained native PAGE gel with wild type LD78, mutant 10, 11, 52 and mixed molecular weight markers. The gel demonstrates the different electrophoretic mobilitie observed for LD78 variants. [Mutant 10 is the subject of Example 7, mutant 11 is the subject of Example 8 and mutant 52 is the subject of Example 64.]

Figure 13:
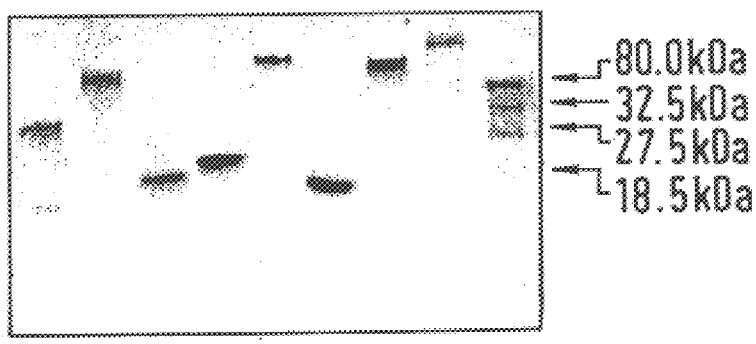

FIG. 13 shows a Coomassie blue stained native PAGE gel with native LD78, 7 mutant constructs and mixed molecular weight markers. The gel demonstrates that mutants 1, 2, 10, 15, 26, 29 and 30 (of Examples 1, 2, 7, 11, 16, 19 and 20, respectively) have different multimerisation properties from wild type exhibiting (to different extents) faster electrophoretic mobility.

Figure 14:
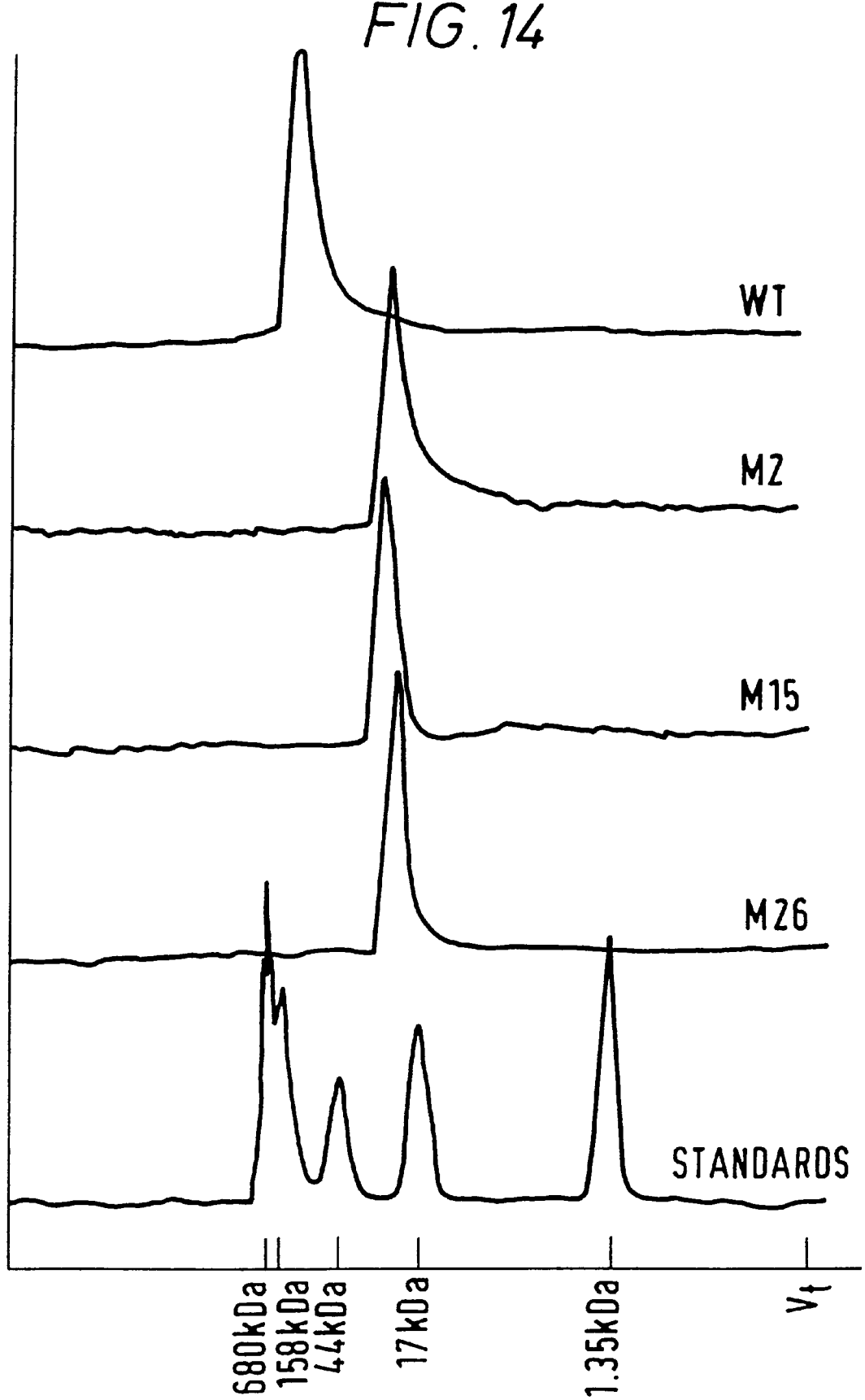

FIG. 14 shows the size exclusion chromatography (SEC) profiles in 150 mM PBS pH7.4 of selected mutant constructs with wild type LD78 for comparison.

Figure 15A:
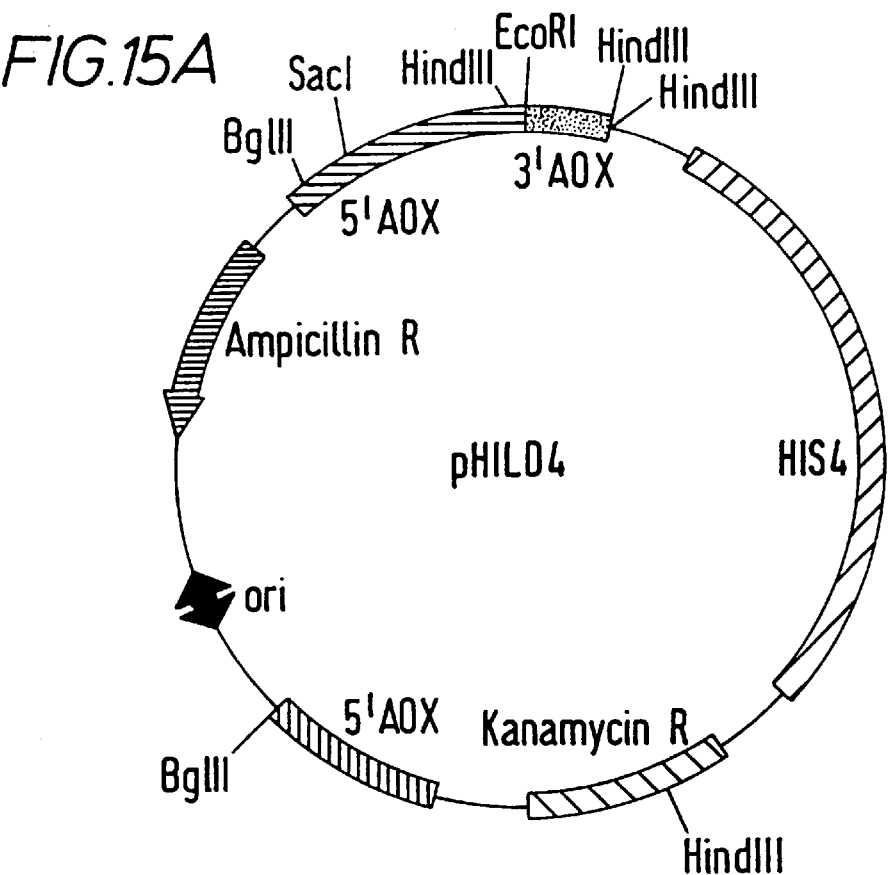

FIG. 15*a* shows the *Pichia pastoris* expression vector pHILD4.

Figure 15B:
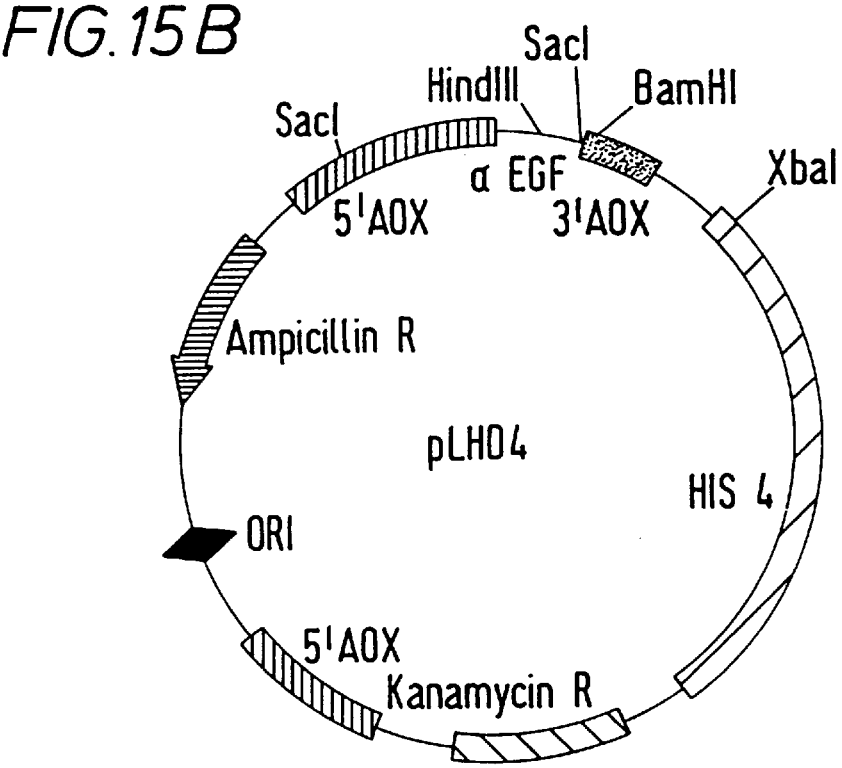

FIG. 15*b* shows the *Pichia pastoris* expression vector pLHD4 which includes an EGF gene fused to the a factor preprosequence.

Figure 16:
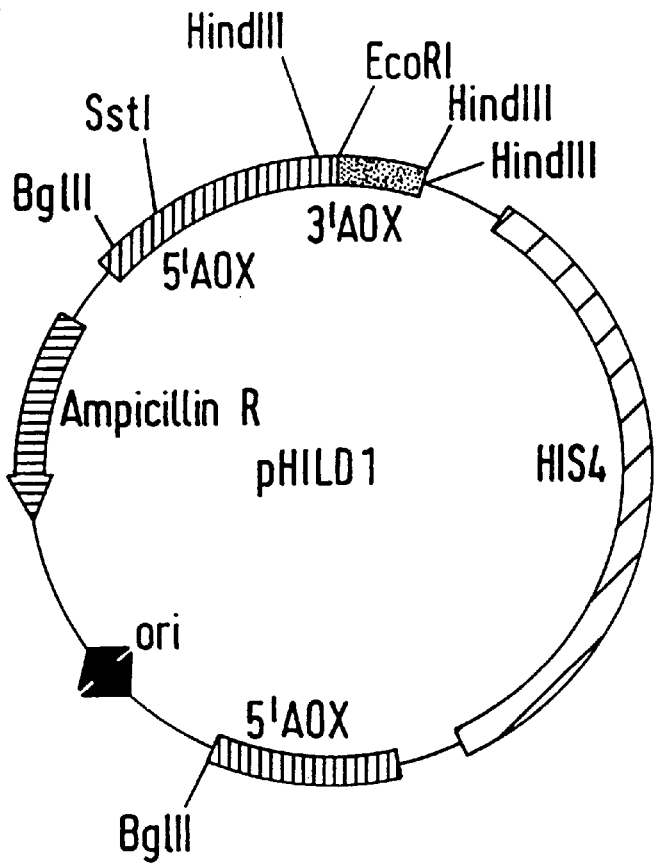

FIG. 16 shows the *Pichia pastoris* expression vector pHILD 1.

Figure 17:
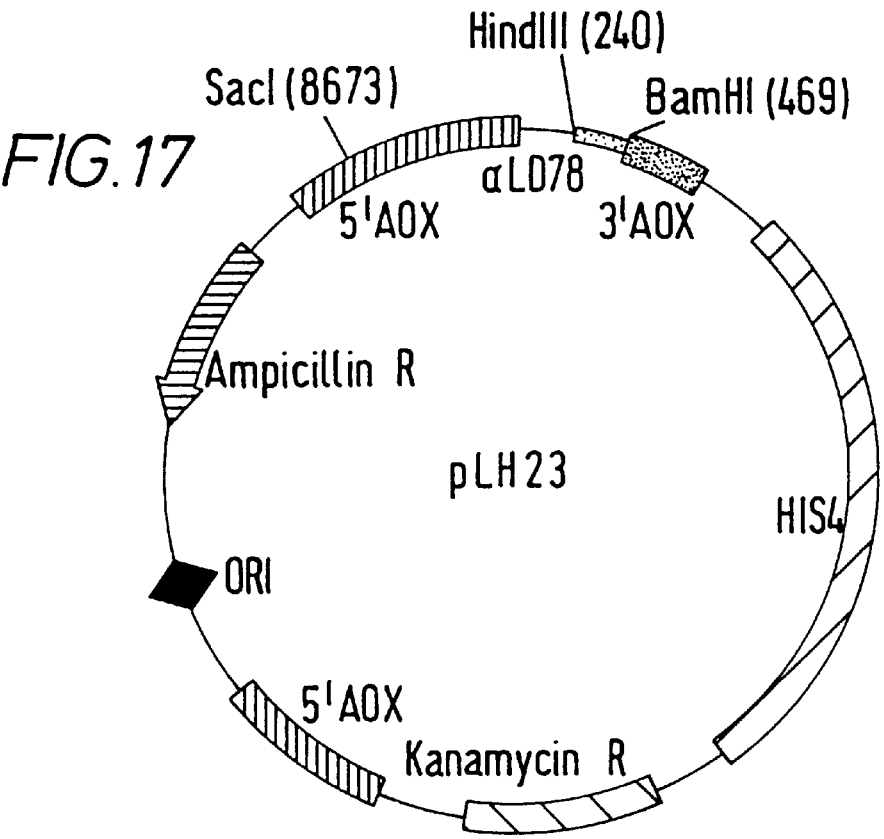

FIG. 17 shows the *Pichia pastoris* expression vector pLH23, which is based on pLHD4 modified to direct expression and secretion of LD78.

Figure 18:
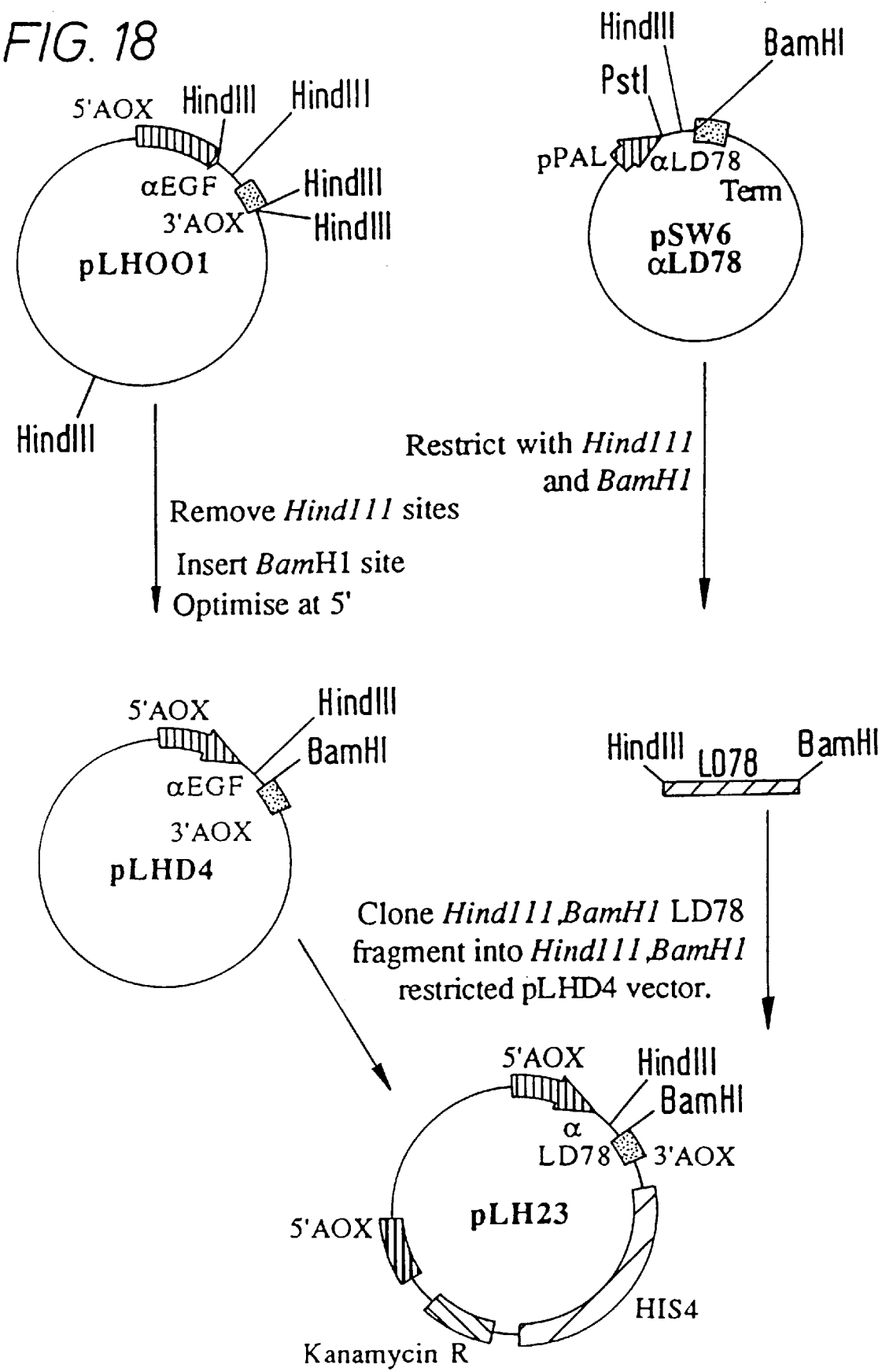

FIG. 18 shows the construction of the optimised *Pichia pastoris* LD78 secretion vector pLH23.

Figure 19:
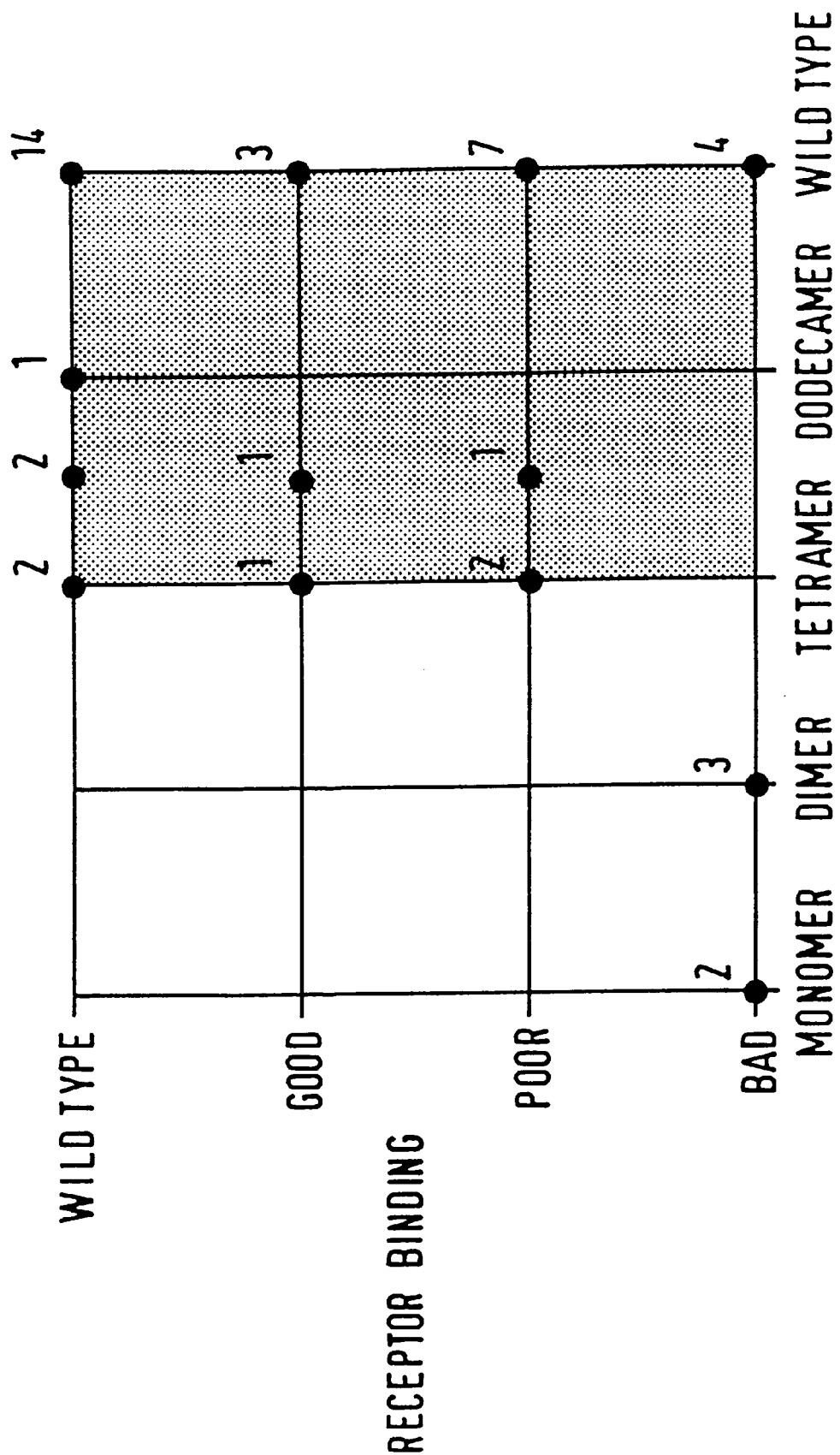

FIG. 19 shows the correlation between multimerisation state and receptor binding.

Figure 20:
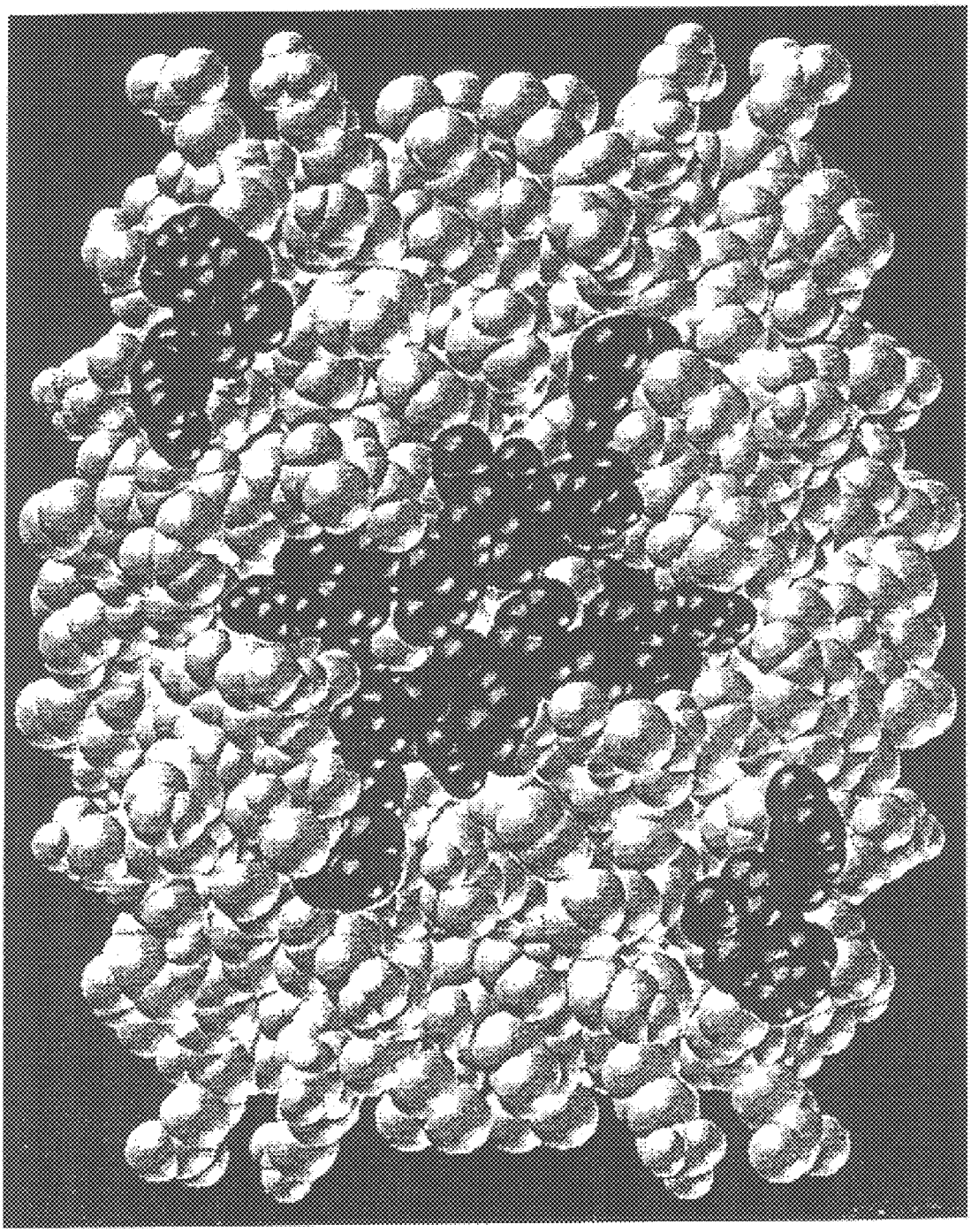

FIG. 20 shows a computer-generated model of the proposed LD78 tetramer with receptor binding residues highlighted in black.

FIG. 21 shows the annealed oligonucleotides for the construction of LD78 synthetic gene (SEQ ID NOS 4–13) with overlapping cohesive ends.

FIG. 22 shows the annealed oligonucleotides used in the construction of the MIP-1α gene (SEQ ID NOS 20–31) with overlapping cohesive ends.

FIG. 23 shows the annealed oligo nucleotides used in the construction of the ACT-2 gene (SEQ ID NOS 37–46) with overlapping cohesive ends.

Figure 24:
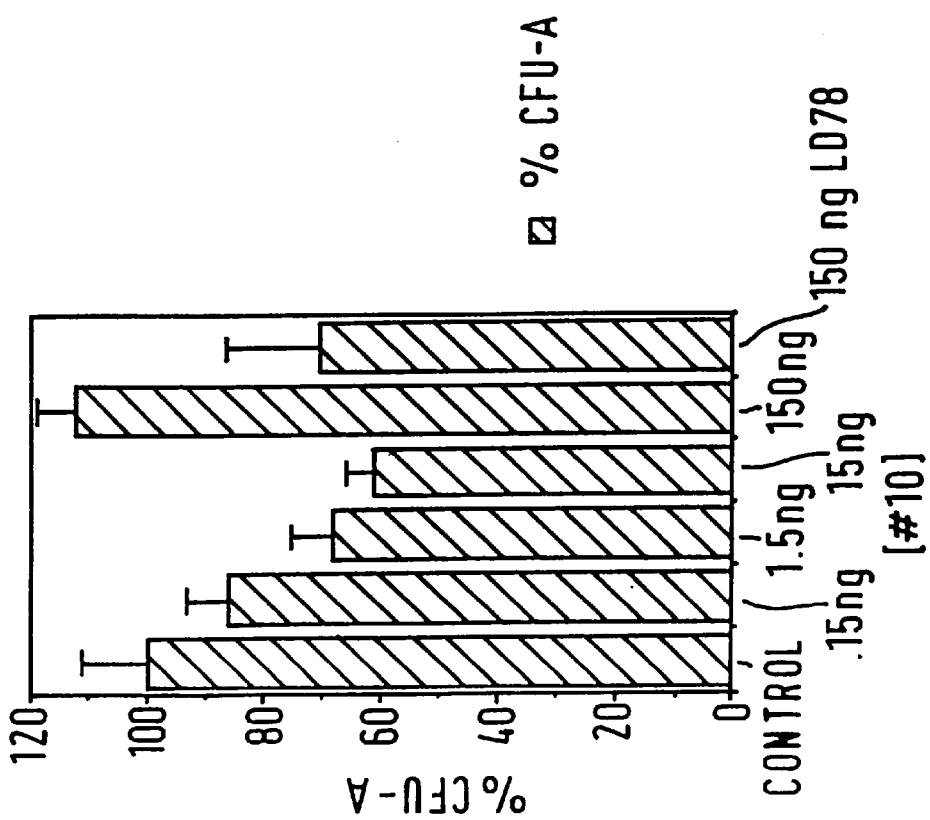

FIG. 24 shows the effect of mutant 10 on in vitro colony formation using purified murine stem cells.

Figure 25:
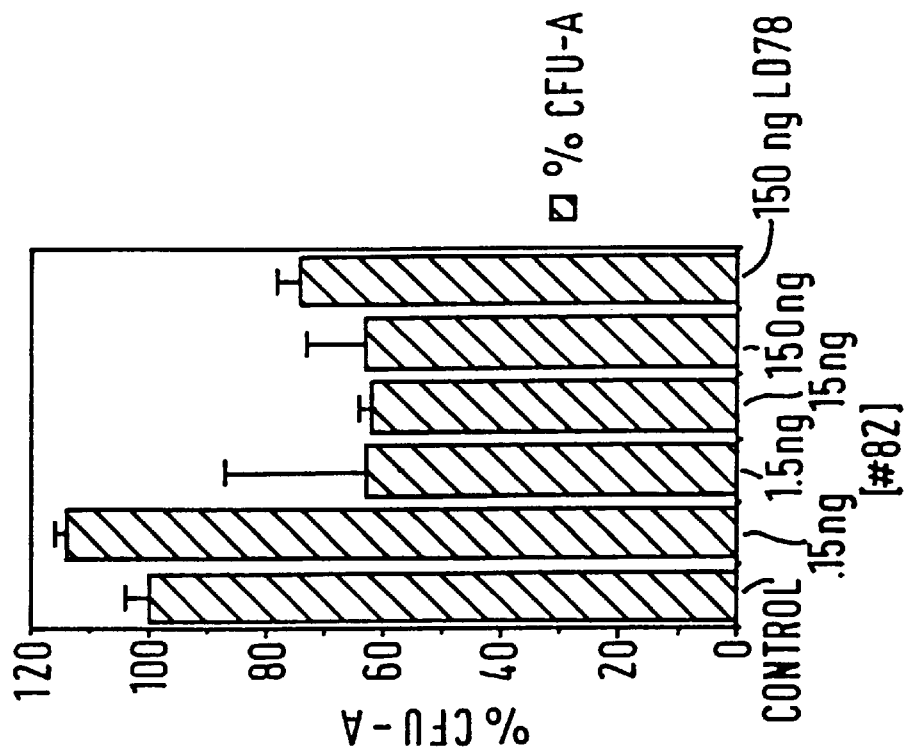

FIG. 25 shows the effect of mutant 82 on in vitro colony formation using purified murine stem cells.

Preparations 1–14 describe the construction of synthetic genes for LD78, MIP-1α and ACT-2, the development of yeast expression vectors and the production and preliminary characterisation of their protein products.

Comparative Examples 1–7 describe the biophysical properties of LD78, MIP-1α and ACT-2, a comparison of their molecular weight under a range of solution conditions and a spectroscopic assay for the extent of LD78 multimerisation.

Examples 1–124 describe the design and construction of LD78 variants and their incorporation into expression vectors. Example 125 discloses a convenient gel screen for the detection of variants with altered multi-merisation properties. Examples 126–153 describe the effect on multimerisation of mutations at particular residues. Example 154 shows that previously described variants of LD78 are wild-type with respect to their multimerisation characteristics. Example 155 discloses the molecular faces involved in LD78 multimerisation.

Examples 156–157 disclose the unexpected observation that LD78 variants exhibiting reduced multimerisation give higher expression levels in *S. cerevisiae* than wild-type LD78. Examples 158–163 describe the construction of an improved *Pichia pastoris* expression vector, the construction of LD78 producing strains and the unexpectedly high yields of wild-type LD78 that are obtained, and demonstrate that further increases in yield are observed with variants exhibiting reduced multimerisation.

Example 164 demonstrates that variants exhibiting reduced multimerisation are active in an in vitro model of receptor binding. Example 165 shows that demultimerised mutants can inhibit the proliferation of haematopoietic progenitor cells (day 12 CFU-S).

Methodology

The techniques of genetic engineering and genetic manipulation used in the manufacture of the genes described and in their further manipulation for construction of expression vectors are well known to those skilled in the art. Descriptions of modem techniques can be found in the laboratory manuals "Current Protocols in Molecular Biology", Volumes 7 and 2, edited by F. M. Ausubel et al, published by Wiley-Interscience, New York and in "Molecular Cloning, A Laboratory Manual" (second edition) edited by Sambrook, Fritsch and Maniatis published by Cold Spring Harbor Laboratories, New York. M13mp18, M13mp19 and pUC18 and pUC19 DNAs were purchased from Pharmacia Ltd., Midsummer Boulevard, Central Milton Keynes, Bucks, MK9 3HP, United Kingdom. Restriction endonucleases were purchased either from Northumbria Biologicals Limited, South Nelson Industrial Estate, Cramlington, Northumberland, NE23 9HL, United Kingdom or from New England Biolabs, 32 Tozer Road, Beverly, Mass. 01915-5510 USA.

Preparation 1—Construction of a Synthetic Gene for Human LD78

Gene Design

The published amino acid sequence for LD78 was reverse-translated to give a gene sequence. The codon usage was then optimised to maximise expression in *S. cerevisiae*. The 5' end of the synthetic gene was designed to include codons for the last five amino acid residues (Ser Leu Asp Lys Arg) of the yeast mating type factor alpha. The sequence was then modified to include a HindIII restriction site at the 5' end and a BamHI restriction site at the 3' end (SEQ ID: 1).

The gene sequence was divided into 12 oligonucleotides (SEQ ID: 4 to SEQ ID: 13). Each internal oligonucleotide was designed so that a unique 7 base cohesive end is left after anealling each pair of complementary oligonucleotides. This allows for perfect oligo matching during gene construction. FIG. 21 shows the annealed oligonucleotides with overlapping cohesive ends.

Oligonucleotide Synthesis

The oligonucleotides were synthesised on an Applied Biosystems 380B Gene Synthesiser, using cyanoethyl phosphoramidite chemistry. The methodology is now widely used and has been described (Beaucage, S. L. and Caruthers, M. H. *Tetrahedron Letters* 24. 245 (1981)).

Gene Construction

In order to create a full length gene, 100 pmole of each oligonucleotide was dried down in a vacuum dessicator. The 5' ends of internal oligonucleotides were kinased to provide a 5' phosphate to allow subsequent ligation. 100 pmoles of dried oligomer was resuspended in 20 μl of kinase buffer (70 mM Tris, pH7.6, 10 mM $MgCl_2$, 1 mM ATP, 0.2 mM spermidine, 0.5 mM dithiothreitol). T4 polynucleotide kinase (2 μl. 10,000 U/ml) was added and the mixture was incubated at 37° C. for 30 minutes. The kinase was then inactivated by heating at 70° C. for 10 minutes. Note that end oligonucleotides BB5615 and BB5624 were not kinased to prevent concatemerisation during the construction (SEQ ID: 2).

Complementary pairs of oligonucleotides were annealed in single pairs (90° C., 5 minutes, followed by slow cooling to room temperature). The 6 annealed pairs were then mixed together, heated at 50° C. for 5 minutes, and ligated overnight at 14° C. using T4 DNA ligase. The ligated full length product was then separated from non-ligated material by electrophoresis on a 2% low melting temperature agarose gel. The DNA fragment corresponding to the LD78 gene was excised and extracted from the gel. The purified fragment was then ligated to HindIII and BamHI treated pUC18 plasmid DNA. The ligated products were transformed into a suitable *E. coli* host strain using standard methodology. The strain used was HW87 which has the following genotype:

araD139Δ(ara-leu) 7697Δ(lacIPOZY)74 galU galK hsdR rpsL srl recA56

The use of this particular strain is not critical: any suitable recipient could be used (eg MC1061, available from the American Type Culture Collection (ATCC)). Transformants were selected on L-agar carbenicillin plates. Twelve carbenicillin-resistant colonies were picked and used to prepare plasmid DNA for sequence analysis. Double stranded dideoxy sequence analysis using a universal sequencing primer (United States Biochemical Corporation, (5'-GTTTTCCCAGTCACGAC-3' (SEQ ID NO 14)), was used to identify a correct clone pUC18-LD78. The pUC18-LD78 vector was used as a source of the LD78 gene to construct the expression vector.

Preparation 2—Construction of a Yeast Expression Vector for Human LD78

An expression vector was designed to enable secretion of LD78 to the extracellular medium after expression in *S. cerevisiae*. Secretion aids purification and rapid analysis of LD78. The secretion signals from the yeast mating type factor alpha were used to direct export of the LD78 protein.

Figure 1B:
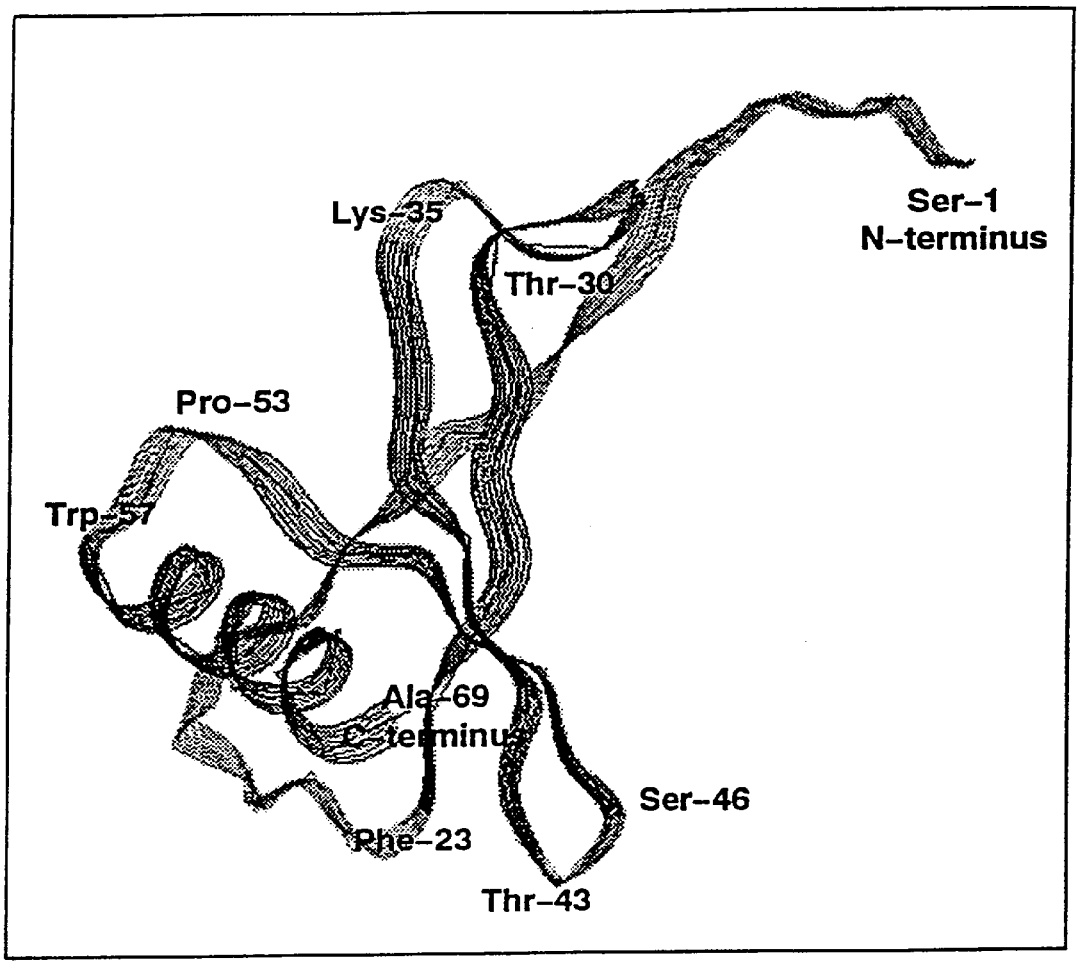
Figure 1C:
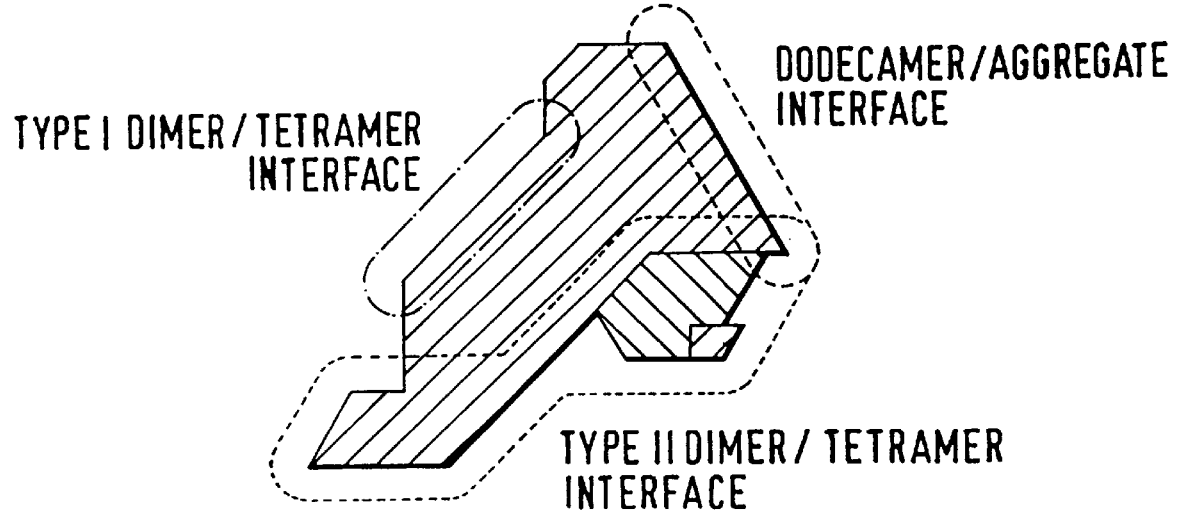
Figure 1D:
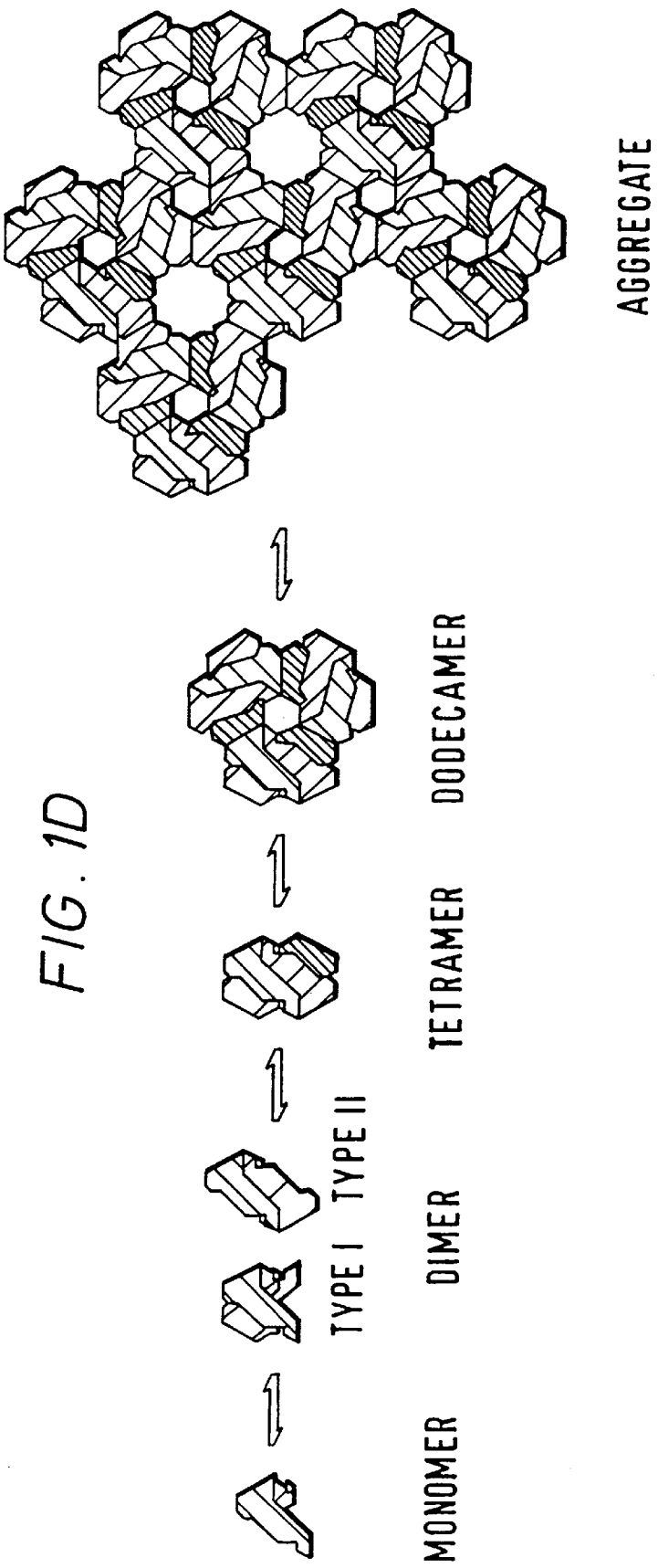
Figure 2:
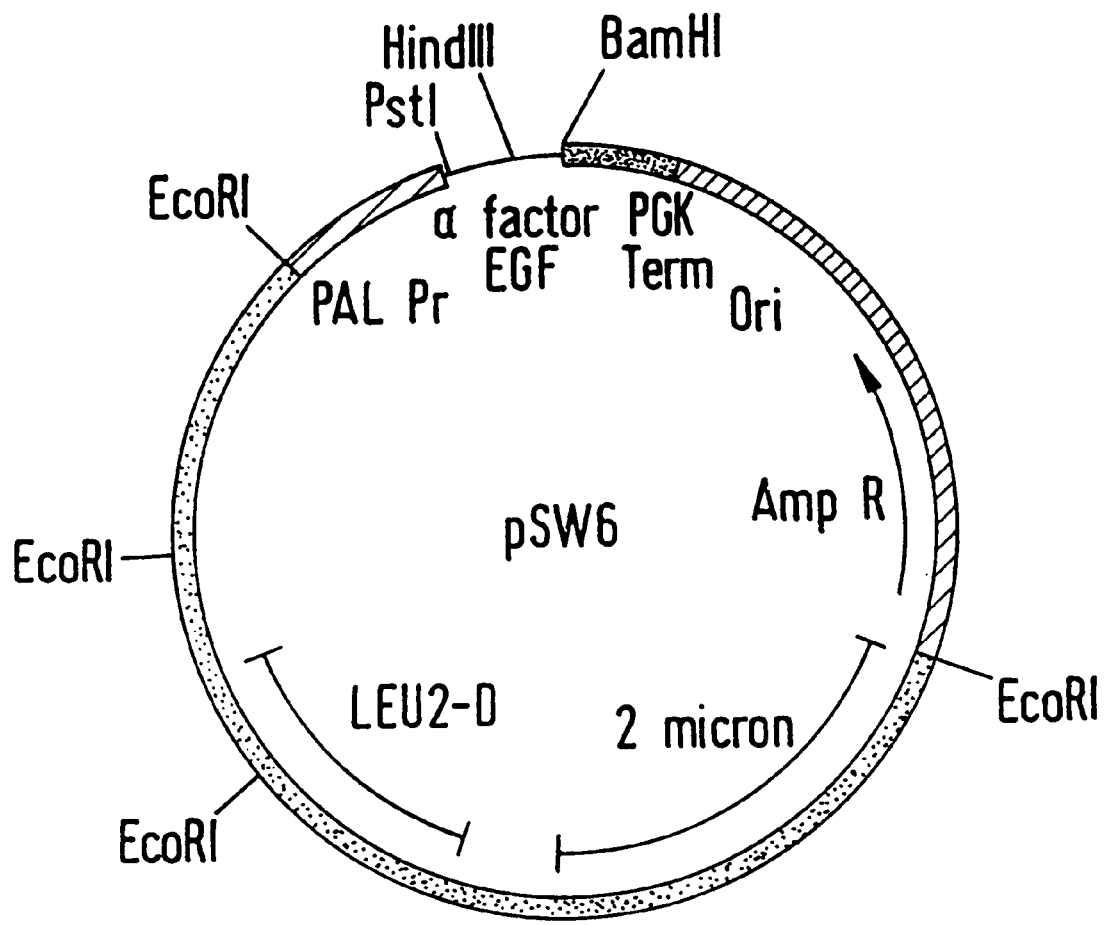

The yeast expression vector pSW6 (SEQ ID NO 15, FIG. 2) is based on the 2 micron circle from *S. cerevisiae*. (pSW6 was deposited in *S. cerevisiae* strain BJ2168 at the National Collection of Industrial and Marine Bacteria Limited, 23 St. Machar Drive, Aberdeen AB2 1RY, Scotland United Kingdom on Oct. 23rd, 1990 under Accession No. NCIMB 40326.) pSW6 is a shuttle vector capable of replication in both *E. coli* and *S. cerevisiae* and contains an origin of DNA replication for both organisms, the leu 2 gene (a selectable marker for plasmid maintenance in the yeast host) and the ampicillin resistance locus for selection of plasmid maintenance in *E. coli*. (The DNA sequence for the vector has been determined; the *E. coli* sequences are derived from the *E. coli* ColE1-based replicon pAT153.) The full sequence is given in SEQ ID NO 15. The ability to passage this vector through *E. coli* greatly facilitates its genetic manipulation and ease of purification. pSW6 contains an alpha-factor pre-pro-peptide gene fused in-frame to a gene encoding human epidermal growth factor (EGF). The expression of this fusion is under the control of an efficient galactose regulated promoter which contains hybrid DNA sequences from the *S. cerevisiae* GAL 1-10 promoter and the *S. cerevisiae* phosophoglycerate kinase (PGK) promoter.

Transcription of the EGF gene is terminated in this vector by the natural yeast PGK terminator. The EGF gene in pSW6 can be removed by digestion with restriction endonucleases HindIII and BamHI. This removes DNA encoding both EGF and 5 amino acids from the C-terminus of the alpha-factor pro-peptide. Genes to be inserted into the pSW6 expression vector must therefore have the general composition: HindIII site-alpha factor adaptor-gene-BamHI site.

After digestion with HindIII and BamHI endonucleases, the pSW6 vector contains the alpha factor gene minus the codons for the last five amino acid residues. To construct the alpha factor-LD78 fusion gene in the pSW6 vector, the pUC18-LD78 vector of Preparation 1 was treated with HindIII and BamHI endonucleases. The products of this digestion reaction were separated by electrophoresis on a 1% low gelling temperature agarose gel. The DNA fragment (ca. 235 bp) corresponding to the LD78 gene was excised and purified from the gel matrix. This DNA fragment was then ligated into HindIII and BamHI treated pSW6 DNA (the vector DNA fragment lacking the EGF insert was purified for use in this ligation). The recombinant ligation products were transformed into competent HW87 *E. coli* cells. Transformants were selected on L-agar ampicillin plates. 12 Ampicillin resistant transformants were screened by preparation of plasmid DNA and restriction endonuclease analysis with HindIII and BamHI followed by agarose gel electrophoresis. A clone (pSW6-LD78) with the correct electrophoretic pattern was selected. A plasmid preparation of this vector was prepared and the integrity of the construct was confirmed by dideoxy sequence analysis on the plasmid DNA using sequencing primer BB1330 (5'-AGGATGGGGAAAGAGAA-3') (SEQ ID NO: 16). This plasmid is the expression vector used for wild-type LD78 expression.

Preparation 3—Expression of Human LD78 Synthetic gene in *S. cerevisiae* pSW6-LD78 plasmid DNA of Preparation 2 was prepared and electroporated into yeast (*S. cerevisiae*) strain MC2 which has the following genotype: prc1-407 prb1-1122, pep4-3, leu23-112, trp1 ura3-52 mating type α. The use of strain MC2 is not critical for use either in this preparation or in the invention in general. Any suitable strain can be used, such as for example strain BJ2168, which is genetically almost identical to MC2 and is deposited (see Preparation 2 above).

Using the method described in the Bio-Rad manual (Gene Pulser™ transfection apparatus, Operating Instructions and Applications Guide, Version 10-90, Bio-Rad Laboratories, 3300 Regatta Boulevard, Richmond, Calif. 94804 USA) the plasmid DNA was electroporated. Briefly, yeast strain MC2 was grown overnight in YPD medium at 30° C. overnight. Cells were harvested by centrifugation at 3000 r.p.m for 5 mins in a Beckman GS-6KR centrifuge, washed in sterile water and resuspended in 1M sorbitol, and then added in 40 μl aliquots to various amounts (0.1 μg–1 μg) of plasmid DNA. The resulting mixtures were subjected to a pulse of 1500 volts for 5 msec, and added to 300 μl of 1M sorbitol. The electroporated cells were then plated out onto agar-sorbitol plates and allowed to grow for 4–5 days at 30° C.

All yeast media were as described by Sherman et al., "Methods in Yeast Genetics", Cold Spring Harbor Laboratory, (1986)).

Yeast Expression and Purification

After 4–5 days, electroporatants were picked and plated onto fresh agar plates. Single colonies were obtained after a further 1–2 days growth at 30° C. Single colonies were then used to inoculate 5 ml of YPD medium and the cultures were grown overnight at 30° C. This 5 ml overnight culture was then used to inoculate 0.5 liter shake flasks containing 50 ml of 0.67% synthetic complete medium, yeast nitrogen base, with amino acids minus leucine and 1% glucose as a carbon source and grown overnight at 30° C. After 24 hrs growth, cells were harvested by centrifugation at 3000 rpm for 5 minutes in a Sorvall™ RC3-B centrifuge and used to inoculate 100 ml of the same synthetic complete medium (except that 1% galactose and 0.2% glucose were used as the carbon source). This induces gene expression from the hybrid PGK promoter. Induction was carried out by growth in the galactose containing medium at 30° C. for 48–72 hours.

After either 48 or 72 hrs the culture supernatant was collected by centrifugation in a Sorvall™ RC3-B centrifuge at 3000 rpm for 5 minutes to remove cells. This supernatant was used for further analysis and purification of LD78 according to the methods described in Preparation 4.

Preparation 4—Purification of human LD78 expressed from a synthetic gene in yeast Supernatant from the shake flasks described in preparation 3 was spun at 6500 rpm (Sorvall™ RCS-B centrifuge) for 15 minutes to clarify. Typically 3 liters of yeast supernatant were adjusted to pH8 and 30 ml of Q-Sepahrose™ ion exchange resin (Pharmacia) pre-equilibrated in 50 mM Tris pH8.0 was added. Protein was batch adsorbed overnight at 4° C. with gentle agitation. The resin was then allowed to settle and the supernatant removed. The resin was then poured into a column 1.6 cm in diameter and washed with 10 volumes of 50 mM Tris pH8.0, the protein was then eluted in 0.5M NaCl, 50 mM Tris pH8.0 (typically 50 ml total volume of eluent). The eluent was transferred into prewetted Spectrapor™ dialysis membrane (3000 Da cutoff) and dialysed against 10×volume 50 mM Tris pH8.0 at 4° C. with one change of buffer. The sample was adjusted to 20% acetonitrile (final concentration) and the pH brought to 3.0 with hydrochloric acid. The protein sample was then pumped directly (bypassing the Rheodyne injection loop) onto a 20 ml Vydac™ C-18 (10μ pore-size) semi-preparative reverse phase HPLC column pre-equilibrated at 3 ml/min in 20% acetonitrile, 0.1% trifluoracetic acid (TFA) and eluted with a linear gradient from 20% to 50% acetonitrile, 0.1% TFA over 40 minutes. Eluting fractions were detected by u.v. absorbance at 280 nm and analysed by SDS-PAGE Phastgel™ (as described in Preparation 11). The pure LD78 protein was found to elute around 43% acetonitrile, 0.1% TFA. Purified LD78 was freeze-dried and stored at −20° C. The sequence of the protein is given as SEQ ID NO 2.

Preparation 5—Construction of a Synthetic Gene for Murine MIP-1α

Gene Design

The published amino acid sequence for MIP-1α was reverse-translated to give a gene sequence. The codon usage was then optimised to maximise expression in S. cerevisiae. SEQ ID NO 17 shows the sequence of the synthetic gene, the protein sequence is given as SEQ ID NO 18 and the antisense strand of the gene is SEQ ID NO 19. The method of Preparation 1 was followed for the construction of the MIP-1α gene except that the oligonucleotides differ from those in preparation 1. FIG. 22 shows the annealed oligonucleotides used in the construction of the MIP-1α gene (SEQ ID NOS 20–31). The synthetic gene was cloned into plasmid pUC18 to create pUC18MIP-1α.

Preparation 6—Construction of a Yeast Expression Vector for Murine MIP-1α

With the exception of the changes detailed below, the method of Preparation 2 was followed for the construction of a yeast expression vector designed to enable secretion of MIP-1α from S. cerevisiae.

The MIP-1α synthetic gene in pUC18MIP-1α vector of Preparation 5 must be engineered prior to its inclusion into the pSW6 expression vector. This is because the synthetic MIP-1α gene lacks sequences at the 5' end suitable for the construction of an in frame fusion to the alpha factor gene in the pSW6 vector. To rebuild the DNA encoding the amino acids at the C-terminal end of the alpha-factor pro-peptide and to fuse this to the synthetic MIP-1α gene, an oligo nucleotide adapter BB985 (5'-AGCTTGGATAAAAGA-3' (SEQ ID 32, top strand), BB986 5'-TCTTTTATCCA-3' (SEQ ID 33, bottom strand)) containing a HindIII site and codons encoding the Ser, Leu, Asp, Lys and Arg from the C-terminal end of the alpha-factor pro-peptide was constructed. The alpha factor adaptor was ligated to the synthetic MIP-1α gene such that the recombinant gene encoded an in-frame alpha-factor pro-peptide fusion to MIP-1α. The pUC18MIP-1α plasmid of Preparation 5 was first cleaved with BspMI and the overhanging ends were filled using DNA polymerase I to create a blunt ended linear DNA fragment. The linearised DNA fragment was separated from uncut plasmid DNA on a 1% low gelling temperature agarose gel matrix, then further treated with HindIII. The fragment was then ligated to the alpha-factor adaptor described above. Note that the two strands of the adaptor were annealed prior to ligation. The recombinant ligation products were transformed into competent cells of E. coli HW87. Ampicillin-resistant transformants were analysed by preparation of plasmid DNA, digestion with HindIII and BamHI and agarose gel electrophoresis. A correct recombinant plasmid was identified. The integrity of this vector was confirmed by dideoxy sequencing analysis using sequencing primers BB3376 and BB3379. (BB3376 and BB3379 are shown together in SEQ. ID: 5.)

This plasmid was used as a source of DNA for construction of the yeast expression vector. The method of Preparation 2 was followed. Briefly the modified pUC18 MIP-1α vector now containing the alpha factor adaptor was digested with HindIII and BamHI and the MIP-1α DNA fragment was purified. This fragment was ligated to HindIII and BamHI treated pSW6 DNA according to the method in Preparation 2. The MIP-1α expression vector, the subject of Preparation 7, was called pSW6MIP-1α. This vector was used for subsequent expression.

Preparation 7—Expression of Synthetic Murine MIP-1α in Yeast

The method of Preparation 3 was used for the expression of the murine MIP-1α gene with the exception that the expression vector used was pSW6MIP-1α and transformation was used in place of electroporation. The method of Sherman F. et al., ("Methods in Yeast Genetics", Cold Spring Harbor Laboratory, (1986)) was used for transformation.

Preparation 8—Purification of murine MIP-1α expressed from a synthetic gene in yeast Supernatant from the shake flasks described in Preparation 7 was centrifuged at 5000 rpm in a Sorvall™ RC-SB centrifuge to clarify. Typically 5 liters of clarified supernatant were adjusted to 20% acetonitrile, 0.1% TFA (final concentration) and 30 g of C-18 silica resin was added as a dry powder. Protein was batch adsorbed onto the resin overnight at 4° C. with gentle agitation. The silica resin was then allowed to settle and the supernatant removed. Resin was then poured into a 2.5 cm (diameter) column, washed with 10 column volumes of 25% acetonitrile, 0.1% TFA and eluted with 50% acetonitrile, 0.1% TFA; 30 ml fractions were collected manually. Aliquots of these fractions were dried and analysed by SDS-PAGE Phastgel™ (Pharmacia) as described in Preparation 13. The protein concentration was estimated from the absorbance at 280 nm in a 1 cm pathlength cell and a calculated absorbance of 1.37 for a 1 mg/ml protein solution under the same conditions. The eluted fractions were then freeze-dried. For further purification, the dried fractions were reconstituted in 0.1% TFA (final concentration) and 4 mg aliquots loaded onto a 20 ml Dynamax™ semi-preparative C-18 reverse phase column (10μ pore-size) at 3 ml/min equilibrated in 25% acetonitrile, 0.1% TFA. MIP-1α was eluted using a linear 25–45% acetonitrile, 0.1% TFA gradient over 50 minutes. Eluting fractions were detected by u.v. absorbance at 280 nm and collected manually. Purified MIP-1α was freeze dried and stored at −20° C.

Preparation 9—Construction of a Synthetic Gene for Human ACT-2

Gene Design

The published amino acid sequence for human ACT-2 was reverse-translated to give a gene sequence. The codon usage was then optimised to maximise expression in S. cerevisiae. SEQ ID NOS 34 and 36 show the sequence of the two strands of the synthetic gene and the protein sequence is given as SEQ ID NO 35. The method of Preparation 1 was followed for the construction of the ACT-2 gene except that the oligonucleotides differ from those in preparation 1. FIG. 23 shows the annealed oligo nucleotides used in the construction of the ACT-2 gene. The synthetic gene was cloned into plasmid pUC18 to create pUC18ACT-2.

Preparation 10—Construction of a Yeast Expression Vector for Human ACT2

The method of Preparation 2 was followed except that the ACT-2 gene from pUC18 ACT-2 was used in place of the pUC18-LD78. The resultant ACT-2 expression vector was called pSW6 ACT-2.

Preparation 11—Expression of Human ACT-2 Synthetic Gene in Yeast

The method of Preparation 3 was followed except that pSW6 ACT-2 DNA was a used as the expression vector.

Preparation 12—Purification of human ACT2 expressed from a synthetic gene in yeast Supernatant from the shake flasks described in Preparation 11 was spun at 6500 rpm for 15 minutes to clarify. Typically 3 liters of yeast supernatant were adjusted to pH8 and 30 ml of Q-Sepahrose™ pre-equilibrated in 50 mM Tris pH8.0 added. Protein was batch-adsorbed onto the resin overnight at 4° C. with gentle agitation. The resin was allowed to settle and the supernatant removed. Resin was poured into a column 1.6 cm in diameter, washed with 10×volumes 50 mM Tris pH8.0, then eluted in 0.5M NaCl, 50 mM Tris pH8.0 (typically 50 ml total eluent). The eluent was transferred into a prewetted Spectrapor™ dialysis membrane (3000 dalton cutoff) and dialysed against 10×volumes of 50 mM Tris pH8.0 at 4° C. with one change of buffer. The sample was then loaded onto an 8 ml Heparin-Sepharose™ column (1.6 cm diameter) equilibrated in 50 mM Tris pH8.0 and the column washed with the same buffer. ACT-2 was eluted in 50 mM Tris, 1M NaCl pH8.0. The eluent was then transferred to a prewetted Spectrapor™ dialysis membrane (3000 dalton cutoff) and dialysed against 10×volume 0.1% TFA at 4° C. with one change of buffer. After dialysis the sample was adjusted to 25% acetonitrile (final concentration). The protein sample was then loaded onto a 20 ml Vydac™ C-18 (10μ pore-size) semi-preparative reverse phase HPLC column pre-equilibrated at 3 ml/min in 20% acetonitrile, 0.1% Trifluoracetic acid (TFA) and eluted with a linear gradient from 20% to 50% acetonitrile, 0.1% TFA over 40 minutes. Eluting fractions were detected by u.v. absorbance at 280 nm and collected manually. The ACT-2 protein was found to elute around 43% acetonitrile, 0.1% TFA. Purified ACT-2 was freeze-dried and stored at −20° C.

Preparation 13—Confirmation of the Identity and Purity of Human LD78. Human ACT-2 and Murine MIP-1α expressed from Synthetic Genes in Yeast A purity of greater than 97% was confirmed using a range of analytical procedures. Small aliquots (5 μg in 5 μl of sample buffer as described in Comparative Example 2) of the dried material were analysed with sodium dodecyl sulphate polyacrylamide gel electrophoresis (SDS-PAGE) using an 8–25% acrylamide gradient PhastGel™ (Pharmacia) using the manufacturers' recommended sample buffer and running programme. Gels were stained and destained according to the manufacturers' recommended procedures.

Analytical reverse phase-HPLC was carried out using a 2 ml Vydac™ C-18 analytical reverse-phase column (5μ pore-size) equilibrated in 20% acetonitrile, 0.1% TFA at 1 ml/min. Approximately 10–50 μg of protein was loaded and eluted with a linear gradient of 20–50% acetonitrile, 0.1% TFA at a flow rate of 1 ml/min over 20 minutes.

Near ultra-violet absorbance spectroscopy in the 240–320 nm range, with a 1 cm pathlength and 1 nm bandwidth was used to ensure that no turbidity (light scattering) arising from aggregated rSCI was present in the purified preparation.

The identity of the purified proteins were confirmed from the N-terminal sequence and the mass of the product. Electrospray mass spectroscopy was carried out on a VG BIO-Q™ spectrometer with 50 μg of sample dissolved in 1:1 (v/v) methanol/water containing 1% acetic acid. In some cases, substantial populations of LD78 protein+metal adduct mass peaks were observed. Typically potassium and copper were noted. Major copper contamination was found to originate from a metal line within the spectrometer, however, the LD78 proteins were shown to tightly hold this metal ion even in the large electric field applied on injection. The strength of association suggests that LD78 has an ability to bind this divalent metal ion with reasonable affinity if exposed to significant quantities.

N-terminal sequencing was carried out using an Applied Biosystems 471A sequenator, Applied Biosystems Ltd, Kelvin Close, Birchwood Science Park North, Warrington WA3 7PB. Typically 250 picomoles of protein dissolved in 0.1%TFA was loaded onto a Biobrene™ precycled glass fibre disc and subjected to 14 cycles of automated Edman degradation. All procedures and sequencing cycles were as recommended by the manufacturer.

COMPARATIVE EXAMPLES

Comparative Example 1

Conformational Analysis of Recombinant Human LD78, Human ACT-2 and Murine MIP-1α

Near and far ultra-violet circular dichroism (u.v. c.d.) measurements of MIP-1α, LD78 and ACT-2 were carried out using a Jobin-Yvon Dichrographe VI. Samples were reconstituted in 10 mM acetic acid pH3.2 and a u.v. absorbance scan from 240–320 nm used to confirm the absence of protein aggregates. The protein concentration was determined using calculated values for the absorbance of a 1 mg/ml solution at 280 nm with a 1 cm pathlength of 1.37 for MIP-1α, 1.25 for LD78 and 1.57 for ACT-2. Mean residue weights were calculated to be 114, 113.7 and 113.3 for MIP-1α, LD78 and ACT-2 respectively. Near u.v. c.d. spectra (250–320 nm) were collected using a scan speed of 5 nm/min, 1 second response, 2 nm bandwidth and a 1 cm pathlength. Far u.v. c.d. spectra (190–250 nm) were collected using a 10 nm/min scan speed, 1 second response, 2 nm bandwidth and either a 0.01 cm or 0.05 cm pathlength. All spectra are calculated and displayed as a mean residue molar ellipticity [θ] with baseline subtracted.

Analysis of the far ultra-violet circular dichroism of these sequence related proteins using the Ccontin™ programme (Provencher, *Comput. Phys. Commun.*, 27, 229–242, (1982); Provencher & Gloeckner, *Biochemistry*, 20, 33–37, (1981)) has confirmed that MIP-1α, LD78 and ACT-2 contain 14–18% helix and a high proportion of β-sheet structure which is consistent with the known secondary structure contents of IL-8 (Clore et al., *J.Biol.Chem.*, 264, 18907–18911, (1989)) and PF-4 (St. Charles et al., *J.Biol.Chem.*, 264, 2092–2099, (1989)).

In the 250–320 nm wavelength range, circular dichroism spectra arise from disulphide bonds and aromatic groups such as tyrosine, tryptophan and to a lesser extent phenylalanine (Strickland, *C.R.C.Crit.Rev. Biochem.*, 2, 113–175, (1974)). Circular dichroism bands in the near u.v. often (but not always) coincide with their chromophore absorption bands. The magnitude, sign (positive/negative) and wavelength position of the c.d. bands are highly sensitive to the conformational environment of the contributing side-chain. Whilst no definitive set of rules exist for interpretation of the contributions to near u.v. c.d. spectra, the intensity and position of shoulders, shape and maxima or minima can nevertheless be used to identify side-chain types. For example, characteristic tyrosine bands are often observed with minima centred at 276 nm and 268 nm, in single tryptophan proteins the $0\_0^1L_b$ band is observed characteristically at 288–293 nm. Phenylalanine produces fine structure, often seen as shoulders in c.d. spectra, in the 250–270 nm range. Disulphide bonds have very broad featureless contributions which are variable in intensity and can extend from 250 nm up to 360 nm.

Figure 3:
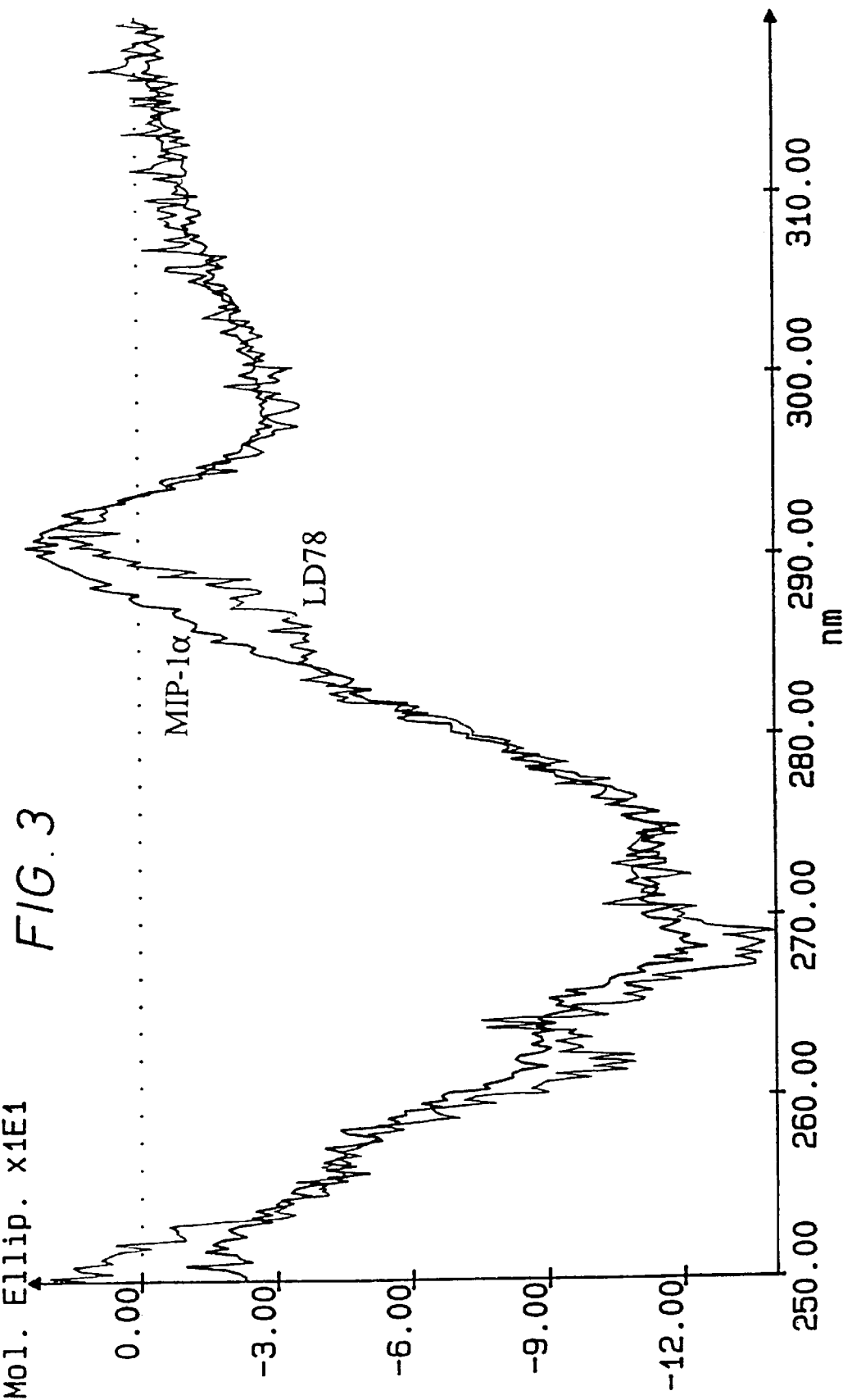

Excepting Tyr3 of MIP-1α, the tyrosines and the single tryptophan residues are conserved in the sequence of LD78 and MIP-1α. The near u.v. circular dichroism spectra of LD78 and MIP-1α are almost superimposable (FIG. 3). The intense negative ellipticity below 290 nm with the minima centred at 268 nm and 276 nm is characteristic of tyrosine with some phenylalanine fine structure superimposed. The intensity of the spectra between 250–290 nm may reflect coupling of transitions between a tyrosine residue and another aromatic group. The broad trough of negative ellipticity observed above 290 nm appears to exhibit a minima at 296 nm with a broad trail to higher wavelength. This shape is somewhat unusual for a tryptophanyl band and it might, therefore, reflect a disulphide contribution. The data demonstrate that Tyr3 of MIP-1α is not contributing to the spectrum. Given that the N-terminal regions of IL-8 and PF-4 are known to be disordered then the absence of Tyr3 c.d. in MIP-1α is not unexpected.

The near ultra-violet circular dichroism spectra demonstrate that the environment of aromatic amino acids in LD78 and MIP-1α is almost identical. These data demonstrate that the two homologues have the same tertiary structure and conformation.

Figure 4:
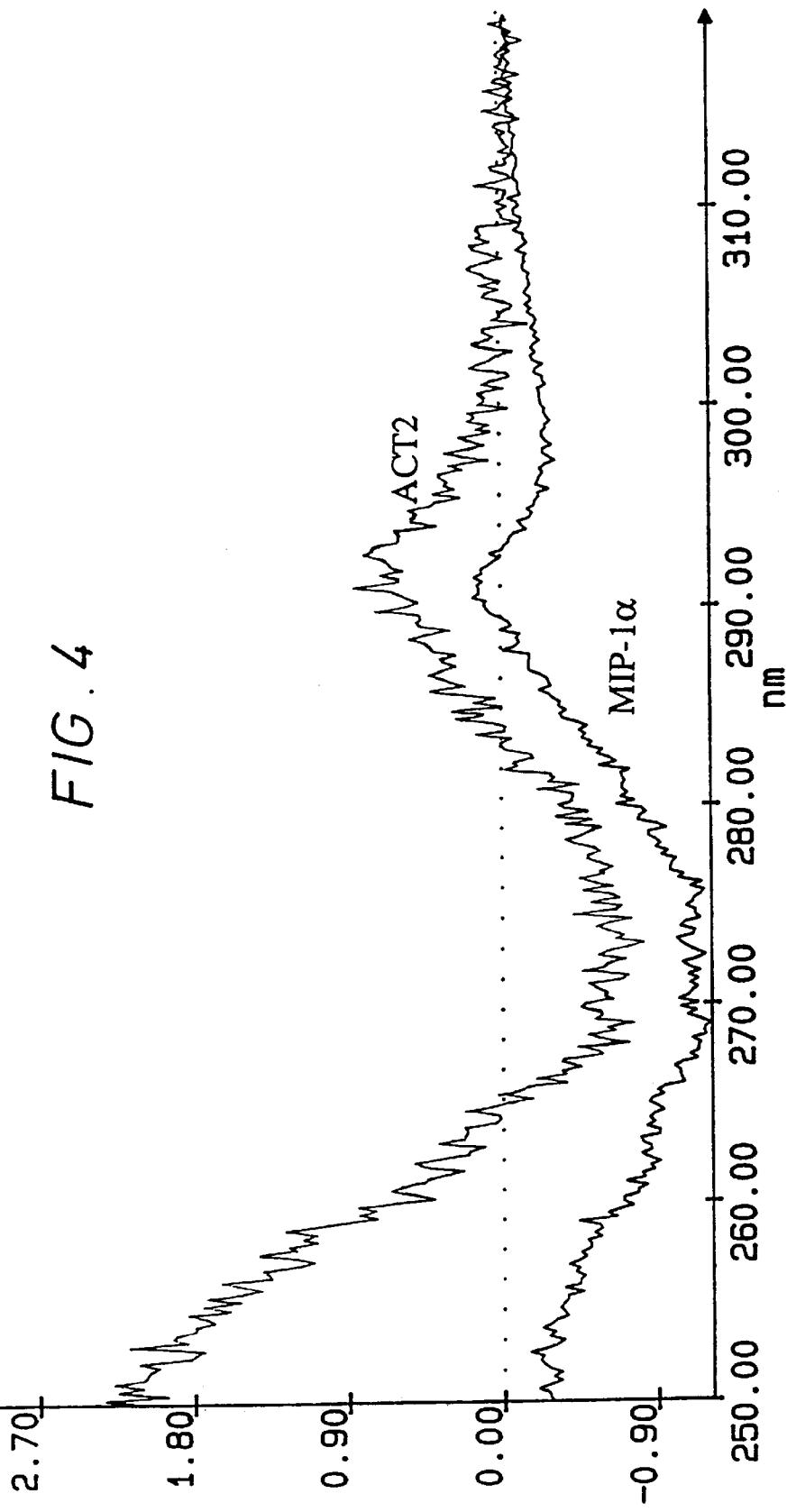

Comparison of the near u.v. c.d. of ACT-2 with MIP-1α highlights distinct differences in the shape and intensity of the spectra (FIG. 4). The ACT-2 spectrum shows a less intense negative tyrosine contribution combined with a distinct $0\_0^1L_b$ tryptophan contribution from the (conserved) single tryptophan residue-58. The only sequence difference between the proteins likely to contribute to the near u.v. c.d. is Tyr29 in ACT-2 (Phe28 in MIP-1α). The nature of the shape and intensity changes observed for the ACT-2 c.d. are not consistent with addition or cancellation simply of a tyrosine band. The data demonstrate, therefore, that there are distinct differences in the conformation of ACT-2 compared to that of MIP-1α and LD78. These proteins all have similar multimerisation properties as detailed in Comparative Example 3. The variation in conformation for ACT-2 is not therefore a result of different quaternary structure.

Comparative Example 2

LD78 is Immunologically Cross-Reactive with Anti-MIP-1α

5 μg each of MIP-1α, LD78, ACT-2 and human epidermal growth factor (as a standard marker) were dissolved in 5 μl of sample buffer (25 mM Tris pH6.8, 2.3% sodium dodecyl sulphate, 5% β-mercaptoethanol, 10% glycerol, 0.01% bromophenol blue) and heated at 90° C. for 5 minutes to reduce and denature the protein. Approximately 1 μg of protein per track was loaded onto 2 identical 8–25% (acrylamide) SDS-PAGE PhastGels™; pre-stained low molecular weight markers (Bethesda Research Laboratories) were also run on each gel. The gels were electrophoresed using the manufacturers' recommended conditions. Following electrophoresis, one of the gels was stained with 0.02% PhastGel Blue R™, 30% methanol, 10% acetic acid followed by destaining in 30% methanol, 10% acetic acid. The second gel was sandwiched between nitrocellulose membrane and electroblotted for 40 minutes at 100 volts using 25 mM Tris, 192 mM glycine, 20% methanol transfer buffer. After transfer of protein onto the nitrocellulose membrane, the membrane was incubated in 0.5% casein, 154 mM NaCl, 20 mM Tris pH7.4, 0.05% Triton blocking buffer for 1 hour at room temperature. The membrane was then incubated for an hour with a 1:5000 (v/v) dilution of the primary antibody (polyclonal rabbit anti-MIP-1α, generated by standard immunological techniques following immunisation with the protein of Preparation 8) in blocking buffer at room temperature. After washing 3×5 min with blocking buffer, the second antibody (anti-rabbit peroxidase conjugated (Sigma)) was incubated with the membrane at 1:10000 (v/v) in blocking buffer for a further 1 hour at room temperature (Sigma Chemical Company Ltd, Fancy Road, Poole, Dorset BH17 7BR). After 3×5 min washes in 150 mM phosphate buffered saline pH7.4 (PBS) the blot was developed in 25 ml of developing solution (0.04% 3,3'-diaminobenzadine tetrahydrochloride, PBS, 0.015% cobalt chloride, 0.015% ammonium nickel sulphate, 0.2% hydrogen peroxide). Development was stopped by washing the membrane with distilled water. The membrane was then dried and photographed.

Figure 5:
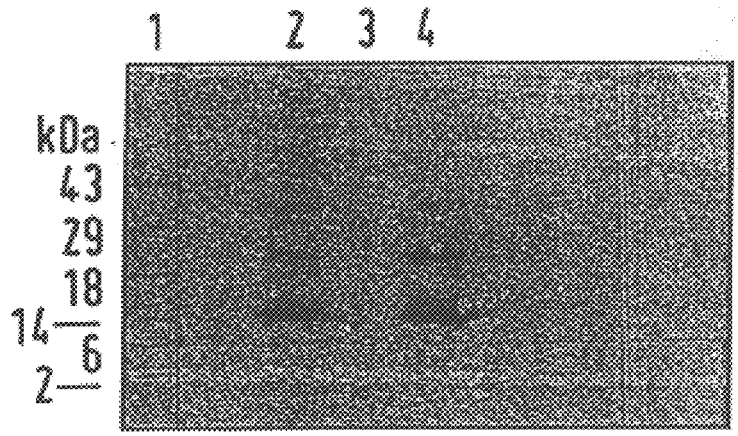
FIG. 5 illustrates a western blot of MIP-1α, LD78 and ACT2 with anti-MIP-1α antibody. The result demonstrates cross-reaction of LD78 but not ACT2 with anti-MIP-1α.

The immunoblot (FIG. 5; 8–25% SDS-PAGE (Reducing)) demonstrates that there 5 is no cross-reaction of anti-MIP-1α with ACT-2, however, there is a strong cross-reaction with LD78. MIP-1α and LD78 have the same epitope and immunological profile whereas ACT-2 is immunologically distinct. Together with the conformational data of Comparative Example 1, this evidence strongly supports the suggestion that LD78 is the human homologue of murine MIP-1α.

Comparative Example 3

Characterization of the molecular weight of LD78 and MIP-1α (expressed from synthetic genes in yeast) under physiological conditions LD78 and MIP-1α are non-glycosylated, with theoretical molecular weights of 7712 Da and 7866 Da, respectively. ACT-2 has a theoretical molecular weight of 7704 Da, though the authentic molecule is thought to be glycosylated. Size exclusion chromatography (SEC) was carried out using a Superose 12™ column attached to an Fast Protein Liquid Chromatography system (Pharmacia). The column was calibrated at 1 ml/min in 150 mM phosphate buffered saline, pH 7.4 (Sigma) using blue dextran, aldolase, bovine serum albumin, carbonic anhydrase and lysozyme as standards. Samples (50–100 μg) of MIP-1α, LD78 and ACT-2 were dissolved in 0.2 ml of 150 mM phosphate buffered saline, pH 7.4 (Sigma) and loaded onto the column running at the calibrated speed of 1 ml/min. Eluting fractions were detected by u.v. absorbance at 280 nm.

Reconstitution of each of lyophilized recombinant LD78, MIP-1α and ACT-2 as described above yields a product which is predominantly a soluble multimeric complex when analysed by size exclusion chromatography (FIG. 6). The soluble multimers range in size from 100,000 Da to>>200,000 Da with the predominant weights apparently in the region of 350,000 Da. The column excludes particles of greater than 180,000 Da; therefore, accurate determinations of masses above this limit are impossible. Over a period of hours the multimeric complexes can form insoluble aggregates which visibly precipitate. A population of low molecular weight species is observed in the SEC profile of all three proteins. In view of the elution at >20,000 Da, and given that the SDS-PAGE results (described in Comparative Example 2) show stable tetramers, it is suggested that these proteins associate to stable tetramers similar to their sequence homologue PF-4. The results described in detail in Comparative Examples 4 and 5 confirm that a basic quaternary structural unit of these molecules is a tetramer.

Samples of LD78, MIP-1α and ACT-2 were also analysed using native polacrylamide gel electrophoresis. 5 μg of each protein were reconstituted in 25 mM Tris pH6.8, 10% glycerol, 0.01% bromophenol blue. Samples were loaded with high molecular weight markers (Flowgen) and human EGF standard and electrophoresed on a 5–50% Gradipore Hylinx™ native gel (Flowgen) at 100 volts for 15 minutes in 0.0825M Tris, 0.0808M boric acid, 0.003M EDTA, pH8.3. The gel was subsequently Coomassie blue-stained and destained (as described in Comparative Example 2).

Figure 7:
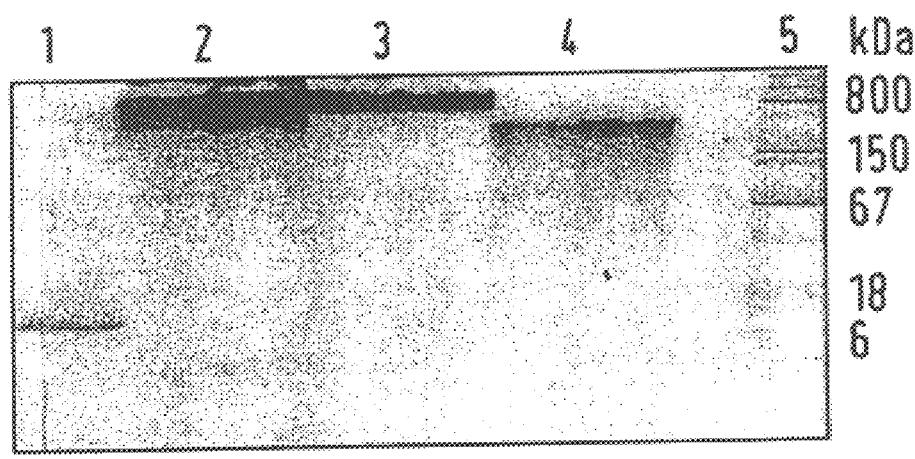
FIG. 7 shows a Coomassie-stained native PAGE analysis of LD78, MIP-1α and ACT-2 with mixed molecular weight markers and EGF standard. The gel demonstrates that the three proteins all run as high molecular weight multimers under native conditions.

The stained gel (FIG. 7) shows that human EGF (6,200 daltons) standard runs at the correct weight under native conditions. MIP-1α, LD78 and ACT-2 however, all run at the top of the gel with broad smearing bands demonstrating a range of molecular weight species. No low molecular weight species are observed.

The two techniques described above provide some quantitative estimates of the molecular size of LD78 and MIP-1α in solution. In both cases, however, a solid support resin is present (acrylamide or Sephaces™) which can affect equilibrium populations of molecules. The recognized method of absolute molecular mass determination in solution is by Sedimentation Equilibrium in the analytical ultracentrifuge (see for example Yphantis (1964) or Harding et al. (1992)).

Using a Beckman Optima™ XL-A analytical ultracentrifuge, protein solute distributions can be recorded by u.v. absorbance during sedimentation equilibrium experiments (for example see Morgan et al, (1992)). In a population of protein molecules distributed at equilibrium through the rotor cell, approximate values for the smallest (protein) mass in solution are obtained from the cell meniscus ($M_w(\zeta=0)$), and the largest (protein) mass in solution determined from the cell base ($M_w(\zeta=1)$). This technique provides the whole-cell weight average molecular weight ($M°_w$) (i.e. the average molecular weight of solute distributed through the rotor cell). In this manner the self-association properties (if present) of a protein molecule can accurately be determined from the measured polydispersity in the observed mass ranges. Characteristically, such polydisperse solutions show an upward curvature when logarithm of absorbance is plotted as a function of the normalised radial displacement parameter ($\zeta$) in analyses of the type detailed by Creeth & Harding (*J.Biochem. Biophys.Methods,* 7 25–34 (1982)) and Creeth & Pain, (*Prog. Biophys & Mol. Biol.* 17 217–287 (1967)). Proteins which exist in solution at a single defined mass (i.e. a monodisperse population) exhibit linear plots of Ln A vs $\zeta$. Non-ideal solution conditions typically yield a downward curvature of Ln A vs $\zeta$. It is possible for the effects of polydispersity and non-ideality to cancel each other and give a linear plot of Ln A vs $\zeta$ (Creeth & Pain, loc. cit. (1967)). This must be considered during data interpretation.

The sedimentation equilibrium behaviour of pure wild type LD78 was measured at 20° C. with a protein concentration of 0.5 mg/ml using the Optima™ XL-A ultracentrifuge with a rotor speed of 9000, 10000 or 12000 r.p.m. and absorbance detection at 278 nm. For masses in the range of monomers, a rotor speed of 28000 r.p.m. is necessary at 20° C. The methodology and analysis were as described by Morgan et al, (1992). The results (FIG. 8) showed that wild type LD78 exists in solution as a polydisperse population of protein species ranging in mass from approx. 10,000 Da ($M_w(\zeta=0)$) to 250,000 Da ($M_w(\zeta=1)$). The whole cell weight average molecular weight ($M°_w$) was found to be 160,000 Da.

Pure MIP-1α was analysed in the same manner except that the rotor speed was 15,000 r.p.m. In this case, the protein was shown to exist as a polydisperse solution of protein species ranging in mass from 230,000 Da ($M_w(\zeta=0)$) to 350,000 Da ($M_w(\zeta=1)$) with ($M°_w$)=310,000 Da.

The results from the independent techniques described above confirm that MIP-1α, LD78 and ACT-2 form large, soluble, heterogenous, multimeric complexes on reconstitution in low ionic strength aqueous buffers.

It is known that 0.5M NaCl prevents formation of the high molecular weight forms of MIP-1α and that in culture medium, around 5% of the total protein is a low molecular weight form (Oh et al.(1991)). Our studies demonstrate that in the absence of salt (i.e. in native PAGE sample buffer) no low molecular weight forms are present. In physiological ionic strength (150 mM phosphate buffered saline, pH7.4), a distinct population of low molecular weight protein species is present as seen in the size exclusion profiles. An equilibrium is, therefore, present between the high and low molecular weight species. This equilibrium is influenced by the ionic strength of the buffer—see Comparative Example 4.

Comparative Example 4

Characterization of the molecular weight of LD78 and MIP-1α (expressed from synthetic genes in yeast) in 10 mM MES. 500 mM NaCl pH6.5

Salt concentrations of 0.5M have been claimed to prevent formation of high molecular weight forms of MIP-1α (Wolpe and Cerami (1989). In order to characterize fully the effect of salt and to elucidate the association pathway of SCI multimers, the molecular weight of LD78 and MIP-1α were examined in conditions of high ionic strength.

Size exclusion chromatography was carried out using a Superose 12™ column attached to an FPLC system (Pharmacia). The column was calibrated at 1 ml/min in 20 mM MES (Sigma), 500 mM NaCl pH6.5 using the standards described in Comparative Example 3. Samples (100 μg) of MIP-1α and LD78 were dissolved in 0.2 ml of 10 mM MES (Sigma), 500 mM NaCl pH6.5 and loaded onto the column running at the calibrated speed of 1 ml/min. Eluted fractions were detected by u.v. absorbance at 280 nm.

Reconstitution of the lyophilized recombinant LD78 under these conditions gives an SEC elution profile containing a single symmetrical peak of mass around 20–25 KDa. The peak symmetry indicates that a single homogenous population of protein molecules exists. It is unclear from the determined mass whether trimeric or tetrameric LD78 represents the observed species.

Reconstitution of lyophilized recombinant MIP-1α under these conditions gives an SEC elution profile containing an asymmetric peak of approximate mass 25 kDa trailing down to around 5 kDa. The shape of the peak suggests the protein exists in a number of mass species under these conditions. The elution profile most probably reflects the presence of tetramer, dimer and monomer populations in solution.

Figure 8:
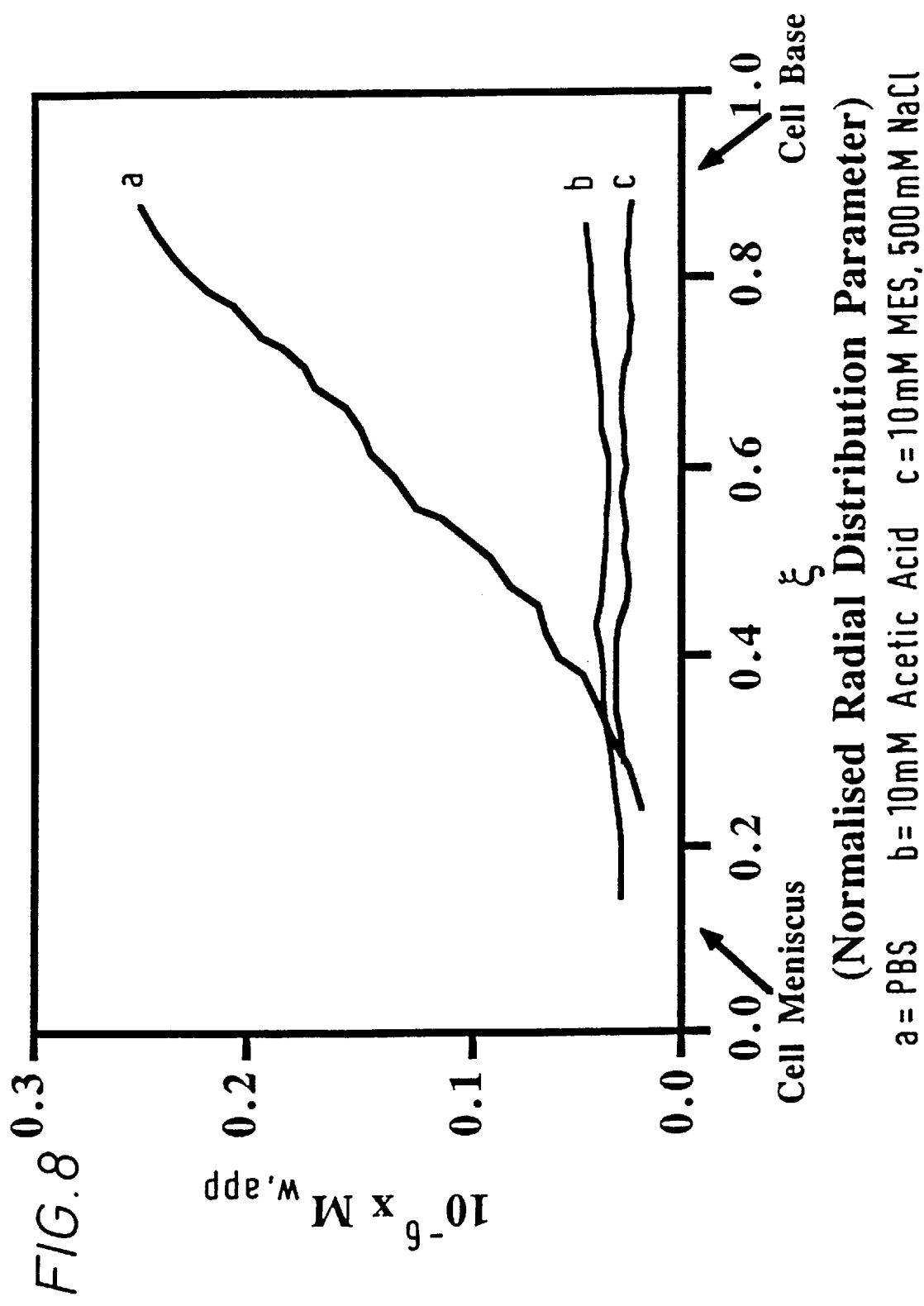
FIG. 8 shows the distribution of protein solute mass in the analytical ultracentrifuge cell at equilibrium for LD78 wild type in various buffer conditions.

Analytical ultracentrifugation of LD78 was carried out in these buffer conditions as described in Comparative Example 3. The whole cell weight average molecular weight was calculated to be a single population with molecular mass of 29±2 kDa. Under these conditions of 10 mM MES, 500 mM NaCl pH6.4, LD78 exists in solution as a defined tetramer in the absence of higher and lower molecular weight forms (FIG. 8).

These data demonstrate that ionic interactions play a key role in the association of LD78 tetramers to form the large heterogeneous multimers.

Comparative Example 5

Characterization of the molecular weight of LD78 (expressed from a synthetic gene in yeast) in 50 mM Tris. 1M Glycine pH 8.3

In order to correllate the molecular mass profiles obtained on native PAGE immunoblots described in Comparative Example 3 with data generated from other methods of mass determination, SEC was carried out in native PAGE buffer. Superdex 75™ FPLC resin has a comparable mass resolution range (3–70 kDa) as the Biorad (Miniprotean™ 12% acrylamide) pre-cast gels. This size exclusion column was, therefore, used to recreate the gel conditions as closely as possible. 100 μg of LD78 was reconstituted in 0.2 ml of 50 mM Tris, 1M Glycine pH8.3 buffer and injected at a flow rate of 1 ml/min onto the Superdex 75™ column equilibrated in the same buffer. Eluting fractions were detected by u.v. absorbance at 280 nm.

The SEC elution profile of LD78 shows a major asymmetric peak of high molecular weight (>70 kDa) protein partially excluded from the column, a small dimer peak at approx. 15 KDa and a major symmetrical peak corresponding to the monomer mass around 8,000 Da. The presence of a large population of monomeric LD78 in equilibrium with high molecular weight multimers suggests that the quaternary structure of LD78 is extremely sensitive either to:

(i) a 0.9 unit shift in pH between this buffer system and that in Comparative Example 3
or
(ii) the presence of significant concentrations of the free amino acid glycine.

Sedimentation equilibrium studies of LD78 (method as described in Comparative Example 3) at a protein concentration of 0.5 mg/ml under these buffer conditions reveal the presence of a polydisperse population of mass species ranging from 8,000 Da ($M_w(\zeta=0)$) to >300,000 Da ($M_w(\zeta=1)$).

As described in Preparation 13, electrospray mass spectroscopy reveals the presence of mono-valent and di-valent metal ions bound to purified LD78. Many chemical methods involve the use of metal ions to chelate to free amino and carboxyl groups of amino acids to enable the modification of side-chain groups in reaction mixtures (Chemistry of the Amino Acids, Volume 1—Chapter 6, Krieger Publishing Florida, ed. Greenstein & Winitz (1961)). The glycine present in this buffer could therefore act as a chelator for metal ions. Only a small population of dimeric LD78 is evident in the SEC profile and no tetrameric species are observed. It is suggested, therefore, that metal ions can play a role in the stabilization of both the LD78 tetramer and dimer units.

Comparative Example 6

Characterization of the molecular weight of LD78 (expressed from a synthetic gene in yeast) in 10 mM acetic acid pH3.2

The stem cell inhibitor protein LD78 is very soluble in mild acidic conditions. Size exclusion chromatography is not ideal under acidic conditions, therefore, analytical ultracentrifugation of LD78 was carried out. At a protein concentration of 0.5 mg/ml in 10 mM acetic acid pH3.2, a monodisperse mass species of 33±3 kDa was observed (FIG. 8). This mass equates to a monodisperse population of tetramers.

The relatively low ionic strength acidic conditions may titrate Glu and/or Asp groups involved in the electrostatic interactions involved in the association of tetramers to multimers described in Comparative Example 4.

Comparative Example 7

Spectroscopic assay for the state of multimerisation of LD78 protein expressed from a synthetic gene in yeast LD78 exists in solution as a tetramer in 10 mM acetic acid pH3.2 and 10 mM MES, 500 mM NaCl pH 6.4 (Comparative Example 4 & 6). In solutions such as 150 mM PBS pH7.4 the protein is present as a heterogeneous population of soluble multimeric complexes stabilized by electrostatic interactions between charged side-chains (Comparative Example 3).

Figure 9:
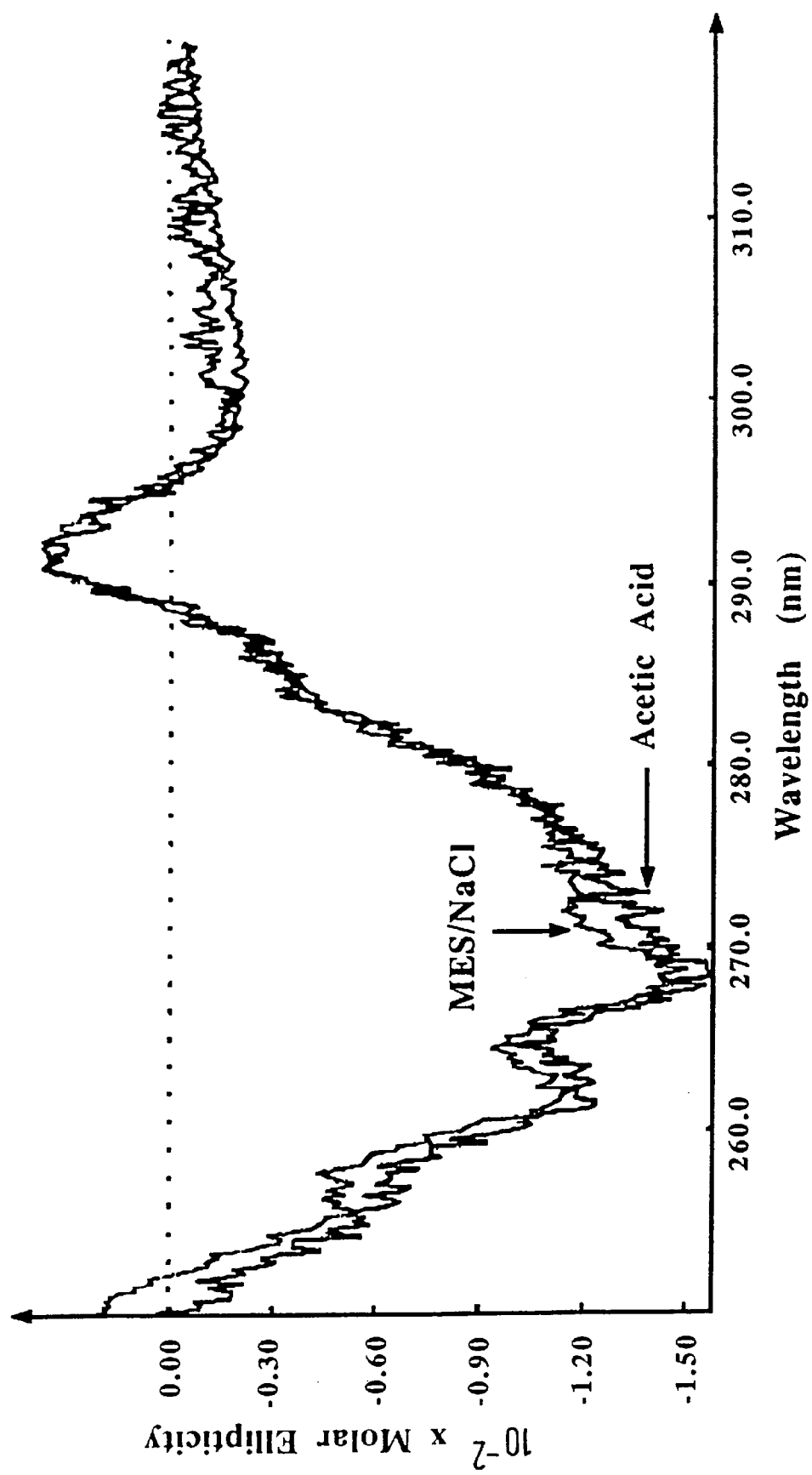
FIG. 9 shows the near u.v. circular dichroism spectra of tetrameric LD78 is independent of the buffer conditions used to achieve the defined structure.

The near u.v. c.d. spectra of LD78 (measured as described in Comparative Example 1) in 10 mM acetic acid pH3.2 and 10 mM MES, 500 mM NaCl pH6.4 are identical (FIG. 9). This data demonstrates that the buffer conditions used to produce tetrameric LD78 do not affect the tertiary conformation of the protein.

Figure 10:
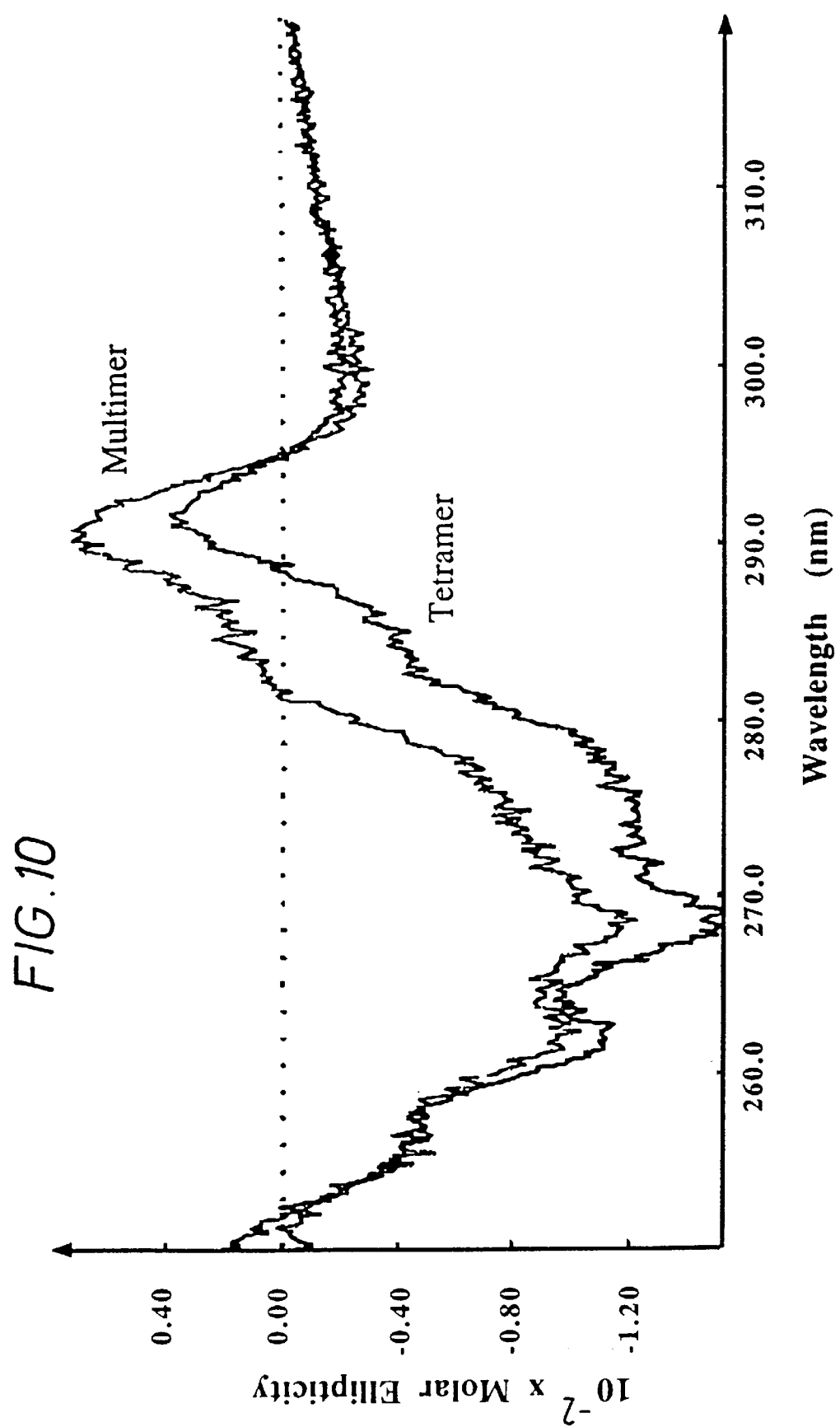
FIG. 10 shows that the near u.v. c.d. spectrum of tetrameric LD78 is different to that of the high molecular weight multimer form.

Comparison of the near u.v. c.d. spectrum of tetrameric LD78 with that of the high molecular weight multimers in 150 mM PBS pH7.4 (FIG. 10) shows that the asymmetric environment of Trp57 is different in the two states (See Comparative Example 1 for discussion of c.d. spectra interpretation).

Figure 11:
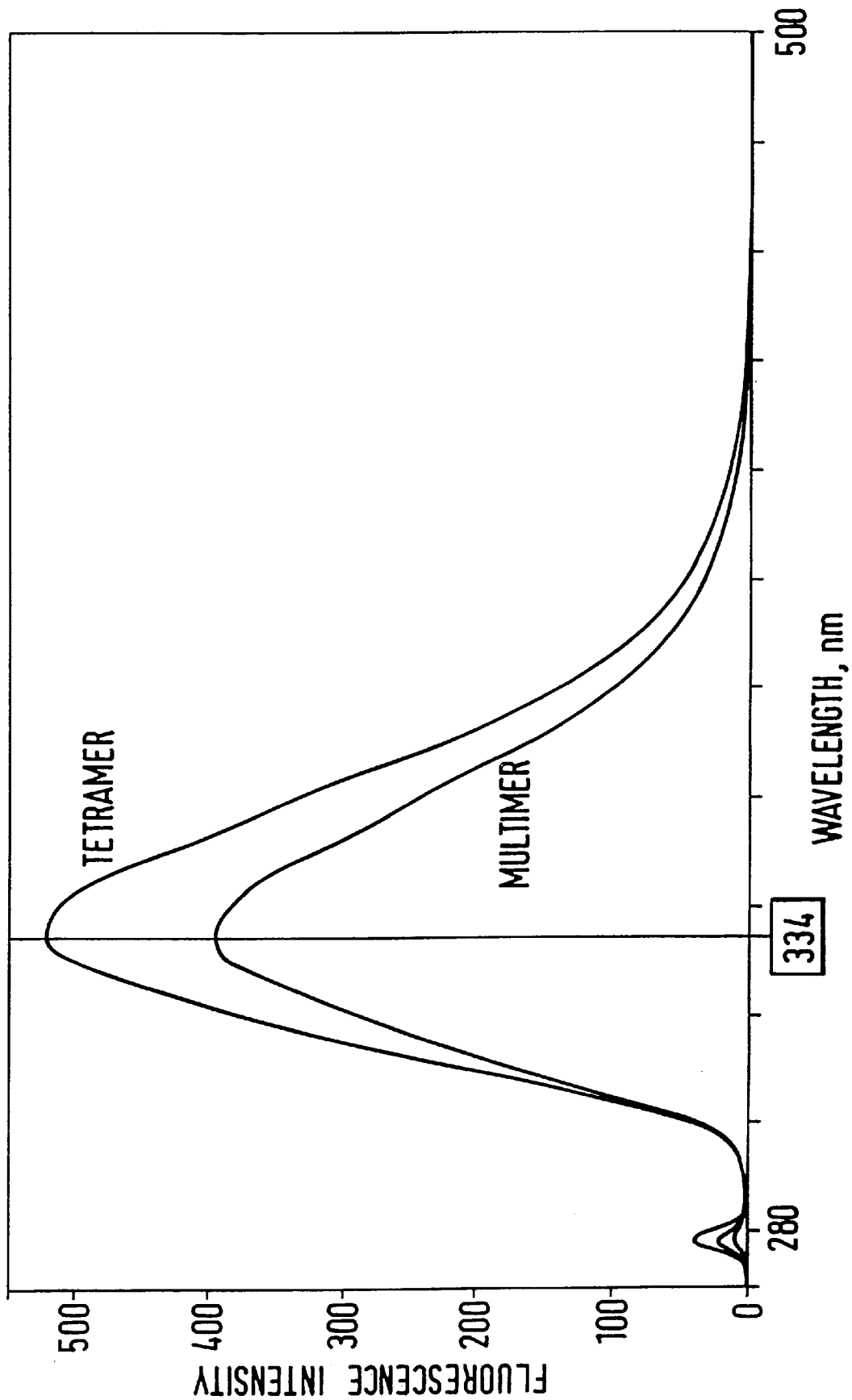
FIG. 11 shows that quenching of Trp-57 fluorescence emission energy occurs is present in the multimeric complexes but not in the tetramer. This quenching of emission energy arises due to the presence of an electrostatic interaction unique to the multimers which is proximal to Trp-57.

Examination of the steady state fluorescence emission spectra (method as described in Comparative Example 1) of LD78 in 10 mM acetic acid, 10 mM MES, 500 mM NaCl pH6.4 and 150 mM PBS pH7.4 (FIG. 11) shows that in the high molecular weight multimers, quenching of emission intensity occurs. The fact that $\lambda_{max}$ has not shifted, indicates that no conformational changes have occurred giving rise to quenching. It is known that electrostatic interactions proximal to tryptophan residues will quench the emission of fluorescence energy (Lackowicz (1983)). Stabilizing interactions between acidic and basic amino acids are known to be key for the association of tetramers to form multimeric complexes (Comparative Example 4). The change in environment observed for Trp-57 is entirely consistent with the formation of an ionic interaction spatially close to the side-chain.

Near u.v. c.d. and/or fluorescence emission spectroscopy can provide a sensitive probe for the multimer state of LD78.

EXAMPLES

Example 1

Design and Construction of LD78 Variant Gln48>Glu (Mutant 1) and Construction of an LD78 Gln48>Glu Expression Vector The strategy for construction of an LD78 variant (eg. Gln48>Glu) by oligonucleotide directed mutagenesis and molecular cloning is described below. Mutagenesis was carried out according to the method of Kunkel et al., *Methods in Enzymology* 154 367–382 (1987). Host strains and methods are described below.

*E. coli* strains

RZ1032 is a derivative of *E. coli* that lacks two enzymes of DNA metabolism: (a) dUTPase (dut), the lack of which results in a high concentration of intracellular dUTP, and (b) uracil N-glycosylase (ung) which is responsible for removing mis-incorporated uracils from DNA (Kunkel et al., oc. cit.). A suitable alternative strain is CJ236, available from Bio-Rad Laboratories, Watford WD1 8RP, United Kingdom. The principal benefit is that these mutations lead to a higher frequency of mutants in site directed mutagenesis. RZ1032 has the following genotype:

HfrKL16PO/45[lysA961-62), dut1, ung1, thi1, recA, Zbd-279::Tn10, supE44

JM103 is a standard recipient strain for manipulations involving M13 based vectors. The genotype of JM103 is Δ (lac-pro), thi, supE, strA, endA, sbcB15, hspR4, F' traD36, proAB, laciq, lacZΔM15. A suitable commercially available alternative *E. coli* strain is *E. coli* JM109, available from Northumbria Biologicals Ltd.

Mutagenesis

Prior to mutagenesis it was necessary to transfer the LD78 gene into a suitable vector. This was accomplished as described below.

pSW6 LD78 plasmid DNA of Preparation 2 was prepared and an aliquot was treated with restriction enzymes HindIII and BamHI. A ca. 235 bp DNA fragment from this digestion was gel purified and ligated to HindIII and BamHI treated *E. coli* bacteriophage M13 mp19 DNA. The products of the ligation reaction were transfected into competent cells of *E. coli* strain JM103. Single stranded DNAs from 6 putative recombinant plaques were then prepared and sequenced, by the dideoxy method, with a universal primer BB22 (5'-GTTTTCCCAGTCACGAC-3' (SEQ ID NO 47)).

Single stranded DNA of M13mp19-LD78 was prepared from *E. coli* RZ1032 and used as a template for oligonucleotide directed mutagenesis as described by Kunkel et al., using 22-mer oligonucleotide BB6298 (5'-GCACAGACTTCTCTCGAGCGCT-3' (SEQ ID NO 48)). The required mutant (pGHC600) was identified by dideoxy sequence analysis of single stranded DNAs prepared from putative mutant plaques. Primer BB22 (see above) was used as the sequencing primer in all cases. Double stranded replicative form (RF) DNA was prepared from the bacteriophage carrying the required mutation. The RF DNA was then digested with HindIII and BamHI. The DNA fragment carrying the LD78 Gln48>Glu gene was then purified after electrophoretic separation on a low gelling temperature agarose gel by standard methods. This fragment was then ligated to HindIII and BamHI treated pSW6 DNA to create an expression vector for the LD78 Gln48>Glu gene. The sequence of a correct clone (pSJE50) was verified by plasmid DNA sequencing. Expression of the mutant LD78 protein was achieved according to methods described in Preparation 3.

Example 2

Design and Construction of LD78 Variant Lys44>Glu Arg45>Gln Mutant 2) and Construction of an LD78 Lys44>Glu Arg45>Gln Expression Vector LD78 Lys44>Glu Arg45>Gln was constructed and cloned into the pSW6 yeast expression vector as described in Example 1. A 30-mer oligonucleotide BB6299 (5'-GACTTGTCTCGATTGCTCAGTCAAGAAGAT-3' (SEQ ID NO 49)) was used to mutate the LD78 gene and a correct clone identified (pGHC601). The mutant gene was cloned into the expression vector to create pSJE51. Expression of the mutant LD78 protein was achieved according to methods described in Preparation 3.

Example 3

Design and Construction of LD78 Variant Ala9>Ser (Mutant 3) and Construction of an LD78 Ala9>Ser Expression Vector LD78 Ala9>Ser was constructed and cloned into the pSW6 yeast expression vector as described in Example 1. A 22-mer oligonucleotide BB6300 (5'AAACAACAAGAGGTTGGAGTGT-3' (SEQ ID NO 50)) was used to mutate the LD78 gene and a correct clone identified (pGHC602). The mutant gene was cloned into the expression vector to create pSJE52. Expression of the mutant LD78 protein was achieved according to methods described in Preparation 3.

Example 4

Design and Construction of LD78 Variant Phe28>Ser Mutant 4) and Construction of an LD78 Phe28>Ser Expression Vector LD78 Phe28>Ser was constructed and cloned into the pSW6 yeast expression vector as described in Example 1. A 25-mer oligonucleotide BB6381 (5'-GAAGAAGTTTCA(G/CIT)AGTAGTCAGCAA-3' SEQ ID NO 51) was used to mutate the LD78 gene and a correct clone identified (pGHC603). The mutant gene was cloned into the expression vector to create pSJE53. Expression of the mutant LD78 protein was achieved according to methods described in Preparation 3.

Example 5

Design and Construction of LD78 Variant Arg17>Ser (Mutant 5) and Construction of an LD78 Arg17>Ser Expression Vector LD78 Arg17>Ser was constructed and cloned into the pSW6 yeast expression vector as described in Example 1. A 25-mer oligonucleotide BB6302 (5'-GTGGAATTTGAGAAGAGGTGTAAGA-3' SEQ ID NO 52) was used to mutate the LD78 gene and a correct clone identified (pGHC604). The mutant gene was cloned into the expression vector to create pSJE54. Expression of the mutant LD78 protein was achieved according to methods described in Preparation 3.

Example 6

Design and Construction of LD78 Variant Phe23>Asn Ile24>Thr (Mutant 6) and Construction of an LD78 Phe23>Asn Ile24>Thr Expression Vector LD78 Phe23>Asn Ile24>Thr was constructed and cloned into the pSW6 yeast expression vector as described in Example 1. A 27-mer oligonucleotide BB6303 (5'-GTAGTCAGCAGTGTTATTTTGTGGAAT-3' SEQ ID NO 53) was used to mutate the LD78 gene and a correct clone identified (pGHC605). The mutant gene was cloned into the expression vector to create pSJE55. Expression of the mutant LD78 protein was achieved according to methods described in Preparation 3.

Example 7

Design and Construction of LD78 Variant Asp26>Ala (Mutant 10) and Construction of an LD78 Asp26>Ala Expression Vector LD78 Asp26>Ala was constructed and cloned into the pSW6 yeast expression vector as described in Example 1. A 25-mer oligonucleotide BB6625 (5'-TTTCAAAGTAG(G/A)CAGCAATGAAATT-3' SEQ ID NO 54) was used to mutate the LD78 gene and a correct clone identified (pGHC609). The mutant gene was cloned into the expression vector to create pSJE59. Expression of the mutant LD78 protein was achieved according to methods described in Preparation 3.

Example 8

Design and Construction of LD78 Variant Phe12>Gln (Mutant 11) and Construction of an LD78 Phe12>Gln Expression Vector LD78 Phe12>Gln was constructed and cloned into the pSW6 yeast expression vector as described in Example 1. A 24-mer oligonucleotide BB6301 (5'-AGGTGTAAGATTGACAACAAGCGG-3' SEQ ID NO 55) was used to mutate the LD78 gene and a correct clone identified (pGHC610). The mutant gene was cloned into the expression vector to create pSJE60. Expression of the mutant LD78 protein was achieved according to methods described in Preparation 3.

Example 9

Design and Construction of LD78 Variant Ile24>Thr (Mutant 13) and Construction of an LD78 Ile24>Thr Expression Vector LD78 Ile24>Thr was constructed and cloned into the pSW6 yeast expression vector as described in Example 1. A 25-mer oligonucleotide BB6382 (5'-AGTAGTCAGCA(G/C/T)TGAAATTTTGTGG-3' SEQ ID NO 56) was used to mutate the LD78 gene and a correct clone identified (pGHC612). The mutant gene was cloned into the expression vector to create pSJE62. Expression of the mutant LD78 protein was achieved according to methods described in Preparation 3.

Example 10

Design and Construction of LD78 Variant Ile40>Arg Mutant 14) and Construction of an LD78 Ile40>Arg Expression Vector LD78 Ile40>Arg was constructed and cloned into the pSW6 yeast expression vector as described in Example 1. A 24-mer oligonucleotide BB6383 (5'-TAGTCAAGAATCTGACACCTGGCT-3' SEQ ID NO 57) was used to mutate the LD78 gene and a correct clone identified (pGHC613). The mutant gene was cloned into the expression vector to create pSJE63. Expression of the mutant LD78 protein was achieved according to methods described in Preparation 3.

Example 11

Design and Construction of LD78 Variant Arg47>Glu (Mutant 15) and Construction of an LD78 Arg47>Glu Expression Vector LD78 Arg47>Glu was constructed and cloned into the pSW6 yeast expression vector as described in Example 1. A 26-mer oligonucleotide BB6384 (5'-GCACAGACTTGTTCCGAGCGCTTAGT-3' SEQ ID NO 58) was used to mutate the LD78 gene and a correct clone identified (pGHC614). The mutant gene was cloned into the expression vector to create pSJE64. Expression of the mutant LD78 protein was achieved according to methods described in Preparation 3.

Example 12

Design and Construction of LD78 Variant Lys60>Gln Asp64>Asn (Mutant 16) and Construction of an LD78 Lys60>Gln Asp64>Asn Expression Vector LD78 Lys60>Gln Asp64>Asn was constructed and cloned into the pSW6 yeast expression vector as described in Example 1. A 35-mer oligonucleotide BB6385 (5'-AATTCCAAGTTAGAAACATATTGTTGAACCCATTC-3' SEQ ID NO 59) was used to mutate the LD78 gene and a correct clone identified (pGHC615). The mutant gene was cloned into the expression vector to create pSJE65. Expression of the mutant LD78 protein was achieved according to methods described in Preparation 3.

Example 13

Design and Construction of LD78 Variant Phe28>Glu (Mutant 17) and Construction of an LD78 Phe28>Glu Expression Vector LD78 Phe28>Glu was constructed and cloned into the pSW6 yeast expression vector as described in Example 1. A 25-mer oligonucleotide BB6345 (5'-GAAGAAGTTTCTTCGTAGTCAGCAA-3' SEQ ID NO 60) was used to mutate the LD78 gene and a correct clone identified (pGHC616). The mutant gene was cloned into the expression vector to create pSJE66. Expression of the mutant LD78 protein was achieved according to methods described in Preparation 3.

Example 14

Design and Construction of LD78 Variant Ile24>Asn (Mutant 24) and Construction of an LD78 Ile24>Asn Expression Vector LD78 Ile24>Asn was constructed and cloned into the pSW6 yeast expression vector as described in Example 1. A 25-mer oligonucleotide BB6382 (5'-AGTAGTCAGCA(G/C/T)TGAAATTTTGTGG-3' SEQ ID NO 56) was used to mutate the LD78 gene and a correct clone identified (pGHC623). The mutant gene was cloned into the expression vector to create pSJE73. Expression of the mutant LD78 protein was achieved according to methods described in Preparation 3.

Example 15

Design and Construction of LD78 Variant Phe28>Glue Gln48>Glue (Mutant 25) and Construction of an LD78 Phe28>Glue Gln48>Glu Expression Vector LD78 Phe28>Glu Gln48>Glu was constructed and cloned into the pSW6 yeast expression vector essentially as described in Example 1. A 27-mer oligonucleotide BB7015 (5'-TGAGAAGAAGTTTCTTCGTAGTCAGCA-3' SEQ ID NO 61) was used to mutate the LD78 Gln48>Glue gene (pGHC600 of Example 1) and a correct clone identified (pGHC624). The mutant gene was cloned into the expression vector to create pSJE74. Expression of the mutant LD78 protein was achieved according to methods described in Preparation 3.

Example 16

Design and Construction of LD78 Variant Phe28>Glu Arg47>Glu (Mutant 26) and Construction of an LD78 Phe28>Glu Arg47>Glu Expression Vector LD78 Phe28>Glu Arg47>Glu was constructed and cloned into the pSW6 yeast expression vector essentially as described in Example 1. A 27-mer oligonucleotide BB7015 (5'-TGAGAAGAAGTTTCTTCGTAGTCAGCA-3' SEQ ID NO 61) was used to mutate the LD78 Arg47>Glu gene (pGHC614 of Example 11) and a correct clone identified (pGHC625). The mutant gene was cloned into the expression vector to create pSJE75. Expression of the mutant LD78 protein was achieved according to methods described in Preparation 3.

Example 17

Design and Construction of LD78 Variant Glu55>Arg Glu56>Arg Mutant 27) and Construction of an LD78 Glu55>Arg Glu56>Arg Expression Vector LD78 Glu55>Arg Glu56>Arg was constructed and cloned into the pSW6 yeast expression vector as described in Example 1. A 27-mer oligonucleotide BB9112 (5'-TTGAACCCAGCGGCGAGATGGGTCAGC-3' SEQ ID NO 62) was used to mutate the LD78 gene and a correct clone identified (pGHC626). The mutant gene was cloned into the expression vector to create pSJE76. Expression of the mutant LD78 protein was achieved according to methods described in Preparation 3.

Example 18

Design and Construction of LD78 Variant Glu29>Arg (Mutant 28) and Construction of an LD78 Glu29>Arg Expression Vector LD78 Glu29>Arg was constructed and cloned into the pSW6 yeast expression vector as described in Example 1. A 24-mer oligonucleotide BB9109 (5'-TTGAGAAGAAGTTCTAAAGTAGTC-3' SEQ ID NO 63) was used to mutate the LD78 gene and a correct clone identified (pGHC627). The mutant gene was cloned into the expression vector to create pSJE77. Expression of the mutant LD78 protein was achieved according to methods described in Preparation 3.

Example 19

Design and Construction of LD78 Variant Gln18>Glu (Mutant 29) and Construction of an LD78 Gln18>Glu Expression Vector LD78 Gln 18>Glu was constructed and cloned into the pSW6 yeast expression vector as described in Example 1. A 24-mer oligonucleotide BB9110 (5'-ATTTTGTGGAATTTCTCTAGAGGT-3' SEQ ID NO 64) was used to mutate the LD78 gene and a correct clone identified (pGHC628). The mutant gene was cloned into the expression vector to create pSJE78. Expression of the mutant LD78 protein was achieved according to methods described in Preparation 3.

Example 20

Design and Construction of LD78 Variant Arg17>Ser Gln18>Glu (Mutant 30) and Construction of an LD78 Arg17>Ser Gln18>Glu Expression Vector LD78 Arg17>Ser Gln18>Glu was constructed and cloned into the pSW6 yeast expression vector as described in Example 1. A 30-mer oligonucleotide BB9111 (5'-ATTTTGTGGAATTTCAGAAGAGGTGTAAGA-3' SEQ ID NO 65) was used to mutate the LD78 gene and a correct clone identified (pGHC629). The mutant gene was cloned into the expression vector to create pSJE79. Expression of the mutant LD78 protein was achieved according to methods described in Preparation 3.

Example 21

Design and Construction of LD78 Variant Ser-Ala-LD78 (Mutant 31) and Construction of a Ser-Ala-LD78 Expression Vector Ser-Ala-LD78 was constructed and cloned into the pSW6 yeast expression vector as described in Example 1. A 30-mer oligonucleotide BB9104 (5'-AGCAGCCAAGGAAGCAGATCTTTTATCCAA-3'SEQ ID NO 66) was used to mutate the LD78 gene and a correct clone identified (pGHC630). The mutant gene was cloned into the expression vector to create pSJE80. Expression of the mutant LD78 protein was achieved according to methods described in Preparation 3.

Example 22

Design and Construction of LD78 Variant Leu-Ser-Ala-Ser1>Pro LD78 (Mutant 32) and Construction of a Leu-Ser-Ala-Ser1>Pro LD78 Expression Vector Leu-Ser-Ala-Ser1>Pro LD78 (in which the residues Leu, Ser and Ala have been added to the N-terminus of LD78 and in which Pro has been substituted for Ser1) was constructed and cloned into the pSW6 yeast expression vector as described in Example 1. A 36-mer oligonucleotide BB9105 (5'-GTCAGCAGCCAATGGAGCAGACAATCTTTTATCCAA-3' SEQ ID NO 67) was used to mutate the LD78 gene and a correct clone identified (pGHC631). The mutant gene was cloned into the expression vector to create pSJE81. Expression of the mutant LD78 protein was achieved according to methods described in Preparation 3.

Example 23

Design and Construction of an LD78 Variant With the First Three N-terminal Amino Acids Deleted (N1-3 LD78) (Mutant 33) and Construction of an N1-3 LD78 Expression Vector N1-3 LD78 was constructed and cloned into the pSW6 yeast expression vector as described in Example 1. A 24-mer oligonucleotide BB9106 (5'-TGGAGTGTCAGCTCTTTTATCCAA-3' SEQ ID NO 68) was used to mutate the LD78 gene and a correct clone identified (pGHC632). The mutant gene was cloned into the expression vector to create pSJE82. Expression of the mutant LD78 protein was achieved according to methods described in Preparation 3.

Example 24

Design and Construction of LD78 Variant Ala-Ser1>Pro LD78 (Mutant 34) and Construction of an Ala-Ser1>Pro LD78 Expression Vector Ala-Ser1>Pro LD78 (in which the residue Ala has been added to the N-terminus of LD78 and in which Pro has been substituted for Ser1) was constructed and cloned into the pSW6 yeast expression vector as described in Example 1. A 30-mer oligonucleotide BB9103 (5'-GTCAGCAGCCAATGGAGCTCTTTTATCCAA-3' SEQ ID NO 69) was used to mutate the LD78 gene and a correct clone identified (pGHC633). The mutant gene was cloned into the expression vector to create pSJE83. Expression of the mutant LD78 protein was achieved according to methods described in Preparation 3.

Example 25

Design and Construction of LD78 Variant Leu-Ser-Ala-Ser1>Pro Gly38>Ser Ser46>Gly (Mutant 35) and Construction of a Leu-Ser-Ala-Ser1>Pro Gly38>Ser Ser46>Gly Expression Vector LD78 Leu-Ser-Ala-Ser1>Pro Gly38>Ser Ser46>Gly (in which the residues Leu, Ser and Ala have been added to the N-terminus of LD78 and in which Pro has been substituted for Ser1, Ser has been substituted for Gly 38 and Gly has been substituted for Ser 46) was constructed and cloned into the pSW6 yeast expression vector essentially as described in Example 1. A 48-mer oligonucleotide BB9108 (5'-ACAGACTTGTCTACCGCGCTTAGTCAAGAAGATGA CAGATGGCTTGGA-3' SEQ ID NO 70) was used to mutate the Leu-Ser-Ala-Ser1>Pro LD78 gene (pGHC631 of Example 22) and a correct clone identified (pGHC634). The mutant gene was cloned into the expression vector to create pSJE84. Expression of the mutant LD78 protein was achieved according to methods described in Preparation 3.

Example 26

Design and Construction of an LD78 Variant With the First Three N-terminal Amino Acids Deleted (N1-3) and Thr15>Phe (Mutant 36) and Construction of an (N1-3) Thr15>Phe LD78 Expression Vector N1-3 Thr15>Phe LD78 was constructed and cloned into the pSW6 yeast expression vector essentially as described in Example 1. A 24-mer oligonucleotide BB9107 (5'-AATTGTCTAGAGAAGTAAGAGAA-3' SEQ ID NO 71) was used to mutate the N1-3 LD78 gene (pGHC632 of Example 23) and a correct clone identified (pGHC635). The mutant gene was cloned into the expression vector to create pSJE85. Expression of the mutant LD78 protein was achieved according to methods described in Preparation 3.

Example 27

Design and Construction of LD78 Variant Gln48>Ser (Mutant 70) and Construction of an LD78 Gln48>Ser Expression Vector LD78 Gln48>Ser was constructed and cloned into the pSW6 yeast expression vector as described in Example 1. A 21-mer oligonucleotide BB9512 (5'-CAGCACAGACAGATCTCGAGC-3' SEQ ID NO 72) was used to mutate the LD78 gene and a correct clone identified (pGHC670). The mutant gene was cloned into the expression vector to create pRC59/70. Expression of the mutant LD78 protein was achieved according to methods described in Preparation 3.

Example 28

Design and Construction of LD78 Variant Asp26>Ser (Mutant 39) and Construction of an LD78 Asp26>Ser Expression Vector LD78 Asp26>Ser was constructed and cloned into the pSW6 yeast expression vector as described in Example 1.

An 18-mer oligonucleotide BB9432 (5'-CAAAGTAGGAAGCAATGA-3' SEQ ID NO 73) was used to mutate the LD78 gene and a correct clone identified (pGHC638). The mutant gene was cloned into the expression vector to create pSJE88. Expression of the mutant LD78 protein was achieved according to methods described in Preparation 3.

Example 29

Design and Construction of LD78 Variant Phe12>Ala (Mutant 77) and Construction of an LD78 Phe12>Ala Expression Vector LD78 Phe12>Ala was constructed and cloned into the pSW6 yeast expression vector as described in Example 1. A 19-mer oligonucleotide BB9519 (5'-GTGTAAGAGGCACAACAAG-3' SEQ ID NO 74) was used to mutate the LD78 gene and a correct clone identified (pGHC676). The mutant gene was cloned into the expression vector to create pDB127. Expression of the mutant LD78 protein was achieved according to methods described in Preparation 3.

Example 30

Design and Construction of LD78 Variant LD78 Phe28>Ala (Mutant 85) and Construction of an LD78 Phe28>Ala Expression Vector LD78 Phe28>Ala was constructed and is cloned into the pSW6 yeast expression vector as described in Example 1. A 19-mer oligonucleotide BB9527 (5'-GAAGTTTCAGCGTAGTCAG-3' SEQ ID NO 75) was used to mutate the LD78 gene and a correct clone identified (pGHC684). The mutant gene was cloned into the expression vector to create pDB130. Expression of the mutant LD78 protein was achieved according to methods described in Preparation 3.

Example 31

Design and Construction of LD78 Variant Ile24>Ala (Mutant 38) and Construction of an LD78 Ile24>Ala Expression Vector LD78 Ile24>Ala was constructed and cloned into the pSW6 yeast expression vector as described in Example 1. A 21-mer oligonucleotide BB9431 (5'-GTAGTCAGCAGCGAAATTTTG-3' SEQ ID NO 76) was used to mutate the LD78 gene and a correct clone identified (pGHC637). The mutant gene was cloned into the expression vector to create pSJE87. Expression of the mutant LD78 protein was achieved according to methods described in Preparation 3.

Example 32

Design and Construction of LD78 Variant Ile40>Ala (Mutant 92) and Construction of an LD78 Ile40>Ala Expression Vector LD78 Ile40>Ala was constructed and cloned into the pSW6 yeast expression vector as described in Example 1. A 19-mer oligonucleotide BB9534 (5'-GTCAAGAAGGCGACACCTG-3' SEQ ID NO 77) was used to mutate the LD78 gene and a correct clone identified (M13DB104). The mutant gene was cloned into the expression vector to create pDB114. Expression of the mutant LD78 protein was achieved according to methods described in Preparation 3.

Example 33

Design and Construction of LD78 Variant LD78 Arg47>Ser (Mutant 44) and Construction of an LD78 Arg47>Ser Expression Vector LD78 Arg47>Ser was constructed and cloned into the pSW6 yeast expression vector as described in Example 1. A 21-mer oligonucleotide BB9437 (5'-CACAGACTTGAGACGAGCGCT-3' SEQ ID NO 78) was used to mutate the LD78 gene and a correct clone identified (pGHC643). The mutant gene was cloned into the expression vector to create pDB144. Expression of the mutant LD78 protein was achieved according to methods described in Preparation 3.

Example 34

Design and Construction of LD78 Variant Glu29>Ser (Mutant 40) and Construction of an LD78 Glu29>Ser Expression Vector LD78 Glu29>Ser was constructed and cloned into the pSW6 yeast expression vector as described in Example 1. A 22-mer oligonucleotide BB9433 (5'-GAGAAGAAGTAGAAAAGTAGTC-3' SEQ ID NO 79) was used to mutate the LD78 gene and a correct clone identified (pGHC639). The mutant gene was cloned into the expression vector to create pDB135. Expression of the mutant LD78 protein was achieved according to methods described in Preparation 3.

Example 35

Design and Construction of LD78 Variant Gln18>Ser (Mutant 64 and Construction of an LD78 Gln18>Ser Expression Vector LD78 Gln18>Ser was constructed and cloned into the pSW6 yeast expression vector as described in Example 1. A 21-mer oligonucleotide BB9506 (5'-TTTGTGGAATAGATCTAGAGG-3' SEQ ID NO 80) was used to mutate the LD78 gene and a correct clone identified (pGHC663). The mutant gene was cloned into the expression vector to create pRC59/64. Expression of the mutant LD78 protein was achieved according to methods described in Preparation 3.

Example 36

Design and Construction of LD78 Variant Asp5>Arg (Mutant 104) and Construction of an LD78 Asp5>Arg Expression Vector LD78 Asp5>Arg was constructed and cloned into the pSW6 yeast expression vector as described in Example 1. A 23-mer oligonucleotide BB10194 (5'-GGTTGGAGTGCGAGCAGCCAAGG-3' SEQ ID NO 81) was used to mutate the LD78 gene and a correct clone identified (pGHC566). The mutant gene is cloned into the expression vector according to the method of Example 1 and expression of the mutant LD78 protein is achieved according to methods described in Preparation 3.

Example 37

Construction of LD78 Variant Arg17>Glu, (Gln. Ile, Pro) Insertion between residues 20 and 21 (Mutant 105) and Construction of an LD78 Arg17>Glu (Gln. Ile, Pro) Insertion between residues 20 and 21 Expression Vector LD78 Arg17>Glu (Gln, Ile, Pro) Insertion between residues 20 and 21 is constructed and cloned into the pSW6 yeast expression vector as described in Example 1. A 22-mer oligonucleotide BB10195 (5'-GGAATTTGTTCAGAGGTGTAAG-3' SEQ ID NO 82) was used to mutate the LD78 gene and a clone containing the desired site-directed sequence mutation and an additional unintentional three amino-acid insertion identified (M13DB120). The mutant gene was cloned into the expression vector to create pDB138. Expression of the mutant LD78 protein was achieved according to methods described in Preparation 3.

Example 38

Design and Construction of LD78 Variant Ser46>Glu (Mutant 106) and Construction of an LD78 Ser46>Glu Expression Vector LD78 Ser46>Glu is constructed and cloned into the pSW6 yeast expression vector as described in Example 1. A 27-mer oligonucleotide BB10196 (5'-GCACAGACTTGTCTTTCGCGCTTAGTC-3' SEQ ID NO 83) was used to mutate the LD78 gene and a correct clone was identified (M13DB121). The mutant gene was cloned into the expression vector to create pDB146. Expression of the mutant LD78 protein was achieved according to methods described in Preparation 3.

Example 39

Design and Construction of LD78 Variant Leu2>Glu (Mutant 107) and Construction of an LD78 Leu2>Glu Expression Vector LD78 Leu2>Glu is constructed and cloned into the pSW6 yeast expression vector as described in Example 1. A 29-mer oligonucleotide BB10197 (5'-GGAGTGTCAGCAGCTTCGGATCTTTTATC-3' SEQ ID NO 84) was used to mutate the LD78 gene and a correct clone identified (M13DB122). The mutant gene was cloned into the expression vector to create pDB139. Expression of the mutant LD78 protein was achieved according to methods described in Preparation 3.

Example 40

Design and Construction of LD78 Variant Ala3>Glu (Mutant 108) and Construction of an LD78 Ala3>Glu Expression Vector LD78 Ala3>Glu is constructed and cloned into the pSW6 yeast expression vector as described in Example 1. A 22-mer oligonucleotide BB10198 (5'-GGAGTGTCAGCTTCCAAGGATC-3' SEQ ID NO 85) was used to mutate the LD78 gene and a correct clone identified (M13DB123). The mutant gene is cloned into the expression vector according to the method of Example 1 and expression of the mutant LD78 protein is achieved according to methods described in Preparation 3.

Example 41

Design and Construction of LD78 Variant Ala4>Glu (Mutant 109) and Construction of an LD78 Ala4>Glu Expression Vector LD78 Ala4>Glu is cloned and cloned into the pSW6 yeast expression vector as described in Example 1. A 23-mer oligonucleotide BB10199 (5'-GGTTGGAGTGTCTTCAGCCAAGG-3' SEQ ID NO 86) was used to mutate the LD78 gene and a correct clone identified (M13DB126). The mutant gene was cloned into the expression vector to create pDB147. Expression of the mutant LD78 protein was achieved according to methods described in Preparation 3.

Example 42

Design and Construction of LD78 Variant Arg17>Glu Gln18>Glu (Mutant 110) and Construction of an LD78 Arg17>Glu Gln18>Glu Expression Vector LD78 Arg17>Glu Gln18>Glu is constructed and cloned into the pSW6 yeast expression vector as described in Example 1. A 22-mer oligonucleotide BB10200 (5'-GGAATTTCTTCAGAGGTGTAAG-3' SEQ ID NO 87) was used to mutate the LD78 gene and a correct clone identified (M13DB124). The mutant gene was cloned into the expression vector to create pDB140. Expression of the mutant LD78 protein was achieved according to methods described in Preparation 3.

Example 43

Design and Construction of LD78 Variant Leu67>Glu (Mutant 111) and Construction of an LD78 Leu67>Glu Expression Vector LD78 Leu67>Glu is constructed and cloned into the pSW6 yeast expression vector as described in Example 1. A 28-mer oligonucleotide BB10201 (5'-CCTTATTAGGCAGATTCTTCCAAGTCAG-3' SEQ ID NO 88) was used to mutate the LD78 gene and a correct clone identified (M13DB125). The mutant gene was cloned into the expression vector to create pDB141. Expression of the mutant LD78 protein was achieved according to methods described in Preparation 3.

Example 44

Design and Construction of LD78 Variant Ser46>Ala (Mutant 95) and Construction of an LD78 Ser46>Ala Expression Vector LD78 Ser46>Ala was constructed and cloned into the pSW6 yeast expression vector as described in Example 1. A 20-mer oligonucleotide BB9537 (5'-GACTTGTCTAGCGCGCTTAG-3' SEQ ID NO 89) was used to mutate the LD78 gene and a correct clone identified (M13DB107). The mutant gene was cloned into the expression vector to create pDB117. Expression of the mutant LD78 protein was achieved according to methods described in Preparation 3.

Example 45

Design and Construction of LD78 Variant Leu2>Ala Mutant 55) and Construction of an LD78 Leu2>Ala Expression Vector LD78 Leu2>Ala was constructed and cloned into the pSW6 yeast expression vector as described in Example 1. A 19-mer oligonucleotide BB9497 (5'-GTCAGCAGCAGCGGATCTT-3' SEQ ID NO 90) was used to mutate the LD78 gene and a correct clone identified (pGHC654). The mutant gene was cloned into the expression vector to create pDB102. Expression of the mutant LD78 protein was achieved according to methods described in Preparation 3.

Example 46

Design and Construction of LD78 Variant Ala3>Ser (Mutant 56) and Construction of an LD78 Ala3>Ser Expression Vector LD78 Ala3>Ser was constructed and cloned into the pSW6 yeast expression vector as described in Example 1. A 17-mer oligonucleotide BB9498 (5'-GTCAGCAGACAAGGATC-3' SEQ ID NO 91) was used to mutate the LD78 gene and a correct clone identified (pGHC655). The mutant gene was cloned into the expression vector to create pDB123. Expression of the mutant LD78 protein was achieved according to methods described in Preparation 3.

Example 47

Design and Construction of LD78 Variant Ala4>Ser (Mutant 57) and Construction of an LD78 Ala4>Ser Expression Vector LD78 Ala4>Ser was constructed and cloned into the pSW6 yeast expression vector as described in Example 1. An 18-mer oligonucleotide BB9499 (5'-GAGTGTCAGAAGCCAAGG-3' SEQ ID NO 92) was used to mutate the LD78 gene and a correct clone identified (pGHC656). The mutant gene was cloned into the expression vector to create pDB124. Expression of the mutant LD78 protein was achieved according to methods described in Preparation 3.

Example 48

Design and Construction of LD78 Variant Leu67>Ala (Mutant 75) and Construction of an LD78 Leu67>Ala Expression Vector LD78 Leu67>Ala was constructed and cloned into the pSW6 yeast expression vector as described in Example 1. A 22-mer oligonucleotide BB9517 (5'-ATTAGGCAGAGGCTTCCAAGTC-3' SEQ ID NO 93) was used to mutate the LD78 gene and a correct clone identified (pRC58/75). The mutant gene was cloned into the expression vector to create pRC59/75. Expression of the mutant LD78 protein was achieved according to methods described in Preparation 3.

Example 49

Design and Construction of LD78 Variant with the First Six Amino Acids Deleted (N1-6) and Pro7>Ser mutant 103) and Construction of an N1-6 Pro7>Ser Expression Vector N1-6 Pro7>Ser LD78 was constructed and cloned into the pSW6 yeast expression vector as described in Example 1. A 34-mer oligonucleotide BB9781 (5'-GAGAAACAACAAGCGGTAGATCTTTTATCCAAGC-3' SEQ ID NO 94) was used to mutate the LD78 gene and a correct clone identified (pRC58/103). The mutant gene was cloned in to the expression vector to create pRC59/103. Expression of the mutant LD78 protein was achieved according to methods described in Preparation 3.

Example 50

Design and Construction of LD78 Variant Phe28>Tyr (Mutant 12) and Construction of an LD78 Phe28>Tyr Expression Vector LD78 Phe28>Tyr was constructed and cloned into the pSW6 yeast expression vector as described in Example 1. A 25-mer oligonucleotide BB6381 (5'-GAAGAAGTTTCA(G/C/T)AGTAGTCAGCAA-3' SEQ ID NO 51) was used to mutate the LD78 gene and a correct clone identified (pGHC611). The mutant gene was cloned into the expression vector to create pRC59/12. Expression of the mutant LD78 protein was achieved according to methods described in Preparation 3.

Example 51

Design and Construction of LD78 Variant Asp5>Ser (Mutant 37) and Construction of an LD78 Asp5>Ser Expression Vector LD78 Asp5>Ser was constructed and cloned into the pSW6 yeast expression vector as described in Example 1. A 20-mer oligonucleotide BB9430 (5'-GTTGGAGTGGAAGCAGCCAA-3' SEQ ID NO 95) was used to mutate the LD78 gene and a correct clone identified (pGHC636). The mutant gene was cloned into the expression vector to create pDB134. Expression of the mutant LD78 protein was achieved according to methods described in Preparation 3.

Example 52

Design and Construction of LD78 Variant Phe23>Ala (Mutant 83) and Construction of an LD78 Phe23>Ala Expression Vector LD78 Phe23>Ala was constructed and cloned into the pSW6 yeast expression vector as described in Example 1. An 18-mer oligonucleotide BB9525 (5'-CAGCAATGGCATTTTGTG-3' SEQ ID NO 96) was used to mutate the LD78 gene and a correct clone identified (M13DB119). The mutant gene was cloned into the expression vector to create pDB137. Expression of the mutant LD78 protein was achieved according to methods described in Preparation 3.

Example 53

Design and Construction of LD78 Variant Lys44>Ser (Mutant 42) and Construction of an LD78 Lys44>Ser Expression Vector LD78 Lys44>Ser was constructed and cloned into the pSW6 yeast expression vector as described in Example 1. A 21-mer oligonucleotide BB9435 (5'-GTCTCGAGCGAGAAGTCAAGA-3' SEQ ID NO 97) was used to mutate the LD78 gene and a correct clone identified (pGHC641). The mutant gene was cloned into the expression vector to create pSJE91. Expression of the mutant LD78 protein was achieved according to methods described in Preparation 3.

Example 54

Design and Construction of LD78 Variant Arg45>Ser (Mutant 43) and Construction of an LD78 Arg45>Ser Expression Vector LD78 Arg45>Ser was constructed and cloned into the pSW6 yeast expression vector as described in Example 1. An 18-mer oligonucleotide BB9436 (5'-GTCTCGAGGACTTAGTCA- 3' SEQ ID NO 98) was used to mutate the LD78 gene and a correct clone identified (pGHC642). The mutant gene was cloned into the expression vector to create pRC59/43. Expression of the mutant LD78 protein was achieved according to methods described in Preparation 3.

Example 55

Design and Construction of LD78 Variant Glu55>Ser (Mutant 46) and Construction of an LD78 Glu55>Ser Expression Vector LD78 Glu55>Ser was constructed and cloned into the pSW6 yeast expression vector as described in Example 1. A 22-mer oligonucleotide BB9423 (5'-GAACCCATTCAGAAGATGGGTC-3' SEQ ID NO 99) was used to mutate the LD78 gene and a correct clone identified (pGHC645). The mutant gene was cloned into the expression vector to create pSJE95. Expression of the mutant LD78 protein was achieved according to methods described in Preparation 3.

Example 56

Design and Construction of LD78 Variant Glu56>Ser (Mutant 47) and Construction of an LD78 Glu56>Ser Expression Vector LD78 Glu56>Ser is constructed and cloned into the pSW6 yeast expression vector as described in Example 1. A 21-mer oligonucleotide BB9424 (5'-TTTGAACCCAAGATTCAGATG-3' SEQ ID NO 100) is used to mutate the LD78 gene. The mutant gene was cloned into the expression vector according to the method of Example 1 and expression of the mutant LD78 protein was achieved according to methods described in Preparation 3.

Example 57

Design and Construction of LD78 Variant Lys60>Ser (Mutant 48) and Construction of an LD78 Lys60>Ser Expression Vector LD78 Lys60>Ser was constructed and cloned into the pSW6 yeast expression vector as described in Example 1. A 21-mer oligonucleotide BB9425 (5'-CAGAAACATAAGATTGAACCC-3' SEQ ID NO 101) was used to mutate the LD78 gene and a correct clone identified (pGHC647). The mutant gene was cloned into the expression vector to create pSJE97. Expression of the mutant LD78 protein was achieved according to methods described in Preparation 3.

Example 58

Design and Construction of LD78 Variant Asp64>Ser (Mutant 50) and Construction of an LD78 Asp64>Ser Expression Vector LD78 Asp64>Ser was constructed and cloned into the pSW6 yeast expression vector as described in Example 1. A 20-mer oligonucleotide BB9427 (5'-CAATTCCAAGGAAGAAACAT-3' SEQ ID NO 102) was used to mutate the LD78 gene and a correct clone identified (pGHC649). The mutant gene was cloned into the expression vector to create pSJE99. Expression of the mutant LD78 protein was achieved according to methods described in Preparation 3.

Example 59

Design and Construction of an LD78 Variant With the Five C-terminal Amino Acids Deleted (C65-69) (Mutant 61) and Construction of an C65-69 LD78 Expression Vector C65-59 LD78 was constructed and cloned into the pSW6 yeast expression vector as described in Example 1. A 17-mer oligonucleotide BB9503 (5'-CCTTATTAGTCAGAAAC-3' SEQ ID NO 103) was used to mutate the LD78 gene and a correct clone identified (M13DB113). The mutant gene was cloned into the expression vector to create pDB103. Expression of the mutant LD78 protein was achieved according to methods described in Preparation 3.

Example 60

Design and Construction of LD78 Variant Asp26>Ala Glu29>Arg (Mutant 101) and Construction of an LD78 Asn26>Ala Glu29>Arg Expression Vector

LD78 Asp26>Ala Glu29>Arg was constructed and cloned into the pSW6 yeast expression vector as described in Example 1. A 33-mer oligonucleotide BB9443 (5'-TTGAGAAGAAGTTCTAAAGTAGGCAGCAATGAA-3' SEQ ID NO 104) was used to mutate the LD78 gene. The mutant gene was cloned into the expression vector to create pDB133. Expression of the mutant LD78 protein was achieved according to methods described in Preparation 3.

Example 61

Design and Construction of LD78 Variant Asp26>Ala Glu29>Arg Arg47>Glu (Mutant 102) and Construction of an LD78 Asp26>Ala Glu29>Arg Arg47>Glu Expression Vector

LD78 Asp26>Ala Glu29>Arg Arg47>Glu is constructed and cloned into the pSW6 yeast expression vector essentially as described in Example 1. A 33-mer oligonucleotide BB9443 (5'-TTGAGAAGAAGTTCTAAAGTAGGCAGCAATGAA-3' SEQ ID NO 104) was used to mutate the LD78 Arg47>Glu gene (pGHC614 of Example 11) and a correct clone identified (pRC58/102). The mutant gene was cloned into the expression vector to create pRC59/102. Expression of the mutant LD78 protein was achieved according to methods described in Preparation 3.

Example 62

Design and Construction of LD78 Variant Lys36>Ser (Mutant 41) and Construction of an LD78 Lys36>Ser Expression Vector

LD78 Lys36>Ser was constructed and cloned into the pSW6 yeast expression vector as described in Example 1. A 20-mer oligonucleotide BB9434 (5'-GACACCTGGAGAGGAACATT- 3' SEQ ID NO 105) was used to mutate the LD78 gene and a correct clone identified (pGHC640). The mutant gene was cloned into the expression vector to create pRC59/41. Expression of the mutant LD78 protein was achieved according to methods described in Preparation 3.

Example 63

Design and Construction of LD78 Variant Leu65>Ala (Mutant 51) and Construction of an LD78 Leu65>Ala Expression Vector

LD78 Leu65>Ala was constructed and cloned into the pSW6 yeast expression vector as described in Example 1. A 22-mer oligonucleotide BB9428 (5'-CAGACAATTCAGCGTCAGAAAC-3' SEQ ID NO 106) was used to mutate the LD78 gene and a correct clone identified (pGHC650). The mutant gene was cloned into the expression vector to create pSJE100. Expression of the mutant LD78 protein was achieved according to methods described in Preparation 3.

Example 64

Design and Construction of LD78 Variant Glu66>Ser (Mutant 52) and Construction of an LD78 Glu66>Ser Expression Vector

LD78 Glu66>Ser was constructed and cloned into the pSW6 yeast expression vector as described in Example 1. A 20-mer oligonucleotide BB9429 (5'-GGCAGACAAAGACAAGTCAG-3' SEQ ID NO 107) was used to mutate the LD78 gene and a correct clone identified (pGHC651). The mutant gene was cloned into the expression vector to create pSJE101. Expression of the mutant LD78 protein was achieved according to methods described in Preparation 3.

Example 65

Design and Construction of LD78 Variant Ala69>Ser (Mutant 53) and Construction of an LD78 Ala69>Ser Expression Vector

LD78 Ala69>Ser is constructed and cloned into the pSW6 yeast expression vector as described in Example 1. A 19-mer oligonucleotide BB9495 (5'-CTTATTAGGAAGACAATTC-3' SEQ ID NO 108) was used to mutate the LD78 gene and a correct clone identified (pRC58/53). The mutant gene was cloned into the expression vector to create pRC59/53. Expression of the mutant LD78 protein was achieved according to methods described in Preparation 3.

Example 66

Design and Construction of LD78 Variant Ser1>Ala (Mutant 54) and Construction of an LD78 Ser1>Ala Expression Vector

LD78 Ser1>Ala was constructed and cloned into the pSW6 yeast expression vector as described in Example 1. A 19-mer oligonucleotide BB9496 (5'-CAGCCAAGGCTCTTTTATC-3' SEQ ID NO 109) was used to mutate the LD78 gene and a correct clone identified (pGHC653). The mutant gene was cloned into the expression vector to create pDB101. Expression of the mutant LD78 protein was achieved according to methods described in Preparation 3.

Example 67

Design and Construction of LD78 Variant Gln33>Ser (Mutant 67) and Construction of an LD78 Gln33>Ser Expression Vector

LD78 Gln33>Ser was constructed and cloned into the pSW6 yeast expression vector as described in Example 1. A 20-mer oligonucleotide BB9509 (5'-CTTGGAACAAGAAGAAGAAG-3' SEQ ID NO 110) was used to mutate the LD78 gene and a correct clone identified (M13DB127). The mutant gene was cloned into the expression vector to create pDB143. Expression of the mutant LD78 protein was achieved according to methods described in Preparation 3.

Example 68

Design and Construction of LD78 Variant Tyr61>Ala Mutant 73) and Construction of an LD78 Tyr61>Ala Expression Vector

LD78 Tyr61>Ala was constructed and cloned into the pSW6 yeast expression vector as described in Example 1. A 19-mer oligonucleotide BB9515 (5'-GTCAGAAACAGCTTTTTGA-3' SEQ ID NO 111) was used to mutate the LD78 gene and a correct clone identified (M13DB115). The mutant gene was cloned into the expression vector to create pDB106. Expression of the mutant LD78 protein was achieved according to methods described in Preparation 3.

Example 69

Design and Construction of LD78 Variant Ser31>Ala (Mutant 87) and Construction of an LD78 Ser31>Ala Expression Vector

LD78 Ser31>Ala was constructed and is cloned into the pSW6 yeast expression vector as described in Example 1. A 19-mer oligonucleotide BB9529 (5'-CATTGAGAAGCAGTTTCAA-3' SEQ ID NO 112) was used to mutate the LD78 gene and a correct clone identified (pGHC686). The mutant gene was cloned into the expression vector to create pDB132. Expression of the mutant LD78 protein was achieved according to methods described in Preparation 3.

Example 70

Design and Construction of LD78 Variant Ser32>Ala (Mutant 88) and Construction of an LD78 Ser32>Ala Expression Vector

LD78 Ser32>Ala was constructed and cloned into the pSW6 yeast expression vector as described in Example 1. A 19-mer oligonucleotide BB9530 (5'-GAACATTGAGCAGAAGTTT-3' SEQ ID NO 113) was used to mutate the LD78 gene and a correct clone identified (M13DB101). The mutant gene was cloned into the expression vector to create pDB110. Expression of the mutant LD78 protein was achieved according to methods described in Preparation 3.

Example 71

Design and Construction of LD78 Variant Leu42>Ala (Mutant 94) and Construction of an LD78 Leu42>Ala Expression Vector

LD78 Leu42>Ala was constructed and cloned into the pSW6 yeast expression vector as described in Example 1. A 21-mer oligonucleotide BB9536 (5'-GCGCTTAGTAGCGAAGATGAC-3' SEQ ID NO 114) was used to mutate the LD78 gene and a correct clone identified (M13DB106). The mutant gene was cloned into the expression vector to create pDB116. Expression of the mutant LD78 protein was achieved according to methods described in Preparation 3.

Example 72

Design and Construction of LD78 Variant Asp52>Ser (Mutant 45) and Construction of an LD78 Asp52>Ser Expression Vector

LD78 Asp52>Ser was constructed and cloned into the pSW6 yeast expression vector as described in Example 1. A 22-mer oligonucleotide BB9422 (5'-CTTCAGATGGAGAAGCACAGAC-3' SEQ ID NO 115) was used to mutate the LD78 gene and a correct clone identified (pGHC644). The mutant gene was cloned into the expression vector to create pSJE94. Expression of the mutant LD78 protein was achieved according to methods described in Preparation 3.

Example 73

Design and Construction of LD78 Variant Val62>Ala (Mutant 49) and Construction of an LD78 Val62>Ala Expression Vector

LD78 Val62>Ala was constructed and cloned into the pSW6 yeast expression vector as described in Example 1. A 21-mer oligonucleotide BB9426 (5'-CAAGTCAGAAGCATATTTTTG-3' SEQ ID NO 116) was used to mutate the LD78 gene and a correct clone identified (pGHC648). The mutant gene was cloned into the expression vector to create pDB100. Expression of the mutant LD78 protein was achieved according to methods described in Preparation 3.

Example 74

Design and Construction of LD78 Variant Ser13>Ala (Mutant 62) and Construction of an LD78 Ser13>Ala Expression Vector

LD78 Ser13>Ala was constructed and cloned into the pSW6 yeast expression vector as described in Example 1. A 17-mer oligonucleotide BB9504 (5'-GGTGTAAGCGAAACAAC-3' SEQ ID NO 117) was used to mutate the LD78 gene and a correct clone identified (pGHC661). The mutant gene was cloned into the expression vector to create pSJE111. Expression of the mutant LD78 protein was achieved according to methods described in Preparation 3.

Example 75

Design and Construction of LD78 Variant Ser16>Ala (Mutant 63) and Construction of an LD78 Ser16>Ala Expression Vector

LD78 Ser16>Ala was constructed and cloned into the pSW6 yeast expression vector as described in Example 1. A 19-mer oligonucleotide BB9505 (5'-ATTTGTCTAGCGGTGTAAG-3' SEQ ID NO 118) was used to mutate the LD78 gene and a correct clone identified (pGHC662). The mutant gene was cloned into the expression vector to create pSJE1 12. Expression of the mutant LD78 protein was achieved according to methods described in Preparation 3.

Example 76

Design and Construction of LD78 Variant Pro20>Ala (Mutant 65) and Construction of an LD78 Pro20>Ala Expression Vector

LD78 Pro20>Ala was constructed and cloned into the pSW6 yeast expression vector as described in Example 1. A 20-mer oligonucleotide BB9507 (5'-GAAATTTTGAGCAATTTGTC-3' SEQ ID NO 119) was used to mutate the LD78 gene and a correct clone identified (pGHC664). The mutant gene was cloned into the expression vector to create pDB104. Expression of the mutant LD78 protein was achieved according to methods described in Preparation 3.

Example 77

Design and Construction of LD78 Variant Ser35>Ala (Mutant 68) and Construction of an LD78 Ser35>Ala Expression Vector

LD78 Ser35>Ala was constructed and cloned into the pSW6 yeast expression vector as described in Example 1. An 18-mer oligonucleotide BB9510 (5'-CTGGCTTGGCACATTGAG-3' SEQ ID NO 120) was used to mutate the LD78 gene and a correct clone identified (pGHC668). The mutant gene was cloned into the expression vector to create pSJE117. Expression of the mutant LD78 protein was achieved according to methods described in Preparation 3.

Example 78

Design and Construction of LD78 Variant Gln59>Ser (Mutant 72) and Construction of an LD78 Gln59>Ser Expression Vector LD78 Gln59>Ser was constructed and cloned into the pSW6 yeast expression vector as described in Example 1. A 23-mer oligonucleotide BB9514 (5'-GAAACATATTTAGAAACCCATTC-3' SEQ ID NO 121) was used to mutate the LD78 gene and a correct clone identified (M13DB114). The mutant gene was cloned into the expression vector to create pDB105. Expression of the mutant LD78 protein was achieved according to methods described in Preparation 3.

Example 79

Design and Construction of LD78 Variant Ser68>Ala (Mutant 76) and Construction of an LD78 Ser68>Ala Expression Vector LD78 Ser68>Ala was constructed and cloned into the pSW6 yeast expression vector as described in Example 1. A 19-mer oligonucleotide BB9518 (5'-ATTAGGCAGCCAATTCCAA-3' SEQ ID NO 122) was used to mutate the LD78 gene and a correct clone identified (M13DB100). The mutant gene was cloned into the expression vector to create pDB107. Expression of the mutant LD78 protein was achieved according to methods described in Preparation 3.

Example 80

Design and Construction of LD78 Variant Tyr14>Ala (Mutant 78) and Construction of an LD78 Tyr14>Ala Expression Vector LD78 Tyr14>Ala was constructed and cloned into the pSW6 yeast expression vector as described in Example 1. A 19-mer oligonucleotide BB9520 (5'-CTAGAGGTGGCAGAGAAAC-3' SEQ ID NO 123) was used to mutate the LD78 gene and a correct clone identified (M13DB116). The mutant gene was cloned into the expression vector to create pDB108. Expression of the mutant LD78 protein was achieved according to methods described in Preparation 3.

Example 81

Design and Construction of LD78 Variant Ile19>Ala (Mutant 80) and Construction of an LD78 Ile19>Ala Expression Vector LD78 Ile19>Ala was constructed and cloned into the pSW6 yeast expression vector as described in Example 1. A 19-mer oligonucleotide BB9522 (5'-TTTTGTGGAGCTTGTCTAG-3' SEQ ID NO 124) was used to mutate the LD78 gene and a correct clone identified (M13DB117). The mutant gene was cloned into the expression vector to create pDB109. Expression of the mutant LD78 protein was achieved according to methods described in Preparation 3.

Example 82

Design and Construction of LD78 Variant Pro37>Ala (Mutant 89) and Construction of an LD78 Pro37>Ala Expression Vector LD78 Pro37>Ala was constructed and cloned into the pSW6 yeast expression vector as described in Example 1. A 20-mer oligonucleotide BB9531 (5'-GATGACACCAGCCTTGGAAC-3' SEQ ID NO 125) was used to mutate the LD78 gene and a correct clone identified (M13DB102). The mutant gene was cloned into the expression vector to create pDB111. Expression of the mutant LD78 protein was achieved according to methods described in Preparation 3.

Example 83

Design and Construction of LD78 Variant Gly38>Ala (Mutant 90) and Construction of an LD78 Gly38>Ala Expression Vector LD78 Gly38>Ala was constructed and cloned into the pSW6 yeast expression vector as described in Example 1. A 20-mer oligonucleotide BB9532 (5'-GAAGATGACAGCTGGCTTGG-3' SEQ ID NO 126) was used to mutate the LD78 gene and a correct clone identified (M13DB103). The mutant gene was cloned into the expression vector to create pDB112. Expression of the mutant LD78 protein was achieved according to methods described in Preparation 3.

Example 84

Design and Construction of LD78 Variant Val39>Ala (Mutant 91) and Construction of an LD78 Val39>Ala Expression Vector LD78 Val39>Ala was constructed and cloned into the pSW6 yeast expression vector as described in Example 1. An 18-mer oligonucleotide BB9533 (5'-AGAAGATGGCACCTGGCT-3' SEQ ID NO 127) was used to mutate the LD78 gene and a correct clone identified (M13DB118). The mutant gene was cloned into the expression vector to create pDB113. Expression of the mutant LD78 protein was achieved according to methods described in Preparation 3.

Example 85

Design and Construction of LD78 Variant Thr6>Ala (Mutant 58) and Construction of an LD78 Thr6>Ala Expression Vector LD78 Thr6>Ala was constructed and cloned into the pSW6 yeast expression vector as described in Example 1. A 17-mer oligonucleotide BB9500 (5'-GGTTGGAGCGTCAGCAG-3' SEQ ID NO 128) was used to mutate the LD78 gene and a correct clone identified (pRC58/58). The mutant gene was cloned into the expression vector to create pRC59/58. Expression of the mutant LD78 protein was achieved according to methods described in Preparation 3.

Example 86

Design and Construction of LD78 Variant Gln21>Ser (Mutant 81) and Construction of an LD78 Gln21>Ser Expression Vector LD78 Gln21>Ser was constructed and cloned into the pSW6 yeast expression vector as described in Example 1. A 22-mer oligonucleotide BB9523 (5'-CAATGAAATTAGATGGAATTTG-3' SEQ ID NO 129) was used to mutate the LD78 gene and a correct clone identified (M13DB118). The mutant gene was cloned into the expression vector to create pDB136. Expression of the mutant LD78 protein was achieved according to methods described in Preparation 3.

Example 87

Design and Construction of LD78 Variant Thr43>Ala (Mutant 69) and Construction of an LD78 Thr43>Ala Expression Vector LD78 Thr43>Ala was constructed and is cloned into the pSW6 yeast expression vector as described in Example 1. A 17-mer oligonucleotide BB9511 (5'-GCGCTTAGCCAAGAAGA-3' SEQ ID NO 130) was used to mutate the LD78 gene and a correct clone identified (pGHC669). The mutant gene was cloned into the expression vector to create pRC59/69. Expression of the mutant LD78 protein was achieved according to methods described in Preparation 3.

Example 88

Design and Construction of LD78 Variant Pro7>Ala (Mutant 59) and Construction of an LD78 Pro7>Ala Expression Vector LD78 Pro7>Ala was constructed and cloned into the pSW6 yeast expression vector as described in Example 1. A 19-mer oligonucleotide BB9501 (5'-CAAGCGGTAGCAGTGTCAG-3' SEQ ID NO 131) was used to mutate the LD78 gene and a correct clone identified (pGHC658). The mutant gene was cloned into the expression vector to create pDB125. Expression of the mutant LD78 protein was achieved according to methods described in Preparation 3.

Example 89

Design and Construction of LD78 Variant Thr8>Ala (Mutant 60) and Construction of an LD78 Thr8>Ala Expression Vector LD78 Thr8>Ala was constructed and cloned into the pSW6 yeast expression vector as described in Example 1. An 18-mer oligonucleotide BB9502 (5'-ACAAGCGGCTGGAGTGTC-3' SEQ ID NO 132) was used to mutate the LD78 gene and a correct clone identified (pRC58/60). The mutant gene was cloned into the expression vector to create pRC59/60. Expression of the mutant LD78 protein was achieved according to methods described in Preparation 3.

Example 90

Design and Construction of LD78 Variant Tyr27>Ala (Mutant 66) and Construction of an LD78 Tyr27>Ala Expression Vector LD78 Tyr27>Ala was constructed and cloned into the pSW6 yeast expression vector as described in Example 1. An 18-mer oligonucleotide BB9508 (5'-GTTTCAAAGGCGTCAGCA-3' SEQ ID NO 133) was used to mutate the LD78 gene and a correct clone identified (pGHC665). The mutant gene was cloned into the expression vector to create pDB126. Expression of the mutant LD78 protein was achieved according to methods described in Preparation 3.

Example 91

Design and Construction of LD78 Variant Pro53>Ala (Mutant 71) and Construction of an LD78 Pro53>Ala Expression Vector LD78 Pro53>Ala was constructed and cloned into the pSW6 yeast expression vector as described in Example 1. A 20-mer oligonucleotide BB9513 (5'-TTCTTCAGATGCGTCAGCAC-3'SEQ ID NO 134) was used to mutate the LD78 gene and a correct clone identified (pRC58/71). The mutant gene was cloned into the expression vector to create pRC59/71. Expression of the mutant LD78 protein was achieved according to methods described in Preparation 3.

Example 92

Design and Construction of LD78 Variant Ser63>Ala Mutant 74) and Construction of an LD78 Ser63>Ala Expression Vector LD78 Ser63>Ala was constructed and cloned into the pSW6 yeast expression vector as described in Example 1. An 18-mer oligonucleotide BB9516 (5'-CAAGTCAGCAACATATTT-3' SEQ ID NO 135) was used to mutate the LD78 gene and a correct clone identified (pGHC674). The mutant gene was cloned into the expression vector to create pDB145. Expression of the mutant LD78 protein was achieved according to methods described in Preparation 3.

Example 93

Design and Construction of LD78 Variant Thr15>Ala (Mutant 79) and Construction of an LD78 Thr15>Ala Expression Vector LD78 Thr15>Ala was constructed and cloned into the pSW6 yeast expression vector as described in Example 1. A 17-mer oligonucleotide BB9521 (5'-GTCTAGAGGCGTAAGAG-3' SEQ ID NO 136) was used to mutate the LD78 gene and a correct clone identified (pGHC678). The mutant gene was cloned into the expression vector to create pDB128. Expression of the mutant LD78 protein was achieved according to methods described in Preparation 3.

Example 94

Design and Construction of LD78 Variant Asn22>Ser (Mutant 82) and Construction of an LD78 Asn22>Ser Expression Vector LD78 Asn22>Ser was constructed and cloned into the pSW6 yeast expression vector as described in Example 1. An 18-mer oligonucleotide BB9524 (5'-CAATGAAAGATTGTGGAA-3' SEQ ID NO 137) was used to mutate the LD78 gene and a correct clone identified (pGHC681). The mutant gene was cloned into the expression vector to create pDB129. Expression of the mutant LD78 protein was achieved according to methods described in Preparation 3.

Example 95

Design and Construction of LD78 Variant Ala25>Ser Mutant 84) and Construction of an LD78 Ala25>Ser Expression Vector LD78 Ala25>Ser was constructed and cloned into the pSW6 yeast expression vector as described in Example 1. A 17-mer oligonucleotide BB9526 (5'-GTAGTCAGAAATGAAAT-3' SEQ ID NO 138) was used to mutate the LD78 gene and a correct clone identified (pRC58/84). The mutant gene was cloned into the expression vector to create pRC59/84. Expression of the mutant LD78 protein was achieved according to methods described in Preparation 3.

Example 96

Design and Construction of LD78 Variant Thr30>Ala (Mutant 86) and Construction of an LD78 Thr30>Ala Expression Vector LD78 Thr30>Ala was constructed and cloned into the pSW6 yeast expression vector as described in Example 1. An 18-mer oligonucleotide BB9528 (5'-GAGAAGAAGCTTCAAAGT-3' SEQ ID NO 139) was used to mutate the LD78 gene and a correct clone identified (pGHC685). The mutant gene was cloned into the expression vector to create pDB131. Expression of the mutant LD78 protein was achieved according to methods described in Preparation 3.

Example 97

Design and Construction of LD78 Variant Phe41>Ala (Mutant 93) and Construction of an LD78 Phe41>Ala Expression Vector LD78 Phe41>Ala was constructed and cloned into the pSW6 yeast expression vector as described in Example 1. A 20-mer oligonucleotide BB9535 (5'CTTAGTCAAGGCGATGACAC-3' SEQ ID NO 140) was used to mutate the LD78 gene and a correct clone identified (M13DB105). The mutant gene was cloned into the expression vector to create pDB115. Expression of the mutant LD78 protein was achieved according to methods described in Preparation 3.

Example 98

Design and Construction of LD78 Variant Val49>Ala (Mutant 96) and Construction of an LD78 Val49>Ala Expression Vector LD78 Val49>Ala was constructed and cloned into the pSW6 yeast expression vector as described in Example 1. A 20-mer oligonucleotide BB9538 (5'-GTCAGCACAGGCTTGTCTCG-3' SEQ ID NO 141) was used to mutate the LD78 gene and a correct clone identified (M13DB108). The mutant gene was cloned into the expression vector to create pDB118. Expression of the mutant LD78 protein was achieved according to methods described in Preparation 3.

Example 99

Design and Construction of LD78 Variant Ala51>Ser (Mutant 97) and Construction of an LD78 Ala51>Ser Expression Vector LD78 Ala51>Ser was constructed and cloned into the pSW6 yeast expression vector as described in Example 1. A 17-mer oligonucleotide BB9539 (5'-TGGGTCAGAACAGACTT-3' SEQ ID NO 142) was used to mutate the LD78 gene and a correct clone identified (M13DB109). The mutant gene was cloned into the expression vector to create pDB119. Expression of the mutant LD78 protein was achieved according to methods described in Preparation 3.

Example 100

Design and Construction of LD78 Variant Ser54>Ala (Mutant 98) and Construction of an LD78 Ser54>Ala Expression Vector LD78 Ser4>Ala was constructed and cloned into the pSW6 yeast expression vector as described in Example 1. A 19-mer oligonucleotide BB9540 (5'-CATTCTTCAGCTGGGTCAG-3' SEQ ID NO 143) was used to mutate the LD78 gene and a correct clone identified (M13DB110). The mutant gene was cloned into the expression vector to create pDB120. Expression of the mutant LD78 protein was achieved according to methods described in Preparation 3.

Example 101

Design and Construction of LD78 Variant Trp57>Ala (Mutant 99) and Construction of an LD78 Trp57>Ala Expression Vector LD78 Trp57>Ala was constructed and cloned into the pSW6 yeast expression vector as described in Example 1. A 20-mer oligonucleotide BB9541 (5'-ATTTTTGAACAGCTTCTTCA-3' SEQ ID NO 144) was used to mutate the LD78 gene and a correct clone identified (M13DB111). The mutant gene was cloned into the expression vector to create pDB121. Expression of the mutant LD78 protein was achieved according to methods described in Preparation 3.

Example 102

Design and Construction of LD78 Variant Val58>Ala (Mutant 100) and Construction of an LD78 Val58>Ala Expression Vector LD78 Val58>Ala was constructed and cloned into the pSW6 yeast expression vector as described in Example 1. A 22-mer oligonucleotide BB9542 (5'-CATATTTTTGAGCCCATTCTTC-3' SEQ ID NO 145) was used to mutate the LD78 gene and a correct clone identified (M13DB132). The mutant gene was cloned into the expression vector to create pDB122. Expression of the mutant LD78 protein was achieved according to methods described in Preparation 3.

Example 103

Design and Construction of LD78 Variant Trp57>Leu (Mutant 112) and Construction of an LD78 Trp57>Leu Expression Vector LD78 Trp57>Leu was constructed and cloned into the pSW6 yeast expression vector as described in Example 1. A 21-mer oligonucleotide BB10374 (5'-TTTTTGAACCAATTCTTCAGA-3' SEQ ID NO 146) was used to mutate the LD78 gene and a correct clone identified (pRC58/112). The mutant gene was cloned into the expression vector to create pRC59/112. Expression of the mutant LD78 protein was achieved according to methods described in Preparation 3.

Example 104

Design and Construction of LD78 Variant Lys60>Asp (Mutant 113) and Construction of an LD78 Lys60>Asp Expression Vector LD78 Lys60>Asp was constructed and cloned into the pSW6 yeast expression 5 vector as described in Example 1. A 21-mer oligonucleotide BB10375 (5'-CAGAAACATAATCTTGAACCC-3' SEQ ID NO 147) was used to mutate the LD78 gene and a correct clone identified (pRC58/113). The mutant gene was cloned into the expression vector to create pDB142. Expression of the mutant LD78 protein was achieved according to methods described in Preparation 3.

Example 105

Design and Construction of LD78 Variant Tyr61>Asp (Mutant 114) and Construction of an LD78 Tyr61>Asp Expression Vector LD78 Tyr61>Asp was constructed and cloned into the pSW6 yeast expression vector as described in Example 1. A 19-mer oligonucleotide BB10376 (5'-GTCAGAAACATCTTTTTGA-3' SEQ ID NO 148) was used to mutate the LD78 gene and a correct clone identified (pRC58/114). The mutant gene was cloned into the expression vector to create pRC59/114. Expression of the mutant LD78 protein was achieved according to methods described in Preparation 3.

Example 106

Design and Construction of LD78 Variant Phe12>Asp (Mutant 115) and Construction of an LD78 Phe12>Asp Expression Vector LD78Phe12>Asp was constructed and cloned into the pSW6 yeast expression vector as described in Example 1. A 19-mer oligonucleotide BB10377 (5'-GTGTAAGAATCACAACAAG-3' SEQ ID NO 149) was used to mutate the LD78 gene and a correct clone identified (pRC58/115). The mutant gene was cloned into the expression vector to create pRC59/115. Expression of the mutant LD78 protein was achieved according to methods described in Preparation 3.

Example 107

Design and Construction of LD78 Variant Thr8>Glu (Mutant 116) and Construction of an LD78 Thr8>Glu Expression Vector LD78 Thr8>Glu is constructed and is cloned into the pSW6 yeast expression vector as described in Example 1. A 23-mer oligonucleotide BB11235 (5'-GAAACAACAAGCTTCTGGAGTGT-3' SEQ ID NO 150) is used to mutate the LD78 gene. The mutant gene is cloned into the expression vector according to the methods of Example 1 and expression of the mutant LD78 protein is achieved according to methods described in Preparation 3.

Example 108

Design and Construction of LD78 Variant Ser68>Glu (Mutant 117) and Construction of an LD78 Ser68>Glu Expression Vector LD78 Ser68>Glu was constructed and is cloned into the pSW6 yeast expression vector as described in Example 1. A 19-mer oligonucleotide BB10379 (5'-ATTAGGCTTCCAATTCCAA-3' SEQ ID NO 151) was used to mutate the LD78 gene and a correct clone identified (pRC58/117). The mutant gene is cloned into the expression vector according to the methods of Example 1 and expression of the mutant LD78 protein is achieved according to methods described in Preparation 3.

Example 109

Design and Construction of LD78 Variant Leu67>Asp (Mutant 118) and Construction of an LD78 Leu67>Asp Expression Vector LD78 Leu67>Asp was constructed and cloned into the pSW6 yeast expression vector as described in Example 1. A 22-mer oligonucleotide BB10380 (5'-ATTAGGCAGAATCTTCCAAGTC-3' SEQ ID NO 152) was used to mutate the LD78 gene and a correct clone identified (M13DB130). The mutant gene was cloned into the expression vector to create pDB148. Expression of the mutant LD78 protein was achieved according to methods described in Preparation 3.

Example 110

Design and Construction of LD78 Variant Asp64>Arg (Mutant 119) and Construction of an LD78 Asp 64>Arg Expression Vector LD78 Asp64>Arg was constructed and was cloned into the pSW6 yeast expression vector as described in Example 1. A 20-mer oligonucleotide BB10381 (5'-CAATTCCAATCTAGAAACAT-3' SEQ ID NO 153) is used to mutate the LD78 gene and a correct clone identified (pGHC569). The mutant gene is cloned into the expression vector according to the methods of Example 1 and expression of the mutant LD78 protein is achieved according to methods described in Preparation 3.

Example 111

Design and Construction of LD78 Variant Ser31>Glu (Mutant 120) and Construction of an LD78 Ser31>Glu Expression Vector LD78 Ser31>Glu is constructed and is cloned into the pSW6 yeast expression vector as described in Example 1. A 19-mer oligonucleotide BB10382 (5'-CATTGAGATTCAGTTTCAA-3' SEQ ID NO 154) is used to mutate the LD78 gene. The mutant gene is cloned into the expression vector according to the methods of Example 1 and expression of the mutant LD78 protein is achieved according to methods described in Preparation 3.

Example 112

Design and Construction of LD78 Variant Ile40>Asn (Mutant 121) and Construction of an LD78 Ile40>Asn Expression Vector LD78 Ile40>Asn was constructed and cloned into the pSW6 yeast expression vector as described in Example 1. A 19-mer oligonucleotide BB10383 (5'-GTCAAGAAGTTGACACCTG-3' SEQ ID NO 155) was used to mutate the LD78 gene and a correct clone identified (pRC58/121). The mutant gene was cloned into the expression vector to create pRC59/121. Expression of the mutant LD78 protein was achieved according to methods described in Preparation 3.

Example 113

Design and Construction of LD78 Variant Leu42>Asn (Mutant 122) and Construction of an LD78 Leu42>Asn Expression Vector LD78 Leu42>Asn was constructed and was cloned into the pSW6 yeast expression vector as described in Example 1. A 21-mer oligonucleotide BB10964 (5'-GCGCTTAGTGTTGAAGATGAC-3' SEQ ID NO 156) is used to mutate the LD78 gene and a correct clone identified (pGHC568). The mutant gene is cloned into the expression vector according to the methods of Example 1 and expression of the mutant LD78 protein is achieved according to methods described in Preparation 3.

Example 114

Design and Construction of LD78 Variant Cys10, Cys11>Cys-Gln-Cys (Mutant 123) and Construction of an LD78 Cys10, Cys11>Cys-Gln-Cys Expression Vector LD78 Cys10, Cys11>Cys-Gln-Cys was constructed and cloned into the pSW6 yeast expression vector as described in Example 1. A 27-mer oligonucleotide BB10385 (5'-GTAAGAGAAACATTGACAAGCGGTTGG-3' SEQ ID NO 157) was used to mutate the LD78 gene and a correct clone identified (pRC58/123). The mutant gene was cloned into the expression vector to create pRC59/123. Expression of the mutant LD78 protein was achieved according to methods described in Preparation 3.

Example 115

Design and Construction of LD78 Variant Glu55>Gln, Glu56>Gln (Mutant 124) and Construction of an LD78 Glu55>Gln, Glu56>Gln Expression Vector LD78 Glu55>Gln, Glu56>Gln is constructed and is cloned into the pSW6 yeast expression vector as described in Example 1. A 24-mer oligonucleotide BB10386 (5'-TTGAACCCATTGTTGAGATGGGTC-3' SEQ ID NO 158) is used to mutate the LD78 gene. The mutant gene is cloned into the expression vector according to the methods of Example 1 and expression of the mutant LD78 protein is achieved according to methods described in Preparation 3.

Example 116

Design and Construction of LD78 Variant Asp26>Gln (Mutant 125) and Construction of an LD78 Asp26>Gln Expression Vector LD78 Asp26>Gln was constructed and cloned into the pSW6 yeast expression vector as described in Example 1. A 21-mer oligonucleotide BB10529 (5'-GTTTCAAAGTATTGAGCAATG-3' SEQ ID NO 159) was used to mutate the LD78 gene and a correct clone identified (pRC58/125). The mutant gene was cloned into the expression vector to create pRC59/125. Expression of the mutant LD78 protein was achieved according to methods described in Preparation 3.

Example 117

Design and Construction of LD78 Variant Lys36>Glu (Mutant 126) and Construction of an LD78 Lys36>Glu Expression Vector LD78 Lys36>Glu was constructed and cloned into the pSW6 yeast expression vector as described in Example 1. A 26-mer oligonucleotide BB10530 (5'-GATGACACCTGGTTCGGAACATTGAG-3' SEQ ID NO 160) was used to mutate the LD78 gene and a correct clone identified (pRC58/126). The mutant gene was cloned into the expression vector to create pRC59/126. Expression of the mutant LD78 protein was achieved according to methods described in Preparation 3.

Example 118

Design and Construction of LD78 Variant Lys44>Glu (Mutant 127) and Construction of an LD78 Lys44>Glu Expression Vector LD78 Lys44>Glu was constructed and cloned into the pSW6 yeast expression vector as described in Example 1. A 26-mer oligonucleotide BB10531 (5'-CTTGTCTCGAGCGTTCAGTCAAGAAG-3' SEQ ID NO 161) was used to mutate the LD78 gene and a correct clone identified (pRC58/127). The mutant gene was cloned into the expression vector to create pRC59/127. Expression of the mutant LD78 protein was achieved according to methods described in Preparation 3.

Example 119

Design and Construction of LD78 Variant Ar245>Glu (Mutant 128) and Construction of an LD78 Arg45>Glu Expression Vector LD78 Arg45>Glu was constructed and cloned into the pSW6 yeast expression vector as described in Example 1. A 25-mer oligonucleotide BB10532 (5'-GACTTGTCTCGATTCCTTAGTCAAG-3' SEQ ID NO 162) was used to mutate the LD78 gene and a correct clone identified (pRC58/128). The mutant gene was cloned into the expression vector to create pRC59/128. Expression of the mutant LD78 protein was achieved according to methods described in Preparation 3.

Example 120

Design and Construction of LD78 Variant Asp52>Gln (Mutant 129) and Construction of an LD78 Asp52>Gln Expression Vector LD78 Asp52>Gln was constructed and cloned into the pSW6 yeast expression vector as described in Example 1. A 27-mer oligonucleotide BB10533 (5'-CCATTCTTCAGATGGTGGAGCACAGAC-3' SEQ ID NO 163) was used to mutate the LD78 gene and a correct clone identified (M13DB131). The mutant gene was cloned into the expression vector to create pDB149. Expression of the mutant LD78 protein was achieved according to methods described in Preparation 3.

Example 121

Design and Construction of LD78 Variant Glu66>Gln (Mutant 130) and Construction of an LD78 Glu66>Gln Expression Vector LD78 Glu66>Gln was constructed and cloned into the pSW6 yeast expression vector as described in Example 1. A 19-mer oligonucleotide BB10534 (5'-GCAGACAATTGCAAGTCAG-3' SEQ ID NO 164) was used to mutate the LD78 gene and a correct clone identified (pRC58/130). The mutant gene was cloned into the expression vector to create pRC59/130. Expression of the mutant LD78 protein was achieved according to methods described in Preparation 3.

Example 122

Design and Construction of LD78 Variant Ile24>Leu (Mutant 131) and Construction of an LD78 Ile24>Leu Expression Vector LD78 Ile24>Leu was constructed and is cloned into the pSW6 yeast expression vector as described in Example 1. A 21-mer oligonucleotide BB10535 (5'-GTAGTCAGCCAAGAAATTTTG-3' SEQ ID NO 165) was used to mutate the LD78 gene and a correct clone identified (M13DB128). The mutant gene is cloned into the expression vector according to the methods of Example 1 and expression of the mutant LD78 protein is achieved according to methods described in Preparation 3.

Example 123

Design and Construction of LD78 Variant Ile24>Val (Mutant 132) and Construction of an LD78 Ile24>Val Expression Vector LD78 Ile24>Val was constructed and cloned into the pSW6 yeast expression vector as described in Example 1. A 21-mer oligonucleotide BB10536 (5'-GTAGTCAGCGACGAAATTTTG-3' SEQ ID NO 166) was used to mutate the LD78 gene and a correct clone identified (M13DB129). The mutant gene was cloned into the expression vector to create pDB150. Expression of the mutant LD78 protein was achieved according to methods described in Preparation 3.

Example 124

Design and Construction of LD78 Variant Arg17>Glu (Mutant 133) and Construction of an LD78 Arg17>Glu Expression Vector LD78 Arg17>Glu was constructed and cloned into the pSW6 yeast expression vector as described in Example 1. A 22-mer oligonucleotide BB10195 (5'GGAATTTGTTCAGAGGTGTAAG-3' SEQ ID NO 167) was used to mutate the LD78 gene and a correct clone identified (pGHC567). The mutant gene is cloned into the expression vector according to the methods of Example 1 and expression of the mutant LD78 protein is achieved according to methods described in Preparation 3.

Example 125

Primary screening of LD78 mutants to identify non-multimerising variant molecules In order to screen mutant LD78 molecules for non-multimerising properties, supernatants of the expressed constructs were initially analysed by native PAGE and the molecular weight of the LD78 variant protein identified by immunoblot with a rabbit anti-MIP-1α polyclonal antiserum.

Mutant constructs (described in Examples 1–124) were expressed and grown in shake-flasks according to the methods described in Preparation 3. 100 µl aliquots of the culture supernatant were dried using a SPEEDIVAC™ concentrator and reconstituted in 7 µl of native PAGE sample buffer (25 mM Tris, 10% glycerol, 0.02% bromophenol blue). 5 µl of sample was loaded onto a 5–50% GRADIPORE HYLINX™ native acrylamide gel (Flowgen) together with high molecular weight range RAINBOW™ markers (Amersham International plc, Amersham Place, Little Chalfont, Amersham, Bucks HP7 9NA) and standard LD78 (purified as described in Preparation 4). The gel was electrophoresed at 100 volts for 15 minutes according to the manufacturers' instructions as detailed in Comparative Example 3. The gel was then sandwiched between sheets of nitrocellulose and electroblotted at 100 mV for 30 minutes in 125 mM Tris, 20 mM glycine, 10% methanol, pH8.8 buffer.

After the protein was blotted onto the nitrocellulose membrane, the membrane was placed in 20 ml of blocking buffer (0.5 % casein, 154 mM NaCl, 20 mM Tris pH7.4, 0.05% Triton) for 30 minutes at room temperature. The membrane was then incubated for 30 minutes at room temperature with a 1:2,000 (v/v) dilution (in blocking buffer) of the primary antibody (polyclonal rabbit anti-MIP-1α produced using standard techniques) with gentle rotation. The membrane was then given 3×5 minute washes in blocking buffer. Following the last wash, the membrane was incubated with a 1:10,000 (v/v) dilution (in blocking buffer) of the secondary antibody goat anti-rabbit peroxidase (Sigma) for 30 minutes with gentle rotation at room temperature. Following this incubation, the membrane was given 3 successive 5 minute washes with 150 mM phosphate buffered saline, pH7.4, and developed as described in Comparative Example 2.

Whilst this system proved a useful screen, estimates of molecular weight could not be made due to the sharp (5–50%) acrylamide gradient required to effect separation of a broad mass range.

In order to focus more directly on the mass range expected for non-multimerising variants (8,000–100,000 daltons), 12% acrylamide BIORAD™ native gels (pre-cast in 0.375M Tris-HCl pH8.8, electrophoresis as per manufacturers' instructions with 25 mM Tris, 192 mM glycine, pH8.3, running buffer) have been used to screen both expressed supernatants and Q-SEPHAROSE™ purified (method described in Preparation 4) LD78 variants prepared for electrophoresis as described above. The gels were electrophoresed at 150V for 60 minutes and then electroblotted or stained as described above. A coomassie stained example of the results obtained in this native PAGE system as shown in FIGS. 12 and 13. The results clearly demonstrate (from the mobility of protein bands during electrophoresis) that LD78 (Glu44;Gln45, (mutant 2 of Example 2)), LD78(Glu47, (mutant 15 of Example 11)) and LD78(Glu28;Glu47, (mutant 26 of Example 16)), LD78(Ser17;Glu18 (mutant 30 of Example 20)) and LD78(Gln12 (mutant 11 of Example 8)) do not form large multimeric complexes. The results in FIGS. 12 and 13 also show that LD78(Ala26 (mutant 10 of Example 7)), LD78(Glu48 (mutant 1 of Example 1)), LD78 (Glu18 (mutant 29 of Example 19)) and LD78(Ser66 (mutant 52 of Example 64)) have increased mobility of electrophoresis, suggesting non-wild-type multimerisation. Known LD78 variants such as LD78 (Leu, Ser, Ala, Pro1, Ser38 ,Gly46, (mutant 35 of Example 25)) and LD78(Ala, Pro1 (mutant 34 of Example 24)) were observed to have the same low mobility, high molecular weight bands as the wild type control.

Table 1 details the results of the native PAGE primary analysis of LD78 variants where those identified to have non-wild type multimerisation properties are classed as "small", "mix" or "large" according to the classification in Table 1. Some variants were expressed very poorly and could not be definitively examined. Variants in Examples 1 to 124 not listed in Table 1 showed wild type electrophoretic mobility. It is probable in these cases that the mutated sites are key structural residues leading to destabilization of the protein. Selected variants identified in this screen were purified to >95% homogeneity (as described in preparation 4) for analysis by SEC and analytical ultracentrifugation as described in Comparative Example 3. The results of these analyses are detailed in subsequent examples.

It should be noted that the gel screen does not always tally with the analytical centrifuge data (see for example LD78 (Glu 48) mutant 1 in Example 135), and that selection of optimum embodiments of the invention should preferably not be undertaken on the basis of gel screen data alone. Possible scientific rationales for this are: (i) in the gel screen TRIS glycine buffers may chelate metal ions, thus destabilising aggregation and (ii) changing the number and/or type of charged side chains can affect the mass/charge ratio on electrophoresis. Also, the concentration used in the analytical ultracentrifuge assays is 0.5 mg/ml, which is not the case in the gel screen assays shown.

TABLE 1

| # Mutation | Size by Native PAGE | SEC kDa | $M_w^\circ$ kDa | $M_w\zeta = 0$ | $M_w\zeta = 1$ |
|---|---|---|---|---|---|
| Wt LD78 | Large Wt | Excl | 160 | 10 | >250 |
| 1 Glu-48 (E135) | Large | 131 (excl) | 400 | 100 | 600 |
| 2 Glu-44; Glu-45 (E128) | Small | 21 | 16-5 | — | — |
| 5 Ser-17 (E129) | Small | 29 | 57.5 | 30 | 100* |
| 10 Ala-26 (E133) | Large | 24.5 | 30 | — | —* |
| 11 Glu-12 (E132) | Small | 12.8 | 98 | 45 | 140 |
| 15 Glu-47 (E127) | Small | 21 | 17.5 | — | — |
| 17 Glu-28 (E153) | Small | n.d. | n.d. | n.d. | n.d. |
| 24 Asn-24 (E153) | Small | n.d. | n.d. | n.d. | n.d. |
| 25 Glu-28, Glu-48 (E136) | Small | 60 | n.d. | n.d. | n.d. |
| 26 Glu-28, Glu-47 (E126) | Small | 21 | 15 | — | — |
| 28 Arg-29 (E134) | Small | 24 | n.d. | n.d. | n.d. |
| 29 Glu-18 (E130) | Large | 48.5 | 130 | 75 | 170 |
| 30 Ser-17; Glu-18 (E131) | Mix* | 25 | 41 | 37 | 50 |
| 34 (E24) (154) | Small | Excl | 350 | 260 | 480 |
| 35 (E25) (154) | Small | Excl | 155 | 90 | 200 |
| 42 Ser-44 (E138) | Small | — | 45 | 35 | 48 |
| 43 Ser-45 (E137) | Small | — | 25 | — | — |
| 51 Ala-65 (E139) | Large | — | 120 | — | — |
| 52 Ser-66 (E140) | Large | — | 27 | — | — |
| 59 Ala-7 (E141) | Small | — | 1000 | 400 | 1200 |
| 64 Ser-18 (E142) | Large | — | 200 | — | — |
| 73 Ala-61 (E143) | Mix* | — | 400 | — | — |
| 77 Ala-12 (E147) | Small | — | 150 | 110 | 170 |
| 79 Ala-15 (E150) | Small | — | 180 | 110 | 250 |
| 80 Ala-19 (E144) | Mix* | — | 6 | — | — |
| 81 Ser-21 (E152) | Large | — | 112 | — | — |
| 91 Ala-39 (E145) | Mix* | — | 8.2 | — | — |
| 109 Glu-5 (E149) | Small | — | 72 | — | — |
| 115 Asp-12 (E148) | Small | — | 30 | — | — |
| 126 Glu-36 (E151) | Small | — | 200 | 100 | 250 |
| MIP-1α | Large Wt | Excl | 310 | 230 | 350 |
| 110 Glu17; Glu18 (E146) | Small | — | 30 | — | — |

$M_w^\circ$ = Whole cell weight average molecular weight
$M_w\zeta = 0$ Point average molecular weight at the meniscus
$M_w\zeta = 1$ Point average molecular weight at the cell base
[where no values for $M_w\zeta = 0$ and $M_w\zeta = 1$ are given with $M_w^\circ$, the sample is monodisperse]
E = Example No. of size analysis
* = large and small species present
Large Wt = Electrophoretic mobility on Native PAGE equivalent to Wt LD78
Large = Minor increase in electrophoretic mobility compared to Wt LD78 on Native PAGE
Small = Major increase in electrophoretic mobility compared to Wt LD78 on Native PAGE
Extl = Excluded from the SEC gel matrix Example 126

Mutation of residues Phe28 to Glu and Arg47 to Glu prevents the association of LD78 dimers to form tetramers As detailed in Table 1, pure LD78(Glu28;Glu47, (mutant 26 of Example 16)) protein has been studied in 150 mM PBS pH7.4 buffer using Size Exclusion Chromatography on SUPERDEX 75™ resin and by Sedimentation Equilibrium with wild type LD78 for comparison. The SEC profile (FIG. 14) of this LD78 mutant is a single, symmetrical peak demonstrating a defined, homogenous population of 21 kDa mass. Analysis of the sedimentation equilibrium data shows that LD78(Glu28;Glu47) exists as a monodisperse population of protein species with a mass ($M^\circ_w$) of 15.2 kDa corresponding to dimers.

The 21 kDa mass measured by SEC in 150 mM PBS pH7.4 is close to that expected for an LD78 trimer. The model of association for this molecule does not predict formation of this mass species. The absolute mass determination by sedimentation equilibrium in this buffer gives very precise data proving the molecule is a single molecular species of 15.2 kDa. The anomalously high mass by SEC arises due to the asymmetrical shape of the LD78 dimer causing non-ideal (non-globular) hydrodynamic behaviour on chromatography.

These results demonstrate that in physiological ionic strength and pH, i.e. 150 mM PBS pH7.4, at a concentration of 0.5 mg/ml, LD78(Glu28;Glu47) exists as a single, defined, dimeric species with no large multimers apparently present, under the methods of analysis used.

Example 127

Mutation of residue Arg47 to Glu prevents the formation of high molecular weight LD78 multimeric complexes As detailed in Table 1, pure LD78(Glu47 (mutant 15 of Example 11)) protein has been studied in 150 mM PBS pH7.4 buffer using Size Exclusion Chromatography on SUPERDEX 75™ resin and by Sedimentation Equilibrium with wild type LD78 for comparison. The SEC profile of this LD78 mutant is a single, symmetrical peak demonstrating a defined, homogenous population of 21 kDa mass. Analysis of the sedimentation equilibrium data shows that LD78 (Glu47) exists as a monodisperse population of protein species with a mass ($M^\circ_w$) of 17 kDa corresponding to dimers.

The 21 kDa mass measured by SEC in 150 mM PBS pH7.4 is close to that expected for an LD78 trimer. Our model of association for this molecule does not predict formation of this mass species. The absolute mass determination by sedimentation equilibrium in this buffer gives very precise data proving the molecule is a single molecular species of 15.2 kDa. The anomalously high mass by SEC arises due to the asymmetrical shape of the LD78 dimer causing non-ideal (non-globular) hydrodynamic behaviour on chromatography.

These results demonstrate that in physiological ionic strength and pH, i.e. 150 mM PBS pH7.4, at a concentration of 0.5 mg/ml, LD78(Glu47) exists as a single, defined, dimeric species with no large multimers apparently present under conditions of analysis used.

Example 128

Mutation of residues Lys44 to Glu and Arg 45 to Gln prevents the formation of high molecular weight LD78 multimeric complexes As detailed in Table 1, pure LD78(Glu44; Gln45, (mutant 2 of Example 2)) protein has been studied in 150 mM PBS pH7.4 buffer using Size Exclusion Chromatography on SUPERDEX 75™ resin and by Sedimentation Equilibrium with wild type LD78 for comparison. The SEC profile of this LD78 variant is a single peak, FIG. 14, demonstrating a defined population of mass 21 kDa. Analysis of the sedimentation equilibrium data shows that LD78(Glu44; Gln45) exists as a monodisperse population of protein species with a mass ($M^o_w$) of 16.5 kDa corresponding to dimers.

The 21 kDa mass measured by SEC in 150 mM PBS pH7.4 is close to that expected for an LD78 trimer. The model of association for this molecule does not predict formation of this mass species. The absolute mass determination by sedimentation equilibrium in this buffer gives very precise data proving the molecule is a single molecular species of 16.5 kDa. The anomalously high mass by SEC arises due to the asymmetrical shape of the LD78 dimer causing non-ideal (non-globular) hydrodynamic behaviour on chromatography.

These results demonstrate that in physiological ionic strength and pH, i.e. 150 mM PBS pH7.4, at a concentration of 0.5 mg/ml, LD78(Glu44; Gln45) exists as a single, defined, dimeric species with no large multimers apparently present under the conditions of analysis used.

Example 129

Mutation of residue Arg17 to Ser disrupts formation of high molecular weight LD78 multimeric complexes As detailed in Table 1, pure LD78(Ser17, (mutant 5 of Example 5)) protein has been studied at 0.5 mg/ml in 150 mM PBS pH 7.4 buffer, using Size Exclusion Chromatography on SUPERDEX 75™ resin and by Sedimentation Equilibrium with wild type LD78 for comparison. The size exclusion profile is a single peak of mass 29 kDa. The tetrameric LD78 molecule is expected to be symmetrical and globular, and, therefore, should chromatograph correctly. The observed elution of this LD78 mutant correlates with the tetramer species. Analysis of the sedimentation equilibrium data reveals the presence of mixed molecular weight species ranging. from 30 kDa (tetramer) to 100 kDa (dodecamer). No masses higher than a dodecamer are observed.

These results demonstrate that mutation of Arg17>Ser in LD78 gives a molecule that is incapable of associating to heterogenous high molecular weight complexes. The mutation does not completely block association of tetramers to dodecamers, however, it would appear to energetically favour the equilibrium shifting to the tetramer.

Example 130

Mutation of residue Gln18 to Glu disrupts association of high molecular weight LD78 multimeric complexes As detailed in Table 1, pure LD78(Glu18, (mutant 29 of Example 19)) protein has been studied in 150 mM PBS pH 7.4 buffer, using Size Exclusion Chromatography on SUPERDEX 75™ resin and by Sedimentation Equilibrium with wild type LD78 for comparison. The size exclusion profile is a large broad peak, of mass centred at 48.5 kDa with a smaller component at 160 kDa. The tetrameric LD78 molecule is expected to be symmetrical and globular, and, therefore, should chromatograph correctly. The observed elution of this LD78 mutant is anomalously high to correlate with the tetramer species. Analysis of the sedimentation equilibrium data reveals the presence of mixed molecular weight species ranging from 75 kDa to 170 kDa.

These results demonstrate that mutation of Gln-18>Glu in LD78 gives a molecule that still has some ability to form heterogenous high molecular weight complexes at physiological ionic strength. It is clear from the results, however, that the mutation does have some disruptive effect on the association equilibrium. The mass range observed for this mutant is smaller than that seen for wild type LD78 (Table 1), and the SEC profile demonstrates that the molecule has significantly smaller solution mass. Whilst the mutation of Gln18>Glu does not completely stop the formation of high molecular weight LD78 multimers, it is obvious from the behaviour of the mutant molecule that this residue plays some role in stabilising the multimeric complexes. At protein concentrations <0.5 mg/ml in physiological ionic strength, this mutant may well exist as a smaller defined mass species.

Example 131

Mutation of residues Arg17 to Ser and Gln18 to Glu disrupts formation of high molecular weight LD78 complexes As detailed in Table 1, pure LD78(Ser17; Glu18, (mutant 30 of Example 20)) protein has been studied in 150 mM PBS pH 7.4 buffer, using Size Exclusion Chromatography on SUPERDEX 75™ resin and by Sedimentation Equilibrium with wild type LD78 for comparison. The size exclusion profile is a single peak of mass 25 kDa. The tetrameric LD78 molecule is expected to be symmetrical and globular, and, therefore, should chromatograph correctly. The observed elution of this LD78 mutant is slightly lower than expected for the tetramer species, however, the shift in molecular mass compared to wild type is marked. Analysis of the sedimentation equilibrium data reveals the presence of mixed molecular weight species ranging from 37 kDa to 50 kDa. No masses higher than 50 kDa are observed.

These results demonstrate that the combined mutation of Arg17>Ser and Gln18>Glu in LD78 gives a molecule that is incapable of associating (at 0.5mg/ml in physiological ionic strength) to high molecular weight complexes. In fact the LD78 mutant does not appear to form any molecular weight species higher than 50 kDa. It is suggested that the results reflect the LD78 mutant exists as a tetramer, though some unstable, limited associations can occur.

Example 132

Mutation of residue Phe12 to Gln disrupts formation of high molecular weight LD78 multimeric complexes As detailed in Table 1, pure LD78(Gln12, (mutant 11 of Example 8)) protein has been studied at 0.5 mg/ml in 150 mM PBS pH7.4 buffer using Size Exclusion Chromatography on SUPERDEX™ 75 and by sedimentation equilibrium with wild type LD78 for comparison. The observed SEC elution for this molecule is a single peak of 12.8 kDa, the smallest mass yet seen for an LD78 mutant. Given the non-ideal behaviour of dimeric LD78 on SEC (e.g. Example 126), this profile suggests that the mutant exists as a monomer. The sedimentation equilibrium, however, indicates that the LD78(Gln12) is a dodecamer in solution. The original native gel screen (Example 125) showed the presence of a small species. The data in Table 1 may reflect an equilibrium between a dodecamer and a smaller species and the presence of the sephadex resin may have some physical effect on the actual equilibrium. Alternatively, the protein may adhere to the resin during chromatography and elute much later with an apparent smaller mass.

Despite the anomaly in mass determination for this mutant, it is obvious that mutation of Phe12>Gln gives a LD78 variant that does not multimerise to the same extent as wild type. The N-terminal region of this molecule may play a role in stabilizing more than one state on the equilibrium association pathway.

Example 133

Mutation of Asp26 to Ala disrupts formation of high molecular weight LD78 multimeric complexes As detailed in Table 1 pure LD78 (Ala26, (mutant 10 of Example 7)) has been studied at 0.5 mg/ml in 150 mM PBS pH7.4 using Size Exclusion Chromatography on SUPERDEX™ 75 resin and sedimentation equilibrium with wild type LD78 for comparison. The elution profile gives a single peak of mass 24.5 kDa. Analysis of the sedimentation equilibrium data demonstrates that the protein exists as a monodisperse mass population with $M°_w$=30 kDa.

This result demonstrates that mutation of Asp26 to Ala gives an LD78 molecule which exists at physiological ionic strength as a homogeneous tetramer.

Example 134

Mutation of Glu29 to Arg disrupts association of LD78 dimers to form tetramers As detailed in Table 1, pure LD78 (Arg29, (mutant 28 of Example 18)) has been studied at 0.5 mg/ml in 150 mM PBS pH7.4 using Size Exclusion Chromatography on SUPERDEX™ 75 resin. The elution profile gives a single peak of mass 24 kDa. As discussed in Example 86, this observed mass most probably relates to a homogeneous dimeric species.

This result demonstrates that mutation of Glu29 to Arg gives an LD78 molecule which exists at physiological ionic strength as a single dimeric species.

Example 135

Mutation of Gln 48 to Glu does not affect the multimerisation properties of LD78

As detailed in Table 1, pure LD78 (Glu48, (mutant 1 of Example 1)) protein has been studied at 0.5 mg/ml in 150 mM PBS pH7.4 buffer using Size Exclusion Chromatography on SUPERDEX™ 75 and by sedimentation equilibrium with wild type LD78 for comparison. The observed SEC elution for this molecule is a single, broad, excluded peak of estimated mass 131 kDa. The sedimentation equilibrium shows that LD78(Glu48) exists as a heterogenous range of species from 100 kDa to 600 kDa. Even though this mutant was observed to have increased mobility on native PAGE, the two independent size analyses confirm that at this concentration in physiological buffer, the protein has wild type multimerisation.

In actual fact the observed mass ranges at equilibrium in the ultracentrifuge appear to show this mutant forms larger more stable multimers than wild type. In this case, therefore, introduction of a negative charge at this site may have a stabilizing effect.

Example 136

Mutation of Phe28 to Glu and Gln48 to Glu disrupts formation of high molecular weight LD78 multimers As detailed in Table 1, pure LD78 (Glu28; Glu48, (mutant 25 of Example 15)) has been studied at 0.5 mg/ml in 150 mM PBS pH7.4 using Size Exclusion Chromatography on SUPERDEX™ 75 resin. The elution profile shows a single, broad asymmetric peak at a molecular mass of approximately 60 kDa. The broad asymmetry suggests a heterogeneous mix of mass species. The combined mutations produce a variant that has markedly different multimerisation properties to wild type.

Example 137

Mutation of Arg45 to Ser disrupts formation of high molecular weight LD78 multimeric complexes As detailed in Table 1, pure LD78 (Ser45, (Mutant 43 of Example 54)) protein has been studied at 0.5 mg/ml in 150 mM PBS pH7.4 buffer by sedimentation equilibrium with wild type LD78 for comparison. Analysis of the sedimentation equilibrium data demonstrates that the protein exists as a monodisperse mass population with $M°_w$=25 kDa. This mass is anomalously high for a dimer and low for a tetramer. Given that stable trimers are unlikely to form, this mass most probably represents a homogeneous tetramer species.

Example 138

Mutation of Lys44 to Ser disrupts formation of high molecular weight LD78 multimeric complexes As detailed in Table 1, pure LD78 (Ser44,(Mutant 42 of Example 53)) protein has been studied at 0.5 mg/ml in 150 mM PBS pH7.4 buffer by sedimentation equilibrium with wild type LD78 for comparison. Analysis of the sedimentation equilibrium data demonstrates that the protein exists as a polydisperse population of species ranging in mass from 35–48 kDa.

This result demonstrates that the mutation of Lys44 to Ser in LD78 gives a molecule that is incapable of associating (at 0.5 mg/ml in physiological ionic strength) to high molecular weight complexes. The fact that no molecular weight species higher than 48 kDa is observed suggests that the mutation destabilizes the association of tetramers to form dodecamers.

This result is very similar to that obtained for LD78 (Ser17;Glu18,(mutant 30 of example 20)) described in Example 131. It is suggested, therefore, that the results reflect the LD78 mutant exists as a tetramer, though some unstable, limited associations between a tetramer and dimer (or monomers) can occur.

Example 139

Mutation of Leu65 to Ala stabilizes a homogeneous high molecular weight LD78 multimeric complex As detailed in Table 1, pure LD78 (Ala65, (Mutant 51 of Example 63)) protein has been studied at 0.5 mg/ml in 150 mM PBS pH7.4 buffer by sedimentation equilibrium with wild type LD78 for comparison. Analysis of the sedimentation equilibrium data demonstrates that the protein exists as a monodisperse mass population with $M°_w$=120 kDa.

The mutation of Leu65 to Ala gives an LD78 molecule that can associate to a stable, homogeneous complex at 0.5 mg/ml in physiological ionic strength. No other molecular weight species are observed under these conditions, therefore, the wild-type self-association properties of LD78 have been modified.

Example 140

Mutation of Glu66 to Ser disrupts formation of high molecular weight LD78 multimeric complexes As detailed in Table 1, pure LD78 (Ser66,(Mutant 52 of Example 64)) protein has been studied at 0.5 mg/ml in 150 mM PBS pH7.4 buffer by sedimentation equilibrium with wild type LD78 for comparison. Analysis of the sedimentation equilibrium data demonstrates that the protein exists as a monodisperse mass population with $M°_w$=27 kDa.

The results demonstrate that in physiological ionic strength and pH, i.e. 150 mM PBS pH7.4, at a concentration of 0.5 mg/ml, LD78(Ser66) exists as a single, defined, tetrameric species with no large multimers present.

Example 141

Mutation of Pro7 to Ala promotes formation of heterogeneous high molecular weight LD78 multimeric complexes As detailed in Table 1, pure LD78 (Ala7, (Mutant 59 of Example 88)) protein has been studied at 0.5 mg/ml in 150 mM PBS pH7.4 buffer by sedimentation equilibrium with wild type for comparison. Analysis of the sedimentation equilibrium data demonstrates that the protein exists as a polydisperse population of mass species ranging from 400–1000 kDa.

The results demonstrate that in physiological ionic strength and pH, i.e. 150 mM PBS pH7.4 at a concentration of 0.5 mg/ml, LD78(Ala7) exists as a heterogeneous range of large multimeric complexes. The mass range observed for these complexes is much greater than normally observed for wild type LD78 under the same conditions (Comparative Example 3).

The mutation of Pro7 to Ala, therefore, promotes the self-association properties of LD78 and the results suggest that the N-terminal arm of the protein plays a major role in the multimerisation of this molecule.

Example 142

Mutation of Gln18 to Ser stabilizes a homogeneous high molecular weight LD78 multimeric complex As detailed in Table 1, pure LD78 (Ser18,(Mutant 64 of Example 35)) protein has been studied at 0.5 mg/ml in 150 mM PBS pH7.4 buffer by sedimentation equilibrium with wild type for comparison. Analysis of the sedimentation equilibrium data demonstrates that the protein exists as a monodisperse mass population with $M°_w$=200 kDa.

The mutation of Gln18 to Ser gives an LD78 molecule that can associate to a stable, homogeneous complex of 26 monomers at 0.5 mg/ml in physiological ionic strength. No other molecular weight species are observed under these conditions, therefore, the wild-type self-association properties of LD78 have been significantly modified.

Example 143

Mutation of Tyr61 to Ala stabilizes a homogeneous high molecular weight LD78 multimeric complex As detailed in Table 1, pure LD78 (Ala 61, (Mutant 73 of Example 68)) protein has been studied at 0.5 mg/ml in 150 mM PBS pH7.4 buffer by sedimentation equilibrium with wild type for comparison. Analysis of the sedimentation equilibrium data demonstrates that the protein exists essentially as a monodisperse mass population with $M°_w$=400 kDa though a slight upward curvature of Ln A vs $\xi$ was evident.

The mutation of Tyr61 to Ala gives an LD78 molecule that can associate to a stable, homogeneous complex at 0.5 mg/ml in physiological ionic strength. No other molecular weight species are observed under these conditions, therefore, the wild-type self-association properties of LD78 have been significantly modified.

Example 144

Mutation of Ile19 to Ala gives a homogeneous LD78 monomer

As detailed in Table 1, pure LD78 (Ala 19, (Mutant 80 of Example 81)) protein has been studied at 0.5 mg/ml in 150 mM PBS pH7.4 buffer by sedimentation equilibrium with wild type for comparison. Analysis of the sedimentation equilibrium data demonstrates that the protein exists as a monodisperse mass population with $M°_w$=6 kDa.

The mutation of Ile19 to Ala gives an LD78 molecule that exists as a homogeneous monomer at 0.5 mg/ml in physiological ionic strength. No other molecular weight species are observed under these conditions, therefore, the wild-type self-association properties of LD78 have been completely inhibited.

Example 145

Mutation of Val39 to Ala gives a homogeneous LD78 monomer

As detailed in Table 1, pure LD78 (Ala 39, (Mutant 91 of Example 84)) protein has been studied at 0.5 mg/ml in 150 mM PBS pH7.4 buffer by sedimentation equilibrium with wild type for comparison. Analysis of the sedimentation equilibrium data demonstrates that the protein exists as a monodisperse mass population with $M°_w$=8 kDa.

The mutation of Val39 to Ala gives an LD78 molecule that exists as a homogeneous monomer at 0.5 mg/ml in physiological ionic strength. No other molecular weight species are observed under these conditions, therefore, the wild-type self-association properties of LD78 have been completely inhibited.

Example 146

Mutation of Arg17 to Glu and Gln18 to Glu disrupts formation of high molecular weight LD78 multimeric complexes As detailed in Table 1, pure LD78 (Glu17;Glu18,(Mutant 110 of Example 42)) protein has been studied at 0.5 mg/ml in 150 mM PBS pH7.4 buffer by sedimentation equilibrium with wild type for comparison. Analysis of the sedimentation equilibrium data demonstrates that the protein exists as a monodisperse mass population with $M°_w$=30 kDa.

This result demonstrates that the combined mutation of Arg17 to Glu and Gln18 to Glu in LD78 gives a molecule that is incapable of associating (at 0.5 mg/ml in physiological ionic strength) to multimeric complexes greater than a tetramer. Comparison with the results obtained for mutant 30 described in Example 131 shows that the more radical substitution of Arg17 to Glu combined with Gln18 to Glu completely disrupts the further association of tetrameric units.

Example 147

Mutation of Phe12 to Ala partially disrupts the multimerisation properties of LD78

As detailed in Table 1, pure LD78 (Ala12(mutant 77 of Example 29)) protein has been studied at 0.5 mg/ml in 150 mM PBS pH7.4 buffer by sedimentation equilibrium with wild type LD78 for comparison. Analysis of the sedimentation equilibrium data demonstrates that the protein exists as a polydisperse population of species ranging in mass from 110–170 kDa.

This result demonstrates that despite an apparent high mobility in Native PAGE, this variant displays only slight differences in self-association compared to wild type LD78 at 0.5 mg/ml in physiological ionic strength (Table 1 and Comparative Example 3). This may reflect a protein concentration dependence of association such that at the low protein concentrations in Native PAGE the variant exists as a significantly smaller mass. It is clear from the results obtained for LD78 variants containing substitutions of Phe12 to Gln or Asp (mutants 11 and 115 described in Examples 132 and 148 respectively) that radical mutation is required at this site to prevent formation of high molecular weight multimers at higher protein concentrations.

Example 148

Mutation of Phe12 to Asp prevents formation of high molecular weight LD78 multimeric complexes As detailed in Table 1, pure LD78 (Asp12(mutant 115 of Example 106)) protein has been studied at 0.5 mg/ml in 150 mM PBS pH7.4 buffer by sedimentation equilibrium with wild-type LD78 for comparison. Analysis of the sedimentation equilibrium data demonstrates that the protein exists as a monodisperse mass population with $M°_w$=30 kDa.

The mutation of Phe12 to Asp gives an LD78 molecule that exists as a homogeneous tetramer at 0.5 mg/ml in physiological ionic strength. No other molecular weight species are observed under these conditions, therefore, this mutation inhibits the association of tetramers to higher order structures.

Example 149

Mutation of Ala4 to Glu disrupts formation of high molecular weight LD78 multimeric complexes As detailed in Table 1, pure LD78 (Glu4(mutant 109 of Example 41)) protein has been studied at 0.5 mg/ml in 150 mM PBS pH7.4 buffer by sedimentation equilibrium with wild-type LD78 for comparison. Analysis of the sedimentation equilibrium data demonstrates that the protein exists as a monodisperse mass population with $M°_w$=71 kDa.

The mutation of Ala4 to Glu gives an LD78 molecule that associates to a stable homogeneous complex of mass 71 kDa at 0.5 mg/ml in physiological ionic strength. The self-association of LD78 has, therefore, been dramatically reduced by this mutation demonstrating that the N-terminal arm of the protein is directly involved in the multimerisation process.

Example 150

Mutation of Thr15 to Ala does not significantly affect the multimerisation properties of LD78

As detailed in Table 1, pure LD78 (Ala15(mutant 79 of Example 93)) protein has been studied at 0.5 mg/ml in 150 mM PBS pH7.4 buffer by sedimentation equilibrium with wild-type LD78 for comparison. Analysis of the sedimentation equilibrium data demonstrates that the protein exists as a polydisperse population of species ranging in mass from approximately 100–250 kDa with $M°_w$=200 kDa.

This result demonstrates that the mutation of Thr15 to Ala gives a molecule that has wild-type association properties at 0.5 mg/ml in physiological ionic strength. The increased mobility observed on Native PAGE may reflect a concentration dependence of self-association with smaller mass species predominating at the low concentrations loaded onto gels. A more radical substitution to a polar or charged amino acid would elucidate this possibility further.

Example 151

Mutation of Lys36 to Glu does not significantly affect the multimerisation properties of LD78

As detailed in Table 1, pure LD78 (Glu36(mutant 126 of Example 117)) protein has been studied at 0.5 mg/ml in 150 mM PBS pH7.4 buffer by sedimentation equilibrium with wild-type LD78 for comparison. Analysis of the sedimentation equilibrium data demonstrates that the protein exists as a polydisperse population of species ranging in mass from approximately 100–250 kDa with $M°_w$=200 kDa.

This result demonstrates that the mutation of Lys36 to Glu gives a molecule that has wild-type association properties at 0.5 mg/ml in physiological ionic strength. The increased mobility observed on Native PAGE may reflect a concentration dependence of self-association with smaller mass species predominating at the low concentrations loaded onto gels.

Example 152

Mutation of Gln21 to Ser partially disrupts formation of high molecular weight LD78 multimeric complexes As detailed in Table 1, pure LD78 (Ser2l(mutant 81 of Example 86)) protein has been studied at 0.5 mg/ml in 150 mM PBS pH7.4 buffer by sedimentation equilibrium with wild-type LD78 for comparison. Analysis of the sedimentation equilibrium data demonstrates that the protein exists as a monodisperse mass population with $M°_w$=112 kDa.

The mutation of Gln21 to Ser gives an LD78 molecule that can associate to a stable homogeneous complex of mass 112 kDa at 0.5 mg/ml in physiological ionic strength. No other molecular weight species are observed under these conditions, therefore, the wild-type self association properties of LD78 have been modified.

Example 153

Further LD78 molecules containing amino-acid substitutions which show higher mobility than wild-type in Native PAGE In the Native PAGE screening assay described in Example 125, a number of other LD78 variants have been identified as a single species with greatly increased mobility than wild type. These variants are- LD78 (Glu28,(mutant 17 of Example 13)), LD78 (Asn24,(mutant 24 of Example 14)), LD78 (Gln26,(mutant 125 of Example 116)), LD78 (Glu44, (mutant 127 of Example 118)), LD78 (Glu45,(mutant 128 of Example 119)) and LD78 (Gln66,(mutant 130 of Example 121)).

In addition four variants have been identified which exhibit a mixture of high and low molecular weight species on Native PAGE. These variants are: LD78 (Ala43(mutant 69 of Example 87)), LD78 (Ser48(mutant 70 of Example 27)), LD78 (Ser51(mutant 97 of Example 99)) and LD78 (Alas8(mutant 100 of Example 102)).

A further 5 variants have been observed to run with a slight increase in mobility compared to wild-type on Native PAGE which suggests that though large, they also reflect in a modification of the LD78 self-association properties. This conclusion is supported by the analysis of mutants 10, 51, 52 and 64 (of Examples 133, 139, 140 & 142 respectively) which showed only slight increases in gel mobility and very striking difference to wild type when examined by sedimentation equilibrium. These variants are: LD78 (Ser26(mutant 39 of Example 28)), LD78 (Ala13(mutant 62 of Example 74)), LD78 (Ala23(mutant 83 of Example 52)), LD78 (Ala32(mutant 88 of Example 70)) and (Ala49(mutant 96 of Example 98)).

Some of the variants identified above contain substitutions at sites known to be involved in multimerisation described in the previous Examples and it is not unexpected, therefore, to observe changes in gel mobility. The remaining sites, however, are, subject to the limitations of the gel screen, likely to be involved either directly or indirectly with the LD78 self-association process.

Example 154

Known natural variants of LD78 exhibit the same multimerisation properties as the recombinant wild type molecule

As detailed in Table 1, the natural variants LD78 (Leu-Ser-Ala; Pro1; Ser38; Gly46, (mutant 35 of Example 25)) and LD78 (Ala; Pro1, (mutant 34 of Example 24)) have been studied by Size Exclusion Chromatography using a SUPERDEX™ 75 resin and by sedimentation equilibrium with wild type as a control. Both variants are excluded from the SEC resin and the sedimentation equilibrium data shows that they exist as polydisperse masses of 90–200 kDa and 230–350 kDa respectively. The N-terminal extensions and amino acid substitutions in these variants do not, therefore, disrupt the multimerisation properties of the LD78 protein.

Example 155

Definition of the molecular faces involved in LD78 association

Residues important for Monomer→Dimer association

From the examples above, it can be seen that at least residues 19 and 39 are important for monomer association to dimers.

Residues important for the Dimer→Tetramer association

From the examples outlined above, two distinct regions of sequence are identified as important for the stable association of dimers to form tetramers.

(i) Individual mutation of residues Phe28>Glu and Glu29>Arg gives rise to a homogeneous population of dimeric LD78. It is clear, therefore, that residues projecting away from the face of the dimer on strand 1 & 1' of the beta sheet form key non-covalent, intermolecular bonds in the tetramer interface.

(ii) Mutation individually of Arg47>Glu or a combination of Lys44>Glu & Arg45>Gln produces stable LD78 dimers in the absence of higher molecular weight forms. The sequence of residues 43–47 in the turn region linking strands. 2 (2') and 3 (3') of the beta sheet is, therefore, key for the association of LD78 dimers to form tetramers.

Residues important for tetramer→dodecamer and dodecamer→higher order multimer

Mutations of Arg 17>Glu, Gln 18>Glu, Phe12>Asp, Asp26>Ala, Glu66>Ser and Ala4>Glu appear to disrupt the tetramer to dodecamer association. Mutations of Gln21 >Ser, Leu65>Ala and Phe12>Gln appear to disrupt the dodecamer to multimer association.

Current evidence suggests that these interfaces may overlap or be one and the same. Mutation of Arg17>Ser and Gln18>Glu individually or in combination appear to disrupt both of the associations outlined above. In this case it is predicted that the sequence region involving residues 16–21 on the N-terminal side of strand 1 (1') of the beta sheet are key for the associations.

The data so far generated for mutation at residue 48 is ambiguous; however, it may be that this residue also plays a role in the higher order association of the LD78 molecule.

Example 156

S. cerevisiae Batch fermentation of wild-type LD78, LD78 (Glu44, Gln45) and LD78 (Glu47).

A convenient way of assessing the potential of a transformed Saccharomyces cerevisiae strain to produce recombinant protein is to use a batch fermentation process. This process relies upon providing a controlled environment in which all of the essential growth nutrients are present in the medium prior to inoculation. Once inoculation has occurred the culture is maintained in an environment appropriate for recombinant protein expression. Scale-up of recombinant protein expression from shake-flask cultures is achieved using fermenter cultures. The Saccharomyces cerevisiae strain used for recombinant gene expression in fermenters is MC2 (see Preparation 3). This strain was isolated from a chemostat culture of S. cerevisiae strain BJ2168 (see Preparation 3) where galactose was used as a sole and limiting carbon source. Unlike BJ2168, MC2 exhibits a wild-type phenotype when growing on galactose as a sole carbon source. The batch and fed-batch fermentation strategies developed are designed to complement this phenotypic characteristic.

The transformed strains used for this example were prepared as previously described in Preparation 2. The plasmids used to express different forms of the molecule are described in Preparation 3 (wild-type LD78), Example 2 (Lys44>Glu; Arg45>Gln) and Example 11 (Arg47>Glu).

Method

A 1 ml glycerol stock culture (stored at −70° C. in 20% glycerol) was thawed and used to inoculate 50 ml of sc/glc medium (6.7 g/L yeast nitrogen base w/o amino acids, 10 g/L glucose and 20 ml/L amino acid solution containing 1 g adenine, 1 g arginine, 5 g aspartic acid, 5 g glutamic acid, 1 g histidine, 15 g iso-leucine, 1.5 g lysine, 1 g methionine, 2.5 g phenylalanine, 17.5 g serine, 10 g threonine, 2 g tryptophan, 1.5 g tyrosine, 1 g uracil, 6.7 g valine). The culture was incubated at 30° C. for 24 hrs on a shaking platform after which time 5 ml was aseptically removed and used to seed 500 ml of the same sc/glc medium. This culture was incubated at 30° C. on a shaking platform for 24 hr at which point it was used to seed a fermenter (prepared as below).

A 5 L fermenter (LSL Biolafitte) was filled with 3.5L of the defined medium NAMC#4 containing 41 g ammonium sulphate (($NH_4)_2SO_4$), 5.25 g potassium dihydrogen orthophosphate ($KH_2PO_4$), 2.85 g magnesium sulphate ($MgSO_4.7H_2O$), 55 mg calcium chloride ($CaCl_2$), 16 mg manganous sulphate ($MnSO_4.4H_2O$), 18.5 mg copper sulphate ($CUSO_4.5H_2O$), 5 mg zinc sulphate ($ZnSO_4.7H_2O$), 1 mg potassium iodide (KI), 9 mg sodium molybdate ($Na_2MoO_4.2H_2O$), 4 mg ferric chloride ($FeCl_3.6H_2O$) and 2 ml $PPG_{2000}$ (antifoam agent). Once sterilised the fermenter was allowed to cool and the medium within the fermenter was completed with the aseptic addition of 400 ml of a filter sterilised sugar/vitamin concentrate containing 15 g glucose, 100 g galactose, 10 mg biotin, 63 mg calcium pantothenate, 63 mg pyridoxine hydrochloride, 50 mg thiamine, 50 mg nicotinic acid, 4 mg p-amino benzoic acid, 100 mg myo-inositiol together with 100 ml of a filter sterilised amino acid stock (as for seed culture).

Once the medium was complete the fermenter was set up to maintain the following environment; temperature –30° C., pH –5.0 (using 3M sodium hydroxide and 3M phosphoric acid as titrants), impeller –750 rpm, air flow rate –2.5 L/min and dissolved oxygen tension above 40% saturation (using increasing impeller rates). After obtaining the running conditions the fermenter was inoculated with the seed culture (described previously) and the running conditions were maintained for 65 hrs. At this point the cell density of the culture was quantified using a spectrophotometer ($A_{600}$) and LD78 levels assessed (in the culture supernatant) using reverse phase HPLC (Comparative Example 3) using a standard curve of LD78 concentration to give peak height/area.

Using the batch protocol the following data have been collected

| LD78 Species | Final Biomass Level ($OD_{600}$) | Final LD78 Level (mg/L) | Specific Productivity (wild-type = 1) |
|---|---|---|---|
| Wild-type | 26.6 | 7 | 1 |
| LD78 (Lys44>Glu; Arg45>Gln) | 24.3 | 41 | 6.4 |
| LD78 (Arg47>Glu) | 26.0 | 27 | 3.9 |

Higher productivities from strains expressing disaggregated variants of LD78 is clearly demonstrated in this experiment.

Example 157

S. cerevisiae Fed-batch fermentation of wild-type LD78 and LD78 variants

The fed-batch strategy is an adaptation of the batch process which promotes higher cell densities within the fermentation culture and thus increases the volumetric level of the recombinant protein. The strains used for the expression of wild-type and mutant LD78 species were as in Example 156. Transformants were produced as described in Preparation 2 and the plasmids used are described in Preparation 2 (wild-type), Example 2 (Lys44>Glu; Arg45>Gln), Example 16 (Phe28>Glu; Arg47 >Glu), Example 53 (Lys44 >Ser), Example 64 (Glu66 >Ser), Example 42 (Arg17>Glu; Gln18>Glu) and Example 19 (Gln18>Glu).

Method

A fermenter was set up as in Example 156. At 18 hr post inoculation a feed was applied to the culture. The feed was 1L in volume and consisted of 300 g galactose, 8.3 g ammonium sulphate (($NH_4)_2SO_4$), 1.05 g potassium dihydrogen orthophosphate ($KH_2PO_4$), 0.57 g magnesium sulphate ($MgSO_4.7H_2O$), 11 mg calcium chloride ($CaCl_2$), 3 mg manganous sulphate ($MnSO_4.4H_2O$), 4 mg copper sulphate ($CuSO_4.5H_2O$), 1 mg zinc sulphate ($ZnSO_4.7H_2O$), 0.2 mg potassium iodide (KI), 2 mg sodium molybdate ($Na_2MoO_4.2H_2O$), 1 mg ferric chloride ($FeCl_3.6H_2O$), 4 mg boric acid ($H_3BO_3$), 2 mg biotin, 12 mg calcium pantothenate, 12 mg pyridoxine hydrochloride, 10 mg thiamine, 10 mg nicotinic acid, 1 mg p-amino, benzoic acid, 20 mg myo-inositiol in addition to 100 ml of the amino acid stock used in the seed stage. The feed was pumped into the vessel at a rate of 0.22 ml/min. After 48 hrs the feed was stopped and a 250 ml pulse of constituents (same as the feed without galactose) was batched into the vessel. This batch phase was then allowed to continue for a further 36 hr after which time the cell density and culture supernatant were assayed as before (Example 156).

Using transformed MC2 cells and the fed-batch protocol described above the following data have been collected

| LD78 Species | Mutant No | Final Biomass Level ($OD_{600}$) | Final LD78 Level (mg/L) | Specific Productivity (wild-type = 1) | Multimerisation Status |
|---|---|---|---|---|---|
| Wild-type LD78 | 0 | 45.3 | 20 | 1 | Wt |
| LD78 (Lys44>Glu; Arg45>Gln) | 2 | 45.8 | 108 | 5.3 | Dimer |
| LD78 (Phe28>Glu; Arg47>Glu) | 26 | 50.4 | 120 | 5.4 | Dimer |
| LD78 (Lys44>Ser) | 42 | 43.5 | 50 | 2.5 | Tetramer/ Dodecamer |
| LD78 (Glu66>Ser) | 52 | 39.7 | 50 | 2.5 | Tetramer |
| LD78 (Arg17>Glu; | 110 | 35.3 | 100 | 5.0 | Tetramer |

-continued

| LD78 Species | Mutant No | Final Biomass Level (OD$_{600}$) | Final LD78 Level (mg/L) | Specific Productivity (wild-type = 1) | Multimerisation Status |
|---|---|---|---|---|---|
| Glu18>Glu) LD78 (Gln18>Glu) | 29 | 39.3 | 40 | 2.0 | Dodecamer |

Higher productivities from strains expressing demultimerised variants of LD78 is clearly demonstrated in this experiment.

Example 158

Construction of a *Pichia pastoris* expression vector for Human LD78

The methylotrophic yeast *Pichia pastoris* has been used for the production of several proteins. High level expression has been obtained for a number of proteins in this host but some proteins prove difficult to produce. There is no obvious correlation between the properties of a particular polypeptide and its ability to be highly expressed in the Pichia system. The *Pichia pastoris* expression system has particular advantages in its ease of scalability for large scale production. Expression of LD78 was investigated in the Pichia host strain GS115 (obtainable from the Phillips Petroleum Company, Bartlesville, Okla., U.S.A.).

The pSW6-LD78 plasmid was used as a source of the α-factor LD78 fusion for cloning into the *P. pastoris* expression vector pHILD4. The expression vector pHILD4 is a shuttle vector capable of propagation in *E. coli* and the methylotrophic yeast *P. pastoris*. The vector comprises sequences derived from the *E. coli* vector pBR322 and sequences derived from the genome of *P. pastoris*. The essential features of the vector are the 5' region of the Pichia AOX1 gene including the regulatable AOX1 promoter for high level transcription, the 3' region from the AOX1 gene containing the transcriptional terminator, a further region from the 3' AOX1 gene which is included together with the 5' AOX1 region to enable site directed integration of the expression cassette into the host genome. The *P. pastoris* histidinol dehydrogenase gene HIS4 is carried and used to complement the defective his4 gene in Pichia host strains. The ampicillin resistance gene is carried to allow selection in *E. coli* hosts during genetic manipulation. This vector is similar to the pHILD1 vector described in Example 159 except that it also contains a kanamycin resistance cassette which enables selection for multicopy integrants when the vector is introduced into Pichia host strains. The pHILD4 vector is illustrated in FIG. 15a. Genes for expression may be cloned into the EcoR1 expression cloning site of the pHILD4 vector. pHILD4 can be obtained under licence from Phillips Petroleum Company, Bartlesville, Okla., U.S.A.

The pSW6-LD78 vector of preparation 2 was used as a source of the wild-type LD78 gene fused to the Saccharomyces mating type α factor pre-pro leader sequence. Sequences encoding this fusion may be isolated from pSW6-LD78 as a linear DNA fragment following digestion with BglII & BamHI restriction endonucleases. To render the ends of this linear fragment compatible with cloning into the EcoR1 expression cloning site of the pHILD4 vector it was first necessary to fill in the single stranded overhangs which result from the BglII/BamHI digestions. This was achieved using the Klenow fragment of *E. coli* DNA polymerase I together with the required deoxynucleoside triphosphates according to standard methodology. The resultant flush ended fragment was then cloned into the pHILD4 vector that had been treated with EcoR1 and then blunt ended as above. The integrity of the resultant plasmid pLH12 was checked by a combination of restriction digestion and sequence analysis.

Expression host strains containing pLH12 were constructed using the method described in Example 159 below.

Example 159

Construction of an improved *Pichia pastoris* expression vector for variants of Human LD78

Whilst pLH12 of Example 158 was used for the early expression analysis, this vector was improved upon as shown in this example and the resultant improved vector pLH23 was used for the construction of Pichia expression vectors for LD78 variants.

Pichia expression vector pHILD1 (FIG. 16) is a shuttle vector capable of propagation in both *E. coli* (for ease of genetic manipulation) and in the methylotrophic yeast *Pichia pastoris*. The *S. cerevisiae* mating type factor alpha secretion signals were incorporated into the pHILD1 vector to enable export of the LD78 protein to the medium. pHILD1 can be obtained under licence from the Phillips Petroleum Company, Bartlesville Okla., U.S.A. The vector comprises sequences derived from the *E. coli* vector pBR322 and sequences derived from the genome of *Pichia pastoris*. The essential features are the 5' region of the Pichia alcohol oxidase (AOX1) gene including the regulatable AOX1 promoter for high level transcription, the 3' region from the AOX1 gene containing the alcohol oxidase transcriptional terminator sequence, a further region from the 3' part of the AOX1 gene is included which together with the 5' AOX1 region is required for site-directed integration of the expression cassette into the host genome. The *P. pastoris* histidinol dehydrogenase gene HIS4 is carried and used to complement the defective his4 gene in Pichia host strains. The ampicillin resistance gene is carried to enable selection in the *E. coli* hosts used during genetic manipulation. The pHILD1 vector was manipulated to allow expression of the synthetic LD78 gene (obtained from pUC18-LD78) of Preparation 1 under the control of the alpha factor secretion signal. pHILD1 does not carry any sequences encoding secretion signals to allow export of heterologous proteins. To include such a signal, the vector was manipulated by the addition of sequences from the *S. cerevisiae* alpha-factor leader. The vector was further engineered to provide a more optimal promoter context and to remove undesirable HindIII restriction sites which may interfere with the cloning of the LD78 gene from pSW6-LD78 of Preparation 2, a BamHI site was then introduced 3' to the remaining HindIII to allow cloning of the LD78 gene (pUC18-LD78 of Preparation 1) on a HindIII - BamHI restriction site and to include a kanamycin resistance cassette enabling the selection of multicopy integrants in transformed Pichia host strains. The stages of the manipulations are below. An outline of the strategy used is shown in FIG. 18.

Inclusion of alpha-factor secretion signals

The alpha-factor sequences were cloned into the pHILD1 vector from the *S. cerevisiae* expression vector pSW6 (FIG. 2) (see Preparation 2 for details). The alpha-factor sequences were isolated from pSW6 on a ca 430 bp BglII-BamHI DNA fragment, this fragment contains the alpha-factor sequences fused to a human epidermal growth factor synthetic gene (EGF). The overhanging ends of this DNA fragment were first filled in using klenow fragment of *E. coli* DNA polymerase I together with the required deoxynucleoside triphosphates according to standard methodology. The flush-ended fragment was then cloned into the pHILD1 vector that had been treated with EcoRI and then blunt-ended as above. The integrity of the resultant plasmid pLH001 was checked by a combination of restriction digestion and DNA sequence analysis. The primer use for sequence analysis was BB5769 (5'- GCATTCTGACATCCTCT-3' SEQ ID NO 168). The sequence of the α factor coding sequence was confirmed.

Mutagenesis to optimise vector for variant LD78 expression

The pLH001 vector was further modified to remove unwanted HindIII restriction sites, to optimise the promoter region and to introduce a BamHI site. Relevant fragments were cloned into a bacteriophage M13 vector for site-directed mutagenesis. The fragments cloned, the primers used for mutagenesis, and the primers used for sequencing are detailed below. Furthermore, a kanamycin resistance cassette was modified for introduction into the final expression vector to allow selection for multicopy integrants when the vector is introduced into Pichia host strains.

A ca 1220 bp SacI-SacI fragment was isolated from pLH001 and cloned into M13 mp19. This M13 construct was then used for mutagenesis in which a HindIII site was removed using oligonucleotide primer BB6040 (5'-CGTTAAAATCAACAACTTGTCAATTGGAACC-3' SEQ ID NO 169), the mutants were identified by sequence analysis with sequencing primer BB6296 (5'-GGAAATCTCACAGATCT-3' SEQ ID NO 170). This fragment was further modified by deletion mutagenesis to optimise the 5' untranslated leader region preceding the AOX1 promoter, which is now identical to that found in the natural 5' untranslated leader of the AOX1 gene on the Pichia genome. Having the correct context around the 5' untranslated leader is preferred for maximal expression. The mutagenesis primer used for this step was BB8461 (5'GAAGGAAATCTCATCGTTTGAATA-3' SEQ ID NO 171). The mutant was identified by sequence analysis with sequencing primer BB8740 (5'- GCTAATGCGGAGGATGC-3' SEQ ID NO 172).

Two further HindIII sites were removed from the ca 770 bp SacI-XbaI fragment of pLH001 by mutagenesis. The SacI-XbaI fragment of pLH001 was first cloned into M13 mp18 and one of the HindIII sites was removed using the primer BB6394 (5'-CCGGCATTACAACTTATCGATAAGCTTGCAC-3' SEQ ID NO 173). The identity of this mutant was confirmed by sequence analysis using the sequencing primer BB6037 (5'-GCGCATTGTTAGATTTC-3' SEQ ID NO 174). A second HindIII site was removed from this newly mutagenised fragment using mutagenesis primer BB6841 (5'-CTTATCGATCAACTTGCACAAACG-3' SEQ ID NO 175). The correct mutant was identified by sequence analysis using sequence primer BB6037 (see above).

Before reassembly, a BamHI site was introduced into the HindIII deleted SacI-XbaI fragment to allow subsequent cloning of the LD78 gene of Preparation 2 on a HindIII-BamHI fragment. The mutagenesis primer used to introduce the BamHI site was BB6189 (5' GTCATGTCTAAGGCGGATCCTTATTAAC-3' SEQ ID NO 176). The identity of the mutant was identified using sequencing primer BB5769 (5'-GCATTCTGACATCCTCT-3' SEQ ID NO 168).

Modification of the Kanamycin resistance cassette

A kanamycin resistance cassette was purchased from Pharmacia Biosystems Limited, Davy Avenue. Knowlhill, Milton Keynes, MK5 8PH. Great Britain. This cassette is supplied as an EcoRI fragment by Pharmacia and this was cloned into M13mp19 as an EcoRI fragment. The internal HindIII restriction site was deleted using mutagenesis primer BB8661 (5'-GAGAATGGCAACAACTTATGCATT-3' SEQ ID NO 177). The mutation was confirmed using sequencing primer BB6038 (5'-CCAACATCAATACAACC-3' SEQ ID NO 178).

Reassembly of expression vector

The vector was reconstructed in a stepwise manner using the Phillips petroleum vector pHILD1 as a backbone for the cloning.

To rebuild the expression vector including the mutagenised fragments, the modified ca 770 bp SacI-XbaI fragment was first ligated into SacI -XbaI treated pHILD1 vector. The integrity of the recombinant construct was then confirmed by restriction analysis and DNA sequence analysis using the oligonucleotide sequencing primer BB6037 (5'-GCGCATTGTTAGATTTC-3' SEQ ID NO 174), the construct was called intermediary vector 1. The modified SacI-SacI fragment was next cloned into intermediary vector 1 which had been treated with SacI and calf intestinal phosphatase. The resultant construct, named intermediary vector 2, was again confirmed by restriction analysis and DNA sequence analysis with oligonucleotide primers BB6296 (5'-GGAAATCTCATAGATCT-3' SEQ ID NO 170) to read through the deleted HindIII site and BB8740 (5'-GCTAATGCGGAGGATGC-3' SEQ ID NO 172) to read through the optimised 5' untranslated leader region. Intermediary vector 2 is a homologue of pHILD1 which lacks the unwanted HindIII sites, has an optimised 5' untranslated region, contains sequences encoding the *S. cerevisiae* alpha-factor secretion signals followed by the remaining HindIII site and which has a BamHI site 3' to the HindIII site to allow cloning of the synthetic LD78 gene described in Preparation 1.

A 1,200 bp HincII fragment containing the mutagenised kanamycin cassette was removed from the M13 mp19 mutagenesis vector (used to remove the HindII site from the kanamycin resistance gene) and cloned into the unique NaeI site of the intermediary vector 2. The vector was renamed pLHD4. The integrity of pLHD4 was confirmed by restriction analysis. A map of pLHD4 is shown in FIG. 15*b*. pLHD4 contains the human EGF gene fused to the *S. cerevisiae* alpha factor secretion signal.

Construction of the improved LD78 Pichia expression vector

The improved expression vector for wild-type LD78 expression was constructed by cloning a HindIII - BamHI fragment of pSW6-LD78 (Preparation 2) into pLHD4. (This HindIII-BamHI fragment contains the synthetic LD78 gene fused to the 3' end of a sequence encoding the 5 amino acids of the yeast alpha factor which precede the KEX2 cleavage site required for liberation of the mature peptide following secretion from the Pichia host).

The HindIII-BamHI fragment was obtained by restriction digestion of the *S. cerevisiae* expression vector pSW6-

LD78. This fragment was purified on a 1.5% low melting temperature agarose gel then ligated to HindIII-BamHI, calf intestinal phosphatase treated pLHD4. The resultant recombinant was called pLH23. The vector is shown in FIG. 17. The integrity of the construct was confirmed by restriction analysis and sequencing analysis using the sequencing primer BB5769 (5'-GCATTCTGACATCCTCT -3' SEQ ID NO 168). FIG. 18 shows the strategy for the construction of pLH23.

Example 160

Construction of P. pastoris expression vectors for demultimerised LD78 variants

The improved vector of Example 159 was used as the basic expression vector for all LD78 variants. The DNA encoding the LD78 variants was obtained from the S. cerevisiae vector described in Examples 16, 2, 11, 5, 20, 18, 1, 15 and 8. Briefly, the plasmid DNA from these various examples was digested with HindIII and BamHI restriction endonucleases. This releases a fragment containing sequences which encode the LD78 variant fused to a sequence encoding the last 5 amino-acids of the S. cerevisiae mating factor type alpha. The HindIII/BamHI DNA fragments were ligated into HindIII/BamHI-treated pLH23. The resultant vectors together with the LD78 variant carried can be seen in the table below

| Mutant No | Mutation | Pichia Vector |
|---|---|---|
| 26 | Arg47>Glu; Phe28>Glu | pLH 25 |
| 2 | Lys44>Glu; Arg45>Glu | 26 |
| 15 | Arg47>Glu | 27 |
| 5 | Arg17>Ser | 28 |
| 30 | Arg17>Ser; Gln18>Glu | 30 |
| 28 | Glu29>Arg | 29 |
| 1 | Gln48>Glu | 31 |
| 25 | Phe28>Glu; Gln48>Glu | 24 |
| 11 | Phe12>Gln | 32 |

Expression hosts for these various plasmids were constructed according to the method described in Example 161 below.

Example 161

Construction of Pichia expression strains pLH12 plasmid DNA prepared as in Example 158 was linearised by cutting with the restriction endonuclease Sac I. This was to enable the expression cassette to integrate via homologous recombination of sequences on the expression cassette and the host chromosome. The linearised plasmid was then transformed into P. pastoris strain GS115 (NRRL Y-1585) which has the genotype his4. The use of strain GS115 is not critical for use either in this preparation or in the invention in general. Any suitable strain can be used, such as, for example, strain KM71 or SMD1163 which have the genotypes his4, AOX1::ARG4 and his4, prB1, pep4 respectively. Strains GS115 and KM71 are described in Phillips patent number AU-B-63882/86. These hosts can be obtained under licence from the Phillips Petroleum Company, Bartlesville, Okla., U.S.A.

Using the method described below the plasmid DNA was transformed into the host strain.

Briefly, yeast strain GS115 was grown overnight in 200 mL of YEPD medium at 30° C. on an orbital shaker. Cultures at an $A_{600}$ of between 0.1 and 0.3 were harvested by centrifugation at 300 rpm for 5 mins, washed in sterile water, recentrifuged, washed in SED buffer (Appendix A at the end of the Examples), recentrifuged, washed in 1M sorbitol, recentrifuged and resuspended in 20 mL SCE buffer (Appendix A). Cells were then incubated at 30° C. with the enzyme zymolyase to remove the cell wall. Spheroplasting was allowed to continue until approximately 70% of the cells had been turned into spheroplasts. These were then collected by gentle centrifugation (750xg 10 mins). Spheroplasts were then washed in 1M sorbitol and resuspended in 600 μL CAS buffer (Appendix A). 100 μL aliquots of spheroplasts were then incubated for 10 mins with 10 μg of the linearised DNA. 1 mL of PEG buffer was then added and incubated for a further 10 mins. After collecting the spheroplasts by gentle centrifugation and aspirating the PEG solution the cells were resuspended in 150 μL of SOS medium (Appendix A) and incubated for 20 mins. After the addition of 850 μL of 1M sorbitol the cells were ready for plating on regeneration agarose.

100 μL of transformed spheroplasts were then added to 10 mL of molten (42° C.) agarose-sorbitol regeneration medium and poured onto agarose-sorbitol base plates and allowed to grow for 5–7 days at 30° C.

All yeast media and transformation buffers were as described in the appendix.

After 5–7 days transformants were collected along with the agarose overlay they had been growing in, transferred to a 50 mL centrifuge tube and resuspended in 50 mM sodium phosphate buffer pH6 and after suitable mixing and agitation to remove the cells from the agarose they were diluted and plated onto YEPD agar plates containing the antibiotic G418 at concentrations between 0 and 2,000 μg/mL. Only cells in which several copies of the expression cassette had integrated into the host chromosome would be able to grow on high levels of antibiotic by virtue of their enhanced kanamycin resistance. Such cells are deemed desirable since they will also be carrying several copies of the LD78 gene. Previous work has shown such multicopy integrants to be high producers under conditions were the foreign gene is expressed (Clare et al (1991)). Plates were incubated at 30° C. for 5–7 days. Colonies occurring on plates containing high concentrations of the antibiotic were then picked and streaked onto fresh MD agar plates. Single colonies were obtained after 3–4 days growth at 30° C.

In order to determine the number of copies of the expression cassette that had integrated onto the host chromosome a Southern blotting technique based on that described by Clare et al. (1991) was employed.

Briefly, chromosomal DNA was prepared from transformed cells and digested with the restriction endonuclease BglII. The resulting DNA fragments were separated by gel electrophoresis and transferred to nitrocellulose by electroblotting. The resulting Southern blot was then incubated with a labelled probe that recognises one of the DNA sequences on the expression cassette (for example HIS4). The probe will also recognise the single copy of the his4 gene present on the host chromosome. By comparing the intensity of the signal from the known single copy with the unknown multicopy signal (by scanning densitometry) it is possible to quantify the number of copies present.

Exactly the same method was employed for transformation and construction of expression strains from the LD78 variant expression vectors described in Example 160.

Example 162

Expression of wt LD78 in Pichia pastoris

Wild-type expression hosts contained pLH12 as described in Example 158.

Single colonies of transformed strains were used to inoculate 5 mL of BMGC medium (Appendix A) and the cultures were grown overnight at 30° C. on an orbital shaker. This 5 mL overnight culture was then used to inoculate 2L baffled shake flasks containing 50 mL of the medium BMGC. After 24 h growth at 30° C. on an orbital incubator cells were harvested by centrifugation at 300 rpm for 5 min and resuspended in 50 mL of BMMC (Appendix A). This induces gene expression from the AOX1 promoter. Induction was carried out by growth in the methanol containing medium at 30° C. for 48–72 h.

After either 48 h or 72 h the culture supernatant was collected by centrifugation at 300 rpm for 5 min to remove cells. This supernatant was used for further analysis and purification of LD78 according to the methods described in Preparations 3 and 4. Levels of wild-type LD78 produced using this method are typically 3–5 mg/L as determined by HPLC.

Such levels can be improved by growing the producing strain in a fermenter. A single colony was inoculated into 5 mL of MD medium (Appendix A) and grown overnight at 30° C. in an orbital incubator. This culture was then used to inoculate 500 mL of YEPGlycerol medium (Appendix A) in a 2L baffled flask. This culture was grown for between 24–48 h and used as an inoculum for the fermentor. The 5 L fermenter was autoclaved with 3.5L of the High Cell Density (HCD) medium (Appendix A). After adjusting the pH to 5.85 with ammonia solution and the addition of 10 mL of a trace element solution ($PTM_1$, (Appendix A)) the fermenter was inoculated with the culture described above. Growth conditions are typically pH5.85 (maintained by the addition of ammonia solution on demand), 29.8° C., 800–1200 rpm, 1–2 vvm air, 20–100% DOT. After 20–24 h the carbon source in the medium was exhausted and a methanol feed (containing 5 mL/L of trace element solution $PTM_1$ and 2 mL/L biotin stock solution –0.2 g/L) started at 3.4 g/h. After 24–30 hours the feed rate was increased to 6 g/h for approximately 20 h. After this the feed rate was increased or decreased to keep the residual methanol concentration in the broth between 1 and 10 g/L (as determined by gas chromatography). The fermentation was run for between 70–180 h and wild-type LD78 levels in the broth were determined to be 60–100 mg/L by HPLC.

The material produced using the Pichia expression system was purified and characterised using the techniques applied to the material produced by Saccharomyces (see Preparation 3, 4 and 13).

Example 163

Enhanced expression of demultimerised mutants

The expression constructs for the demultimerised variants as described in Example 160 were introduced into Pichia host strain GS115 according to the method of Example 161.

It was generally noted that mutations of the LD78 gene that resulted in a demultimerised form of the molecule gave higher levels of expression into culture supernatants than did the wild-type LD78 molecule.

As mentioned in Example 162, the expression level in shake flask inductions was determined to be 3–5 mg/L for the wild-type LD78 molecule. When production strains containing integrated expression cassettes of demultimerised mutants were grown as detailed in Example 157 expression levels were seen to be elevated to the order of 50–200 mg/L (specifically mutant 26 (LD78 Glu28, Glu47) –158 mg/L, mutant 2 (LD78 Glu44, Gln45) –76 mg/L, mutant 15 (LD78 Glu47) –63 mg/L, mutant 5 (LD78 Ser17) –79 mg/L, mutant 30 (LD78 Ser17, Glu18) –138 mg/L, mutant 28 (LD78 Arg29) –169 mg/L). This phenomenon was not restricted to the Pichia system but was also noted with the Saccharomyces system (see Examples 156 and 157).

When production strains containing the demultimerised mutant expression cassettes were grown in fermenters expression levels were again enhanced. Glycerol stock cultures were used to inoculate 500 mL of YEPGlycerol medium in a 2L baffled shake flask. This was grown for 18–24 h at 30° C. in an orbital shaker. This culture was used as an inoculum for the fermenter. The 5L fermenter was prepared as detailed in Example 162. After the batch phase carbon was exhausted a limiting glycerol feed (500 g/L glycerol, 5 mL/L trace elements $PTM_1$, 2 mL/L biotin stock solution 0.2 g/L) was started and run for 3–6 h at 14 g/h. Then the glycerol feed rate was reduced to 10 g/h and a methanol feed (methanol plus 5 mL/L trace elements $PTM_1$ and 2 mL/L biotin stock solution 0.2 g/L) started at 5 g/h. The methanol feed was increased exponentially with time to arrive at a final feed rate of 30 g/h after a total elapsed fermentation time of 75 h. During this period growth conditions were as detailed in Example 162. This process resulted in the production of 1.5 g/L of demultimerised mutant 26 (LD78 Glu28, Glu47) into the fermentation broth, compared with 60–100 mg/L of the wild-type LD78 molecule. Clearly, expression levels may be dependent on the number of expression cassettes integrated into the host chromosome. In order to compare expression levels of demultimerised mutants with those of the wild-type, differences in copy number must be taken into account. The strain producing wild-type LD78 has 4 copies of the expression cassette compared to 42 for the mutant 26 producing strain. Even allowing for this difference, however, mutant 26 is produced at higher than expected levels (3.1 mg/L/copy as opposed to 0.75–1.25 mg/L/copy for wild-type).

This phenomenon of enhanced expression of demultimerised mutants in a fermenter was also observed with the Saccharomyces system (see Example 157).

Example 164

Demultimerised mutants are active in an in vitro receptor binding assay

The effect of the mutations on LD78 biological activity was assessed initially by measuring their ability to displace radio-labelled LD78 from the murine stem cell line FDCP cell mix (A4 cells) (Dexter et al., *J. Exp. Med.* 152 1036 (1980)). The A4 FDCP cell mix cell line is available on request from the Paterson Cancer Research Institute, Department of Haematology, Wilmslow Road, Manchester, M20 9BX, United Kingdom).

The assay procedure is as follows: FDCP-mix A4 cells are diluted with fresh growth medium on the day before use to give $1-2\times10^5$/ml (usually 2–4 fold). On the day of the assay, cells are counted and then harvested by centrifugation. After washing once in serum free medium and once in binding medium, the cells are resuspended at $5\times10^6$/ml in binding medium (RPMI 1640+20 mM HEPES +1 mg/ml BSA). 200 µl of the cell suspension is pipetted into Eppendorf tubes, followed by 25 µl of unlabelled competitor, made up at 10× the required final concentration, and 25 µl label prepared in the same way. The final concentration of labelled ligand used is 0.5 nM, i.e. 3.85 ng/ml. The tubes are incubated on a suspension mixer for 2 hours at room temperature. 1 ml of cold PBS is then added and the tubes centrifuged at 200 rpm.

After washing in 2 further volumes of PBS the cells are finally transferred to vials and the radioactivity measured by counting using a Packard Cobra Auto-Gamma counter. The assay was performed in triplicate, and the binding of $^{125}$I-LD78 in the presence of excess cold LD78 or LD78 mutant was compared to binding in the absence of cold material.

LD78 or LD78 mutant was diluted in binding medium to provide a range of concentrations. Routinely, concentrations of 3.85 μg/ml and 0.385 μg/ml were prepared, which following a ten-fold dilution into the assay, yielded concentrations of cold material that were 100- and 10-fold the concentration of $^{125}$I-LD78 respectively. $^{125}$I-LD78 was prepared by Amersham plc.

For more detailed characterisation of selected variants, a range of sample concentrations from 0.01–100 ng/ml was employed to construct a detailed dose response curve. To ensure comparability between assays, the activity of LD78 variants was expressed as percentage of the wild-type activity based on IC50 values. Wild-type LD78 was always included as a control. Thus wild-type activity is represented as 100%; a variant that with an IC50 ten times that of wild-type as 10% (i.e. binds the receptor 1/10 as well) and a variant with an IC50 ½ that of wild-type as 200% (i.e. binds the receptor twice as well).

The receptor binding data for 53 LD78 variants are shown in Table 2, along with a summary of the relevant physicochemical data relating to their multimerisation state.

TABLE 2

BIOLOGICAL ACTIVITY OF SCI MUTANTS

| Mutant No. | Residue No. | Mutation | Size on Native Gel | AUC [mean] | Structure | Receptor Binding | % WT |
|---|---|---|---|---|---|---|---|
| 0 | | LD78 | WT | 160 | Wt | 1 | 100 |
| 1 | 48 | Gln>Glu | Large? | 400 | Wt | 2 | |
| 2 | 44 | Lys>Glu | Small | 16 | D | 4 | 5 |
| | 45 | Arg>Gln | | | | | |
| 5 | 17 | Arg>Ser | Mixed | 57.5 | T/Do | 2 | 25 |
| 10 | 26 | Asp>Ala | Small | 35 | T | 1 | 77.4 |
| 11 | 12 | Phe>Gln | Mixed | 98 | T/Do | 1 | 34 |
| 26 | 28 | Phe>Glu | Small | 16 | D | 4 | 1 |
| | 47 | Arg>Glu | | | | | |
| 28 | 29 | Glu>Arg | Small | | T | 2 | 7.7 |
| 29 | 18 | Gln>Glu | Small | 130 | Do | 1 | |
| 30 | 17 | Arg>Ser | Small | 41 | T | 3 | 4.2 |
| | 18 | Gln>Glu | | | | | |
| 35 | -3 | >Leu | WT | 155 | Wt | 4 | 3 |
| | -2 | >Ser | | | | | |
| | -1 | >Ala | | | | | |
| | 1 | Ser>Pro | | | | | |
| | 38 | Gly>Ser | | | | | |
| | 46 | Ser>Gly | | | | | |
| 37 | 5 | Asp>Ser | WT | | Wt | 1 | 45 |
| 38 | 24 | Ile>Ala | WT | | Wt | 1 | 50 |
| 40 | 29 | Glu>Ser | WT | | | 4 | |
| 42 | 44 | Lys>Ser | Small | 45 | T/Do | 1 | 18 |
| 43 | 45 | Arg>Ser | Small | 25 | T | 3 | |
| 45 | 52 | Asp>Ser | WT | | | 4 | |
| 48 | 60 | Lys>Ser | WT | | | 1 | |
| 52 | 66 | Glu>Ser | Large | 27 | T | 1 | 161.5 |
| 54 | 1 | Ser>Ala | WT | | | 1 | 145 |
| 60 | 8 | Thr>Ala | WT | | | 1 | |
| 62 | 13 | Ser>Ala | Large | 370 | Wt | 1 | 66 |
| 63 | 16 | Ser>Ala | WT | | | 3 | |
| 64 | 18 | Gln>Ser | Large | 200 | Wt | 4 | |
| 66 | 27 | Tyr>Ala | WT | | | 2 | 47 |
| 68 | 35 | Ser>Ala | WT | | Wt | 1 | 125 |
| 70 | 48 | Gln>Ser | Mixed | | | 2 | |
| 71 | 53 | Pro>Ala | WT | | | 3 | |
| 75 | 67 | Leu>Ala | WT | | | 1 | |
| 77 | 12 | Phe>Ala | Small | 150 | | 3 | |
| 79 | 15 | Thr>Ala | Small | 180 | | 1 | |
| 82 | 22 | Asn>Ser | WT | | | 1 | |
| 84 | 25 | Ala>Ser | WT | | | 1 | |
| 85 | 28 | Phe>Ala | WT | | | 3 | |
| 87 | 31 | Ser>Ala | WT | | | 3 | |
| 94 | 42 | Leu>Ala | WT | | | 1 | |
| 97 | 51 | Ala>Ser | Mixed | | | 2 | |

TABLE 2-continued

BIOLOGICAL ACTIVITY OF SCI MUTANTS

| Mutant No. | Residue No. | Mutation | Size on Native Gel | AUC [mean] Structure | Receptor Binding | % WT |
|---|---|---|---|---|---|---|
| 101 | 26 | Asp>Ala | WT | | 2 | |
| | 29 | Glu>Arg | | | | |
| 102 | 26 | Asp>Ala | Small | | 4 | |
| | 29 | Glu>Arg | | | | |
| | 47 | Arg>Glu | | | | |

KEY:
AUC = Analytical Ultra Centrifugation (kDa)
Receptor Binding:
1 = Wild-type
2 = $\frac{1}{10}$ to $\frac{1}{2}$ Wt
3 = $\frac{1}{100}$–$\frac{1}{10}$ Wt
4 = Inactive
T = Tetramer
T/Do = Tetramer/Dodecamer equilibrium
D = Dimer
WT = Wild type The following facts emerge from this analysis:
1) The majority of the variants with wild-type or minimally affected multimerisation properties exhibit wild-type or close to wild-type receptor binding.
2) There is a clear subset of variants which, though wild-type with respect to size, are clearly affected in their ability to compete with wild-type LD78 for receptor binding. The mutations in these variants presumably define the residues involved in interacting with the receptor. These key residues include Lys-44, Arg-45, Arg-17, Gln-18, Phe-28 and Glu-29.
3) Most of the de-multimerised variants appear to be compromised in receptor binding. This implies either that the residues involved in multimerisation are also involved in receptor binding, or that receptor binding requires a multimeric form of LD78. Wild-type receptor binding activity has not been seen in variants smaller than a tetramer. This is summarised in FIG. 19. The numerals refer to the number of mutants found in each category. Mutants shown lying between the tetramer and dodecamer positions represent an equilibrium between the two states.
4) Variants in which the N terminus of LD78 are extended show greatly diminished ability to compete for receptor binding. Surprisingly, these include the forms of LD78 described previously such as in variant #35 (WO-A-9104274) and variant #34 (JP-A-03228683). In contrast, deletion of N-terminal residues appears to have minimal effect on receptor binding. The other N-terminal form described in the literature (Pragnell et al., CRC Beatson Laboratories Scientific Report, Beatson Institute for Cancer Research, Glasgow, Scotland) does not express in the yeast expression systems described in this application.
5) The residues implicated in receptor binding map to two defined regions on the surface of the LD78 model described above. One region flanks the N-terminal serine and includes residues in the β-turn around residues 44–48 (Lys-Arg-Ser-Arg-Gln).

Taken together, these data suggest that the active form of LD78 is a tetramer. FIG. 20 shows a view of the model of tetrameric LD78, showing the dramatic clustering of residues implicated in receptor binding. In this model of LD78 structure and function, mutations at the interface between dimers exert their effect on receptor binding indirectly, by disrupting the formation of the active, tetrameric species. A second implication of this model is that the N-terminal extended forms of LD78 are probably inactive proforms of the molecule, at least as regards the receptor present on A4 cells.

Both of these conclusions are surprising in view of the prior art. In WO-A-9104274 the N-termini of the LD78 forms they describe was not defined. The material was apparently biologically active, perhaps as a result of processing by proteases present in their in vitro assay of colony formation, or in view of the high concentrations of material used.

Although the active species of the SCI family of molecules has been a matter for speculation, it was recently asserted that for LD78 the active species is a monomer (Mantel et al., (1992), loc. cit.). This was based on the observation that *E. coli*-derived LD78, disaggregated in 30% acetonitrile & 0.1% TFA, was 1000-fold more active in various in vitro colony forming unit assays on the haematosis lineage precursors BFU-E and GM-CFC cells. We can only speculate that this large difference reflects a problem with the activity of the aggregated *E. coli* derived material.

Example 165

Demultimerised mutants can inhibit the proliferation of haemopoietic progenitor cells (Day 12 CFU-S)

The ability of mutant #10 (Example 7) to inhibit the formation of murine day 12 CFU-S cell colonies was measured in vitro according to the following method. The activity was compared to that of mutant #82 (Example 94), which is wild-type with respect to structure and receptor binding.

Day 12 CFU-S cells were sorted from normal murine bone marrow cells as described in Lord and Spooncer (1986) *Lymphokine Research* 5:59–72. Sorted cells (between 500–1000) were plated in soft agar and assayed for their colony forming ability according to the method described in Heyworth and Spooncer (1992) in "Haemopoiesis—A Practical Approach" page 37 IRL Press (Testa and Molineux, Eds).

Growth factors were supplied from conditioned medium of L cells and AF1-19T cells. Each of the conditioned media was used at 10% as described in Pragnell et al., (1988) *Blood* 72:196–201. LD78 mutant 10 or 82 was added at 150 ng/ml, 15 ng/ml, 1.5 ng/ml or 0.15 ng/ml to the top agar in 10 μl of PBS and allowed to diffuse through the plate. The plates were then incubated at 37° C. in 5% $O_2$, 5% $CO_2$ for 14 days. Colonies were counted with an inverted microscope. All assays were run in triplicate. 150 ng/ml of LD78 wild type protein of Preparations 1 to 4 and PBS were used as controls in this experiment.

Results were expressed as a percentage of the control treated with carrier PBS alone. The Mutant 10 used in this assay will inhibit colony formation fo day 12 CFU-S cells at concentrations down to 1.5 ng/ml. Both mutant 10 (FIG. 24) and 82 (FIG. 25) show similar potency with optimum inhibitors at 15 ng/ml. This shows that a demultimerised variant can exert functional effects as well as binding to the receptor.

Appendix A
Media recipes
BMGC
Quantities per liter:

| | |
|---|---|
| Sodium phosphate buffer 1M, pH 6 | 100 mL |
| Casamino acids (100 g/L) | 100 mL |
| Yeast Nitrogen Base (13.4 g/L) | 100 mL |
| Biotin (0.2 g/L) | 2 mL |
| Glycerol | 10 mL |

Filter sterilise
BMMC
As above but replace glycerol with 5 mL of methanol.
YEPD

| | |
|---|---|
| Yeast extract | 10 g/L |
| Peptone | 20 g/L |
| Glucose | 10 g/L |

For solid medium add 15 g/L agar
Autoclave at 121° C. 15 mins
YEPGlycerol
As above but replace glucose with glycerol
HCD

| | |
|---|---|
| $H_3PO_4$ (85%) | 21 mL/L |
| $CaSO_4.H_2O$ | 0.9 g/L |
| $K_2SO_4$ | 14.28 g/L |
| $MgSO_4.7H_2O$ | 11.7 g/L |
| KOH | 3.9 g/L |
| Glycerol | 50 g/L | pH is about 1.7 when made up. Bring pH to 4 in the fermentor with ammonia solution (prior to sterilization). Sterilize in the fermentor and bring pH to 5.85 with ammonia solution prior to inoculation.

To the 3.5L of medium in the fermentor add 10 mL of the following trace element solution ($PTM_1$)

| | |
|---|---|
| $CuSO_4.5H_2O$ | 6 g/L |
| KI | 0.8 g/L |
| $MnSO_4.H_2O$ | 3.0 g/L |
| $NaMoO_4.2H_2O$ | 0.2 g/L |
| $H_3BO_3$ | 0.02 g/L |
| $CoCl_2.6H_2O$ | 0.5 g/L |
| $ZnSO_4$ | 20 g/L |
| $H_2SO_4$ | 5 mL/L |
| $FeSO_4.7H_2O$ | 65 g/L |
| Biotin | 0.2 g/L |

MD

| | |
|---|---|
| Yeast nitrogen base | 13.4 g/L |
| Biotin | 0.4 g/L |
| Glucose | 20 g/L |

Filter sterilise
For solid medium add 15 g/L agar
Transformation buffers and reagents
SED

| | | |
|---|---|---|
| Sorbitol | | 1 M |
| EDTA | (pH 8) | 25 mM |
| DTT | | 50 mM (add just prior to use) |

SCE

| | |
|---|---|
| Sorbitol | 1 M |
| EDTA | 1 mM |
| Sodium citrate buffer pH 5.8 | 10 mM |

CAS

| | |
|---|---|
| Sorbitol | 1 M |
| Tris-Cl pH 7.5 | 10 mM |
| $CaCl_2$ | 10 mM |

PEG solution

| | |
|---|---|
| PEG 3350 | 200 g/L |
| Tris-Cl pH 7.5 | 10 mM |
| $CaCl_2$ | 10 mM |

Prepare fresh and filter sterilise. Discard if pH is below 7.
SOS

| | |
|---|---|
| Sorbitol | 1 M |
| YEPD | ×0.3 |
| $CaCl_2$ | 10 mM |

Regeneration medium (RD)

| | |
|---|---|
| Sorbitol | 186 g/L |
| Agarose | 10 g/L |
| Glucose | 20 g/L |

-continued

| Yeast nitrogen base | 1.34 g/L |
| Biotin | 400 ug/L |
| Histidine assay medium* | 2 g/L |
| Glutamic acid | 50 mg/L |
| Methionine | 50 mg/L |
| Lysine | 50 mg/L |
| Leucine | 50 mg/L |
| Isoleucine | 50 mg/L |

*DIFCO Ltd

For base plates use agarose at 20 g/L

ADDITIONAL REFERENCES

Clare et al. BIO/TECHNOLOGY, 9, 455–460, (1991).
Clore et al., J. Biol. Chem., 264, 18907–18911, (1989).
Clore et al., Biochemistry, 29, 1689–1696, (1990).
Clore & Gronenbom, J. Mol. Biol., (1991).
Creeth & Harding J. Biochem. Biophys. Methods, 7, 25–34 (1982)
Creeth & Pain Prog. Biophys. Mol. Biol. 17 217–287 (1967).
Dodson, Meeting Abstracts, Prospects in Protein Engineering, Groningen, Netherlands, 49–53, (1989).
Graham et al, Nature (London), 344, 442-, (1990).
Gronenbom & Clore, Protein Engineering, 4, 263–269, (1991).
Harding et al Ed.s, Analytical Ultracentrifugation in Biochemistry and Polymer Science, Royal Society Of Chemistry Press (Cambridge), (1992)
Lackowitz, Principles of Fluorescence Microscopy, Plenum. Pub. (New York) (1983).
Lord et al, Brit. J. Haematol., 34, 441-, (1976).
Lord & Wright, Blood Cells, 6, 581-, (1980).
Mantel et al., Expt. Haematol. 20: No. 368 800 (1992).
Mayo & Chen, Biochemistry, 28, 9469–9478, (1989).
Moore et al., Biochim. Biophys. Acta., 379, 379–384, (1975).
Morgan et al., Beckman OPTIMA XL-A Technical Bulletin, (1992).
Oh et al, J. Immunology, 147, 2978–2983, (1991).
Provencher, Comput. Phys. Commun., 27, 229–242, (1982).
Provencher & Gloeckner, Biochemistry, 20, 33–37, (1981).
Schall, Cytokine, 3, 165–183 (1991).
Sherry et al, J. Exp. Med., 168, 2251-, (1988).
St. Charles et al., J. Biol. Chem., 264, 2092–2099, (1989).
Strickland, C. R. C. Crit. Rev. Biochem., 2, 133–175, (1974).
Wingfield et al, Eur. J. Biochem., 173, 65–72, (1988). Patent number AU-B-63882/86
Wolpe and Cerami, FASEB, J. 3 2565–2573 (1989)
Yphantis, Biochemistry, 3, 297–317, (1964)

We claim:

1. A proteinaceous molecule comprising an LD78 or MIP-1α analogue with stem cell inhibition (SCI) activity, the molecule being an analogue of a wild-type LD78 molecule or MIP-1α molecule, the analogue being substantially incapable at physiological ionic strength of forming a stable multimer higher than a dodecamer as determined by Sedimentation Equilibrium Analytical Ultracentrifugation (AUC).

2. A molecule as claimed in claim 1, in which, relative to the wild-type LD78 or MIP-1α molecule, one or more amino acid residues involved in promoting and/or stabilizing association of the components of a dimeric, tetrameric, dodecameric or higher order complex is altered to have a lesser promoting and/or stabilizing effect.

3. A molecule as claimed in claim 2, wherein the alteration is a substitution.

4. A molecule as claimed in claim 1, which is substantially incapable at physiological ionic strength of forming a stable multimer higher than a tetramer.

5. A molecule as claimed in claim 1, which is substantially incapable at physiological ionic strength of forming a stable multimer higher than a dimer.

6. A molecule as claimed in claim 1, which is substantially incapable at physiological ionic strength of forming a stable multimer higher than a monomer.

7. A composition comprising a proteinaceous molecule as claimed in claim 1 and a pharmaceutically acceptable carrier.

8. A process for producing a proteinaceous molecule as claimed in claim 1 comprising expressing nucleic acid coding for said proteinaceous molecule in a S. cerevisiae host cell containing said nucleic acid and under conditions to produce said proteinaceous molecule.

9. A process for producing a proteinaceous molecule as claimed in claim 1 comprising expressing nucleic acid coding for said proteinaceous molecule in a P. pastoris host cell containing said nucleic add and under conditions to produce said proteinaceous molecule.

10. A proteinaceous molecule with stem cell inhibition (SCI) activity, the molecule being an analogue of a chemotactic cytokine superfamily molecule having SCI activity and a tendency to aggregate at physiological ionic strength, the analogue being substantially incapable at physiological ionic strength of forming a stable multimer higher than a dodecamer as determined by Sedimentation Equilibrium Analytical Ultracentrifugation (AUC), wherein the analogue is an LD78 analogue with a mutation at one or more of the amino acid residues with respect to wild-type LD78 selected from the group consisting of: Ser1, Leu2, Ala3, Ala4, Asp5, Thr6, Ala9, Phe12, Ser13, Tyr14, Ser16, Arg17, Gln18, Ile19, Pro20, Gln21, Phe23, Ile24, Asp26, Tyr27, Phe28, Glu29, Ser31, Ser32, Gln33, Ser35, Lys36, Pro37, Gly38, Val39, Ile40, Leu42, Thr43, Lys44, Arg45, Ser46, Arg47, Gln48, Asp52, Glu55, Glu56, Gln59, Lys60, Tyr61, Val62, Asp64, Leu65, Glu66, Leu67, Ser68 and Ala69.

11. A molecule as claimed in claim 10, wherein there are only two mutation substitutions.

12. A proteinaceous molecule with stem cell inhibition (SCI) activity, the molecule being an analogue of a chemotactic cytokine superfamily molecule having SCI activity and a tendency to aggregate at physiological ionic strength, the analogue being substantially incapable at physiological ionic strength of forming a stable multimer higher than a dodecamer as determined by Sedimentation Equilibrium Analytical Ultracentrifugation (AUC), wherein the analogue is an LD78 analogue and has at least one of the following substitutions with respect to wild-type LD78, wherein the substitutions are selected from the group consisting of: Ile24>Asn, Tyr27>Asn, Phe28>Glu, Glu29>Arg, Lys44>Glu and Arg 45>Glu.

13. A molecule as claimed in claim 12, wherein the analogue possesses both Lys44>Glu and Arg45>Gln substitutions.

14. A proteinaceous molecule with stem cell inhibition (SCI) activity, the molecule being an analogue of a chemotactic cytokine superfamily molecule having SCI activity and a tendency to aggregate at physiological ionic strength, the analogue being substantially incapable at physiological ionic strength of forming a stable multimer higher than a dodecamer as determined by Sedimentation Equilibrium Analytical Ultracentrifugation (AUC), wherein the analogue is an LD78 analogue and has at least one of the following substitutions with respect to wild-type LD78, wherein the substitutions are selected from the group consisting of: Lys44>Glu with Arg45>Gln, Arg47>Glu, Phe28>Glu, Phe28>Glu with Gln48>Glu, Phe28>Glu with Arg47>Glu, Arg17>Ser with Gln18>Glu, Phe12>Ala, Val39>Ala, Ile40>Ala, Asp26>Ala with Glu29>Arg and Arg47>Glu, Arg17>Ser, Glu29>Arg, Gln18>Glu, Asp26>Ser, Gln48>Ser, Thr15>Ala, Gln21>Ser, Phe23>Ala, Ser32>Ala, Ala51>Ser, Ala4>Glu, Phe12>Asp, Asp26>Gln, Lys36>Glu, Lys44>Glu, Arg45>Glu, Glu66>Gln, Phe12>Gln, Lys44>Ser, Arg17>Glu with Gln18>Glu, Asp26>Ala, Glu66>Ser, Ile19>Ala.

15. A molecule as claimed in claim 14, which is an LD78 analogue having the following substitution with respect to wild-type LD78: Asp26>Ala.

16. A molecule as claimed in claim 14, which is an LD78 analogue having the following substitution with respect to wild-type LD78:Glu66>Ser.

17. A molecule as claimed in claim 14, which is an LD78 analogue having both the following substitution with respect to wild-type LD78: Ile19>Ala and Val39>Ala.

18. A proteinaceous molecule with stem cell inhibition (SCI) activity, the molecule being an analogue of a chemotactic cytokine superfamily molecule having SCI activity and a tendency to aggregate at physiological ionic strength, the analogue being substantially incapable at physiological ionic strength of forming a stable multimer higher than a dodecamer as determined by Sedimentation Equilibrium Analytical Ultracentrifugation (AUC), wherein the analogue is an LD78 analogue with a substitution mutation of asparagine to alanine at amino acid residues 26 with respect to wild-type LD78.

19. A proteinaceous molecule with stem cell inhibition (SCI) activity, the molecule being an analogue of a chemotactic cytokine superfamily molecule having SCI activity and a tendency to aggregate at physiological ionic strength, the analogue being substantially incapable at physiological ionic strength of forming a stable multimer higher than a dodecamer as determined by Sedimentation Equilibrium Analytical Ultracentrifugation (AUC), wherein the analogue is an MIP-1α analogue with a mutation at one or more of the amino acid residues with respect to wild-type MIP-1α selected from the group consisting of: Ala1, Pro2, Tyr3, Gly4, Ala5, Asp6, Thr7, Ala10, Phe13, Ser14, Tyr15, Ser16, Arg17, Lys18, Ile19, Pro20, Arg21, Phe23, Ile24, Asp26, Phe28, Glu29, Ser31, Ser32, Leu33, Ser35, Gln36, Pro37, Gly38, Val39, Ile40, Leu42, Thr43, Lys44, Arg45, Asn46, Arg47, Gln48, Asp52, Glu55, Thr56, Gln59, Glu60, Tyr61, Ile62, Asp64, Leu65, Glu66, Leu67, Asn68 and Ala69.

20. A molecule as claimed in claim 19, wherein there are only two mutation substitutions.

21. A nucleic acid coding for a proteinaceous molecule as claimed in claim 1.

22. A vector comprising the nucleic acid as claimed in claim 21, which is recombinant DNA.

23. A host cell transfected or transformed with a vector as claimed in claim 22.

* * * * *

SEQUENCE LISTING (1) GENERAL INFORMATION:

(iii) NUMBER OF SEQUENCES: 178

(2) INFORMATION FOR SEQ ID NO:1:

(i) SEQUENCE CHARACTERISTICS:
      (A) LENGTH: 229 base pairs
      (B) TYPE: nucleic acid
      (C) STRANDEDNESS: double
      (D) TOPOLOGY: linear (ii) MOLECULE TYPE: DNA (genomic)

(iii) ANTI-SENSE: NO (ix) FEATURE:
      (A) NAME/KEY: CDS
      (B) LOCATION: 1..229
      (D) OTHER INFORMATION: /codon_start= 1
          /product= "LD78 SYNTHTIC GENE"

(ix) FEATURE:
      (A) NAME/KEY: 3'UTR
      (B) LOCATION: 223..225
      (D) OTHER INFORMATION: /function= "NON-TRANSLATED STOP CODON"

(ix) FEATURE:
      (A) NAME/KEY: 3'UTR
      (B) LOCATION: 226..228
      (D) OTHER INFORMATION: /function= "NON-TRANSLATED STOP CODON"

(xi) SEQUENCE DESCRIPTION: SEQ ID NO:1:

```
AGC TTG GAT AAA AGA TCC TTG GCT GCT GAC ACT CCA ACC GCT TGT TGT        48
Ser Leu Asp Lys Arg Ser Leu Ala Ala Asp Thr Pro Thr Ala Cys Cys
 1               5                  10                  15

TTC TCT TAC ACC TCT AGA CAA ATT CCA CAA AAT TTC ATT GCT GAC TAC        96
Phe Ser Tyr Thr Ser Arg Gln Ile Pro Gln Asn Phe Ile Ala Asp Tyr
```

```
                    20                  25                  30
TTT GAA ACT TCT TCT CAA TGT TCC AAG CCA GGT GTC ATC TTC TTG ACT      144
Phe Glu Thr Ser Ser Gln Cys Ser Lys Pro Gly Val Ile Phe Leu Thr
        35                  40                  45

AAG CGC TCG AGA CAA GTC TGT GCT GAC CCA TCT GAA GAA TGG GTT CAA      192
Lys Arg Ser Arg Gln Val Cys Ala Asp Pro Ser Glu Glu Trp Val Gln
 50                  55                  60

AAA TAT GTT TCT GAC TTG GAA TTG TCT GCC TAA TAA G                    229
Lys Tyr Val Ser Asp Leu Glu Leu Ser Ala
 65                  70
```

(2) INFORMATION FOR SEQ ID NO:2:

(i) SEQUENCE CHARACTERISTICS:
        (A) LENGTH: 69 amino acids
        (B) TYPE: amino acid
        (D) TOPOLOGY: linear (ii) MOLECULE TYPE: protein (xi) SEQUENCE DESCRIPTION: SEQ ID NO:2:

```
Ser Leu Ala Ala Asp Thr Pro Thr Ala Cys Cys Phe Ser Tyr Thr Ser
 1               5                  10                  15

Arg Gln Ile Pro Gln Asn Phe Ile Ala Asp Tyr Phe Glu Thr Ser Ser
            20                  25                  30

Gln Cys Ser Lys Pro Gly Val Ile Phe Leu Thr Lys Arg Ser Arg Gln
        35                  40                  45

Val Cys Ala Asp Pro Ser Glu Glu Trp Val Gln Lys Tyr Val Ser Asp
 50                  55                  60

Leu Glu Leu Ser Ala
 65
```

(2) INFORMATION FOR SEQ ID NO:3:

(i) SEQUENCE CHARACTERISTICS:
        (A) LENGTH: 229 base pairs
        (B) TYPE: nucleic acid
        (C) STRANDEDNESS: double
        (D) TOPOLOGY: linear (ii) MOLECULE TYPE: DNA (iii) ANTI-SENSE: YES (xi) SEQUENCE DESCRIPTION: SEQ ID NO:3:

```
CTTATTAGGC AGACAATTCC AAGTCAGAAA CATATTTTTG AACCCATTCT TCAGATGGGT     60

CAGCACAGAC TTGTCTCGAG CGCTTAGTCA AGAAGATGAC ACCTGGCTTG GAACATTGAG    120

AAGAAGTTTC AAAGTAGTCA GCAATGAAAT TTTGTGGAAT TTGTCTAGAG GTGTAAGAGA    180

AACAACAAGC GGTTGGAGTG TCAGCAGCCA AGGATCTTTT ATCCAAGCT                229
```

(2) INFORMATION FOR SEQ ID NO:4:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..45
        (D) OTHER INFORMATION: /product= "OLIGOMER FOR

CONSTRUCTION OF SYNTHETIC LD78 GENE"

(xi) SEQUENCE DESCRIPTION: SEQ ID NO:4:

AGCTTGGATA AAAGATCCTT GGCTGCTGAC ACTCCAACCG CTTGT                45

(2) INFORMATION FOR SEQ ID NO:5:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..48
        (D) OTHER INFORMATION: /product= "OLIGOMER FOR
            CONSTRUCTION OF SYNTHETIC LD78 GENE"

(xi) SEQUENCE DESCRIPTION: SEQ ID NO:5:

AGAAACAACA AGCGGTTGGA GTGTCAGCAG CCAAGGATCT TTTATCCA              48

(2) INFORMATION FOR SEQ ID NO:6:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..50
        (D) OTHER INFORMATION: /product= "OLIGOMER FOR
            CONSTRUCTION OF SYNTHETIC LD78 GENE"

(xi) SEQUENCE DESCRIPTION: SEQ ID NO:6:

TGTTTCTCTT ACACCTCTAG ACAAATTCCA CAAAATTTCA TTGCTGACTA            50

(2) INFORMATION FOR SEQ ID NO:7:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..50
        (D) OTHER INFORMATION: /product= "OLIGOMER FOR
            CONSTRUCTION OF SYNTHETIC LD78 GENE"

(xi) SEQUENCE DESCRIPTION: SEQ ID NO:7:

TTCAAAGTAG TCAGCAATGA AATTTTGTGG AATTTGTCTA GAGGTGTAAG            50

(2) INFORMATION FOR SEQ ID NO:8:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (ix) FEATURE:
   (A) NAME/KEY: misc_feature
   (B) LOCATION: 1..48
   (D) OTHER INFORMATION: /product= "OLIGOMER FOR
       CONSTRUCTION OF LD78 SYNTHETIC GENE"

(xi) SEQUENCE DESCRIPTION: SEQ ID NO:8:

CTTTGAAACT TCTTCTCAAT GTTCCAAGCC AGGTGTCATC TTCTTGAC            48

(2) INFORMATION FOR SEQ ID NO:9:

(i) SEQUENCE CHARACTERISTICS:
       (A) LENGTH: 48 base pairs
       (B) TYPE: nucleic acid
       (C) STRANDEDNESS: single
       (D) TOPOLOGY: linear (ii) MOLECULE TYPE: DNA (ix) FEATURE:
       (A) NAME/KEY: misc_feature
       (B) LOCATION: 1..48
       (D) OTHER INFORMATION: /product= "OLIGOMER FOR
           CONSTRUCTION OF SYNTHETIC LD78 GENE"

(xi) SEQUENCE DESCRIPTION: SEQ ID NO:9:

GCGCTTAGTC AAGAAGATGA CACCTGGCTT GGAACATTGA GAAGAAGT            48

(2) INFORMATION FOR SEQ ID NO:10:

(i) SEQUENCE CHARACTERISTICS:
       (A) LENGTH: 46 base pairs
       (B) TYPE: nucleic acid
       (C) STRANDEDNESS: single
       (D) TOPOLOGY: linear (ii) MOLECULE TYPE: DNA (ix) FEATURE:
       (A) NAME/KEY: misc_feature
       (B) LOCATION: 1..46
       (D) OTHER INFORMATION: /product= "OLIGOMER FOR THE
           CONSTRUCTION OF LD78 SYNTHETIC GENE"

(xi) SEQUENCE DESCRIPTION: SEQ ID NO:10:

TAAGCGCTCG AGACAAGTCT GTGCTGACCC ATCTGAAGAA TGGGTT              46

(2) INFORMATION FOR SEQ ID NO:11:

(i) SEQUENCE CHARACTERISTICS:
       (A) LENGTH: 46 base pairs
       (B) TYPE: nucleic acid
       (C) STRANDEDNESS: single
       (D) TOPOLOGY: linear (ii) MOLECULE TYPE: DNA (ix) FEATURE:
       (A) NAME/KEY: misc_feature
       (B) LOCATION: 1..46
       (D) OTHER INFORMATION: /product= "OLIGOMER FOR
           CONSTRUCTION OF SYNTHETIC LD78 GENE"

(xi) SEQUENCE DESCRIPTION: SEQ ID NO:11:

ATTTTTGAAC CCATTCTTCA GATGGGTCAG CACAGACTTG TCTCGA              46

(2) INFORMATION FOR SEQ ID NO:12:

(i) SEQUENCE CHARACTERISTICS:
       (A) LENGTH: 40 base pairs (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..40
        (D) OTHER INFORMATION: /product= "OLIGOMER FOR
             CONSTRUCTION OF SYNTHETIC LD78 GENE"

(xi) SEQUENCE DESCRIPTION: SEQ ID NO:12:

CAAAAATATG TTTCTGACTT GGAATTGTCT GCCTAATAAG                    40

(2) INFORMATION FOR SEQ ID NO:13:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..37
        (D) OTHER INFORMATION: /product= "OLIGOMER FOR
             CONSTRUCTION OF SYNTHETIC LD78 GENE"

(xi) SEQUENCE DESCRIPTION: SEQ ID NO:13:

GATCCTTATT AGGCAGACAA TTCCAAGTCA GAAACAT                       37

(2) INFORMATION FOR SEQ ID NO:14:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

GTTTTCCCAG TCACGAC                                             17

(2) INFORMATION FOR SEQ ID NO:15:

(i) SEQUENCE CHARACTERISTICS:
        (A) LENGTH: 7859 base pairs
        (B) TYPE: nucleic acid
        (C) STRANDEDNESS: double
        (D) TOPOLOGY: circular (ii) MOLECULE TYPE: DNA (xi) SEQUENCE DESCRIPTION: SEQ ID NO:15:

TTCCCATGTC TCTACTGGTG GTGGTGCTTC TTTGGAATTA TTGGAAGGTA AGGAATTGCC     60

AGGTGTTGCT TTCTTATCCG AAAAGAAATA AATTGAATTG AATTGAAATC GATAGATCAA    120

TTTTTTTCTT TTCTCTTTCC CCATCCTTTA CGCTAAAATA ATAGTTTATT TTATTTTTTG    180

AATATTTTTT ATTTATATAC GTATATATAG ACTATTATTT ACTTTTAATA GATTATTAAG    240

ATTTTTATTA AAAAAAAATT CGTCCCTCTT TTTAATGCCT TTTATGCAGT TTTTTTTTCC    300

CATTCGATAT TTCTATGTTC GGGTTTCAGC GTATTTTAAG TTTAATAACT CGAAAATTCT    360

GCGTTTCGAA AAAGCTCTGC ATTAATGAAT CGGCCAACGC GCGGGGAGAG GCGGTTTGCG    420

-continued

```
TATTGGGCGC TCTTCCGCTT CCTCGCTCAC TGACTCGCTG CGCTCGGTCG TTCGGCTGCG      480

GCGAGCGGTA TCAGCTCACT CAAAGGCGGT AATACGGTTA TCCACAGAAT CAGGGGATAA      540

CGCAGGAAAG AACATGTGAG CAAAAGGCCA GCAAAAGGCC AGGAACCGTA AAAAGGCCGC      600

GTTGCTGGCG TTTTTCCATA GGCTCCGCCC CCCTGACGAG CATCACAAAA ATCGACGCTC      660

AAGTCAGAGG TGGCGAAACC CGACAGGACT ATAAAGATAC CAGGCGTTTC CCCCTGGAAG      720

CTCCCTCGTG CGCTCTCCTG TTCCGACCCT GCCGCTTACC GGATACCTGT CCGCCTTTCT      780

CCCTTCGGGA AGCGTGGCGC TTTCTCATAG CTCACGCTGT AGGTATCTCA GTTCGGTGTA      840

GGTCGTTCGC TCCAAGCTGG GCTGTGTGCA CGAACCCCCC GTTCAGCCCG ACCGCTGCGC      900

CTTATCCGGT AACTATCGTC TTGAGTCCAA CCCGGTAAGA CACGACTTAT CGCCACTGGC      960

AGCAGCCACT GGTAACAGGA TTAGCAGAGC GAGGTATGTA GGCGGTGCTA CAGAGTTCTT     1020

GAAGTGGTGG CCTAACTACG GCTACACTAG AAGGACAGTA TTTGGTATCT GCGCTCTGCT     1080

GAAGCCAGTT ACCTTCGGAA AAAGAGTTGG TAGCTCTTGA TCCGGCAAAC AAACCACCGC     1140

TGGTAGCGGT GGTTTTTTTG TTTGCAAGCA GCAGATTACG CGCAGAAAAA AAGGATCTCA     1200

AGAAGATCCT TTGATCTTTT CTACGGGGTC TGACGCTCAG TGGAACGAAA ACTCACGTTA     1260

AGGGATTTTG GTCATGAGAT TATCAAAAAG GATCTTCACC TAGATCCTTT TAAATTAAAA     1320

ATGAAGTTTT AAATCAATCT AAAGTATATA TGAGTAAACT TGGTCTGACA GTTACCAATG     1380

CTTAATCAGT GAGGCACCTA TCTCAGCGAT CTGTCTATTT CGTTCATCCA TAGTTGCCTG     1440

ACTCCCCGTC GTGTAGATAA CTACGATACG GGAGGGCTTA CCATCTGGCC CCAGTGCTGC     1500

AATGATACCG CGAGACCCAC GCTCACCGGC TCCAGATTTA TCAGCAATAA ACCAGCCAGC     1560

CGGAAGGGCC GAGCGCAGAA GTGGTCCTGC AACTTTATCC GCCTCCATCC AGTCTATTAA     1620

TTGTTGCCGG GAAGCTAGAG TAAGTAGTTC GCCAGTTAAT AGTTTGCGCA ACGTTGTTGC     1680

CATTGCTACA GGCATCGTGG TGTCACGCTC GTCGTTTGGT ATGGCTTCAT TCAGCTCCGG     1740

TTCCCAACGA TCAAGGCGAG TTACATGATC CCCCATGTTG TGCAAAAAAG CGGTTAGCTC     1800

CTTCGGTCCT CCGATCGTTG TCAGAAGTAA GTTGGCCGCA GTGTTATCAC TCATGGTTAT     1860

GGCAGCACTG CATAATTCTC TTACTGTCAT GCCATCCGTA AGATGCTTTT CTGTGACTGG     1920

TGAGTACTCA ACCAAGTCAT TCTGAGAATA GTGTATGCGG CGACCGAGTT GCTCTTGCCC     1980

GGCGTCAACA CGGGATAATA CCGCGCCACA TAGCAGAACT TTAAAAGTGC TCATCATTGG     2040

AAAACGTTCT TCGGGGCGAA AACTCTCAAG GATCTTACCG CTGTTGAGAT CCAGTTCGAT     2100

GTAACCCACT CGTGCACCCA ACTGATCTTC AGCATCTTTT ACTTTCACCA GCGTTTCTGG     2160

GTGAGCAAAA ACAGGAAGGC AAAATGCCGC AAAAAAGGGA ATAAGGGCGA CACGGAAATG     2220

TTGAATACTC ATACTCTTCC TTTTTCAATA TTATTGAAGC ATTTATCAGG GTTATTGTCT     2280

CATGAGCGGA TACATATTTG AATGTATTTA GAAAAATAAA CAAATAGGGG TTCCGCGCAC     2340

ATTTCCCCGA AAAGTGCCAC CTGACGTCTA AGAAACCATT ATTATCATGA CATTAACCTA     2400

TAAAAATAGG CGTATCACGA GGCCCTTTCG TCTTCAAGAA TTCTGAACCA GTCCTAAAAC     2460

GAGTAAATAG GACCGGCAAT TCTTCAAGCA ATAAACAGGA ATACCAATTA TTAAAAGATA     2520

ACTTAGTCAG ATCGTACAAT AAAGCTAGCT TTGAAGAAAA ATGCGCCTTA TTCAATCTTT     2580

GCTATAAAAA ATGGCCCAAA ATCTCACATT GGAAGACATT TGATGACCTC ATTTCTTTCA     2640

ATGAAGGGCC TAACGGAGTT GACTAATGTT GTGGGAAATT GGAGCGATAA GCGTGCTTCT     2700

GCCGTGGCCA GGACAACGTA TACTCATCAG ATAACAGCAA TACCTGATCA CTACTTCGCA     2760

CTAGTTTCTC GGTACTATGC ATATGATCCA ATATCAAAGG AAATGATAGC ATTGAAGGAT     2820
```

```
GAGACTAATC CAATTGAGGA GTGGCAGCAT ATAGAACAGC TAAAGGGTAG TGCTGAAGGA    2880

AGCATACGAT ACCCCGCATG GAATGGGATA ATATCACAGG AGGTACTAGA CTACCTTTCA    2940

TCCTACATAA ATAGACGCAT ATAAGTACGC ATTTAAGCAT AAACACGCAC TATGCCGTTC    3000

TTCTCATGTA TATATATATA CAGGCAACAC GCAGATATAG GTGCGACGTG AACAGTGAGC    3060

TGTATGTGCG CAGCTCGCGT TGCATTTTCG GAAGCGCTCG TTTTCGGAAA CGCTTTGAAG    3120

TTCCTATTCC GAAGTTCCTA TTCTCTAGAA AGTATAGGAA CTTCAGAGCG CTTTTGAAAA    3180

CCAAAAGCGC TCTGAAGACG CACTTTCAAA AAACCAAAAA CGCACCGGAC TGTAACGAGC    3240

TACTAAAATA TTGCGAATAC CGCTTCCACA AACATTGCTC AAAAGTATCT CTTTGCTATA    3300

TATCTCTGTG CTATATCCCT ATATAACCTA CCCATCCACC TTTCGCTCCT TGAACTTGCA    3360

TCTAAACTCG ACCTCTACAT TTTTTATGTT TATCTCTAGT ATTACTCTTT AGACAAAAAA    3420

ATTGTAGTAA GAACTATTCA TAGAGTGAAT CGAAAACAAT ACGAAAATGT AAACATTTCC    3480

TATACGTAGT ATATAGAGAC AAAATAGAAG AAACCGTTCA TAATTTTCTG ACCAATGAAG    3540

AATCATCAAC GCTATCACTT TCTGTTCACA AAGTATGCGC AATCCACATC GGTATAGAAT    3600

ATAATCGGGG ATGCCTTTAT CTTGAAAAAA TGCACCCGCA GCTTCGCTAG TAATCAGTAA    3660

ACGCGGGAAG TGGAGTCAGG CTTTTTTTAT GGAAGAGAAA ATAGACACCA AAGTAGCCTT    3720

CTTCTAACCT TAACGGACCT ACAGTGCAAA AAGTTATCAA GAGACTGCAT TATAGAGCGC    3780

ACAAAGGAGA AAAAAGTAA TCTAAGATGC TTTGTTAGAA AAATAGCGCT CTCGGGATGC    3840

ATTTTTGTAG AACAAAAAAG AAGTATAGAT TCTTTGTTGG TAAAATAGCG CTCTCGCGTT    3900

GCATTTCTGT TCTGTAAAAA TGCAGCTCAG ATTCTTTGTT TGAAAAATTA GCGCTCTCGC    3960

GTTGCATTTT TGTTTTACAA AAATGAAGCA CAGATTCTTC GTTGGTAAAA TAGCGCTTTC    4020

GCGTTGCATT TCTGTTCTGT AAAAATGCAG CTCAGATTCT TTGTTTGAAA AATTAGCGCT    4080

CTCGCGTTGC ATTTTTGTTC TACAAAATGA AGCACAGATG CTTCGTTAAC AAAGATATGC    4140

TATTGAAGTG CAAGATGGAA ACGCAGAAAA TGAACCGGGG ATGCGACGTG CAAGATTACC    4200

TATGCAATAG ATGCAATAGT TTCTCCAGGA ACCGAAATAC ATACATTGTC TTCCGTAAAG    4260

CGCTAGACTA TATATTATTA TACAGGTTCA AATATACTAT CTGTTTCAGG AAAACTCCC    4320

AGGTTCGGAT GTTCAAAATT CAATGATGGG TAACAAGTAC GATCGTAAAT CTGTAAAACA    4380

GTTTGTCGGA TATTAGGCTG TATCTCCTCA AAGCGTATTC GAATATCATT GAGAAGCTGC    4440

ATTTTTTTTT TTTTTATAT ATATTTCAAG GATATACCAT TGTAATGCCT GCCCCTAAGA    4500

AGATCGTCGT TTTGCCAGGT GACCACGTTG GTCAAGAAAT CACAGCCGAA GCCATTAAGG    4560

TTCTTAAAGC TATTTCTGAT GTTCGTTCCA ATGTCAAGTT CGATTTCGAA AATCATTTAA    4620

TTGGTGGTGC TGCTATCGAT GCTACAGGTG TTCCACTTCC AGATGAGGCG CTGGAAGCCT    4680

CCAAGAAGGC TGATGCCGTT TTGTTAGGTG CTGTGGGTGG TCCTAAATGG GGTACCGGTA    4740

GTGTTAGACC TGAACAAGGT TTACTAAAAA TCCGTAAAGA ACTTCAATTG TACGCCAACT    4800

TAAGACCATG TAACTTTGCA TCCGACTCTC TTTTAGACTT ATCTCCAATC AAGCCACAAT    4860

TTGCTAAAGG TACTGACTTC GTTGTTGTTA GAGAATTAGT GGGAGGTATT TACTTTGGTA    4920

AGAGAAAGGA AGACGATGGT GATGGTGTCG CTTGGGATAG TGAACAATAC ACCGTTCCAG    4980

AAGTGCAAAG AATCACAAGA ATGGCCGCTT TCATGGCCCT ACAACATGAG CCACCATTGC    5040

CTATTTGGTC CTTGGATAAA GCTAATGTTT TGGCCTCTTC AAGATTATGG AGAAAAACTG    5100

TGGAGGAAAC CATCAAGAAC GAATTCCCTA CATTGAAAGT TCAACATCAA TTGATTGATT    5160
```

-continued

```
CTGCCGCCAT GATCCTAGTT AAGAACCCAA CCCACCTAAA TGGTATTATA ATCACCAGCA    5220

ACATGTTTGG TGATATCATC TCCGATGAAG CCTCCGTTAT CCCAGGCTCC TTGGGTTTGT    5280

TGCCATCTGC GTCCTTGGCC TCTTTGCCAG ACAAGAACAC CGCATTTGGT TTGTACGAAC    5340

CATGCCATGG TTCCGCTCCA GATTGCCAA AGAATAAGGT CAACCCTATC GCCACTATCT     5400

TGTCTGCTGC AATGATGTTG AAATTGTCAT TGAACTTGCC TGAAGAAGGT AAAGCCATTG    5460

AAGATGCAGT TAAAAAGGTT TTGGATGCAG GTATCAGAAC TGGTGATTTA GGTGGTTCCA    5520

ACAGTACCAC CGAAGTCGGT GATGCTGTCG CCGAAGAAGT TAAGAAAATC CTTGCTTAAA    5580

AAGATTCTCT TTTTTTATGA TATTTGTACA AAAAAAAAAA AAAAAAAAAA AAAAAAAAA    5640

AAAAAAAAAA AAAAAAAAAA AAAATGCAGC GTCACATCGG ATAATAATGA TGGCAGCCAT    5700

TGTAGAAGTG CCTTTTGCAT TTCTAGTCTC TTTCTCGGTC TAGCTAGTTT TACTACATCG    5760

CGAAGATAGA ATCTTAGATC ACACTGCCTT TGCTGAGCTG GATCAATAGA GTAACAAAAG    5820

AGTGGTAAGG CCTCGTTAAA GGACAAGGAC CTGAGCGGAA GTGTATCGTA CAGTAGACGG    5880

AGTATACTAG TATAGTCTAT AGTCCGTGGA ATTCTCATGT TTGACAGCTT ATCATCGATA    5940

AGCTAGCTTT CTAACTGATC TATCCAAAAC TGAAAATTAC ATTCTTGATT AGGTTTATCA    6000

CAGGCAAATG TAATTTGTGG TATTTTGCCG TTCAAAATCT GTAGAATTTT CTCATTGGTC    6060

ACATTACAAC CTGAAAATAC TTTATCTACA ATCATACCAT TCTTAATAAC ATGTCCCTT     6120

AATACTAGGA TCAGGCATGA ACGCATCACA GACAAAATCT TCTTGACAAA CGTCACAATT    6180

GATCCCTCCC CATCCGTTAT CACAATGACA GGTGTCATTT TGTGCTCTTA TGGGACGATC    6240

CTTATTACCG CTTTCATCCG GTGATTGACC GCCACAGAGG GGCAGAGAGC AATCATCACC    6300

TGCAAACCCT TCTATACACT CACATCTACC AGTGATCGAA TTGCATTCAG AAAACTGTTT    6360

GCATTCAAAA ATAGGTAGCA TACAATTAAA ACATGGCGGG CATGTATCAT TGCCCTTATC    6420

TTGTGCAGTT AGACGCGAAT TTTTCGAAGA AGTACCTTCA AAGAATGGGG TCTTATCTTG    6480

TTTTGCAAGT ACCACTGAGC AGGATAATAA TAGAAATGAT AATATACTAT AGTAGAGATA    6540

ACGTCGATGA CTTCCCATAC TGTAATTGCT TTTAGTTGTG TATTTTTAGT GTGCAAGTTT    6600

CTGTAAATCG ATTAATTTTT TTTTCTTTCC TCTTTTTATT AACCTTAATT TTTATTTTAG    6660

ATTCCTGACT TCAACTCAAG ACGCACAGAT ATTATAACAT CTGCATAATA GGCATTTGCA    6720

AGAATTACTC GTGAGTAAGG AAAGAGTGAG GAACTATCGC ATACCTGCAT TTAAAGATGC    6780

CGATTTGGGC GCGAATCCTT TATTTTGGCT TCACCCTCAT ACTATTATCA GGGCCAGAAA    6840

AAGGAAGTGT TTCCCTCCTT CTTGAATTGA TGTTACCCTC ATAAAGCACG TGGCCTCTTA    6900

TCGAGAAAGA AATTACCGTC GCTCGTGATT TGTTTGCAAA AAGAACAAAA CTGAAAAAAC    6960

CCAGACACGC TCGACTTCCT GTCTTCCTAT TGATTGCAGC TTCCAATTTC GTCACACAAC    7020

AAGGTCCTAG CGACGGCTCA CAGGTTTTGT AACAAGCAAT CGAAGGTTCT GGAATGGCGG    7080

GGAAAGGGTT TAGTACCACA TGCTATGATG CCCACTGTGA TCTCCAGAGC AAAGTTCGTT    7140

CGATCGTACT GTACTCTCTC TCTTTCAAAC AGAATTGTCC GAATCGTGTG ACAACAACAG    7200

CCTGTTCTCA CACACTCTTT TCTTCTAACC AAGGGGGTGG TTTAGTTTAG TAGAACCTCG    7260

TGAAACTTAC ATTTACATAT ATATAAACTT GCATAAATTG GTCAATGGAA GAAATACATA    7320

TTTGGTCTTT TCTAATTCGT AGTTTTTCAA GTTCTTAGAT GCTTTCTTTT TCTCTTTTTT    7380

ACAGATCATC AAGGAAGTAA TTATCTACTT TTTACAACAA ATACAAAAGA TCTATGAGAT    7440

TTCCTTCAAT TTTTACTGCA GTTTTATTCG CAGCATCCTC CGCATTAGCT GCTCCAGTCA    7500

ACACTACAAC AGAAGATGAA ACGGCACAAA TTCCGGCTGA AGCTGTCATC GGTTACTTAG    7560
```

```
ATTTAGAAGG GGATTTCGAT GTTGCTGTTT TGCCATTTTC CAACAGCACA AATAACGGGT      7620

TATTGTTTAT AAATACTACT ATTGCCAGCA TTGCTGCTAA AGAAGAAGGG GTAAGCTTGG      7680

ATAAAAGAAA CAGCGACTCT GAATGCCCGC TGAGCCATGA TGGCTACTGC CTGCACGACG      7740

GTGTATGCAT GTATATCGAA GCTCTGGACA AATACGCATG CAACTGCGTA GTTGGTTACA      7800

TCGGCGAACG TTGCCAGTAC CGCGACCTGA AATGGTGGGA GCTCCGTTAA TAAGGATCC      7859
```

(2) INFORMATION FOR SEQ ID NO:16:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:16:

```
AGGATGGGGA AAGAGAA                                                       17
```

(2) INFORMATION FOR SEQ ID NO:17:

(i) SEQUENCE CHARACTERISTICS:
        (A) LENGTH: 228 base pairs
        (B) TYPE: nucleic acid
        (C) STRANDEDNESS: double
        (D) TOPOLOGY: linear (ii) MOLECULE TYPE: DNA (genomic)

(iii) ANTI-SENSE: NO (ix) FEATURE:
        (A) NAME/KEY: CDS
        (B) LOCATION: 1..234
        (D) OTHER INFORMATION: /codon_start= 1
            /product= "MIP-1-ALPHA GENE"

(ix) FEATURE:
        (A) NAME/KEY: 3'UTR
        (B) LOCATION: 223..225
        (D) OTHER INFORMATION: /function= "UNTRANSLATED STOP
            CODON"

(ix) FEATURE:
        (A) NAME/KEY: 3'UTR
        (B) LOCATION: 226..228
        (D) OTHER INFORMATION: /function= "NON-TRANSLATED STOP
            CODON"

(xi) SEQUENCE DESCRIPTION: SEQ ID NO:17:

```
AGC TGG GAT AAA AGA GCG CCT TAT GGA GCT GAC ACC CCG ACT GCA TGC         48
Ser Leu Asp Lys Arg Ala Pro Tyr Gly Ala Asp Thr Pro Thr Ala Cys
1               5                   10                  15

TGC TTC TCC TAC AGC CGG AAG ATT CCA CGC CAA TTC ATC GTC GAC TAT         96
Cys Phe Ser Tyr Ser Arg Lys Ile Pro Arg Gln Phe Ile Val Asp Tyr
            20                  25                  30

TTT GAA ACT AGT AGC CTT TGC TCC CAG CCA GGT GTC ATT TTC CTG ACT        144
Phe Glu Thr Ser Ser Leu Cys Ser Gln Pro Gly Val Ile Phe Leu Thr
        35                  40                  45

AAG AGA AAC CGG CAG ATC TGC GCT GAC TCC AAA GAG ACC TGG GTC CAA        192
Lys Arg Asn Arg Gln Ile Cys Ala Asp Ser Lys Glu Thr Trp Val Gln
    50                  55                  60

GAA TAC ATC ACT GAC CTC GAG CTG AAT GCC TGA TAG                        228
Glu Tyr Ile Thr Asp Leu Glu Leu Asn Ala
65                  70                  75
```

(2) INFORMATION FOR SEQ ID NO:18:

(i) SEQUENCE CHARACTERISTICS:
        (A) LENGTH: 69 amino acids
        (B) TYPE: amino acid
        (D) TOPOLOGY: linear (ii) MOLECULE TYPE: protein (xi) SEQUENCE DESCRIPTION: SEQ ID NO:18:

```
Ala Pro Tyr Gly Ala Asp Thr Pro Thr Ala Cys Cys Phe Ser Tyr
 1               5                  10                  15

Ser Arg Lys Ile Pro Arg Gln Phe Ile Val Asp Tyr Phe Glu Thr
                20                  25                  30

Ser Ser Leu Cys Ser Gln Pro Gly Val Ile Phe Leu Thr Lys Arg
                35                  40                  45

Asn Arg Gln Ile Cys Ala Asp Ser Lys Glu Thr Trp Val Gln Glu
                50                  55                  60

Tyr Ile Thr Asp Leu Glu Leu Asn Ala
                65
```

(2) INFORMATION FOR SEQ ID NO:19:

(i) SEQUENCE CHARACTERISTICS:
        (A) LENGTH: 234 base pairs
        (B) TYPE: nucleic acid
        (C) STRANDEDNESS: double
        (D) TOPOLOGY: linear (ii) MOLECULE TYPE: DNA (iii) ANTI-SENSE: YES (xi) SEQUENCE DESCRIPTION: SEQ ID NO:19:

```
CGGATCCTAT CAGGCATTCA GCTCGAGGTC AGTGATGTAT TCTTGGACCC AGGTCTCTTT      60

GGAGTCAGCG CAGATCTGCC GGTTTCTCTT AGTCAGGAAA ATGACACCTG GCTGGGAGCA     120

AAGGCTACTA GTTTCAAAAT AGTCGACGAT GAATTGGCGT GGAATCTTCC GGCTGTAGGA     180

GAAGCAGCAT GCAGTCGGGG TGTCAGCTCC ATAAGGCGCC ATGGCAGGTA AGCT           234
```

(2) INFORMATION FOR SEQ ID NO:20:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..38
        (D) OTHER INFORMATION: /product= "OLIGOMER FOR
            CONSTRUCTION OF MIP-ALPHA GENE"

(xi) SEQUENCE DESCRIPTION: SEQ ID NO:20:

```
AGCTTACCTG CCATGGCGCC TTATGGAGCT GACACCCC                              38
```

(2) INFORMATION FOR SEQ ID NO:21:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (ix) FEATURE:
    (A) NAME/KEY: misc_feature
    (B) LOCATION: 1..41
    (D) OTHER INFORMATION: /product= "OLIGOMER FOR
        CONSTRUCITON OF MIP1-ALPHA GENE"

(xi) SEQUENCE DESCRIPTION: SEQ ID NO:21:

TGCAGTCGGG GTGTCAGCTC CATAAGGCGC CATGGCAGGT A        41

(2) INFORMATION FOR SEQ ID NO:22:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..44
        (D) OTHER INFORMATION: /product= "OLIGOMER FOR
            CONSTRUCTION OF MIP1-ALPHA GENE"

(xi) SEQUENCE DESCRIPTION: SEQ ID NO:22:

GACTGCATGC TGCTTCTCCT ACAGCCGGAA GATTCCACGC CAAT        44

(2) INFORMATION FOR SEQ ID NO:23:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..43
        (D) OTHER INFORMATION: /product= "OLIGOMER FOR
            CONSTRUCTION OF MIP1-ALPHA GENE"

(xi) SEQUENCE DESCRIPTION: SEQ ID NO:23:

ACGATGAATT GGCGTGGAAT CTTCCGGCTG TAGGAGAAGC AGCA        44

(2) INFORMATION FOR SEQ ID NO:24:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..39
        (D) OTHER INFORMATION: /product= "OLIGOMER FOR
            CONSTRUCTION OF MIP1-ALPHA GENE"

(xi) SEQUENCE DESCRIPTION: SEQ ID NO:24:

TCATCGTCGA CTATTTTGAA ACTAGTAGCC TTTGCTCCC        39

(2) INFORMATION FOR SEQ ID NO:25:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..39
        (D) OTHER INFORMATION: /product= "OLIGOMER FOR
            CONSTRUCTION OF MIP1-ALPHA GENE"

(xi) SEQUENCE DESCRIPTION: SEQ ID NO:25:

CCTGGCTGGG AGCAAAGGCT ACTAGTTTCA AAATAGTCG                       39

(2) INFORMATION FOR SEQ ID NO:26:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..37
        (D) OTHER INFORMATION: /product= "OLIGOMER FOR
            CONSTRUCTION OF MIP1-ALPHA GENE"

(xi) SEQUENCE DESCRIPTION: SEQ ID NO:26:

AGCCAGGTGT CATTTTCCTG ACTAAGAGAA ACCGGCA                         37

(2) INFORMATION FOR SEQ ID NO:27:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..37
        (D) OTHER INFORMATION: /product= "OLIGOMER FOR
            CONSTRUCTION OF MIP1-ALPHA GENE"

(xi) SEQUENCE DESCRIPTION: SEQ ID NO:27:

GCAGATCTGC CGGTTTCTCT TAGTCAGGAA AATGACA                         37

(2) INFORMATION FOR SEQ ID NO:28:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..44
        (D) OTHER INFORMATION: /product= "OLIGOMER FOR THE
            CONSTRUCTION OF MIP1-ALPHA GENE"

(xi) SEQUENCE DESCRIPTION: SEQ ID NO:28:

GATCTGCGCT GACTCCAAAG AGACCTGGGT CCAAGAATAC ATCA                         44

(2) INFORMATION FOR SEQ ID NO:29:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..44
        (D) OTHER INFORMATION: /product= "OLIGOMER FOR
            CONSTRUCTION OF MIP1-ALPHA GENE"

(xi) SEQUENCE DESCRIPTION: SEQ ID NO:29:

AGGTCAGTGA TGTATTCTTG GACCCAGGTC TCTTTGGAGT CAGC                         44

(2) INFORMATION FOR SEQ ID NO:30:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..32
        (D) OTHER INFORMATION: /product= "OLIGOMER FOR
            CONSTRUCTION OF MIP1-ALPHA SYNTHETIC GENE"

(xi) SEQUENCE DESCRIPTION: SEQ ID NO:30:

CTGACCTCGA GCTGAATGCC TGATAGGATC CG                                     32

(2) INFORMATION FOR SEQ ID NO:31:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..29
        (D) OTHER INFORMATION: /product= "OLIGOMER FOR
            CONSTRUCTION OF MIP1-ALPHA GENE"

(xi) SEQUENCE DESCRIPTION: SEQ ID NO:31:

AATTCGGATC CTATCAGGCA TTCAGCTCG                                         29

(2) INFORMATION FOR SEQ ID NO:32:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..15

(D) OTHER INFORMATION: /product= "TOP STRAND OF
                OLIGONUCLEOTIDE ADAPTOR"

(xi) SEQUENCE DESCRIPTION: SEQ ID NO:32:

AGCTTGGATA AAAGA                                                           15

(2) INFORMATION FOR SEQ ID NO:33:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..11
        (D) OTHER INFORMATION: /product= "BOTTOM STRAND OF
            OLIGONUCLEOTIDE ADAPTOR"

(xi) SEQUENCE DESCRIPTION: SEQ ID NO:33:

TCTTTTATCC A                                                               11

(2) INFORMATION FOR SEQ ID NO:34:

(i) SEQUENCE CHARACTERISTICS:
        (A) LENGTH: 229 base pairs
        (B) TYPE: nucleic acid
        (C) STRANDEDNESS: double
        (D) TOPOLOGY: linear (ii) MOLECULE TYPE: DNA (genomic)

(iii) ANTI-SENSE: NO (ix) FEATURE:
        (A) NAME/KEY: CDS
        (B) LOCATION: 1..228
        (D) OTHER INFORMATION: /codon_start= 1
            /product= "HUMAN ACT-2 SYNTHETIC GENE"

(ix) FEATURE:
        (A) NAME/KEY: 3'UTR
        (B) LOCATION: 223..225
        (D) OTHER INFORMATION: /function= "NON-TRANSLATED STOP
            CODON"

(ix) FEATURE:
        (A) NAME/KEY: 3'UTR
        (B) LOCATION: 226..228
        (D) OTHER INFORMATION: /function= "NON-TRANSLATED STOP
            CODON"

(xi) SEQUENCE DESCRIPTION: SEQ ID NO:34:

AGC TTG GAT AAA AGA GCA CCA ATG GGT TCA GAC CCT CCA ACC GCA TGC    48
Ser Leu Asp Lys Arg Ala Pro Met Gly Ser Asp Pro Pro Thr Ala Cys
1               5                   10                  15

TGC TTT TCT TAC ACC GCT AGG AAG TTG CCT AGA AAC TTT GTG GTC GAC    96
Cys Phe Ser Tyr Thr Ala Arg Lys Leu Pro Arg Asn Phe Val Val Asp
            20                  25                  30

TAC TAT GAG ACC TCT TCT TTG TGC TCC CAG CCA GCT GTG GTA TTC CAA   144
Tyr Tyr Glu Thr Ser Ser Leu Cys Ser Gln Pro Ala Val Val Phe Gln
        35                  40                  45

ACC AAA AGA TCC AAG CAA GTC TGT GCT GAC CCG AGT GAA TCC TGG GTC   192
Thr Lys Arg Ser Lys Gln Val Cys Ala Asp Pro Ser Glu Ser Trp Val
    50                  55                  60

CAG GAG TAC GTG TAT GAC TTG GAA TTG AAC TGA TAAG                  229
Gln Glu Tyr Val Tyr Asp Leu Glu Leu Asn 65          70

(2) INFORMATION FOR SEQ ID NO:35:

(i) SEQUENCE CHARACTERISTICS:
        (A) LENGTH: 69 amino acids
        (B) TYPE: amino acid
        (D) TOPOLOGY: linear (ii) MOLECULE TYPE: protein (xi) SEQUENCE DESCRIPTION: SEQ ID NO:35:

Ala Pro Met Gly Ser Asp Pro Pro Thr Ala Cys Cys Phe Ser Tyr Thr
1               5                   10                  15

Ala Arg Lys Leu Pro Arg Asn Phe Val Val Asp Tyr Tyr Glu Thr Ser
            20                  25                  30

Ser Leu Cys Ser Gln Pro Ala Val Val Phe Gln Thr Lys Arg Ser Lys
        35                  40                  45

Gln Val Cys Ala Asp Pro Ser Glu Ser Trp Val Gln Glu Tyr Val Tyr
    50                  55                  60

Asp Leu Glu Leu Asn
65

(2) INFORMATION FOR SEQ ID NO:36:

(i) SEQUENCE CHARACTERISTICS:
        (A) LENGTH: 229 base pairs
        (B) TYPE: nucleic acid
        (C) STRANDEDNESS: double
        (D) TOPOLOGY: linear (ii) MOLECULE TYPE: DNA (genomic)

(iii) ANTI-SENSE: YES (xi) SEQUENCE DESCRIPTION: SEQ ID NO:36:

CTTATCAGTT CAATTCCAAG TCATACACGT ACTCCTGGAC CCAGGATTCA CTCGGGTCAG      60

CACAGACTTG CTTGGATCTT TTGGTTTGGA ATACCACAGC TGGCTGGGAG CACAAAGAAG    120

AGGTCTCATA GTAGTCGACC ACAAAGTTTC TAGGCAACTT CCTAGCGGTG TAAGAAAAGC    180

AGCATGCGGT TGGAGGGTCT GAACCCATTG GTGCTCTTTT ATCCAAGCT              229

(2) INFORMATION FOR SEQ ID NO:37:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..46
        (D) OTHER INFORMATION: /product= "OLIGOMER FOR
            CONSTRUCTION OF HUMAN ACT-2 GENE"

(xi) SEQUENCE DESCRIPTION: SEQ ID NO:37:

AGCTTGGATA AAAGAGCACC AATGGGTTCA GACCCTCCAA CCGCAT                      46

(2) INFORMATION FOR SEQ ID NO:38:

(i) SEQUENCE CHARACTERISTICS:
        (A) LENGTH: 45 base pairs
        (B) TYPE: nucleic acid

```
            (C) STRANDEDNESS: single
            (D) TOPOLOGY: linear (ii) MOLECULE TYPE: DNA (ix) FEATURE:
            (A) NAME/KEY: misc_feature
            (B) LOCATION: 1..45
            (D) OTHER INFORMATION: /product= "OLIGOMER FOR
                CONSTRUCTION OF HUMAN ACT-2 GENE"

(xi) SEQUENCE DESCRIPTION: SEQ ID NO:38:

AGCATGCGGT TGGAGGGTCT GAACCCATTG GTGCTCTTTT ATCCA                45

(2) INFORMATION FOR SEQ ID NO:39:

(i) SEQUENCE CHARACTERISTICS:
            (A) LENGTH: 47 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: misc_feature
            (B) LOCATION: 1..47
            (D) OTHER INFORMATION: /product= "Oligomer for
                construction of human ACT-2 gene"

(xi) SEQUENCE DESCRIPTION: SEQ ID NO:39:

GCTGCTTTTC TTACACCGCT AGGAAGTTGC CTAGAAACTT TGTGGTC              47

(2) INFORMATION FOR SEQ ID NO:40:

(i) SEQUENCE CHARACTERISTICS:
            (A) LENGTH: 51 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: misc_feature
            (B) LOCATION: 1..51
            (D) OTHER INFORMATION: /product= "Oligomer for
                construction of human ACT-2 gene"

(xi) SEQUENCE DESCRIPTION: SEQ ID NO:40:

AGTAGTCGAC CACAAAGTTT CTAGGCAACT TCCTAGCGGT GTAAGAAAAG C         51

(2) INFORMATION FOR SEQ ID NO:41:

(i) SEQUENCE CHARACTERISTICS:
            (A) LENGTH: 46 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: misc_feature
            (B) LOCATION: 1..46
            (D) OTHER INFORMATION: /product= "Oligomer for
                construction of human ACT-2 gene"

(xi) SEQUENCE DESCRIPTION: SEQ ID NO:41:

GACTACTATG AGACCTCTTC TTTGTGCTCC CAGCCAGCTG TGGTAT               46
```

(2) INFORMATION FOR SEQ ID NO:42:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..46
        (D) OTHER INFORMATION: /product= "Oligomer for
             construction of human ACT-2 gene"

(xi) SEQUENCE DESCRIPTION: SEQ ID NO:42:

GTTTGGAATA CCACAGCTGG CTGGGAGCAC AAAGAAGAGG TCTCAT                46

(2) INFORMATION FOR SEQ ID NO:43:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..47
        (D) OTHER INFORMATION: /product= "Oligomer for
             construction of human ACT-2 gene"

(xi) SEQUENCE DESCRIPTION: SEQ ID NO:43:

TCCAAACCAA AAGATCCAAG CAAGTCTGTG CTGACCCGAG TGAATCC               47

(2) INFORMATION FOR SEQ ID NO:44:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..47
        (D) OTHER INFORMATION: /product= "Oligomer for
             construction of human ACT-2 gene"

(xi) SEQUENCE DESCRIPTION: SEQ ID NO:44:

GGACCCAGGA TTCACTCGGG TCAGCACAGA CTTGCTTGGA TCTTTTG               47

(2) INFORMATION FOR SEQ ID NO:45:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..43
        (D) OTHER INFORMATION: /product= "Oligomer for
             construction of human ACT-2 gene"

(xi) SEQUENCE DESCRIPTION: SEQ ID NO:45:

TGGGTCCAGG AGTACGTGTA TGACTTGGAA TTGAACTGAT AAG                43

(2) INFORMATION FOR SEQ ID NO:46:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..40
        (D) OTHER INFORMATION: /product= "Oligomer for
            construction of human ACT-2 gene"

(xi) SEQUENCE DESCRIPTION: SEQ ID NO:46:

GATCCTTATC AGTTCAATTC CAAGTCATAC ACGTACTCCT                    40

(2) INFORMATION FOR SEQ ID NO:47:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:47:

GTTTTCCCAG TCACGAC                                             17

(2) INFORMATION FOR SEQ ID NO:48:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:48:

GCACAGACTT CTCTCGAGCG CT                                       22

(2) INFORMATION FOR SEQ ID NO:49:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..30
        (D) OTHER INFORMATION: /product= "BB6299 oligomer (xi) SEQUENCE DESCRIPTION: SEQ ID NO:49:

GACTTGTCTC GATTGCTCAG TCAAGAAGAT                               30

(2) INFORMATION FOR SEQ ID NO:50:

(i) SEQUENCE CHARACTERISTICS:

(A) LENGTH: 22 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..22
        (D) OTHER INFORMATION: /product= "BB6300 oligomer"

(xi) SEQUENCE DESCRIPTION: SEQ ID NO:50:

AAACAACAAG AGGTTGGAGT GT                                                    22

(2) INFORMATION FOR SEQ ID NO:51:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..25
        (D) OTHER INFORMATION: /product= "BB6381 oligomer"

(xi) SEQUENCE DESCRIPTION: SEQ ID NO:51:

GAAGAAGTTT CABAGTAGTC AGCAA                                                 25

(2) INFORMATION FOR SEQ ID NO:52:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..25
        (D) OTHER INFORMATION: /product= "BB6302 oligomer"

(xi) SEQUENCE DESCRIPTION: SEQ ID NO:52:

GTGGAATTTG AGAAGAGGTG TAAGA                                                 25

(2) INFORMATION FOR SEQ ID NO:53:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..27
        (D) OTHER INFORMATION: /product= "BB6303 oligomer"

(xi) SEQUENCE DESCRIPTION: SEQ ID NO:53:

GTAGTCAGCA GTGTTATTTT GTGGAAT                                               27

(2) INFORMATION FOR SEQ ID NO:54:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: misc_feature
            (B) LOCATION: 1..25
            (D) OTHER INFORMATION: /product= "BB6625 oligomer"

(xi) SEQUENCE DESCRIPTION: SEQ ID NO:54:

TTTCAAAGTA GRCAGCAATG AAATT                                             25

(2) INFORMATION FOR SEQ ID NO:55:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: misc_feature
            (B) LOCATION: 1..24
            (D) OTHER INFORMATION: /product= "BB6301 oligomer"

(xi) SEQUENCE DESCRIPTION: SEQ ID NO:55:

AGGTGTAAGA TTGACAACAA GCGG                                              24

(2) INFORMATION FOR SEQ ID NO:56:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: misc_feature
            (B) LOCATION: 1..25
            (D) OTHER INFORMATION: /product= "BB6382 oligomer"

(xi) SEQUENCE DESCRIPTION: SEQ ID NO:56:

AGTAGTCAGC ABTGAAATTT TGTGG                                             25

(2) INFORMATION FOR SEQ ID NO:57:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: misc_feature
            (B) LOCATION: 1..24
            (D) OTHER INFORMATION: /product= "BB6383 oligomer"

(xi) SEQUENCE DESCRIPTION: SEQ ID NO:57:

TAGTCAAGAA TCTGACACCT GGCT                                              24

(2) INFORMATION FOR SEQ ID NO:58:

```
    (i) SEQUENCE CHARACTERISTICS:
         (A) LENGTH: 26 base pairs
         (B) TYPE: nucleic acid
         (C) STRANDEDNESS: single
         (D) TOPOLOGY: linear (ii) MOLECULE TYPE: DNA (ix) FEATURE:
         (A) NAME/KEY: misc_feature
         (B) LOCATION: 1..26
         (D) OTHER INFORMATION: /product= "BB6384 oligomer"

(xi) SEQUENCE DESCRIPTION: SEQ ID NO:58:

GCACAGACTT GTTCCGAGCG CTTAGT                                          26

(2) INFORMATION FOR SEQ ID NO:59:

(i) SEQUENCE CHARACTERISTICS:
         (A) LENGTH: 35 base pairs
         (B) TYPE: nucleic acid
         (C) STRANDEDNESS: single
         (D) TOPOLOGY: linear (ii) MOLECULE TYPE: DNA (ix) FEATURE:
         (A) NAME/KEY: misc_feature
         (B) LOCATION: 1..35
         (D) OTHER INFORMATION: /product= "BB6385 oligomer"

(xi) SEQUENCE DESCRIPTION: SEQ ID NO:59:

AATTCCAAGT TAGAAACATA TTGTTGAACC CATTC                                 35

(2) INFORMATION FOR SEQ ID NO:60:

(i) SEQUENCE CHARACTERISTICS:
         (A) LENGTH: 25 base pairs
         (B) TYPE: nucleic acid
         (C) STRANDEDNESS: single
         (D) TOPOLOGY: linear (ii) MOLECULE TYPE: DNA (ix) FEATURE:
         (A) NAME/KEY: misc_feature
         (B) LOCATION: 1..25
         (D) OTHER INFORMATION: /product= "BB6345 oligomer"

(xi) SEQUENCE DESCRIPTION: SEQ ID NO:60:

GAAGAAGTTT CTTCGTAGTC AGCAA                                           25

(2) INFORMATION FOR SEQ ID NO:61:

(i) SEQUENCE CHARACTERISTICS:
         (A) LENGTH: 27 base pairs
         (B) TYPE: nucleic acid
         (C) STRANDEDNESS: single
         (D) TOPOLOGY: linear (ii) MOLECULE TYPE: DNA (ix) FEATURE:
         (A) NAME/KEY: misc_feature
         (B) LOCATION: 1..27
         (D) OTHER INFORMATION: /product= "BB7015 oligomer"

(xi) SEQUENCE DESCRIPTION: SEQ ID NO:61:

TGAGAAGAAG TTTCTTCGTA GTCAGCA                                         27
```

(2) INFORMATION FOR SEQ ID NO:62:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..27
        (D) OTHER INFORMATION: /product= "BB9112 oligomer"

(xi) SEQUENCE DESCRIPTION: SEQ ID NO:62:

TTGAACCCAG CGGCGAGATG GGTCAGC                          27

(2) INFORMATION FOR SEQ ID NO:63:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..24
        (D) OTHER INFORMATION: /product= "BB9109 oligomer"

(xi) SEQUENCE DESCRIPTION: SEQ ID NO:63:

TTGAGAAGAA GTTCTAAAGT AGTC                            24

(2) INFORMATION FOR SEQ ID NO:64:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..24
        (D) OTHER INFORMATION: /product= "BB9110 oligomer"

(xi) SEQUENCE DESCRIPTION: SEQ ID NO:64:

ATTTTGTGGA ATTTCTCTAG AGGT                            24

(2) INFORMATION FOR SEQ ID NO:65:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..30
        (D) OTHER INFORMATION: /product= "BB9111 Oligomer"

(xi) SEQUENCE DESCRIPTION: SEQ ID NO:65:

ATTTTGTGGA ATTTCAGAAG AGGTGTAAGA                    30

(2) INFORMATION FOR SEQ ID NO:66:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..30
        (D) OTHER INFORMATION: /product= "BB9104 Oligomer"

(xi) SEQUENCE DESCRIPTION: SEQ ID NO:66:

AGCAGCCAAG GAAGCAGATC TTTTATCCAA                              30

(2) INFORMATION FOR SEQ ID NO:67:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..36
        (D) OTHER INFORMATION: /product= "BB9105 Oligomer"

(xi) SEQUENCE DESCRIPTION: SEQ ID NO:67:

GTCAGCAGCC AATGGAGCAG ACAATCTTTT ATCCAA                       36

(2) INFORMATION FOR SEQ ID NO:68:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..24
        (D) OTHER INFORMATION: /product= "BB9106 oligomer"

(xi) SEQUENCE DESCRIPTION: SEQ ID NO:68:

TGGAGTGTCA GCTCTTTTAT CCAA                                    24

(2) INFORMATION FOR SEQ ID NO:69:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..30
        (D) OTHER INFORMATION: /product= "BB9103 oligomer"

(xi) SEQUENCE DESCRIPTION: SEQ ID NO:69:

GTCAGCAGCC AATGGAGCTC TTTTATCCAA                              30

(2) INFORMATION FOR SEQ ID NO:70:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..48
        (D) OTHER INFORMATION: /product= "BB9108 oligomer"

(xi) SEQUENCE DESCRIPTION: SEQ ID NO:70:

ACAGACTTGT CTACCGCGCT TAGTCAAGAA GATGACAGAT GGCTTGGA                48

(2) INFORMATION FOR SEQ ID NO:71:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..24
        (D) OTHER INFORMATION: /product= "BB9107 oligomer"

(xi) SEQUENCE DESCRIPTION: SEQ ID NO:71:

AATTTGTCTA GAGAAGTAAG AGAA                24

(2) INFORMATION FOR SEQ ID NO:72:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..21
        (D) OTHER INFORMATION: /product= "BB9512 oligomer"

(xi) SEQUENCE DESCRIPTION: SEQ ID NO:72:

CAGCACAGAC AGATCTCGAG C                21

(2) INFORMATION FOR SEQ ID NO:73:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..18
        (D) OTHER INFORMATION: /product= "BB9432 oligomer"

(xi) SEQUENCE DESCRIPTION: SEQ ID NO:73:

CAAAGTAGGA AGCAATGA                    18

(2) INFORMATION FOR SEQ ID NO:74:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..19
        (D) OTHER INFORMATION: /product= "BB9519 oligomer"

(xi) SEQUENCE DESCRIPTION: SEQ ID NO:74:

GTGTAAGAGG CACAACAAG                   19

(2) INFORMATION FOR SEQ ID NO:75:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..19
        (D) OTHER INFORMATION: /product= "BB9527 oligomer"

(xi) SEQUENCE DESCRIPTION: SEQ ID NO:75:

GAAGTTTCAG CGTAGTCAG                   19

(2) INFORMATION FOR SEQ ID NO:76:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..21
        (D) OTHER INFORMATION: /product= "BB9431 oligomer"

(xi) SEQUENCE DESCRIPTION: SEQ ID NO:76:

GTAGTCAGCA GCGAAATTTT G                21

(2) INFORMATION FOR SEQ ID NO:77:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..19
        (D) OTHER INFORMATION: /product= "BB9534 oligomer"

(xi) SEQUENCE DESCRIPTION: SEQ ID NO:77:

```
GTCAAGAAGG CGACACCTG                                                     19

(2) INFORMATION FOR SEQ ID NO:78:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: DNA (ix) FEATURE:
          (A) NAME/KEY: misc_feature
          (B) LOCATION: 1..21
          (D) OTHER INFORMATION: /product= "BB9437 oligomer"

(xi) SEQUENCE DESCRIPTION: SEQ ID NO:78:

CACAGACTTG AGACGAGCGC T                                                  21

(2) INFORMATION FOR SEQ ID NO:79:

(i) SEQUENCE CHARACTERISTICS:
          (A) LENGTH: 22 base pairs
          (B) TYPE: nucleic acid
          (C) STRANDEDNESS: single
          (D) TOPOLOGY: linear (ii) MOLECULE TYPE: DNA (ix) FEATURE:
          (A) NAME/KEY: misc_feature
          (B) LOCATION: 1..22
          (D) OTHER INFORMATION: /product= "BB9433 oligomer"

(xi) SEQUENCE DESCRIPTION: SEQ ID NO:79:

GAGAAGAAGT AGAAAAGTAG TC                                                 22

(2) INFORMATION FOR SEQ ID NO:80:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: DNA (ix) FEATURE:
          (A) NAME/KEY: misc_feature
          (B) LOCATION: 1..21
          (D) OTHER INFORMATION: /product= "BB9506 oligomer"

(xi) SEQUENCE DESCRIPTION: SEQ ID NO:80:

TTTGTGGAAT AGATCTAGAG G                                                  21

(2) INFORMATION FOR SEQ ID NO:81:

(i) SEQUENCE CHARACTERISTICS:
          (A) LENGTH: 23 base pairs
          (B) TYPE: nucleic acid
          (C) STRANDEDNESS: single
          (D) TOPOLOGY: linear (ii) MOLECULE TYPE: DNA (ix) FEATURE:
          (A) NAME/KEY: misc_feature
          (B) LOCATION: 1..23
          (D) OTHER INFORMATION: /product= "BB10194 oligomer"
```

(xi) SEQUENCE DESCRIPTION: SEQ ID NO:81:

GGTTGGAGTG CGAGCAGCCA AGG                                                      23

(2) INFORMATION FOR SEQ ID NO:82:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..22
        (D) OTHER INFORMATION: /product= "BB10195 oligomer"

(xi) SEQUENCE DESCRIPTION: SEQ ID NO:82:

GGAATTTGTT CAGAGGTGTA AG                                                       22

(2) INFORMATION FOR SEQ ID NO:83:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..27
        (D) OTHER INFORMATION: /product= "BB10196 oligomer"

(xi) SEQUENCE DESCRIPTION: SEQ ID NO:83:

GCACAGACTT GTCTTTCGCG CTTAGTC                                                  27

(2) INFORMATION FOR SEQ ID NO:84:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..29
        (D) OTHER INFORMATION: /product= "BB10197 oligomer"

(xi) SEQUENCE DESCRIPTION: SEQ ID NO:84:

GGAGTGTCAG CAGCTTCGGA TCTTTTATC                                                29

(2) INFORMATION FOR SEQ ID NO:85:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..22
        (D) OTHER INFORMATION: /product= "BB10198 oligomer"

(xi) SEQUENCE DESCRIPTION: SEQ ID NO:85:

GGAGTGTCAG CTTCCAAGGA TC                                                        22

(2) INFORMATION FOR SEQ ID NO:86:

(i) SEQUENCE CHARACTERISTICS:
             (A) LENGTH: 23 base pairs
             (B) TYPE: nucleic acid
             (C) STRANDEDNESS: single
             (D) TOPOLOGY: linear (ii) MOLECULE TYPE: DNA (ix) FEATURE:
             (A) NAME/KEY: misc_feature
             (B) LOCATION: 1..23
             (D) OTHER INFORMATION: /product= "BB10199 oligomer"

(xi) SEQUENCE DESCRIPTION: SEQ ID NO:86:

GGTTGGAGTG TCTTCAGCCA AGG                                                       23

(2) INFORMATION FOR SEQ ID NO:87:

(i) SEQUENCE CHARACTERISTICS:
             (A) LENGTH: 22 base pairs
             (B) TYPE: nucleic acid
             (C) STRANDEDNESS: single
             (D) TOPOLOGY: linear (ii) MOLECULE TYPE: DNA (ix) FEATURE:
             (A) NAME/KEY: misc_feature
             (B) LOCATION: 1..22
             (D) OTHER INFORMATION: /product= "BB10200 oligomer"

(xi) SEQUENCE DESCRIPTION: SEQ ID NO:87:

GGAATTTCTT CAGAGGTGTA AG                                                        22

(2) INFORMATION FOR SEQ ID NO:88:

(i) SEQUENCE CHARACTERISTICS:
             (A) LENGTH: 28 base pairs
             (B) TYPE: nucleic acid
             (C) STRANDEDNESS: single
             (D) TOPOLOGY: linear (ii) MOLECULE TYPE: DNA (ix) FEATURE:
             (A) NAME/KEY: misc_feature
             (B) LOCATION: 1..28
             (D) OTHER INFORMATION: /product= "BB10201 oligomer"

(xi) SEQUENCE DESCRIPTION: SEQ ID NO:88:

CCTTATTAGG CAGATTCTTC CAAGTCAG                                                  28

(2) INFORMATION FOR SEQ ID NO:89:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: DNA (ix) FEATURE:
             (A) NAME/KEY: misc_feature
             (B) LOCATION: 1..20

(D) OTHER INFORMATION: /product= "BB9537 oligomer"

(xi) SEQUENCE DESCRIPTION: SEQ ID NO:89:

GACTTGTCTA GCGCGCTTAG                                              20

(2) INFORMATION FOR SEQ ID NO:90:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: misc_feature
            (B) LOCATION: 1..19
            (D) OTHER INFORMATION: /product= "BB9497 oligomer"

(xi) SEQUENCE DESCRIPTION: SEQ ID NO:90:

GTCAGCAGCA GCGGATCTT                                               19

(2) INFORMATION FOR SEQ ID NO:91:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: misc_feature
            (B) LOCATION: 1..17
            (D) OTHER INFORMATION: /product= "BB9498 oligomer"

(xi) SEQUENCE DESCRIPTION: SEQ ID NO:91:

GTCAGCAGAC AAGGATC                                                 17

(2) INFORMATION FOR SEQ ID NO:92:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: misc_feature
            (B) LOCATION: 1..18
            (D) OTHER INFORMATION: /product= "BB9499 oligomer"

(xi) SEQUENCE DESCRIPTION: SEQ ID NO:92:

GAGTGTCAGA AGCCAAGG                                                18

(2) INFORMATION FOR SEQ ID NO:93:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: misc_feature (B) LOCATION: 1..22
        (D) OTHER INFORMATION: /product= "BB9517 oligomer"

(xi) SEQUENCE DESCRIPTION: SEQ ID NO:93:

ATTAGGCAGA GGCTTCCAAG TC                                                      22

(2) INFORMATION FOR SEQ ID NO:94:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..34
        (D) OTHER INFORMATION: /product= "BB9781 oligomer"

(xi) SEQUENCE DESCRIPTION: SEQ ID NO:94:

GAGAAACAAC AAGCGGTAGA TCTTTTATCC AAGC                                          34

(2) INFORMATION FOR SEQ ID NO:95:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..20
        (D) OTHER INFORMATION: /product= "BB9430 oligomer"

(xi) SEQUENCE DESCRIPTION: SEQ ID NO:95:

GTTGGAGTGG AAGCAGCCAA                                                          20

(2) INFORMATION FOR SEQ ID NO:96:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..18
        (D) OTHER INFORMATION: /product= "BB9525 oligomer"

(xi) SEQUENCE DESCRIPTION: SEQ ID NO:96:

CAGCAATGGC ATTTTGTG                                                            18

(2) INFORMATION FOR SEQ ID NO:97:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (ix) FEATURE:

(A) NAME/KEY: misc_feature
        (B) LOCATION: 1..21
        (D) OTHER INFORMATION: /product= "BB9435 oligomer"

(xi) SEQUENCE DESCRIPTION: SEQ ID NO:97:

GTCTCGAGCG AGAAGTCAAG A                                              21

(2) INFORMATION FOR SEQ ID NO:98:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..18
        (D) OTHER INFORMATION: /product= "BB9436 oligomer"

(xi) SEQUENCE DESCRIPTION: SEQ ID NO:98:

GTCTCGAGGA CTTAGTCA                                                  18

(2) INFORMATION FOR SEQ ID NO:99:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..22
        (D) OTHER INFORMATION: /product= "BB9423 oligomer"

(xi) SEQUENCE DESCRIPTION: SEQ ID NO:99:

GAACCCATTC AGAAGATGGG TC                                             22

(2) INFORMATION FOR SEQ ID NO:100:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..21
        (D) OTHER INFORMATION: /product= "BB9424 oligomer"

(xi) SEQUENCE DESCRIPTION: SEQ ID NO:100:

TTTGAACCCA AGATTCAGAT G                                              21

(2) INFORMATION FOR SEQ ID NO:101:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (ix) FEATURE:
            (A) NAME/KEY: misc_feature
            (B) LOCATION: 1..21
            (D) OTHER INFORMATION: /product= "BB9425 oligomer"

(xi) SEQUENCE DESCRIPTION: SEQ ID NO:101:

CAGAAACATA AGATTGAACC C                                              21

(2) INFORMATION FOR SEQ ID NO:102:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: misc_feature
            (B) LOCATION: 1..20
            (D) OTHER INFORMATION: /product= "BB9427 oligomer"

(xi) SEQUENCE DESCRIPTION: SEQ ID NO:102:

CAATTCCAAG GAAGAAACAT                                                20

(2) INFORMATION FOR SEQ ID NO:103:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: misc_feature
            (B) LOCATION: 1..17
            (D) OTHER INFORMATION: /product= "BB9503 oligomer"

(xi) SEQUENCE DESCRIPTION: SEQ ID NO:103:

CCTTATTAGT CAGAAAC                                                   17

(2) INFORMATION FOR SEQ ID NO:104:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: misc_feature
            (B) LOCATION: 1..33
            (D) OTHER INFORMATION: /product= "BB9443 oligomer"

(xi) SEQUENCE DESCRIPTION: SEQ ID NO:104:

TTGAGAAGAA GTTCTAAAGT AGGCAGCAAT GAA                                 33

(2) INFORMATION FOR SEQ ID NO:105:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (ix) FEATURE:
        (A) NAME/KEY: misc_feature
        (B) LOCATION: 1..20
        (D) OTHER INFORMATION: /product= "BB9434 oligomer"

(xi) SEQUENCE DESCRIPTION: SEQ ID NO:105:

GACACCTGGA GAGGAACATT                                                    20

(2) INFORMATION FOR SEQ ID NO:106:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..22
        (D) OTHER INFORMATION: /product= "BB9228 oligomer"

(xi) SEQUENCE DESCRIPTION: SEQ ID NO:106:

CAGACAATTC AGCGTCAGAA AC                                                 22

(2) INFORMATION FOR SEQ ID NO:107:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..20
        (D) OTHER INFORMATION: /product= "BB9429 oligomer"

(xi) SEQUENCE DESCRIPTION: SEQ ID NO:107:

GGCAGACAAA GACAAGTCAG                                                    20

(2) INFORMATION FOR SEQ ID NO:108:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..19
        (D) OTHER INFORMATION: /product= "BB9495 oligomer"

(xi) SEQUENCE DESCRIPTION: SEQ ID NO:108:

CTTATTAGGA AGACAATTC                                                     19

(2) INFORMATION FOR SEQ ID NO:109:

(i) SEQUENCE CHARACTERISTICS:
        (A) LENGTH: 19 base pairs
        (B) TYPE: nucleic acid
        (C) STRANDEDNESS: single
        (D) TOPOLOGY: linear

```
    (ii) MOLECULE TYPE: DNA (ix) FEATURE:
         (A) NAME/KEY: misc_feature
         (B) LOCATION: 1..19
         (D) OTHER INFORMATION: /product= "BB9496 oligomer"

(xi) SEQUENCE DESCRIPTION: SEQ ID NO:109:

CAGCCAAGGC TCTTTTATC                                                    19

(2) INFORMATION FOR SEQ ID NO:110:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (ix) FEATURE:
         (A) NAME/KEY: misc_feature
         (B) LOCATION: 1..20
         (D) OTHER INFORMATION: /product= "BB9509 oligomer"

(xi) SEQUENCE DESCRIPTION: SEQ ID NO:110:

CTTGGAACAA GAAGAAGAAG                                                   20

(2) INFORMATION FOR SEQ ID NO:111:

(i) SEQUENCE CHARACTERISTICS:
         (A) LENGTH: 19 base pairs
         (B) TYPE: nucleic acid
         (C) STRANDEDNESS: single
         (D) TOPOLOGY: linear (ii) MOLECULE TYPE: DNA (ix) FEATURE:
         (A) NAME/KEY: misc_feature
         (B) LOCATION: 1..19

(xi) SEQUENCE DESCRIPTION: SEQ ID NO:111:

GTCAGAAACA GCTTTTTGA                                                    19

(2) INFORMATION FOR SEQ ID NO:112:

(i) SEQUENCE CHARACTERISTICS:
         (A) LENGTH: 19 base pairs
         (B) TYPE: nucleic acid
         (C) STRANDEDNESS: single
         (D) TOPOLOGY: linear (ii) MOLECULE TYPE: DNA (ix) FEATURE:
         (A) NAME/KEY: misc_feature
         (B) LOCATION: 1..19
         (D) OTHER INFORMATION: /product= "BB9529 oligomer"

(xi) SEQUENCE DESCRIPTION: SEQ ID NO:112:

CATTGAGAAG CAGTTTCAA                                                    19

(2) INFORMATION FOR SEQ ID NO:113:

(i) SEQUENCE CHARACTERISTICS:
         (A) LENGTH: 19 base pairs
         (B) TYPE: nucleic acid
         (C) STRANDEDNESS: single
         (D) TOPOLOGY: linear
```

```
        (ii) MOLECULE TYPE: DNA (ix) FEATURE:
              (A) NAME/KEY: misc_feature
              (B) LOCATION: 1..19
              (D) OTHER INFORMATION: /product= "BB9530 oligomer"

(xi) SEQUENCE DESCRIPTION: SEQ ID NO:113:

GAACATTGAG CAGAAGTTT                                                19

(2) INFORMATION FOR SEQ ID NO:114:

(i) SEQUENCE CHARACTERISTICS:
              (A) LENGTH: 21 base pairs
              (B) TYPE: nucleic acid
              (C) STRANDEDNESS: single
              (D) TOPOLOGY: linear (ii) MOLECULE TYPE: DNA (ix) FEATURE:
              (A) NAME/KEY: misc_feature
              (B) LOCATION: 1..21
              (D) OTHER INFORMATION: /product= "BB9536 oligomer"

(xi) SEQUENCE DESCRIPTION: SEQ ID NO:114:

GCGCTTAGTA GCGAAGATGA C                                             21

(2) INFORMATION FOR SEQ ID NO:115:

(i) SEQUENCE CHARACTERISTICS:
              (A) LENGTH: 22 base pairs
              (B) TYPE: nucleic acid
              (C) STRANDEDNESS: single
              (D) TOPOLOGY: linear (ii) MOLECULE TYPE: DNA (ix) FEATURE:
              (A) NAME/KEY: misc_feature
              (B) LOCATION: 1..22
              (D) OTHER INFORMATION: /product= "BB9422 oligomer"

(xi) SEQUENCE DESCRIPTION: SEQ ID NO:115:

CTTCAGATGG AGAAGCACAG AC                                            22

(2) INFORMATION FOR SEQ ID NO:116:

(i) SEQUENCE CHARACTERISTICS:
              (A) LENGTH: 21 base pairs
              (B) TYPE: nucleic acid
              (C) STRANDEDNESS: single
              (D) TOPOLOGY: linear (ii) MOLECULE TYPE: DNA (ix) FEATURE:
              (A) NAME/KEY: misc_feature
              (B) LOCATION: 1..21
              (D) OTHER INFORMATION: /product= "BB9426 oligomer"

(xi) SEQUENCE DESCRIPTION: SEQ ID NO:116:

CAAGTCAGAA GCATATTTTT G                                             21

(2) INFORMATION FOR SEQ ID NO:117:

(i) SEQUENCE CHARACTERISTICS:
              (A) LENGTH: 17 base pairs
              (B) TYPE: nucleic acid
              (C) STRANDEDNESS: single
              (D) TOPOLOGY: linear
```

```
        (ii) MOLECULE TYPE: DNA (ix) FEATURE:
             (A) NAME/KEY: misc_feature
             (B) LOCATION: 1..17
             (D) OTHER INFORMATION: /product= "BB9504 oligomer"

(xi) SEQUENCE DESCRIPTION: SEQ ID NO:117:

GGTGTAAGCG AAACAAC                                                    17

(2) INFORMATION FOR SEQ ID NO:118:

(i) SEQUENCE CHARACTERISTICS:
             (A) LENGTH: 19 base pairs
             (B) TYPE: nucleic acid
             (C) STRANDEDNESS: single
             (D) TOPOLOGY: linear (ii) MOLECULE TYPE: DNA (ix) FEATURE:
             (A) NAME/KEY: misc_feature
             (B) LOCATION: 1..19
             (D) OTHER INFORMATION: /product= "BB9505 oligomer"

(xi) SEQUENCE DESCRIPTION: SEQ ID NO:118:

ATTTGTCTAG CGGTGTAAG                                                  19

(2) INFORMATION FOR SEQ ID NO:119:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: DNA (ix) FEATURE:
             (A) NAME/KEY: misc_feature
             (B) LOCATION: 1..20
             (D) OTHER INFORMATION: /product= "BB9507 oligomer"

(xi) SEQUENCE DESCRIPTION: SEQ ID NO:119:

GAAATTTTGA GCAATTTGTC                                                 20

(2) INFORMATION FOR SEQ ID NO:120:

(i) SEQUENCE CHARACTERISTICS:
             (A) LENGTH: 18 base pairs
             (B) TYPE: nucleic acid
             (C) STRANDEDNESS: single
             (D) TOPOLOGY: linear (ii) MOLECULE TYPE: DNA (ix) FEATURE:
             (A) NAME/KEY: misc_feature
             (B) LOCATION: 1..18
             (D) OTHER INFORMATION: /product= "BB9510 oligomer"

(xi) SEQUENCE DESCRIPTION: SEQ ID NO:120:

CTGGCTTGGC ACATTGAG                                                   18

(2) INFORMATION FOR SEQ ID NO:121:

(i) SEQUENCE CHARACTERISTICS:
             (A) LENGTH: 23 base pairs
             (B) TYPE: nucleic acid
             (C) STRANDEDNESS: single
```

(D) TOPOLOGY: linear (ii) MOLECULE TYPE: DNA (ix) FEATURE:
            (A) NAME/KEY: misc_feature
            (B) LOCATION: 1..23
            (D) OTHER INFORMATION: /product= "BB9514 oligomer"

(xi) SEQUENCE DESCRIPTION: SEQ ID NO:121:

GAAACATATT TAGAAACCCA TTC                                                  23

(2) INFORMATION FOR SEQ ID NO:122:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: misc_feature
            (B) LOCATION: 1..19

(xi) SEQUENCE DESCRIPTION: SEQ ID NO:122:

ATTAGGCAGC CAATTCCAA                                                       19

(2) INFORMATION FOR SEQ ID NO:123:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: misc_feature
            (B) LOCATION: 1..19
            (D) OTHER INFORMATION: /product= "BB9520 oligomer"

(xi) SEQUENCE DESCRIPTION: SEQ ID NO:123:

CTAGAGGTGG CAGAGAAAC                                                       19

(2) INFORMATION FOR SEQ ID NO:124:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: misc_feature
            (B) LOCATION: 1..19
            (D) OTHER INFORMATION: /product= "BB9522 oligomer"

(xi) SEQUENCE DESCRIPTION: SEQ ID NO:124:

TTTTGTGGAG CTTGTCTAG                                                       19

(2) INFORMATION FOR SEQ ID NO:125:

(i) SEQUENCE CHARACTERISTICS:
            (A) LENGTH: 20 base pairs
            (B) TYPE: nucleic acid
            (C) STRANDEDNESS: single (D) TOPOLOGY: linear (ii) MOLECULE TYPE: DNA (ix) FEATURE:
            (A) NAME/KEY: misc_feature
            (B) LOCATION: 1..20
            (D) OTHER INFORMATION: /product= "BB9531 oligomer"

(xi) SEQUENCE DESCRIPTION: SEQ ID NO:125:

GATGACACCA GCCTTGGAAC                                                   20

(2) INFORMATION FOR SEQ ID NO:126:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: misc_feature
            (B) LOCATION: 1..20
            (D) OTHER INFORMATION: /product= "BB9532 oligomer"

(xi) SEQUENCE DESCRIPTION: SEQ ID NO:126:

GAAGATGACA GCTGGCTTGG                                                   20

(2) INFORMATION FOR SEQ ID NO:127:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: misc_feature
            (B) LOCATION: 1..18
            (D) OTHER INFORMATION: /product= "BB9533 oligomer"

(xi) SEQUENCE DESCRIPTION: SEQ ID NO:127:

AGAAGATGGC ACCTGGCT                                                     18

(2) INFORMATION FOR SEQ ID NO:128:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: misc_feature
            (B) LOCATION: 1..17
            (D) OTHER INFORMATION: /product= "BB9500 oligomer"

(xi) SEQUENCE DESCRIPTION: SEQ ID NO:128:

GGTTGGAGCG TCAGCAG                                                      17

(2) INFORMATION FOR SEQ ID NO:129:

(i) SEQUENCE CHARACTERISTICS:
            (A) LENGTH: 22 base pairs
            (B) TYPE: nucleic acid

```
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..22
        (D) OTHER INFORMATION: /product= "BB9523 oligomer"

(xi) SEQUENCE DESCRIPTION: SEQ ID NO:129:

CAATGAAATT AGATGGAATT TG                                          22

(2) INFORMATION FOR SEQ ID NO:130:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..17
        (D) OTHER INFORMATION: /product= "BB9511 oligomer"

(xi) SEQUENCE DESCRIPTION: SEQ ID NO:130:

GCGCTTAGCC AAGAAGA                                                17

(2) INFORMATION FOR SEQ ID NO:131:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION:  1..19
        (D) OTHER INFORMATION: /product= "BB9501 oligomer"

(xi) SEQUENCE DESCRIPTION: SEQ ID NO:131:

CAAGCGGTAG CAGTGTCAG                                              19

(2) INFORMATION FOR SEQ ID NO:132:

(i) SEQUENCE CHARACTERISTICS:
        (A) LENGTH: 18  base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION:  1..18
        (D) OTHER INFORMATION: /product= "BB9502 oligomer"

(xi) SEQUENCE DESCRIPTION: SEQ ID NO:132:

ACAAGCGGCT GGAGTGTC                                               18

(2) INFORMATION FOR SEQ ID NO:133:

(i) SEQUENCE CHARACTERISTICS:
        (A) LENGTH: 18  base pairs
```

```
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..18
        (D) OTHER INFORMATION: /product= "BB9508 oligomer"

(xi) SEQUENCE DESCRIPTION: SEQ ID NO:133:

GTTTCAAAGG CGTCAGCA                                                   18

(2) INFORMATION FOR SEQ ID NO:134:

(i) SEQUENCE CHARACTERISTICS:
        (A) LENGTH: 20  base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..20
        (D) OTHER INFORMATION: /product= "BB9513 oligomer"

(xi) SEQUENCE DESCRIPTION: SEQ ID NO:134:

TTCTTCAGAT GCGTCAGCAC                                                 20

(2) INFORMATION FOR SEQ ID NO:135:

(i) SEQUENCE CHARACTERISTICS:
        (A) LENGTH: 18  base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..18
        (D) OTHER INFORMATION: /product= "BB9516 oligomer"

(xi) SEQUENCE DESCRIPTION: SEQ ID NO:135:

CAAGTCAGCA ACATATTT                                                   18

(2) INFORMATION FOR SEQ ID NO:136:

(i) SEQUENCE CHARACTERISTICS:
        (A) LENGTH: 17  base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..17
        (D) OTHER INFORMATION: /product= "BB9521 oligomer"

(xi) SEQUENCE DESCRIPTION: SEQ ID NO:136:

GTCTAGAGGC GTAAGAG                                                    17

(2) INFORMATION FOR SEQ ID NO:137:

(i) SEQUENCE CHARACTERISTICS:
```

(A) LENGTH: 18  base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: misc_feature
            (B) LOCATION:  1..18
            (D) OTHER INFORMATION: /product= "BB9524 oligomer"

(xi) SEQUENCE DESCRIPTION: SEQ ID NO:137:

CAATGAAAGA TTGTGGAA                                                       18

(2) INFORMATION FOR SEQ ID NO:138:

(i) SEQUENCE CHARACTERISTICS:
            (A) LENGTH: 17  base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: misc_feature
            (B) LOCATION:  1..17
            (D) OTHER INFORMATION: /product= "BB9526 oligomer"

(xi) SEQUENCE DESCRIPTION: SEQ ID NO:138:

GTAGTCAGAA ATGAAAT                                                        17

(2) INFORMATION FOR SEQ ID NO:139:

(i) SEQUENCE CHARACTERISTICS:
            (A) LENGTH: 18  base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: misc_feature
            (B) LOCATION:  1..18
            (D) OTHER INFORMATION: /product= "BB9528 oligomer"

(xi) SEQUENCE DESCRIPTION: SEQ ID NO:139:

GAGAAGAAGC TTCAAAGT                                                       18

(2) INFORMATION FOR SEQ ID NO:140:

(i) SEQUENCE CHARACTERISTICS:
            (A) LENGTH: 20  base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: misc_feature
            (B) LOCATION:  1..20
            (D) OTHER INFORMATION: /product= "BB9535 oligomer"

(xi) SEQUENCE DESCRIPTION: SEQ ID NO:140:

CTTAGTCAAG GCGATGACAC                                                     20

(2) INFORMATION FOR SEQ ID NO:141:

(i) SEQUENCE CHARACTERISTICS:
            (A) LENGTH: 20  base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: misc_feature
            (B) LOCATION: 1..20
            (D) OTHER INFORMATION: /product= "BB9538 oligomer"

(xi) SEQUENCE DESCRIPTION: SEQ ID NO:141:

GTCAGCACAG GCTTGTCTCG                                                  20

(2) INFORMATION FOR SEQ ID NO:142:

(i) SEQUENCE CHARACTERISTICS:
            (A) LENGTH: 17  base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: misc_feature
            (B) LOCATION: 1..17
            (D) OTHER INFORMATION: /product= "BB9539 oligomer"

(xi) SEQUENCE DESCRIPTION: SEQ ID NO:142:

TGGGTCAGAA CAGACTT                                                     17

(2) INFORMATION FOR SEQ ID NO:143:

(i) SEQUENCE CHARACTERISTICS:
            (A) LENGTH: 19  base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: misc_feature
            (B) LOCATION: 1..19
            (D) OTHER INFORMATION: /product= "BB9540 oligomer"

(xi) SEQUENCE DESCRIPTION: SEQ ID NO:143:

CATTCTTCAG CTGGGTCAG                                                   19

(2) INFORMATION FOR SEQ ID NO:144:

(i) SEQUENCE CHARACTERISTICS:
            (A) LENGTH: 20  base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: misc_feature
            (B) LOCATION: 1..20
            (D) OTHER INFORMATION: /product= "BB9541 oligomer"

(xi) SEQUENCE DESCRIPTION: SEQ ID NO:144:

ATTTTTGAAC AGCTTCTTCA                                                  20

(2) INFORMATION FOR SEQ ID NO:145:

(i) SEQUENCE CHARACTERISTICS:
            (A) LENGTH: 22  base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: misc_feature
            (B) LOCATION: 1..22
            (D) OTHER INFORMATION: /product= "BB9542 oligomer"

(xi) SEQUENCE DESCRIPTION: SEQ ID NO:145:

CATATTTTTG AGCCCATTCT TC                                             22

(2) INFORMATION FOR SEQ ID NO:146:

(i) SEQUENCE CHARACTERISTICS:
            (A) LENGTH: 21  base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: misc_feature
            (B) LOCATION: 1..21
            (D) OTHER INFORMATION: /product= "BB10374 oligomer"

(xi) SEQUENCE DESCRIPTION: SEQ ID NO:146:

TTTTTGAACC AATTCTTCAG A                                              21

(2) INFORMATION FOR SEQ ID NO:147:

(i) SEQUENCE CHARACTERISTICS:
            (A) LENGTH: 21  base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: misc_feature
            (B) LOCATION: 1..21
            (D) OTHER INFORMATION: /product= "BB10375 oligomer"

(xi) SEQUENCE DESCRIPTION: SEQ ID NO:147:

CAGAAACATA ATCTTGAACC C                                              21

(2) INFORMATION FOR SEQ ID NO:148:

(i) SEQUENCE CHARACTERISTICS:
            (A) LENGTH: 19  base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: misc_feature
            (B) LOCATION: 1..19
            (D) OTHER INFORMATION: /product= "BB10376 oligomer"

(xi) SEQUENCE DESCRIPTION: SEQ ID NO:148:

GTCAGAAACA TCTTTTTGA                                                 19

```
(2) INFORMATION FOR SEQ ID NO:149:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..19
        (D) OTHER INFORMATION: /product= "BB10377 oligomer"

(xi) SEQUENCE DESCRIPTION: SEQ ID NO:149:

GTGTAAGAAT CACAACAAG                                                19

(2) INFORMATION FOR SEQ ID NO:150:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..23
        (D) OTHER INFORMATION: /product= "BB11235 oligomer"

(xi) SEQUENCE DESCRIPTION: SEQ ID NO:150:

GAAACAACAA GCTTCTGGAG TGT                                           23

(2) INFORMATION FOR SEQ ID NO:151:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..19
        (D) OTHER INFORMATION: /product= "BB10379 oligomer"

(xi) SEQUENCE DESCRIPTION: SEQ ID NO:151:

ATTAGGCTTC CAATTCCAA                                                19

(2) INFORMATION FOR SEQ ID NO:152:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..22
        (D) OTHER INFORMATION: /product= "BB10380 oligomer"

(xi) SEQUENCE DESCRIPTION: SEQ ID NO:152:

ATTAGGCAGA ATCTTCCAAG TC                                            22
```

(2) INFORMATION FOR SEQ ID NO:153:

(i) SEQUENCE CHARACTERISTICS:
        (A) LENGTH: 20   base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION:  1..20
        (D) OTHER INFORMATION: /product= "BB10381 oligomer"

(xi) SEQUENCE DESCRIPTION: SEQ ID NO:153:

CAATTCCAAT CTAGAAACAT                                                    20

(2) INFORMATION FOR SEQ ID NO:154:

(i) SEQUENCE CHARACTERISTICS:
        (A) LENGTH: 19   base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION:  1..19
        (D) OTHER INFORMATION: /product= "BB10382 oligomer"

(xi) SEQUENCE DESCRIPTION: SEQ ID NO:154:

CATTGAGATT CAGTTTCAA                                                     19

(2) INFORMATION FOR SEQ ID NO:155:

(i) SEQUENCE CHARACTERISTICS:
        (A) LENGTH: 19   base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION:  1..19
        (D) OTHER INFORMATION: /product= "BB10383 oligomer"

(xi) SEQUENCE DESCRIPTION: SEQ ID NO:155:

GTCAAGAAGT TGACACCTG                                                     19

(2) INFORMATION FOR SEQ ID NO:156:

(i) SEQUENCE CHARACTERISTICS:
        (A) LENGTH: 21   base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION:  1..21
        (D) OTHER INFORMATION: /product= "BB10964 oligomer"

(xi) SEQUENCE DESCRIPTION: SEQ ID NO:156:

GCGCTTAGTG TTGAAGATGA C                                                  21

(2) INFORMATION FOR SEQ ID NO:157:

(i) SEQUENCE CHARACTERISTICS:
        (A) LENGTH: 27  base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..27
        (D) OTHER INFORMATION: /product= "BB10385 oligomer"

(xi) SEQUENCE DESCRIPTION: SEQ ID NO:157:

GTAAGAGAAA CATTGACAAG CGGTTGG                                        27

(2) INFORMATION FOR SEQ ID NO:158:

(i) SEQUENCE CHARACTERISTICS:
        (A) LENGTH: 24  base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..24
        (D) OTHER INFORMATION: /product= "BB10386 oligomer"

(xi) SEQUENCE DESCRIPTION: SEQ ID NO:158:

TTGAACCCAT TGTTGAGATG GGTC                                              24

(2) INFORMATION FOR SEQ ID NO:159:

(i) SEQUENCE CHARACTERISTICS:
        (A) LENGTH: 21  base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..21
        (D) OTHER INFORMATION: /product= "BB10529 oligomer"

(xi) SEQUENCE DESCRIPTION: SEQ ID NO:159:

GTTTCAAAGT ATTGAGCAAT G                                                  21

(2) INFORMATION FOR SEQ ID NO:160:

(i) SEQUENCE CHARACTERISTICS:
        (A) LENGTH: 26  base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..26
        (D) OTHER INFORMATION: /product= "BB10530 oligomer"

(xi) SEQUENCE DESCRIPTION: SEQ ID NO:160:

GATGACACCT GGTTCGGAAC ATTGAG                                          26

(2) INFORMATION FOR SEQ ID NO:161:

(i) SEQUENCE CHARACTERISTICS:
        (A) LENGTH: 26  base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..26
        (D) OTHER INFORMATION: /product= "BB10531 oligomer"

(xi) SEQUENCE DESCRIPTION: SEQ ID NO:161:

CTTGTCTCGA GCGTTCAGTC AAGAAG                                          26

(2) INFORMATION FOR SEQ ID NO:162:

(i) SEQUENCE CHARACTERISTICS:
        (A) LENGTH: 25  base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..25
        (D) OTHER INFORMATION: /product= "BB10532 oligomer"

(xi) SEQUENCE DESCRIPTION: SEQ ID NO:162:

GACTTGTCTC GATTCCTTAG TCAAG                                           25

(2) INFORMATION FOR SEQ ID NO:163:

(i) SEQUENCE CHARACTERISTICS:
        (A) LENGTH: 27  base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..27
        (D) OTHER INFORMATION: /product= "BB10533 oligomer"

(xi) SEQUENCE DESCRIPTION: SEQ ID NO:163:

CCATTCTTCA GATGGTGGAG CACAGAC                                         27

(2) INFORMATION FOR SEQ ID NO:164:

(i) SEQUENCE CHARACTERISTICS:
        (A) LENGTH: 19  base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..19
        (D) OTHER INFORMATION: /product= "BB10534 oligomer"

(xi) SEQUENCE DESCRIPTION: SEQ ID NO:164:

```
GCAGACAATT GCAAGTCAG                                                19
```

(2) INFORMATION FOR SEQ ID NO:165:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..21
        (D) OTHER INFORMATION: /product= "BB10535 oligomer"

(xi) SEQUENCE DESCRIPTION: SEQ ID NO:165:

```
GTAGTCAGCC AAGAAATTTT G                                             21
```

(2) INFORMATION FOR SEQ ID NO:166:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..21
        (D) OTHER INFORMATION: /product= "BB10536 oligomer"

(xi) SEQUENCE DESCRIPTION: SEQ ID NO:166:

```
GTAGTCAGCG ACGAAATTTT G                                             21
```

(2) INFORMATION FOR SEQ ID NO:167:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..22
        (D) OTHER INFORMATION: /product= "BB10195 oligomer"

(xi) SEQUENCE DESCRIPTION: SEQ ID NO:167:

```
GGAATTTGTT CAGAGGTGTA AG                                            22
```

(2) INFORMATION FOR SEQ ID NO:168:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..17
        (D) OTHER INFORMATION: /product= "BB5769 primer"

(xi) SEQUENCE DESCRIPTION: SEQ ID NO:168:

GCATTCTGAC ATCCTCT                                                           17

(2) INFORMATION FOR SEQ ID NO:169:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..31
        (D) OTHER INFORMATION: /product= "BB6040 primer"

(xi) SEQUENCE DESCRIPTION: SEQ ID NO:169:

CGTTAAAATC AACAACTTGT CAATTGGAAC C                                           31

(2) INFORMATION FOR SEQ ID NO:170:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..17
        (D) OTHER INFORMATION: /product= "BB6296 primer"

(xi) SEQUENCE DESCRIPTION: SEQ ID NO:170:

GGAAATCTCA CAGATCT                                                           17

(2) INFORMATION FOR SEQ ID NO:171:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..24
        (D) OTHER INFORMATION: /product= "BB8461 primer"

(xi) SEQUENCE DESCRIPTION: SEQ ID NO:171:

GAAGGAAATC TCATCGTTTG AATA                                                   24

(2) INFORMATION FOR SEQ ID NO:172:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..17
        (D) OTHER INFORMATION: /product= "BB8740 primer"

```
    (xi) SEQUENCE DESCRIPTION: SEQ ID NO:172:

GCTAATGCGG AGGATGC                                                    17

(2) INFORMATION FOR SEQ ID NO:173:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..31
        (D) OTHER INFORMATION: /product= "BB6394 primer"

(xi) SEQUENCE DESCRIPTION: SEQ ID NO:173:

CCGGCATTAC AACTTATCGA TAAGCTTGCA C                                    31

(2) INFORMATION FOR SEQ ID NO:174:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..17
        (D) OTHER INFORMATION: /product= "BB6037 primer"

(xi) SEQUENCE DESCRIPTION: SEQ ID NO:174:

GCGCATTGTT AGATTTC                                                    17

(2) INFORMATION FOR SEQ ID NO:175:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..24
        (D) OTHER INFORMATION: /product= "BB6841 primer"

(xi) SEQUENCE DESCRIPTION: SEQ ID NO:175:

CTTATCGATC AACTTGCACA AACG                                            24

(2) INFORMATION FOR SEQ ID NO:176:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..28
```

-continued (D) OTHER INFORMATION: /product= "BB6189 primer"

(xi) SEQUENCE DESCRIPTION: SEQ ID NO:176:

GTCATGTCTA AGGCGGATCC TTATTAAC                                28

(2) INFORMATION FOR SEQ ID NO:177:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (ii) MOLECULE TYPE: cDNA (ix) FEATURE:
          (A) NAME/KEY: misc_feature
          (B) LOCATION: 1..24
          (D) OTHER INFORMATION: /product= "BB8661 primer"

(xi) SEQUENCE DESCRIPTION: SEQ ID NO:177:

GAGAATGGCA ACAACTTATG CATT                                    24

(2) INFORMATION FOR SEQ ID NO:178:

(i) SEQUENCE CHARACTERISTICS:
          (A) LENGTH: 17 base pairs
          (B) TYPE: nucleic acid
          (C) STRANDEDNESS: single
          (D) TOPOLOGY: linear (ii) MOLECULE TYPE: cDNA (ix) FEATURE:
          (A) NAME/KEY: misc_feature
          (B) LOCATION: 1..17
          (D) OTHER INFORMATION: /product= "BB6038 primer"

(xi) SEQUENCE DESCRIPTION: SEQ ID NO:178:

CCAACATCAA TACAACC                                            17